United States Patent [19]
Holden

[11] Patent Number: 5,876,931
[45] Date of Patent: Mar. 2, 1999

[54] IDENTIFICATION OF GENES

[75] Inventor: David William Holden, London, United Kingdom

[73] Assignee: RPMS Technology Limited, London, United Kingdom

[21] Appl. No.: 637,759

[22] PCT Filed: Dec. 11, 1995

[86] PCT No.: PCT/GB95/02875

§ 371 Date: Jul. 19, 1997

§ 102(e) Date: Jul. 19, 1997

[87] PCT Pub. No.: WO96/17951

PCT Pub. Date: Jun. 13, 1976

[30] Foreign Application Priority Data

Dec. 9, 1994 [GB] United Kingdom .................... 9424921
Jan. 31, 1995 [GB] United Kingdom .................... 9501881
May 5, 1995 [GB] United Kingdom .................... 9509239

[51] Int. Cl.$^6$ .............................. C12Q 1/02; C12Q 1/68; C12N 15/31; C12N 15/63
[52] U.S. Cl. ................................ 435/6; 435/4; 435/172.3; 536/23.7
[58] Field of Search ............................. 435/172.1, 172.3, 435/252.1, 252.3, 243, 4, 6; 424/93.2, 93.4; 530/350; 536/23.1, 23.7

[56] References Cited

U.S. PATENT DOCUMENTS 5,397,697  3/1995  Lam et al. ................................... 435/6
5,527,674  6/1996  Guerra et al. .
5,700,683  12/1997  Stover et al. .
5,700,928  12/1997  Hodgeson et al. .

FOREIGN PATENT DOCUMENTS

WO 92/01056  1/1992  WIPO .
WO 93/04202  3/1993  WIPO .
WO 94/26933  11/1994  WIPO .

OTHER PUBLICATIONS

Roudier et al. (1992) Characterization of translation termination mutations in the spv operon of the Salmonella virulence plasmid pSDL2. J. Bacteriol. 174:6418–6423, Oct. 1992.
Adachi et al. (1994) (Abstract) *Biochem. Biophys. Res. Comm.* 205, 1808–1814.
Albus et al. (1991) *Infect. Immun.* 59, 1008–1014.
Anthony et al. (1991) (Abstract) *J. Gen. Microbiol.* 137, 2697–2703.
Artiguenave et al. (1997) (Abstract) *FEMS Microbiol. Lett.* 153, 363–369.
Black et al. (1995) *Mol. Biochem. Parasitol.* 74, 55–63.
Bolker et al. (1995) *Mol. Gen. Genet.* 248, 547–552.
Brown et al. (1997) 19th Fungal Genetics Conference, 18–23 Mar. 1997, Asilomar Conference Centre, Pacific Grove, CA.
Cheung et al. (1992) *Proc. Natl. Acad. Sci. USA* 89, 6462–6466.
Chuang et al. (1993) *J. Bacteriol.* 175, 2026–2036.
Chiang & Mekalanos (1998) *Mol. Microbiol.* 27, 797–805.
Correia et al. (1995) (Abstract) *Oral Microbiol. Immunol.* 10, 220–226.
Dolganov & Grossman (1993) (Abstract) *J. Bacteriol.* 175, 7644–7651.
Gaillard et al. (1986) (Abstract) *Infect. Immun.*52, 50–55.
Han et al. (1997) (Abstract) *Mol. Cells*7, 40–44.
Kahrs et al. (1994) *Mol. Microbiol.* 12, 819–831.
Kim et al. (1997) (Abstract) *J. Bacteriol.* 168, 1690–1697.
Leahy et al. (1993) (Abstract) *J. Bacteriol.* 175, 1838–1840.
Mei et al. (1997) *Mol. Microbiol.* 26, 399–407.
Mejia–Ruiz et al. (1997) (Abstract) *FEMS Microbiol Lett* 156(1) 101–106.
Morrison et al. (1984) *J. Bacteriol.* 159, 870–876.
Myers & Myers (1997) (Abstract) *Lett. Appl. Microbiol.* 25, 162–168.
Norgren et al. (1989) (Abstract) *Infect. Immun.* 57, 3846–3850.
Pang et al. (1998) *Trends Microbiol.* 6, 131–133.
Pelicic et al. (1998) *Molecular Microbiology* 28, 413–420.
Polissi et al. (1997) *Fourth European Meeting on the Molecular Biology of the Pneumococcus Abstract A.18.*
Ramakrishnan et al. (1997) *Infect. Immun.* 65, 767–773.
Regue et al. (1991) *Res. Microbiol.* 142, 23–27.
Rella et al. (1985) *Gene* 33, 293–303.

(List continued on next page.)

*Primary Examiner*—Nancy Degen
*Assistant Examiner*—Robert Schwartzman
*Attorney, Agent, or Firm*—Arnall Golden & Gregory LLP

[57] ABSTRACT

A method for identifying a microorganism having a reduced adaptation to a particular environment comprising the steps of:

(1) providing a plurality of microorganisms each of which is independently mutated by the insertional inactivation of a gene with a nucleic acid comprising a unique marker sequence so that each mutant contains a different marker sequence, or clones of the said microorganism;

(2) providing individually a stored sample of each mutant produced by step (1) and providing individually stored nucleic acid comprising the unique marker sequence from each individual mutant;

(3) introducing a plurality of mutants produced by step (1) into the said particular environment and allowing those microorganisms which are able to do so to grow in the said environment;

(4) retrieving microorganisms from the said environment or a selected part thereof and isolating the nucleic acid from the retrieved microorganisms;

(5) comparing any marker sequences in the nucleic acid isolated in step (4) to the unique marker sequence of each individual mutant stored as in step (2); and (6) selecting an individual mutant which does not contain any of the marker sequences as isolated in step (4).

31 Claims, 112 Drawing Sheets

OTHER PUBLICATIONS

Roberts et al. (1988) (Abstract) *J. Bacteriol.* 170, 1445–1451.

Roos et al. (1997) (Abstract) *Methods* 13, 112–122.

Rott et al. (1996) (Abstract) *J. Bacteriol.* 178, 4590–4596.

Schiestl & Petes (1991) *Proc. Natl. Acad. Sci. USA* 88, 7585–7589.

Sharetzsky et al. (1991) (Abstract) *J. Bacteriol.* 173, 1561–1564.

Subramanian et al. (1992) (Abstract) *PCR Methods* 1, 187–192.

Tam & Lefebvre (1993) (Abstract) *Genetics* 135, 375–384.

Trieu–Cuot et al. (1991) *Gene* 106, 21–27.

Wooley et al. (1989) (Abstract) *Plasmid* 22, 169–174.

Maurizi et al., "Sequence and Structure of Clp P, the Proteolytic Component of the ATP–Dependent Clp Protease of *Escherichia coli,*" *J. Biol. Chem.*, 265(21):12536–45 (1990).

Stojiljkovik et al., "Ethanolamine utilization in *Salmonella typhurium:* nucleotide sequence, protein expression, and mutational analysis of the cchA cchB eutE eutJ eutG eutH gene cluster," *J. Bacteriol.*, 177(5)1357–66 (1995).

Aldhous, "Fast Track to Disease Genes", *Science* 265:2008–2010 (1994).

Camilli, et al., "Insertional Mutagenesis Of Listeria Monocytogenes With A Novel Tn917 Derivative That Allows Direct Cloning Of DNA Flanking Transposon Insertions", *J. Bacteriol.*, 172:3738–3744 (1990).

Carter & Collins, "The Route of Enteric Infection In Normal Mice", J. Exp. Med., 139:1189–1203 (1974).

Fields, et al., "A Salmonella Locus That Controls Resistance To Microbicidal Proteins From Phagocytic Cells", *Science*, 243:1059–1062 (1989).

Finlay, et al., "Identification And Characterization Of TnphoA Mutants Of Salmonella That Are Unable to Pass Through A Polarized MDCK Epithelial Cell Monolayer", *Mol. Microbiol.*, 2:757–766 (1988).

Galan, et al., "Molecular And Functional Characterization Of The Salmonella Invasion Gene invA: Homology Of InvA To Memebers Of A New Protein Family", (1992).

Groisman & Ochman, "How To Become A Pathogen", *Trends Microbiol.*, 2:289–293 (1994).

Groisman, et al., "Molecular, Functional And Evolutionary Analysis Of Sequences Specific To Salmonella", *Proc. Natl. Acad. Sci. USA*, 90:1033–1037 (1993).

Groisman, et al., "*Salmonella Typhimurium* phoP Virulence Gene Is A Transcriptional Regulator", *Proc. Natl. Acad. Sci. USA*, 86:7077–7081 (1989).

Groisman & Saie, "Salmonella Virulence: New Clues To Intramacrophage Survival", *Trends in Biochem. Sci.*, 15:30–33 (1990).

Hensel, et al., "Simultaneous Indentication Of Bacterial Virulence Genes By Negative Selection", *Science*, 269:400–403 (1995).

Holland, et al., "Tn916 Insertion Mutagenesis In *Escherichia coli* And Haemophilus Influenzae Type b Following Conjugative Transfer", *J. Gen. Microbiol.*, 138:509–515 (1992).

Lee & Falkow, "Isolation Of Hyperinvasive Mutants Of Salmonella", *Methods Enzymol.*, 265:531–545 (1994).

Lisitsyn, et al., "Cloning The Difference Between Two Complex Genomes", *Science*, 259:946–951 (1993).

Lisitsyn, et al., "Direct Isolation Of Polymorphic Markers Linked To A Trait By Genetically Directed Representational Difference Analysis", *Nature Genetics*, 6:57–63 (1994).

Lu, et al., "Tagged Mutations At The Tox1 Locus Of Cochliobolus Heterostrophus By Restriction Enzyme–Mediated Integration", *Proc. Natl. Acad. Sci. USA*, 91:12649–12653 (1994).

Mahan, et al., "Selection Of Bacterial Virulence Genes That Are Specifically Induced In Host Tissues", *Science*, 259:686–688 (1993).

Miller, et al., "Isolation Of Orally Attenuated *Salmonella Typhimurium* Following TnphoA Mutagenesis", *Infection Immun.*, 57:2758–2763 (1989).

Miller, et al., "A Two–Component Regulartory System (phoPphoQ) Controls *Salmonella Typhimurium* Virulence", *Proc. Natl. Acad. Sci. USA*, 86:5054–5058 (1989).

Nelson, et al., "Genomic Mismatch Scanning: A New Approach To Genetic Linkage Mapping", *Nature Genetics*, 4:11–17 (1993).

Pascopella, et al., "Use Of In Vivo Coplementation In *Mycobacterium Tuberculosis* To Identify A Genomic Fragment Associated With Virulence", *Infection Immun.*, 62:1313–1319 (1994).

Slauch, et al., "In Vivo Expression Techology For Selection Of Bacterial Genes Specifically Induced in Host Tissues", *Methods Enzymol*, 235:481–492 (1994).

Smith, et al., "Virulence Of *Asperaillus Femigatus* Double Mutants Lacking Restriction And An Alkaline Protease In A Low–Dose Model of Invasive Pulmonary Aspergillosis", *Infection Immun.*, (1994).

Smith, et al., "Genetic Footprinting: A Genomic Strategy For Determining A Gene's Function Given Its Sequence", *Proc. Natl. Acad. Sci. USA*, 92:6479–6483 (1995).

Walsh & Cepko, "Wildespread Dispertion Of Neuronal Clones Across Functional Gegions Of THe Cerebral Cortex", *Science*, 255:434–440 (1992).

1 2 3 4 5 6 7 8 9 10 11 12

Inoculum pattern

Spleen pattern

Name: mpcc2 1

J05534 Escherichia coli ATP-dependent clp protease proteolytic component (clpP) gene complete cds. Length = 1236

Minus Strand HSPs:

Score = 453 (125.2 bits), Expect = 4.3e-28, P = 4.3e-28
Identities = 113/141 (80%), Positives = 113/141 (80%),
Strand = Minus Query is our Salmonella sequence ⟶

```
Query:359 CCACCAGCCGCTGGGGTACCAGGGCCAGGCGACGGATATTGA 318
          ||| || |   || |  ||||||||||||| ||||||||||
Sbjct:785 CCAACCGTTGGGCGCTACCAGGGCCAGGCGACCGATATCGA 826
                                              c/pP gene ⟶

Query:317 AATTCACGCCCGCGAAATTTTGAAAGTAAAAGGGCGCATGAA 276
          |||||| ||  |||||||| |||||||||| ||||||||||
Sbjct:827 AATTCATGCCCGTGAAATTCTGAAAGTTAAAGGGCGCATGAA 867

Query:275 TGAACTTATGRMKYKMMATACGGGTCANTCTCTTGA 240
          |||||||||                ||  || |||
Sbjct:868 TGAACTTATGGCGCTTCATACGGGTCAATCATTAGA 904

Query:239 GCAGATTGAASGTGATACTGA 219
          ||||||||||  |||||| ||
Sbjct:905 ACAGATTGAACGTGATACCGA 925
```

Score = 231 (63.8 bits), Expect = 4.0e-24,
Poisson P(2) = 4.03-24
Identities = 55/66 (83%), Positives = 55/66 (83%),
Strand = Minus

```
Query:194 TGAAGCGGGTAGAGTACGGTTTGGTTGACTCAATTTTGACCCA 154
          |||||||| || ||||| |||| |||| || || ||| ||||||
Sbjct:950 TGAAGCGGTGGAATACGGTCTGGTCGATTCGATTCTGACCCA 990

Query:153 TCGTAATTGATGCCCCTGG 135
          ||||||||||||||||| —
Sbjct:991 TCGTAATTGATGCCAGAG 1009

Query:134 ACGCAA 129
          |||||
Sbjct:1010 GCGCAA 1015
```

FIG. 5C

>ECCLPXGNA Z23278 E.coli Clpx gene, complete CDS
  Length = 1945

Minus Strand HSPs:

Score = 364 (100.6 bits), Expect =1.6e-20, P = 1.6e-20
  Identities = 88/107 (82%), Positives = 88/107 (82%),
  Strand = Minus

```
Query:325 GATATTGAAATTCACGCCCCGCGAAATTTGAAAGTAAAAGGG 285
          |||| |||||||| ||| ||| ||||| |||||||| |||||
Sbjct:  1 GATATCGAAATTCATGCCCCGTGAAATTCTGAAAGTTAAAGGG 41

Query:284 CGCATGAATGAACTTATG 266
          ||||||||||||||||||
Sbjct: 42 CGCATGAATGAACTTATG 60

Query:265 RMKYKMMATACGGGTCANTCTCTTGAGCAGATTGAASGTGATACTGA 219
          ||| | ||  ||||||||| || |||||||||||||| |||||| ||
Sbjct: 61 GCGCTTCATACGGGTCAATCATTAGAACAGATTGAACGTGATACCGA 107
```

FIG. 5D

```
Score = 231 (63.8 bits), Expect = 6.8e-24,
Poisson P(2) = 6.8e-24
Identities = 55/66 (83%), Positives = 55/66 (83%),
Strand = Minus Query:194 TGAAGCGGGTAGAGTACGGTTTGGTTGACTCAATTTTGACCCA 154
          ||||||||||   ||||| |||||||| || ||  ||| |||||
Sbjct:132 TGAAGCGGGTGGAATACGGTCTGGTCGATTCGATTCTGACCCA 172

Query:153 TCGTAATTGATGCCCCTGG 135
          |||||||||||||||  ||
Sbjct:173 TCGTAATTGATGCCAGAG 191

Query:134 ACGCAA 129
          | ||||
Sbjct:192 GCGCAA 197
```

Fetch ⟶ Gb_ba:Ecoclppa 265, 12536
— OK then type J Biol Chem
(1990)

A) new virulence factors with similarity to sequenced genes:
1. p1F10
similarity to *clpP* (*E. coli*)
(Figure 5)

2. p2D6
similarity to *lcrD* (*Yersinia spp.*)
sequence p2D6_1_I

GGTCTTAATGTACGGGCATGGTCTGCATCGATAACTCCGGCACGCAAATCG
CCATCGATACTCATTTGTTTGGCTGGCATCCCATCAAGCGAGAAACGTGCG
CTAACTTCCGCCACCCTCTCGATACCTTTTGTAATGACAATAAATTGCACG
ATAGTAATGATGGTAAATACGACCAACCCAACGGTGAGATTTCCTCCTACG
ACAAACTTACCGAAAGCATCCACAAATATTACCGGCATTATGTTGTAACAG
TACCCAGCCGTGATGTGCTGATTGGGGAGTTAACAACCGATTTAT 3. s4C3
probably same gene as p2D6, but different region
similarity to *S. typhimurium invA* and *Yersinia spp.lcrD*
sequence s4C3_1_U GCGCGGACGCTAGTGTGGTGGGTGACAGCCAGACGTTACCGAACGGGATGG
GGCAGATCTGTTGGCTTACAAAGACATGGCCCATAAGGCGCAAGGTTTTG
GGACTGGACGTTTTCGCGGGCAGACAACGTATCTCTGTCTTATTAAAATGT
GTCCTGCTTCGGCATATGTATCGAACCCTCGGAGCAAAGTCGTTTGGGCGC
AGAATTAGTACGTTTGGGTCGGTTGCTGTTATTCCTTGGGCTCGGAAAAAG
AGTGCCAGCGTGAAGGAGTGGGATTTGGCAGACTGGCCGCCTAAT sequence s4C3_1_R CACTATAGGGAAAGCTTGCATGCCTGCAGGTCGACTCTAGAGGATCTACTA
GTCATATGGATTGCACTTGTGTATAAGAGTCAGGATTAGAGGACATGCGCC
GGGAACCATACTATCTTTTTCCGGTGCTTCGACGCCATTTGCGGAAACCAC
AGACTTTTTGCGGCGAATGAGGATAATTGGCAATGCTAACAACGCTGAAAA
GAAAGCGAGAGTGATAAAAGGAAAGCCAGGAATTAAAGCGAGGAGCATTAA
AACCACAGCGGCTAATATGAGCGACTGAGGTTGTCTGGCAATTTG

Figure 6A 4. p3F4
similarity to *invG* (*S. typhimurium*)
sequence p3F4_1_U

TGCAGGCCGACTCTAGAGGATCCCCGGGTACCGGTAATTTCTTTAACCTCG
CATCCCGGTGGATGAAAGGATATTCTGGCTGCGTAAGTAATGAATGAACCG
CCCAGTAGATAAATATTGAAAGTGATAACCTGATGTTTTAATAACGATGC
AGGATATACATATAACATGCTGGCATCAAACCAGGTAAGCAAATCATATTG
TGCTGCCAGGTTATTCAAACTATCGACCGGTGGTCCAGGCGGGAATTTTTC
CACTAAATGTAGGTGGGATCAATGGGCTAATTGGTATAGGCGGAT 5. p7G2
similarity to *yscC* (*Yersinia spp.*)
sequence p7G2_1_U CCTGTGATTCCGGATGAAATAGCTTTTACGAAAGCTGTCAGACNTGCTGAA
GAATACGCTGCAAATGGTAAGCTTGTAACTTTTGGGTATTGTTCCAACGCA
TGCTGAAACGGGTTATGGATATATTCGTCGCGGTGAGTTGATAGGAAATGA
CGCTTATGCAGTGGCTGAATTTGTGGAGAAACCGGATATCGATACCGCCCG
TGACTATTTCAAATCAGGGGAAATATTACTGGCCTAGCGGCGATGTTTTTA
TTTCGCGCAAAGCCCTTATTTAAACGAATTAAACGTATCTATCACCCCCAA
ATTCATACAGCTTGTGAA sequence p7G2_3_O TTACTAAACAGGGCCCCGGACCATGTAAACACCACGCTTGCCAACACTAAA
AAACGATGCTTGCCGTAAAAAATTGAACGTTATTTACTTAATACGCCTAT
TTTATTTACATTATGCACGGACAGAGGGTGAGGATTAAATGGATAATATTG
ATAATAAGTATACTCCACAGCTATGTAAATTTTGGGGCTATATCGGATT
TGGTTGTTTTTAATTTAGCCTTATGGCTTTCACTAGGATGTGTCTATTTTT
TTTGTGGTCAAGCACAGAGATTTATTCCCCAACCACC sequence p7G2_1_I TTTCCTTGCCGTGACAGTCCGGGATGCGAGGTTAACGAAATTACCGGCACC
AAAGCTGTGGAGGTGAGCGGTGTCCCCAGCTGCCTGACTCGTATTAGTCAA
TTAGCTTCAGTGCTGGATAATGCGTTAATCAAACGAAAGACAGTGCGGTG
AGTGTAAGTATATACACGCTTAAGTATGCCACTGCGATGGATACCCAGTAC
CATTATCGCGATCAGTCCGTCGTGGTTCCAGGGGTCGCCTAGTGTATTGCG
TGAGATGAGTAACACCAGCGTCCCGACGTCATCGACGAACAATGG

Figure 6B 6. p9B7
similarity to *fliQ, invX (E. coli)*
sequence p9B7_1_I

CATGAGTAACCTACCCAACTGTAATCTTTACCAATATGCATCATAATCTTC
TGCTGGTAAATGATTGGTAATATCGGAAAGGTAAGTGACATAAGCACGCCA
TTACGTAAAAGTGCGGCCCCTAAACTGCCACTTTTTAATAAGGGAAGTAAT
AAAGAAAGGCTCAATGGTCGAATAAAAGCCACAGCCAATGCAATAAGCCAC
TCATTTACCTGTTGTGCCATTCAACCATGCTCTCCAATTCGTAACATTATC
TGCCGGGTATAATTCAACAGGATACCGCTAAGCCATGGGTAG sequence p9B7_3_O ATTCCAGCCCCCGGGCCATCTAACCACTATGAACAATCATCTTCTGGGTGG
ACAATCATTGGTACCATCGGCCAGGCTTGTGCAATATGTATGTCATCACGT
AAAAGCGCGGCCCCTTAATCTCCCCATTCTTCCTTAAGGGCAGTTATCACG
GCTGGCTCAATGGCCGGCTTAACAGCCACAG 7. s6F5
similarity to *yscU (Y. enterocolitica)*
sequence s6F5_1_O GAGGCGCGTCTTCGGTTGAGGGTCGCCCTCCAGATCTTTATGCTCCTGTTT
TACGTCATCTTTACTCATTTTAAGATCTTTTCTAATCTTATAATATTGAAA
AGAATAGTCCAGTATGCCAACGACGAAATAAAGAAACATCACCCCAACCCA
TAACCATTTTTTCAATGATGAAAGCACAAGCACGCCACAGGCTACACCACA
GCCCGGAGGGGGCCGGAAAGTGCTGGGATCTTGATTAATGAAAAGGCAAA
GGGAAGAGATAGGATGATGCATGCTGGTTGGAGGCAGATTATTCATCTTCG

Figure 6C

B) new sequences without similarity to entries in
DNA or protein database:
1. s4D10
sequence s4D10_1_U AGTTGCCGTATTTATTAAATATTCACCTCAGGTCAATATGGAGGTCTTCCC
GGCTAAAAATCATTGCTTTACTAGAGATATCACTCCCTGGGTTGCAATACA
GTACGATTAGTTATCTTGATGCAGCCTGCTGATTTCAGAATGGCAGCTGAC
GTACCCGCGAGACAAACATTCTGGATTATGGACGTTATCAACGCCAATATA
GGGAAGGTGGTGAAGTGGTTGATGAAATACCCCTATCCCTTGCATGTTATC
GCTGACAGGACTGTTATCAGGAGCGGGCATCCTCGATCGGCT sequence s4D10_1_R CAAGAGACAGATCCAACTCGGGCCGATCGCCATAACGCCAGCAGTTTGAAA
GATGAAAGCCCAGCTTATCCAGCCATTCCGGTACAGCGTAACGAGCAGGTT
GCCAGAAATAACGATAAAGTTGCAACACCTCGGGATCAGGTCGGCTCAAAA
ACGGGGTCTCAGGCAAAAATAGCCGATCAGGATGCCCACTCCTAATAACAG
TCCTGTCAACGATAACATCAACGGATAAGGGTATTTCATCAACCACTTCAC
CACCTTCCCTTTATTGGCGTTGGATAACGTCCATAATCCAGA 2. s4H10
sequence s4H10_1_U AGGGCTTTATTGATTCCATTTTTACACTGATGAATGTTCCGTTGCGCTGCC
CGGATTACAGCCGGATCCTCTAGAGTCGACCTGCAGAACCGAGCCAGGAGC
AAATTAATTTTTTTGGGCAATTGCTGAAAGATGAAGCATCCACCAGTAACG
CCAGTGCTTTATTACCGCAGGTTATGTTGACCAGACAAATAGATTATATGC
AGTTAACGGTAGGCGTCGATTATCTTGTCAGAATATCAGGCGCAGCATCGC
AAGCGCTTAATAAGCTGGGTAACATGGCATGAAGGGGCAACCC sequence s4H10_1_R CACTATAGGGAAAGCTTGCATGCCTGCAGGTCGACTCTAGAGGATCTACTA
GTCATATGGATTCCTAGGCGGCCAGATCTGATCAAGAGACAGATCCAACTC
GGGCCGATCGCCATAACGCCAGCAGTTTGAAAGATGAAAGCCCAGCTTATC
CAGCCATTCCGGTACAGCGTAACGAGCAGGTTGCCAGAAATAACGATAAAG
TTGCAACACCTCGGGATCAGGTCGGCTCAAAAACGGGGTCTCAGGCAAAAA
TAGCCGATCAGGATGCCCACTCCTAATAACAGTCCTGTCAACG

Figure 6D 3. p4G5
sequence p4G5_1_O

CCCCCCCCCTTCTCCTGGCTTACACAGCCCCAGACCGGCGCTGGAAAAGGC
CATTCCCGCCATACAGGAGGCCAGCAACATATTTTCACGCGCCGCCAGATC
GTGGCCGTAACCCACGGCTTTCGGCAGCGATTTGCCAATCATCGCTATCGC
GCCAATCGCCAGGCTGTCGGTAAACGGCGTGGCGTTGAGCGCGCTGTAGGC
CTCAATCGCATGCGTCAACGCATCGATACCGGTCATCGCCGTCACGTTTGG
CGGAACGCCTTCGGTCACGGAAGCATCAAGAATCGCCACGTCCGGC sequence p4G5_1_U CGCGAACGTGCGCCGCAACTGCTTGTGGACGGTGAATTGCAGTTTGACGCC
GCTTTCGTGCCGGAGGTCGCCGCGCAAAAGCGCCTGACAGCCCGCTGCAA
GGCCGCGCCAACGTGATGATTTTCCCGTCGCTGGAGGCGGGCAATATTGGC
TACAAAATCACTCAGCGTCTGGGAGGCTATCGCGCTGTTGGGCCGCTAATT
CAGGGGCTTGGCGCGCCGCTTCACGACCTCTCCCGAGGCTGTAGCGTGCAG
GAAATTATCGAACTGCGGTTGGTGAGAAAACCAA 4. p7A3
sequence p7A3_1_U CGCCCTAGCATGCCTGGCGTTGTCCGGTTATTGCTCGTCAAGCGAACAGAT
GCAAAAGGTGAGAGCGACTCTCGAATCATGGGGGGTCATGTATCGGGATGG
TGTAATCTGTGATGACTTATTGGTACGAGAAGTGCAGGATGTTTTGGATAA
AAATGGGTTACCCGCATGCTGAAGTATCCAGCGAAGGGCCGGGGAGCGTGT
TAATTCATGATGATATACAAATGGATCAGCAATGGCGCAAGGTTCAACCAT
TACTTGCAGATATTCCCGGGTTATTGCACTGGCAGATTAGTCACTCTC sequence p7A3_1_I CCCTTCCCAGGCTCGACAGGTACACAGCCAGCCACTGGTGCAGGCAGTTAC
TTGCTTTCATCATGGGAAGGAGCAATATCCTGATATATTAAAGAAAGAGCG
GGATCCCCTTTCTTTACTGCTGCTAACGTTTCTTGCAAAATGCGTTGATGA
GATTCATCCAGCACACCACTGATAACAAAAGAGCGCCGCATTGGCGTAACA
TTGACAAGCCCCACTAAACCGCTCTCTATTATCGCAGAAATAATATCATCC
CCCTGAGACTGATGAGAGTGACTATTCTGCCAGCGCAAATAACCC 5. p10E11
sequence p10E11_1

ATACCGAGTATTAAGCGGCTGTGTAACATCGTCATCCAACAACATACGCAG
CGAGCCGCCACGCCGGAAAAACCGCATCGTGTCATGTGCCTGTTGTAGGGT
CGGGTCTTTTTTCATGAGTACGTTTCTGCGTATCATACTGGAAATTTCC
CCCCACTTACTGATAAGCCCTGTCAGTTGGGTAAGGACAGAGTTAAGCTCC
TGAGACATTTTTTGGAATGGTTATCTTTCCCCGACTCATAAAATCGGTATT
CCCGCTGGGGGCAATATCCAAAGACGCTTTGGTCGCCCGTAGGGCACC

Figure 6E sequence p10E11_U

GCCGTATGCCTGCAGTTGCCCGGTTATTGCTCGTCAAGCGAACCGATGCCA
AAGGTGAGAGCGACTCTCGAATCATGGGGGGTCATGTATCGGGATGGTGTA
ATCTGTGATGACTTATTGGTACGAGAAGTGCAGGATGTTTTGGTAAAAATG
GGTTACCCCCATGCTGAAGTATCCAGCGAAGGGGCGGGGAGCGTGTTAATT
CACGATGATATTCAAATGGGTCAGCAATGGGGCAAGGTTCAACCCCCACTT
GCAGATATTCCCCCCCTATTGGACTGGCAGATTAGTCACTCTCA 6. s4B9
sequence s4B9_1_O GGGCGACCTGCCCGCGGCGCAACTTTCCCCGAAGCGTTTTCCATTTCCTTG
TTCTTAAATGACCTGGAAAGCTTACCTAAGCCTTGTCTTGCCTATGTGACA
ATACTGCTTGGAGAACACCCGGACGTCCATGATTATGCTATACAGATCACA
GCGGATGGGGGATGGTGAATCGGTTATTATACCACAAGTCGCAGCTCTGAG
CTTATTGCTATTGAGATAGAAAAACACCCCGCTTCAACTTGGATTTTGAAT
AATGTAATACGCAATCACCATACACTATATTCGGGTGGCGTATAA sequence s4B9_1_R TTCGAGCTGGGGCACCGCTAATATCTTTAACCTCGCATCCCGGTGATGAAA
GGATATTCTGGCTGCGTAAGTAATGAATGAACCGCCCAGCAGATAAAATAT
TGACAGTGATAACCCGATGTTTTTTTAACGATGCAGGCTATACATATAACA
TAGCTGGCCACCAACACAGCTGAAGTAAATCATATTGTTGCTGCCAGGCTA
CTTCACACTATTGTCCGGCGGGCCAGCGGGGATTTTCCCCCTAAATCTCGC
TGGTTCTCAAA 7. p4F8
sequence p4F8_1_I AGTCTACGATTTCGCTATATCTTCTCTTAATCATGGCCGCCATTTGTGGAT
GCGATTTTAAAATATCCGGGCGATCTTTCATTAAAAAATAAAGATTCCCCA
TGACTTCACAGATAAAGGTATCGGTATTTTGAGTGATACGTAACAATTCGT
TCTCTTCGTGTGGGTCCATGATGCGAAGAATAATGGTGGCATCATTTTCAT
GAGGATTATGAACCCGAAATCTTTCTCTTTGCGATGCGCAGGCTAACTCTT
TCAACTCAAAAAAATCTCTGTAAGCCGCTCTCGTGTGGGGCGC 8. p7B8
sequence p7B8_1_O GCGCCCCTTTAATTGGTTGAGGCGGCTGGTATTCTTGTAAGGGTAATACTA
GCGAGACCCAGGTTCCACCCCCGGGGACACTTTTTAGTGTCAGATTACCGC
CCATCATTTTAGCCAGGCTTGACGCAATAGTCAGTCCAATTCCTGTACCTT
GCGAATTTGTGTCTGCTTGATAAAAGCAGAAAGATTTGAGACTGCTGCT
GTTTTTCAATCCCCCACCGCTATCGCTAACCAGAAATATTAATTGTTCCT
CACCAAGATTGAGCGCCAGACGTATCCCTCCCCCCTCGGGAAAT

Figure 6F 9. p8G12
sequence p8G12_1_I

GGATAAGATCCCGGATAAGTATGTCAGGCTCGTATGCACAACAGGCATTAT
AAACCTCTAGACCATTTTTAACATGCTCTACTATTTTAAAATGAGGCCAGG
GTAATAAGGCATTCATAATGCCGTTAATGATGATTTCATGATCGTCTACTA
ATAAGATCTTATATTCTTTCATTTGGCTGCCCTCGCGAAAATTAAGATAAT
ATTAAGTAATGGTGTAGGTTGTGGAGATCATACGTATTTTCTGGCGTAAGT
CGGTTAGTTCCTCCAGCGCGATGATTTTCCCCATTTTTACGCGAT 10. p9G4
sequence p9G4_1_O TTCCATATTGCTCGTCCGGGGAGCGTGTTAATTCTTGATGATATACCAATG
GATCTGCAATGGCGCAAGGTTCAACCATTACTTGGAGATATTCCCGGGTTA
TTGTACTGGGAGATTAGTCACTCTCATCAGTCTCAGGGGGTGATGTTATT
TCTGGGATAATAGAGCAACGGCGTTAGCAGGGGTCGGTCAGTAGTCACGGC
CAACTTCGGTGCACTTTTGCGTATCACTGGGGTATCATAACTGAATCTCAT
CCCCCCCACTTTGGTAATCACAC sequence p9G4_1_U AATTCTTTTACCTCCATAAGCTGCGTGGCATAGCGATACAGAGTATTAAGC
GGGTGTGTTACATCGTCATCCAACAACATACGCAGCGAGCCGCCACGCCGG
AAAAACCGCATCGTGTCATGTGCCTGTTGTAGGGTCGGGTCTTTTTTTCAT
GAGTACGTGTTCTGCGCTATCATACTGGAAATTTCCCCCACTTACTGATA
AGCCCTGTCAGTTGGGTAAGGACAGCGTTAAGCTCCTGAGACATTTTTGA
GTTGTTATCTGCCCCCCGACTCATAAGATCGGGTATTCCGCGGTGG 11. p9B6
sequence p9B6_1

ATATCCCTAATGCTTTTCCTTAAAATAAATACCACGGAAGGATACTGGCCA
CCTAGCCAAATTTAGAAAGCAATGAACATCCGGTTTATTCCTGAAAACGAT
TACTCCGGCGCACGTTGTTCTGGCGTTACCTGAGCCAGCAAACGATATAAT
GGGGTGGTGACCCGCATACCGGTCATTGGCATCCATCCACACCGGAGGGA
GTAAAACTCATTAGGCCATAGGTAATATCATTAAGACGCTCTAATAAATGA
GGGTGGGGGGCCCAAACTACCACTCCAGTATGTATTGAGTCA

Figure 6G 12. p6G5
sequence p6G5_2_I

CCCATGGGCGCAATTTGTTGCGCAGCGTTTACCCGACCATCGCGTTTATGA
GCTGTAATTCATGGGGGGTAAAAACGGGCGTGACGACCCCAACGGAAGATA
AGGCCGGGCTTAAACAGGAGATTATTGCTAATGCGCAGCGCAAAGTGTTGC
TGGCGGACAGCAGTAAGTATGGCGCGCATTCGCTCTTTAATGTGGTGCCGC
TTGAGCGCTTTAATGACGTGATTACCGACGTCAATCTGCCGCCGTCAGCGC
AGGTTGAACTGAAAGGGCGCGCTTTTTGCGCTAACG

Figure 6H

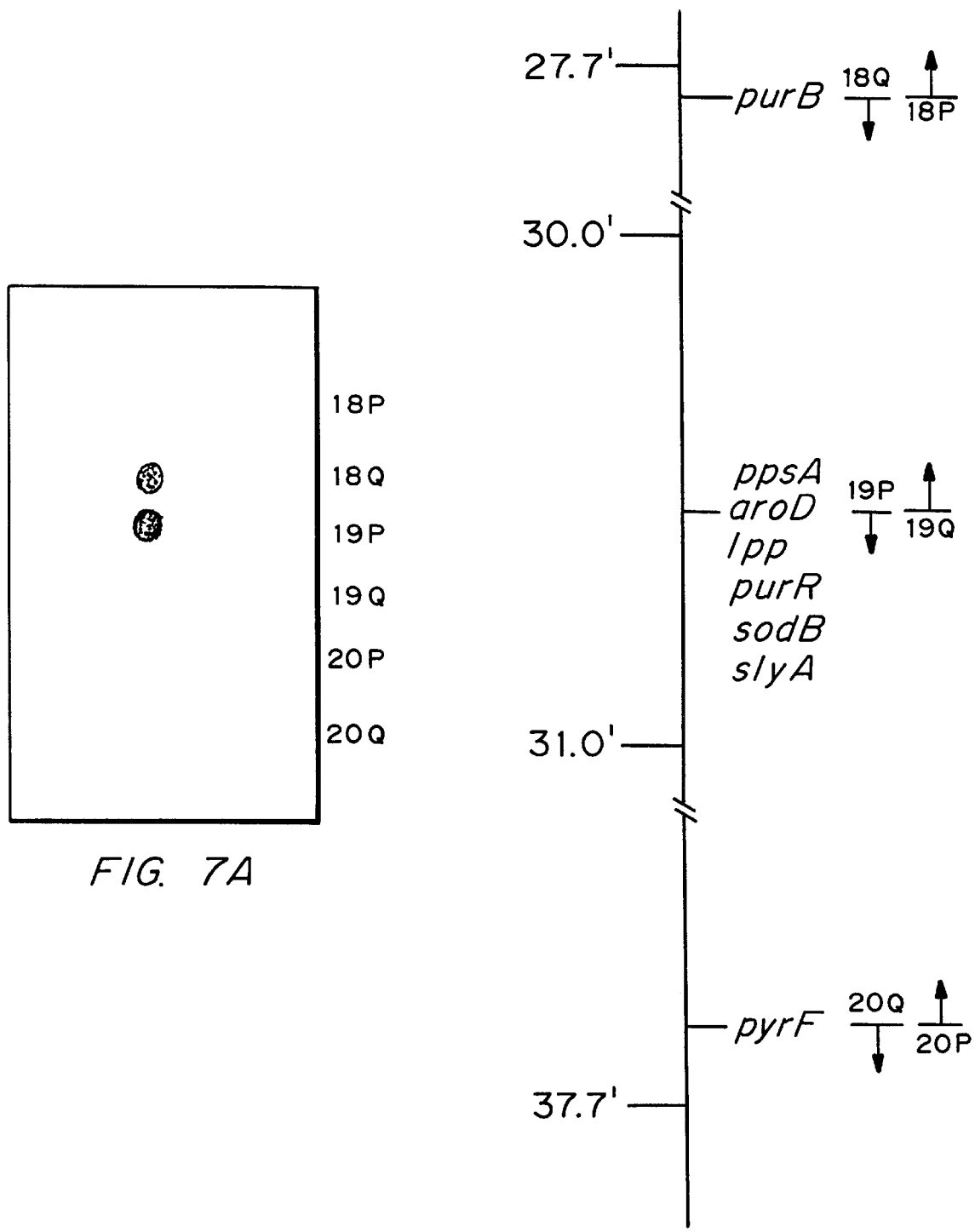

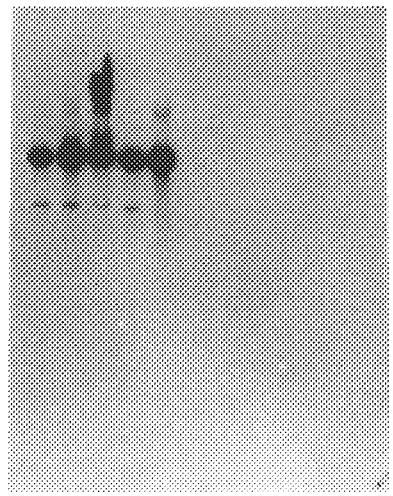
FIG.10A  PstI
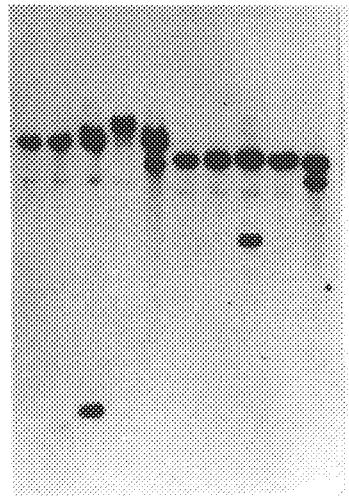
FIG.10B  HindIII  EcoRV

DNA sequence of VGC II from centre to left hand end

```
1   CTGCAGAACCGAGCCAGGAGCAAATTAATTTTTTGAACAATTGCTGAAAGATGAAGCAT   60
    ----+----+----+----+----+----+----+----+----+----+----+----+
    GACGTCTTGGCTCGGTCCTCGTTTAATTAAAAAAACTTGTTAACGACTTTCTACTTCGTA a     L  Q  N  R  A  R  S  K  L  I  F  L  N  C  -  K  M  K  H
b   C  R  T  E  P  G  A  N  -  F  F  -  T  I  A  E  R  -  S  I
c     A  E  P  S  Q  E  Q  I  N  F  F  E  Q  L  L  K  D  E  A  S

61  CCACCAGTAACGCCAGTGCTTTATTACCGCAGGTTATGTTGACCAGACAAATGGATTATA  120
    ----+----+----+----+----+----+----+----+----+----+----+----+
    GGTGGTCATTGCGGTCACGAAATAATGGCGTCCAATACAACTGGTCTGTTTACCTAATAT a     P  P  V  T  P  V  L  Y  Y  R  R  L  C  -  P  D  K  W  I  I
b   H  Q  -  R  Q  C  F  I  T  A  G  Y  V  D  Q  T  N  G  L  Y
c     T  S  N  A  S  A  L  L  P  Q  V  M  L  T  R  Q  M  D  Y  M

121 TGCAGTTAACGGTAGGCGTCGATTATCTTGCCAGAATATCACGGCGCAGCATGCCAAGCG  180
    ----+----+----+----+----+----+----+----+----+----+----+----+
    ACGTCAATTGCCATCCGCAGCTAATAGAACGGTCTTATAGTGCCGCGTCGTACGGTTCGC a     C  S  -  R  -  A  S  I  I  L  P  E  Y  H  G  A  A  C  Q  A
b   A  V  N  G  R  R  R  L  S  C  Q  N  I  T  A  Q  H  A  K  R
c     Q  L  T  V  G  V  D  Y  L  A  R  I  S  R  R  S  M  P  S  A
```

Figure 11A

```
181  CTTAATAAGCTGGATAACATGGCATGAAGGTTCATCGTATAGTATTCTTACTGTCCTTA    240
     ----+----+----+----+----+----+----+----+----+----+----+----+
     GAATTATTCGACCTATTGTACCGTACTTCCAAGTAGCATATCATAAAGAATGACAGGAAT a     L  N  K  L  D  N  M  A  -  R  F  I  V  -  Y  F  L  L  S  L
b     L  -  I  S  W  I  T  W  H  E  G  S  S  Y  S  I  S  Y  C  P  Y
c        -  A  G  -  H  G  M  K  V  H  R  I  V  F  L  T  V  L  T

241  CGTTCTTTCTTACGGCATGTGATGTGGATCTTTATGCTCATTGCCAGAAGATGAAGCGA    300
     ----+----+----+----+----+----+----+----+----+----+----+----+
     GCAAGAAAGAATGCCGTACACTACACCTAGAAATAGCGAGTAACGGTCTTCTACTTCGCT
                                               start yscJ*?
a     R  S  F  L  R  H  V  M  W  M  F  I  A  H  C  Q  K  M  K  R
b     V  L  S  Y  G  M  -  C  G  S  L  S  L  I  A  R  R  -  S  E
c        F  F  L  T  A  C  D  V  D  L  Y  R  S  L  P  E  D  E  A  N 301  ATCAAATGCTGGCATTACTTATGCAGCATCATATTGATGCGAAAAAAACAGGAAGAGGA    360
     ----+----+----+----+----+----+----+----+----+----+----+----+
     TAGTTTACGACCGTAATGAATACGTCGTAGTATAACTACGCTTTTTTTGTCCTTCTCCT
                                         start yscJ*?
a     I  K  C  W  H  Y  L  C  S  I  I  L  M  R  K  K  T  G  R  G
b     S  N  A  G  I  T  Y  A  A  S  Y  -  C  E  K  K  Q  E  E  D
c     Q  M  L  A  L  L  M  Q  H  H  I  D  A  K  K  N  R  K  R  M
```

Figure 11B

```
361  TGGTGTAACCTTACGTGTCGAGCAGTCGGCAGTTTATTAATGCGGTTGAGGCTACTTAGA
     ------+---------+---------+---------+---------+---------+  420
     ACCACATTGGAATGCACAGCTCGTCAGCCGTCAAATAATTACGCCAACTCCGATGAATCT a        W   C   N   L   T   C   R   A   V   G   S   L   L   M   R   L   L   R
b        G   V   T   L   R   V   E   Q   S   A   V   Y   -   C   G   -   G   Y   L   D
c        V   -   P   Y   V   S   S   R   Q   F   I   N   A   V   E   A   T   -   T

421  CTTAACGGTTATCCGCATAGGGCAGTTTACAACGGGGATAAGATGTTTCCGGCTAATCA
     ------+---------+---------+---------+---------+---------+  480
     GAATTGCCAATAGGCGTATCCCGTCAAATGTTGCCCTATTCTACAAAGGCCGATTAGT a        L   N   G   Y   P   H   R   A   V   Y   N   G   G   -   D   V   S   G   -   S
b        L   T   V   I   R   I   G   Q   F   T   T   A   D   K   M   F   P   A   N   Q
c        -   R   L   S   A   -   G   S   L   Q   R   R   I   R   C   F   R   L   I   S

481  GTTAGTGGTATCACCCCAGGAAGAACAGGCAGAAGATTAATTTTTTAAAAGAACAAAGAA
     ------+---------+---------+---------+---------+---------+  540
     CAATCACCATAGTGGGGGTCCTTCTTGTCCGTCTTCTAATTAAAAAATTTTCTTGTTCTT a        V   S   G   I   T   P   G   R   T   G   R   R   L   I   F   -   K   N   K   E
b        L   V   V   S   P   Q   E   E   Q   A   E   D   -   F   F   K   R   T   K   N
c        -   W   Y   H   P   R   K   N   R   Q   K   I   N   F   L   K   E   Q   R   I
```

Figure 11C

```
541  TTGAAGGAATGCTGAGTCAGATGGAGGGCGTGATTAATGGCAAAAGTGACCATTGCGCT
     ---------+---------+---------+---------+---------+---------+  600
     AACTTCCTTACGACTCAGTCTACCTCCCCGCACTAATTACCGTTTTCACTGGTAACGCGA a      L  K  E  C  -  V  R  W  R  G  V  I  N  G  K  S  D  H  C  A
b      -  R  N  A  E  S  D  G  G  A  -  L  M  A  K  V  T  I  A  L
c        E  G  M  L  S  Q  M  E  G  R  D  -  W  Q  K  -  P  L  R  Y

601  ACCGACTTATGATGAGGGAAGTAACGCTTCTCCGAGCTCAGTTGCCGTATTTATAAAATA
     ---------+---------+---------+---------+---------+---------+  660
     TGGCTGAATACTACTCCCTTCATTGCGAAGAGGCTCGAGTCAACGGCATAAATATTTTAT a      T  D  L  -  G  K  -  R  F  S  E  L  S  C  R  I  Y  K  I
b      P  T  Y  D  E  G  S  N  A  S  P  S  S  V  A  V  F  I  K  Y
c        R  L  M  M  R  E  V  T  L  R  A  Q  L  P  Y  L  -  N  I

661  TTCACCTCAGGTCAATATGGAGGCCTTTCGGGTAAAAATTAAAGATTAATAGAGATGTC
     ---------+---------+---------+---------+---------+---------+  720
     AAGTGGAGTCCAGTTATACCTCCGGAAAGCCCATTTTAATTTCTAATTATCTCTACAG a      F  T  S  G  Q  Y  G  G  L  S  G  K  N  -  R  F  N  R  D  V
b      S  P  Q  V  N  M  E  A  F  R  V  K  I  K  D  L  I  E  M  S
c        H  L  R  S  I  W  R  P  F  G  -  K  L  K  I  -  R  C  Q

Figure 11D
```

```
721   AATCCCTGGGTTGCAATACAGTAAGATTAGTATCTTGATGCAGCCTGCTGAATTCAGAAT
      ----------+---------+---------+---------+---------+---------+  780
      TTAGGGACCCAACGTTATGTCATTCTAATCATAGAACTACGTCGGACGACTTAAGTCTTA a         N  P  W  V  A  I  Q  -  D  -  Y  L  D  A  A  C  -  I  Q  N
b         I  P  G  L  Q  Y  S  K  I  S  I  L  M  Q  P  A  E  F  R  M
c         S  L  G  C  N  T  V  R  L  V  S  -  C  S  L  L  N  S  E  W

781   GGTAGCTGACGTACCCGCGAGACAAACATTCTGGATTATGGACGTTATCAACGCCAATAA
      ----------+---------+---------+---------+---------+---------+  840
      CCATCGACTGCATGGGCGCTCTGTTTGTAAGACCTAATACCTGCAATAGTTGCGGTTATT a         G  S  -  R  T  R  E  T  N  I  L  D  Y  G  R  Y  Q  R  Q  -
b         V  A  D  V  P  A  R  Q  T  F  W  I  M  D  V  I  N  A  N  K
c         -  L  T  Y  P  R  D  K  H  S  G  L  W  T  L  S  T  P  I  K

841   AGGGAAGGTGGTGAAGTGGTTGATGAAATACCCTTATCCGTTGATGTTATCGTTGACAGG
      ----------+---------+---------+---------+---------+---------+  900
      TCCCTTCCACCACTTCACCAACTACTTTATGGGAATAGGCAACTACAATAGCAACTGTCC a         R  E  G  G  E  V  V  D  E  I  P  L  S  V  D  V  I  V  D  R
b         G  K  V  V  K  W  L  M  K  Y  P  Y  P  L  M  L  S  L  T  G
c         G  R  W  -  S  G  -  N  T  L  I  R  -  C  Y  R  -  Q  D
```

Figure 11E

```
                    Tn insertion P11H11
                          ⇒
901  ACTGTTATTAGGAGTGGGCATCCTGATCGGCTATTTTTGCCTGAGACGCCGTTTTGAGC  960
     ----------+---------+---------+---------+---------+---------+
     TGACAATAATCCTCACCCGTAGGACTAGCCGATAAAAACGGACTCTGCGGCAAAACTCG a      T  V  I  R  S  G  H  P  D  R  L  F  L  P  E  T  P  F  L  S
b       L  L  G  V  G  I  L  I  G  Y  F  C  L  R  R  R  F  -  A
c        C  Y  -  E  W  A  S  -  S  A  I  F  A  -  D  A  V  F  E  P 961  CGACCTGATCCCGAGGTGTTGCAACTTTATCGTTATTCTGGCAACCTGCTCGTTACGCT  1020
     ----------+---------+---------+---------+---------+---------+
     GCTGGACTAGGGCTCCACAACGTTGAAATAGCAATAAAGACCGTTGGACGAGCAATGCGA a      R  P  D  P  E  V  L  Q  L  Y  R  Y  F  W  Q  P  A  R  Y  A
b       D  L  I  P  R  C  C  N  F  I  V  I  S  G  N  L  L  V  T  L
c        T  -  S  R  G  V  A  T  L  S  L  F  L  A  T  C  S  L  R  C
                                                    Tn insertion P11D10
                                                          ⇒
1021 GTACCGGAATGGCTGGATAAGCTGGGCTTTCATCTTCAAACTGCTGGCGTTATGGCGATC  1080
     ----------+---------+---------+---------+---------+---------+
     CATGGCCTTACCGACCTATTCGACCCGAAAGTAGAAGTTTGACGACCGCAATACCGCTAG a      V  P  E  W  L  D  K  L  G  F  H  L  Q  T  A  G  V  M  A  I
b       Y  R  N  G  W  I  S  W  A  F  I  F  K  L  L  A  L  W  R  S
c        T  G  M  A  G  -  A  G  L  S  S  N  C  W  R  Y  G  D  R
```

Figure 11F

```
1081   GGCCCGAGTTGGATCGTCTTTCTTGACAGAGGCGTTAAATAGACTAAGAGGAAGCTCTGTTA   1140
       ----+----+----+----+----+----+----+----+----+----+----+----+
       CCGGGCTCAACCTAGCAGAAAGAACTGTCTCGCAATTTATCTGATTCTCCTTCGAGACAAT a          G  P  S  W  I  V  F  L  T  E  R  -  I  D  -  E  E  A  L  L
b          A  R  V  G  S  S  -  Q  S  V  K  -  T  K  R  K  L  C
c          P  E  L  D  R  L  D  R  A  L  N  R  L  R  G  S  S  V  I

1141   TTCCAGCCTGTGTTAAATGACAGGCAAAAACGGCAGGTTCGTCTTGCCGTCTATATCGG   1200
       ----+----+----+----+----+----+----+----+----+----+----+----+
       AAGGTCGGACACAATTTACTGTCCGTTTTTGCCGTCCAAGCAGAACGGCGGCATATAGCC a          F  Q  P  V  -  M  T  G  K  N  G  R  F  V  L  R  R  V  Y  R
b          S  S  L  F  K  -  Q  A  K  T  A  G  S  S  C  A  A  Y  I  G
c          P  A  C  L  N  D  R  Q  K  R  Q  V  R  L  A  P  R  I  S  A

1201   CATTTGCCTTTGGGCTGGGATTATTCAAACTCAGGTGTAGTGACTATTTTATGCTACCAG   1260
       ----+----+----+----+----+----+----+----+----+----+----+----+
       GTAAACGGAAACCCGACCCTAATAAGTTTGAGTCCACATCACTGATAAAATACGATGGTC start lcrE*?
a          H  L  P  L  G  W  D  Y  S  N  S  G  V  V  T  I  L  C  Y  Q
b          I  C  L  W  A  G  I  I  Q  T  Q  V  -  L  F  Y  A  T  R
c          F  A  F  G  L  G  L  F  K  L  R  C  S  D  Y  F  M  L  P  E
```

Figure 11G

```
1261  AGTATCGGCAATTGCTTCTACAGTGGTTTAGCGAGGATGAGATCTGGCAGCTATATGGTT  1320
      ----+----+----+----+----+----+----+----+----+----+----+----+
      TCATAGCCGTTAACGAAGATGTCACCAAATCGCTCCTACTCTAGACCGTCGATATACCAA a       S  I  G  N  C  F  Y  S  G  L  A  R  M  R  S  G  S  Y  M  V
b     V  S  A  I  A  S  T  V  V  -  R  G  -  D  L  A  A  I  W  L
c       Y  R  Q  L  L  Q  W  F  S  E  D  E  I  W  Q  L  Y  G  W

1321  GGTTGGGGCAAAGAGATGGCAAATTACTTCCTCCGCAAGTGATGCAACAAACTGCATTGC  1380
      ----+----+----+----+----+----+----+----+----+----+----+----+
      CCAACCCCGTTTCTCTACCGTTTAATGAAGGAGGCGTTCACTACGTTGTTTGACGTAACG a       G  W  G  K  E  M  A  N  Y  F  L  R  K  -  C  N  K  L  H  C
b     V  G  A  K  R  W  Q  I  T  S  S  A  S  D  A  T  N  C  I  A
c       L  G  Q  R  D  G  K  L  L  P  P  Q  V  M  Q  Q  T  A  L  Q

1381  AGATCGGTACCGCCATTCTTAATCGGGAAGCCATGACGATGCGGGTTTTACATGCGCTA  1440
      ----+----+----+----+----+----+----+----+----+----+----+----+
      TCTAGCCATGGCGGTAAGAATTAGCCCTTCGGTACTGCTACGCCCAAAATGTACGCGAT a       R  S  V  P  P  F  L  I  G  K  R  M  T  M  R  V  L  H  A  L
b     D  R  Y  R  H  S  -  S  G  S  A  -  R  C  G  F  Y  M  R  Y
c       I  G  T  A  I  L  N  R  E  A  H  D  D  A  G  F  F  T  C  A  I
```

Figure 11H

```
1441  TTAGTATTATTACCCCCTCCGCAGCGTATACTTTGGCCGAAGACTTCTCTTACCGAGATT  1500
      ------+---------+---------+---------+---------+---------+
      AATCATAATAATGGGGGAGGCGTCGCATATGAAACCGGCTTCTGAAGAGAATGGCTCTAA a         L  V  L  L  P  P  P  Q  R  I  L  W  P  K  T  S  L  T  E  I
b      -  Y  Y  Y  P  L  R  S  V  Y  F  G  R  R  L  L  P  R  L
c         S  I  T  P  S  A  A  Y  T  L  A  E  D  F  S  Y  R  D  Y

1501  ATCTTCATGGAGCATTTGCTATGAGTTTTACTTCACTTCCTCTGACGGAAATTAACCATA  1560
      ------+---------+---------+---------+---------+---------+
      TAGAAGTACCTCGTAAACGATACTCAAAATGAAGTGAAGGAGACTGCCTTTAATTGGTAT a         I  F  M  E  H  L  L  -  V  L  L  H  F  L  -  R  K  L  T  I
b      S  S  W  S  I  C  Y  E  F  F  T  S  S  D  G  N  -  P  -
c         L  H  G  A  F  A  M  S  F  T  S  L  P  L  T  E  I  N  H  K

1561  AGCTACCCGCTCGAAATATTTGAGTCACAGTGGATAACATTAACTTTATTG  1620
      ------+---------+---------+---------+---------+---------+
      TCGATGGGCGAGCTTTATAATAACTCAGTGTCACCTATTGTAATGTTAATTGAAATAAAC a         S  Y  P  L  E  I  L  L  S  H  S  G  -  H  Y  N  -  L  Y  L
b      A  T  R  S  K  Y  Y  -  V  T  V  D  N  I  T  I  N  F  I  C
c         L  P  A  R  N  I  I  E  S  Q  W  I  T  L  Q  L  T  L  F  A
```

Figure 11I

```
1621  CGCAAGAGCAACAAGCTAAGAGAGTTTCACATGCTATTGTGAGCTCCGCTTACCGTAAGG  1680
      ------+---------+---------+---------+---------+---------+
      GCGTTCTCGTTGTTCGATTCTCTCAAAGTGTACGATAACACTCGAGGCGAATGGCATTCC a       R  K  S  N  K  L  R  E  F  H  M  L  L  -  A  P  L  T  V  R
b       A  R  A  T  S  -  E  S  F  T  C  Y  C  E  L  R  L  P  -  G
c       Q  E  Q  Q  A  K  R  V  S  H  A  I  V  S  S  A  Y  R  K  A

1681  CTGAAAAAATCATCCGAGACGCCTATCGTTATCAGCGTGAACAGAAAGTTGAGCAGCAAC  1740
      ------+---------+---------+---------+---------+---------+
      GACTTTTTTAGTAGGCTCTGCGGATAGCAATAGTCGCACTTGTCTTTCAACTCGTCGTTG a       L  K  K  S  S  E  T  P  I  V  I  S  V  N  R  K  L  S  S  N
b       -  K  N  H  P  R  R  L  S  L  S  A  -  T  E  S  -  A  A  T
c       E  K  I  I  R  D  A  Y  R  Y  Q  R  E  Q  K  V  E  Q  Q  Q

1740  AAGAACTAGCCGTGCTTGCCGTAAAAATACGCTGGAAAAATGGAAGTGGAATGGCTGGAAC  1800
      ------+---------+---------+---------+---------+---------+
      TTCTTGATCGGCACGAACGGCATTTTTATGCGACCTTTTTACCTTCACCTTACCGACCTTG a       K  N  -  R  A  C  V  K  I  R  W  K  K  W  K  W  N  G  W  N
b       R  T  S  V  L  A  -  K  Y  A  G  K  K  N  G  S  G  M  A  G  T
c       E  L  A  C  L  R  K  N  T  L  E  K  M  E  V  E  W  L  E  Q
```

Figure 11J

```
1801  AGCATGTAAACATTTACAAGACGATGAAAATCAATTTCGTTCATTGGTCGATCACGCAG  1860
      ----+----+----+----+----+----+----+----+----+----+----+----+
      TCGTACATTTGTAAATGTTCTGCTACTTTTAGTTAAAGCAAGTAACCAGCTAGTGCGTC a     S  M  -  N  I  Y  K  T  M  K  I  N  F  V  H  W  S  I  T  Q
b     A  C  K  T  F  T  R  R  -  K  S  I  S  F  I  G  R  S  R  S
c     H  V  K  H  L  Q  D  D  E  N  Q  F  R  S  L  V  D  H  A  A

1861  CGCATCATATTAAAAATAGTATAGAACAGGTTCTGTTGGCCTGTTCGACCAACAGTCGG  1920
      ----+----+----+----+----+----+----+----+----+----+----+----+
      GCGTAGTATAATTTTTATCATATCTTGTCCAAGACAACCGGACAAGCTGGTTGTCAGCC a     R  I  I  L  K  I  V  -  N  R  F  C  W  P  G  S  T  N  S  R
b     A  S  Y  -  K  -  Y  R  T  G  S  V  G  L  V  R  P  T  V  G
c     H  H  I  K  N  S  I  E  Q  V  L  L  A  W  F  D  Q  Q  S  V

1921  TAGACAGTGTTATGTGCCATCGTCTGGCACGCCAGGCCACGGCTATGGCGGAAGAGGGAG  1980
      ----+----+----+----+----+----+----+----+----+----+----+----+
      ATCTGTCACAATACACGGTAGCAGATGCCGGTCCGGTGCCGATACCGCCTTCTCCCTC a     -  T  V  L  C  A  I  V  W  H  A  R  P  R  L  W  R  K  R  E
b     R  Q  C  Y  V  P  S  S  G  T  P  G  H  G  Y  G  G  R  G  S
c     D  S  V  M  C  H  R  L  A  R  Q  A  T  A  M  A  E  E  G  A
```

Figure 11K

```
                      CGCTTTATTGCGTATTCATCCTGAAAAGAGGCATTGATGCGAGAAACTTTTGGCAAGC
                      ----------+---------+---------+---------+---------+---------+  2040
                      GCGAAATAACGCATAAGTAGGACTTTTTCTCCGTAACTACGCTCTTTGAAAACCGTTCG
  1981
     a                R    F    I    C    V    F    I    L    K    K    R    H  -  C    E    K    L    L    A    S
     b                A    L    F    A    Y    S    S  -  K    R    G    I    D    A    R    N    F    W    Q    A
     c                L    Y    L    R    I    H    P    E    K    E    A    L    M    R    E    T    F    G    K    R

GGTTTACGTTGATTATCGAGCCTGGTTTCTCTCCCGATCAGGCTGAACTTTCCTCAACAC
                      ----------+---------+---------+---------+---------+---------+  2100
                      CCAAATGCAACTAATAGCTCGGACCAAAGAGAGGGCTAGTCCGACTTGAAAGGAGTTGTG
  2040
     a                G    L    R  -  L    S    S    L    V    S    L    P    I    R    L    N    F    P    Q    H
     b                V    Y    V    D    Y    R    A    W    F    L    S    R    S    G  -  T    F    L    N    T
     c                F    T    L    I    E    P    G    F    S    P    D    Q    A    E    L    S    S    T    R

GATATGCCGTTGAATTTCACTTTCTCGTCATTTCAACGCGTTACTGAAATGGTTACGTA
                      ----------+---------+---------+---------+---------+---------+  2160
                      CTATACGGCAACTTAAAGTGAAAGAGCAGTAAAGTTGCGCAATGACTTTACCAATGCAT
  2101
     a                D    M    P    L    N    F    H    F    F    L    V    I    S    T    R    Y  -  N    G    Y    V  -
     b                I    C    R  -  I    F    F    S    L    S    R    H    F    N    A    L    L    K    W    L    R    N
     c                Y    A    V    E    F    S    S    F    Q    R    V    T    E    M    V    T  -
```

Figure 11L

```
              ATGGTGAAGATAAAAGAGGTAGCGATGAATATTAAAATTAATGAGATAAAAATGACGCCC
2161          ------+---------+---------+---------+---------+---------+ 2220
              TACCACTTCTATTTTCTCCATCGCTACTTATAATTTAATTACTCTATTTTTACTGCGGG a              M  V  K  I  K  E  V  A  M  N  I  K  I  N  E  I  K  M  T  P
b              W  -  R  -  K  R  -  R  -  I  L  K  L  M  R  -  K  -  R  P
c              G     E  D  K  R  G  S  D  E  Y  -  N  -  -  D  K  N  D  A  P

CCTACAGCATTTACCCCCTGGCCCAGGTTATAGAGGAACAAGAGGTTATTTCGCCTTCAATG
2221          ------+---------+---------+---------+---------+---------+ 2280
              GGATGTCGTAAATGGGGACCGGGTCCAATATCTCCTTGTTCTCCAATAAAGCGGAAGTTAC a              P  T  A  F  T  P  G  Q  V  I  E  E  Q  E  V  I  S  P  S  M
b              L  Q  H  L  P  L  A  R  L  -  R  N  K  R  L  F  R  L  Q  C
c              Y  S  I  Y  P  W  P  G  Y  R  G  T  R  G  Y  F  A  F  N  V

TTAGCTCTCCAGGAGTTACAGGAAACGGGGCAGCGCTCTATGAGACGATGGAAGAA
2281          ------+---------+---------+---------+---------+---------+ 2340
              AATCGAGAGGTCCTCAATGTCCTTTGCTGCCCCGTCGCGAGATACTCTGCTACCTTCTT a              L  A  L  Q  E  L  Q  E  T  T  G  A  A  L  Y  E  T  M  E  E
b              -  L  S  R  S  Y  R  K  R  R  G  G  Q  R  S  M  R  R  W  K  K
c              S     S  P  G  V  T  G  N  D  G  G  S  A  L  -  D  D  G  R  N
```

Figure 11M

```
         ATAGGAATGGCGCTGAGTGGTAAAACTGCGCGAAAATTATAAATTCACTGATGCTGAGAAA
2341     ------+---------+---------+---------+---------+---------+    2400
         TATCCTTACCGCGACTCACCATTTGACGCGCTTTTAATATTTAAGTGACTACGACTCTTT a          I  G  M  A  L  S  G  K  L  R  E  K  N  Y  K  F  T  D  A  E  K
b          -  E  W  R  -  V  V  N  C  A  K  I  I  N  S  L  M  R  N
c            R  N  G  A  E  W  -  T  A  R  K  L  -  I  H  -  C  -  E  T

CTGGAGCGCAGACAGCAGGCTTTGCTGCGTTTGATAAAACAAATACAGGAGGATAATGGG
2401     ------+---------+---------+---------+---------+---------+    2460
         GACCTCGCGTCTGTCGTCCGAAACGACGCAAACTATTTTGTTTATGTCCTCCTATTACCC a          L  E  R  R  Q  Q  A  L  L  R  L  I  K  Q  I  Q  E  D  N  G
b          W  S  A  D  S  R  L  C  C  V  -  -  N  K  Y  R  R  I  M  G
c            G  A  Q  T  A  G  F  A  A  F  D  K  T  N  T  G  G  -  W  G

GCAACGTTGCGTCCGCTTACCGAAGAGAATAGTGATCCTGATTACAGAATGCGTATCAA
2461     ------+---------+---------+---------+---------+---------+    2520
         CGTTGCAACGCAGGCGAATGGCTTCTCTTATCACTAGGACTAAATGTCTTACGCATAGTT a          A  T  L  R  P  L  T  E  E  N  S  D  P  D  L  Q  N  A  Y  Q
b          Q  R  C  V  R  L  P  K  R  I  V  I  L  I  Y  R  M  R  I  K
c            N  V  A  S  A  Y  R  R  E  -  -  S  -  F  T  E  C  V  S  N
```

Figure 11N

```
       ATTATGCGTCTTGCAATGGCGCTTACTGCCGGGGTTGTCAAAAAGAAAAAACGCGAT
2521   ------+---------+---------+---------+---------+---------+  2580
       TAATAGCGAGAACGTTACCGCGAATGACGGCCCCAACAGTTTTTCTTTTTGCGCTA a       I  I  A  L  A  M  A  L  T  A  G  G  L  S  K  K  K  K  R  D
b       L  S  L  L  Q  W  R  L  L  P  A  G  C  Q  K  R  K  N  A  I
c       Y  R  S  C  N  G  A  Y  C  R  R  V  V  K  K  E  K  T  R  F

TTGCAATCGCAACTGGATACGTTACAGGCGGAGGAGGGATGGGAACTTGCCGTTTTAGTT
2581   ------+---------+---------+---------+---------+---------+  2640
       AACGTTAGCGTTGACCTATGCAATGTCCGCCTCCTCCCTACCCTTGAACGGCAAAATCAA a       L  Q  S  Q  L  D  T  L  Q  R  R  R  D  G  N  L  P  F  L  V
b       C  N  R  N  W  I  R  Y  S  G  G  G  M  G  T  C  R  F  -  F
c       A  I  A  T  G  Y  V  T  A  E  E  G  W  E  L  A  V  F  S  L

TACTGGAACTTGGCGAAGTGGATACCGTACGCTGTCCTCTCTGAAGCGTTTTATGCAACA
2641   ------+---------+---------+---------+---------+---------+  2700
       ATGACCTTGAACCGCTTCACCTATGGCATGCGACAGGAGACTTCGCAAAATACGTTGT a       Y  W  N  L  A  K  W  I  P  Y  A  V  L  S  E  A  F  Y  A  T
b       T  G  T  W  R  S  G  Y  R  T  L  S  S  L  K  R  F  M  Q  Q
c       L  E  L  G  E  V  D  T  V  R  C  P  L  -  S  V  L  C  N  R
```

Figure 110

```
2701  GGCGATAGACAACGATGAAATGCCCTTATCGCAGTGGTTCAGACGCGGTGGCAGACTGGCC
      ------+---------+---------+---------+---------+---------+  2760
      CCGCTATCTGTTGCTACTTTACGGGAATAGCGTCACCAAGTCTGCGCCACCGTCTGACCGG a     G  D  R  Q  R  -  N  A  L  I  A  V  V  Q  T  R  G  R  L  A
b     A  I  D  N  D  E  M  P  L  S  Q  W  F  R  R  V  A  D  W  P
c     R  -  T  T  M  K  C  P  Y  R  S  G  S  D  A  W  Q  T  G  R

2761  GGATCGCTGTGAACGGGTCCGTATTTTGCTAAGAGCAGTAGCCTTTGAACTTAGCATATG
      ------+---------+---------+---------+---------+---------+  2820
      CCTAGCGACACTTGCCCAGGCATAAAACGATTCTCGTCATCGGAAACTTGAATCGTATAC a     G  S  L  -  T  G  P  Y  F  A  K  S  S  L  -  T  -  H  M
b     D  R  C  E  R  V  R  I  L  L  R  A  V  A  F  E  L  S  I  C
c     I  A  V  N  G  S  V  F  C  -  E  Q  -  P  L  N  L  A  Y  A

2821  CATCGAACCCTCGGAGCAAAAGTCGTTTGGCCGCAGCATTAGTACGTTTGCGTCGTTTGCT
      ------+---------+---------+---------+---------+---------+  2880
      GTAGCTTGGGAGCCTCGTTTCAGCAAACCGGCGTCGTAATCATGCAAACGCAGCAAACGA a     H  R  T  L  G  A  K  S  F  G  R  S  I  S  T  F  A  S  F  A
b     I  E  P  S  E  Q  S  R  L  A  A  A  L  V  R  L  R  R  L  L
c     S  N  P  R  S  K  V  V  W  P  Q  H  -  Y  V  C  V  V  C  C
```

```
2881  GTTATTCCTTGGCCTTGAAAAAGAGTGCCAGCGTGAGGAGTGGATTTGCCAGTTGCCGCC  2940
      ------+---------+---------+---------+---------+---------+
      CAATAAGGAACCGGAACTTTTTCTCACGGTCGCACTCCTCACCTAAACGGTCAACGGCGG a      V  I  P  W  P  -  K  R  V  P  A  -  G  V  D  L  P  V  A  A
b      L  F  L  G  L  E  K  K  S  A  S  V  R  S  G  F  A  S  C  R  L
c      Y  S  L  A  L  K  K  K  E  C  Q  R  E  E  W  I  C  Q  L  P  P

2941  TAATACATTACTGCCGCTACTACTCGATATTATTTGTGAGCGCTGGCTTTTCAGTGATTG  3000
      ------+---------+---------+---------+---------+---------+
      ATTATGTAATGACGGCGATGATGAGCTATAATAAACACTCGCGACCGAAAAGTCACTAAC a      -  Y  I  T  A  A  T  T  R  Y  Y  L  -  A  L  A  F  Q  -  L
b      N  T  L  L  P  L  L  L  D  I  I  C  E  R  W  L  F  S  D  W
c      I  H  Y  C  R  Y  Y  S  I  L  F  V  S  A  G  F  S  V  I  G

3001  GTTGCTTGATAGACTTACCGCTATAGTTTCTTCATCGAAGATGTTCAATCGGTTACTCCA  3060
      ------+---------+---------+---------+---------+---------+
      CAACGAACTATCTGAATGGCCGATATCAAAGAAGTAGCTTCTACAAGTTAGCCAATGAGGT a      V  A  -  T  Y  R  Y  S  F  F  I  E  D  V  Q  S  V  T  P
b      L  L  D  R  L  T  L  A  I  V  S  S  K  M  F  N  R  L  L  Q
c      C  L  I  D  L  P  L  -  F  L  H  R  R  C  S  I  G  Y  S  N
```

```
3061  ACAACTTGATGCGCAGTTTATGCTGATACCCGATAACTGTTTTAACGACGAAGATCAACG  3120
      ----+----+----+----+----+----+----+----+----+----+----+----+
      TGTTGAACTACGCGTCAAATACGACTATGGGCTATTGACAAAATTGCTGCTTCTAGTTGC a      T  T  -  C  A  V  Y  A  D  T  R  -  L  F  -  R  R  R  S  T
b      Q  L  D  A  Q  F  M  L  I  P  D  N  C  F  N  D  E  D  Q  R
c      N  L  M  R  S  L  C  -  Y  P  I  T  V  L  T  T  K  I  N  V

3121  TGAACAAATTCTCGAAACGCTTCGTGAAGTAAAGATAAATCAGTTTTATTCTGATACCT  3180
      ----+----+----+----+----+----+----+----+----+----+----+----+
      ACTTGTTTAAGAGCTTTGCGAAGCACTTCATTTCTATTTAGTCCAAAATAAGACTATGGA a      -  T  N  S  R  N  A  S  -  S  K  D  K  S  G  F  I  L  I  P
b      E  Q  I  L  E  T  L  R  E  V  K  -  R  -  I  R  F  Y  S  D  T  W
c      N  K  F  S  K  R  F  V  K  -  R  -  I  R  F  Y  S  D  T  W

3181  GGCTTTCAATATTTAGGTAAAATTGGCTTTTCTGGCTAAATCCGAAGACCGAGTACTCCGCCAGTCCTACCTAAC  3240
      ----+----+----+----+----+----+----+----+----+----+----+----+
      CCGAAAGTTATAAATCCATTTTAACCGAAAGACCGAGTAGTCCGGCAGTCCTACCTAAC a      G  F  Q  Y  L  G  K  L  A  F  W  L  I  M  R  R  Q  D  G  L
b      A  F  N  I  -  V  N  W  L  S  G  S  S  -  G  V  R  M  D  W
c      L  S  I  F  R  -  I  G  F  L  A  H  H  E  A  S  G  W  I  G
```

Figure 11R

```
3241  GGATCTCATTACTGAACGTAATATTCAGCTTTTATTCAATTAGCAGGATTAGCTGAACG
      ----+----+----+----+----+----+----+----+----+----+----+----+  3300
      CCTAGAGTAATGACTTGCATTATAAGTCGAAAAATAAGTTAATCGTCCTAATCGACTTGC a       G  S  H  Y  -  T  -  Y  S  A  F  Y  S  I  S  R  I  S  -  T
b       D  L  I  T  E  R  N  I  Q  L  F  I  Q  L  A  G  L  A  E  R
c        I  S  L  L  N  V  I  F  S  F  L  F  N  -  Q  D  -  L  N  G

3301  GCCTTTAGCAACCAATATGTTCTGGCGGCAAGGACAATATGAAACTATCATAACGGTCGT
      ----+----+----+----+----+----+----+----+----+----+----+----+  3360
      CGGAAATCGTTGGTTATACAAGACCGCCGTTCCTGTTATACTTTGATAGTATTGCCAGCA a       A  F  S  N  Q  Y  V  L  A  A  R  T  I  I  -  N  Y  H  N  G  R
b       P  L  A  T  N  M  F  W  R  Q  G  Q  Y  E  T  I  I  T  V  V
c        L  -  Q  P  I  C  S  G  G  K  D  N  M  K  L  S  -  R  S  Y

3361  ATTCTCTTATGTCAGATACTCAAGCAAACCTTCTTAGACGAAGAACTGCTTTTAAAGCG
      ----+----+----+----+----+----+----+----+----+----+----+----+  3420
      TAAGAGAATACAGTCTATGAGTTCGTTTGGAAGAATCTGCTTCTTGACGAAAAATTCGC a       I  L  L  C  Q  I  L  K  Q  T  F  L  D  E  E  L  L  F  K  A
b       F  S  Y  V  R  Y  S  S  K  P  S  -  T  K  N  C  F  L  K  R
c        S  L  M  S  D  T  Q  A  N  L  L  R  R  R  T  A  F  -  S  V
```

Figure 11S

```
      TTGGCTAACTGGAAACCCGCAGCGTTCCAGGGTATTCCTCAACGATTATTTTGTTGCGC
3421  ------------------------------------------------------------  3480
      AACCGATTGACCCTTTGGGCGTCGCAAGGTCCCATAAGGAGTTGCTAATAAAAACAACGCG a      L  A  N  W  K  P  A  A  F  Q  G  I  P  Q  R  L  F  L  L  R
b      W  L  T  G  N  P  Q  R  S  R  V  P  G  Y  S  S  T  I  F  V  A  R
c      G  -  L  E  T  R  S  V  P  G  Y  S  S  T  I  F  V  A  R

GATGGGCTTGCAATGAGTTGTTCTCCACCTCTTTCCAGCTCCCGCCAGCTCTGGTTACGA
3481  ------------------------------------------------------------  3540
      CTACCCGAACGTTACTCAACAAGAGGTGGAGAAAGGTCGAGGGCTCGAGACCAATGCT a      D  G  L  A  M  S  C  S  P  P  L  S  S  S  A  E  L  W  L  R
b      M  G  L  Q  -  V  V  L  H  L  F  P  A  P  P  S  S  G  Y  D
c      W  A  C  N  E  L  F  S  T  S  F  Q  L  R  R  A  L  V  T  I

TTACATCATCGACAAATAAAATTTCNTGGAGTCGCAATGCGTTCATGGTTAGGTGAGGGA
3541  ------------------------------------------------------------  3600
      AATGTAGTAGCTGTTTATTTTAAAGNACCTCAGCGTTACGCAAGTACCAATCCACTCCCT a      L  H  H  R  Q  I  K  F  X  G  V  A  M  R  S  W  L  G  E  G
b      Y  I  D  K  -  N  F  X  E  S  Q  C  V  H  G  -  V  R  E
c      T  S  S  T  N  K  I  X  W  S  R  N  A  F  M  V  R  -  G  S
```

Figure 11T

```
3601  GTCAGGGGCGCAACAGTGGCTCAGTGTATGCGCGGTCGGCAGGATATGGTTCTGGCGACG
      ------+---------+---------+---------+---------+---------+  3660
      CAGTCCCCGCGTTGTCACCGAGTCACATACGCGCCAGCCGTCCTATACCAAGACCGCTGC start lcrD*
a         V  R  A  Q  Q  W  L  S  V  V  C  A  G  R  Q  D  M  V  L  A  T
b         S  G  R  N  S  G  S  V  Y  A  R  V  G  R  I  W  F  W  R  R
c         Q  G  A  T  V  A  Q  C  M  R  G  S  A  G  Y  G  S  G  D  G 3661  GTGTTATTAATCGCTATTGTGATGATGCTGTTACCCTTGCCGACCTGATGGTTGATATC
      ------+---------+---------+---------+---------+---------+  3720
      CACAATAATTAGCGATAACACTACTACGACAATGGGAACGGCTGGACTACCAACTATAG a         V  L  L  I  A  I  V  M  M  L  L  P  L  P  T  W  M  V  D  I
b         C  Y  -  S  L  L  -  -  C  C  Y  P  C  R  P  G  W  L  I  S
c         V  I  N  R  Y  C  D  D  A  V  T  L  A  D  L  D  G  -  Y  P 3721  CTGATTACTATCAACCCTTATGTTTTCAGTGATCCTGCTCTTAATTGCTATTTATCTTAGT
      ------+---------+---------+---------+---------+---------+  3780
      GACTAATGATAGTTGGAATACAAAAGTCACTAGGACGAGAATTAACGATAAATAGAATCA a         L  I  T  I  N  L  M  F  S  V  I  L  L  L  I  A  I  F  L  S
b         -  L  L  S  T  L  C  F  Q  -  S  C  S  -  L  L  F  I  L  V
c         D  Y  Y  Q  P  Y  V  F  S  D  P  A  L  N  C  Y  L  S  -  -
```

Figure 11U

```
3781   GACCCTCTCGATTTATCGGTATTTCCGTCTTTATTACTACATTATATCGTTTG   3840
       ----+----|----+----|----+----|----+----|----+----|----
       CTGGGAGAGCTAAATAGCCATAAAGGCAGAAATAATGATGTAATATAGCAAAC a       D  P  L  D  L  S  V  F  P  S  L  L  L  I  T  T  L  Y  R  L
b       T  L  S  I  Y  R  Y  F  R  L  Y  Y  L  L  L  H  Y  I  V  C
c       P  S  R  F  I  G  I  S  V  F  I  T  Y  Y  I  I  S  F  V

3841   TCACTCACAATCAGCACATCACGGCTGGTACTGTTACAACATAAATGCCGGTAATATTGTG   3900
       ----+----|----+----|----+----|----+----|----+----|----+----|
       AGTGAGTGTTAGTCGTGTAGTGCCGACCATGACAATGTTGTATTACGGCCATTATAACAC a       S  L  T  I  S  T  S  R  L  V  L  L  Q  H  N  A  G  N  I  V
b       H  S  Q  S  A  H  H  G  W  Y  C  Y  N  I  M  P  V  I  L  W
c       T  H  N  Q  H  I  T  A  G  T  V  T  T  -  C  R  -  Y  C  G

3901   GATGCTTTCGGTAAGTTTGTCGTAGGAGGAAATCTCACCGTTGGGTTGGTCGTATTTACC   3960
       ----+----|----+----|----+----|----+----|----+----|----+----|
       CTACGAAAGCCATTCAAACAGCATCCTCCTTTAGAGTGGCAACCCAACCAGCATAAATGG a       D  A  F  G  K  F  V  V  G  G  N  L  T  V  G  L  W  V  F  T
b       M  L  S  V  S  L  S  -  E  E  K  S  -  I  S  P  L  G  W  S  Y  L  P
c       C  F  R  -  V  C  R  R  K  S  H  R  W  V  G  R  I  Y  H
```

Figure 11V

```
3961  ATCATTACTATCGTGCAATTTATTGTCATTACAAAAGGTATCGAGAGGGTGTGGCGGAAGTT
      ----------+---------+---------+---------+---------+---------+  4020
      TAGTAATGATAGCACGTTAAATAACAGTAATGTTTTCCATAGCTCTCCCACCGCCTTCAA a      I  I  T  I  V  Q  F  I  V  I  T  K  G  I  E  R  V  A  E  V
b      S  L  L  S  C  N  L  L  S  L  Q  K  V  S  R  G  W  R  K  L
c         H  Y  Y  R  A  I  Y  C  H  Y  K  R  Y  R  E  G  G  G  S  -

4021  AGCGCACGTTTCTCGCTTGATGGGATGCCAGGCAAACAAATGAGTATCGATGGCGATTTG
      ----------+---------+---------+---------+---------+---------+  4080
      TCGCGTGCAAAGAGCGAACTACCCTACGGTCCGTTTGTTTACTCATAGCTACCGCTAAAC a      S  A  R  F  S  L  D  G  M  P  G  K  Q  M  S  I  D  G  D  L
b      A  H  V  S  R  L  M  G  C  Q  A  N  K  -  V  S  M  A  I  C
c         R  T  F  F  L  A  -  W  D  A  R  Q  T  N  E  Y  R  W  R  F  A

Tn insertion P2D6
                                              ⇒
4081  CGTGCCGGAGTTATCGATGCAGACCATGCCCGTACATTAAGACAGTCCAGCAGGAA
      ----------+---------+---------+---------+---------+---------+  4140
      GCACGGCCTCAATAGCTACGTCTGGTACGGGCATGTAATTCTGTCGTACAGGTCGTCCTT a      R  A  G  V  I  D  A  D  H  A  R  T  L  R  Q  H  V  Q  Q  E
b      V  P  E  L  S  M  Q  T  M  P  V  H  -  D  S  M  S  S  R  K
c         C  R  S  Y  R  C  R  P  C  P  Y  I  K  T  A  C  P  A  G  K
```

Figure 11W

```
4141  AGCCGCTTTCTCGGTGCCGATGGACGGTGCCGATGAAATTTGTTAAAGGCGATACGATTGCC
      ----+----+----+----+----+----+----+----+----+----+----+----+  4200
      TCGGCGAAAGAGCCACGGCTACCTGCCACGCTACTTTAAACAATTTCCGCTATGCTAACGG a       S  R  F  L  G  A  M  D  G  A  M  K  F  V  K  G  D  T  I  A
b       A  A  F  S  V  R  W  T  V  R  -  N  L  L  K  A  I  R  L  P
c       P  L  S  R  C  D  D  G  R  C  D  E  I  C  -  R  R  Y  D  C  R

4201  GGTATTATTGTTCTGGTGAACATTATCGGGGGTATCATTATCGCTATCGTACAAATAT
      ----+----+----+----+----+----+----+----+----+----+----+----+  4260
      CCATAATAACAAGACCACTTGTAATAGCCCCATAGTAATAGCGATAGCATGTTATA a       G  I  I  V  V  L  V  N  I  I  G  G  I  I  I  A  I  V  Q  Y
b       V  L  L  L  F  W  -  T  L  S  A  V  S  L  S  L  S  Y  N  M
c       Y  Y  C  C  S  G  E  H  Y  R  R  Y  H  Y  R  Y  R  T  I  -

4321  GATATGTCGATGAGTGAGGCTGTGTTCACACTTATAGCGTACTGTCAATCGGAGATGGTTTA
      ----+----+----+----+----+----+----+----+----+----+----+----+  4320
      CTATACAGCTACTCACTCCGACACAAGTGTGAATATCGCATGACAGTTAGCCTCTACCAAAT a       D  M  S  M  S  E  A  V  H  T  Y  S  V  L  S  I  G  D  G  L
b       I  C  R  -  V  R  L  F  T  L  L  I  A  Y  C  Q  S  E  M  V  Y
c       Y  V  D  E  -  G  C  S  H  L  -  R  T  V  N  R  R  W  F  M
```

Figure 11X

```
4381 TGTGGGCAAATTCCATCGCTGCTGATTTCCCTTAGCGCGGAATTATTGTCACCCGTGTC 4380
     ----------+---------+---------+---------+---------+---------+
     ACACCCGTTTAAGGTAGCGACGACTAAAGGGAATCGCGCCCTTAATAACAGTGGCACAG a        C  G  Q  I  P  S  L  L  I  S  L  S  A  G  I  I  V  T  R  V
b        V  G  K  F  H  R  C  -  F  P  L  A  R  E  L  L  S  P  V  S
c        W  A  N  S  I  A  A  D  F  P  -  R  G  N  Y  C  H  P  C  P

4441 CCGGGTGAGAAACGCCAGAACCTGGCCACAGAGTTGAGTTCTCAAATTGCCAGACAACCT 4440
     ----------+---------+---------+---------+---------+---------+
     GGCCCACTCTTTGCGGTCTTGGACCGGTGTCTCAACTCAAGAGTTTAACGGTCTGTTGGA a        P  G  E  K  R  Q  N  L  A  T  E  L  S  S  Q  I  A  R  Q  P
b        R  V  R  N  A  R  T  W  R  Q  S  -  V  L  K  L  P  D  N  L
c        G  -  E  T  P  E  P  G  D  R  V  E  F  S  N  C  Q  T  T  S

4441 CAGTCGCTCATATTAACCGCTGTGTGGTTTTAAATGCTCCCTCGCTTTAATTCCTGGCTTTCCT 4500
     ----------+---------+---------+---------+---------+---------+
     GTCAGCGAGTATAATTGGCGACACCAAAATTTACGAGGAGCGAAATTAAGGACCGAAAGGA a        Q  S  L  I  L  T  A  V  V  L  M  L  A  L  I  P  G  F  F  P
b        S  R  S  Y  -  P  L  W  F  -  C  S  S  L  -  F  L  A  F  L
c        V  A  H  I  N  R  C  G  F  N  A  P  R  F  N  S  W  L  S  F
```

Figure 11Y

```
4501  TTTATCACTCTCGCTTCTTTTCAGCGTGTGTTAGCATTGCCAATTATCCTCATTCGCCGC  4560
      ----+----+----+----+----+----+----+----+----+----+----+----+
      AAATAGTGAGAGCGAAAGAAAAGTCGCACACAATCGTAACGGTTAATAGGAGTAAGCGGCG a      F  I  T  L  A  F  F  S  A  L  L  A  L  P  I  I  L  I  R  R
b        L  S  L  S  L  S  F  Q  R  C  -  H  C  Q  L  S  S  F  A  A
c           Y  H  S  R  F  L  F  S  V  V  S  I  A  N  Y  P  H  S  P  Q

Tn insertion P11C3
                             ⇒
4561  AAAAAGTCTGTGGTTTCCGCAAATGGCGTCGAAGCACCGGAAAAAGATAGTATGGTTCCC  4620
      ----+----+----+----+----+----+----+----+----+----+----+----+
      TTTTTCAGACACCAAAGGCGTTTACCGCAGCTTCGTGGCCTTTTTCTATCATACCAAGGG a      K  K  S  V  V  S  A  N  G  V  E  A  P  E  K  D  S  M  V  P
b        K  S  L  W  F  P  Q  M  A  S  K  H  R  K  K  I  V  W  F  P
c           K  V  C  G  F  R  K  W  R  R  S  T  G  K  R  -  Y  G  S  R 4621  GGCGCATGTCCTCTAATCTTACGTCTTAGCCCGACGTTACATTCTGCCGACCTGATTCGT  4680
      ----+----+----+----+----+----+----+----+----+----+----+----+
      CCGCGTACAGGAGATTAGAATGCAGAATCGGGCTGCAATGTAAGACGGCTGGACTAAGCA a      G  A  C  P  L  I  L  R  L  S  P  T  L  H  S  A  D  L  I  R
b        A  H  V  L  -  S  Y  V  L  A  R  R  Y  I  L  P  T  -  F  V
c           R  M  S  S  N  L  T  S  -  P  D  V  T  F  C  R  P  D  S  -
```

Figure 11Z

```
4681  GATATTGACGCCATGAGATGGTTTTATTTGAGGATACCGGGCGTCCCTCCCTGAGGTG
      -----+---------+---------+---------+---------+---------+ 4720
      CTATAACTGCGGTACTCTACCAAAATAAACTCCTATGGCCGCAGGGAGAGGACTCCAC a      D  I  D  A  M  R  W  F  L  F  E  D  T  G  V  P  L  P  E  V
b       I  L  T  P  -  D  G  F  Y  L  R  I  P  A  S  L  S  L  R  -
c        Y  -  R  H  E  M  V  F  I  -  G  Y  R  R  P  S  P  -  G  E

4721  AATATTGAGGTTTTGCCTGAACCCACCGAAAAATTGACGGTACTGCTATATCAGGAACCC
      -----+---------+---------+---------+---------+---------+ 4800
      TTATAACTCCAAAACGGACTTGGGTGGCTTTTTAACTGCCATGACGATATAGTCCTTGGG a      N  I  E  V  L  P  E  P  T  E  K  L  T  V  L  L  Y  Q  E  P
b       I  L  R  F  C  L  N  P  P  K  N  -  R  Y  C  Y  I  R  N  P
c        Y  -  G  F  A  -  T  H  R  K  I  D  G  T  A  I  S  G  T  R

4801  GTATTTAGTTTATCTATTCCCGCTCAGGCGGATTATTATTGATAGGCGCGGACGCTAGT
      -----+---------+---------+---------+---------+---------+ 4860
      CATAAATCAAATAGATAAGGGCGAGTCCGCCTAATAATAACTATCCGCGCCTGCGATCA a      V  F  S  L  S  I  P  A  Q  A  D  Y  L  L  I  G  A  D  A  S
b       Y  L  V  Y  L  F  P  L  R  R  R  I  I  Y  -  A  R  T  L  V
c        I  -  F  I  Y  S  R  S  G  G  L  F  I  D  R  R  G  R  -  C
```

Figure 11AA

```
      GTGGTGGGTGACAGCCAGACGTTACCGAACGGGATGGGCAGATCTGTTGGCTTACAAAA
4861  ------+---------+---------+---------+---------+---------+  4920
      CACCACCCACTGTCGGTCTGCAATGGCTTGCCCTACCCGTCTAGACAACGAATGTTTT a      V  V  G  D  S  Q  T  L  P  N  G  M  G  Q  I  C  W  L  T  K
b      W  W  V  T  A  R  R  Y  R  T  G  W  G  R  S  V  G  L  Q  K
c      G  G  -  Q  P  D  V  T  E  R  D  G  A  D  L  L  A  Y  K  R

GACATGGCCCATAAGGCGCAAGGTTTTTGGACTGGACGTTTTCGCGGCAGCCAACGTATC
4921  ------+---------+---------+---------+---------+---------+  4980
      CTGTACCGGGTATTCCGCGTTCCAAAACCTGACCTGCAAAAGCGCCCGTCGGTTGCATAG a      D  M  A  H  K  A  Q  G  F  G  L  D  V  F  A  G  S  Q  R  I
b      T  W  P  I  R  R  K  V  L  D  W  T  F  S  R  A  A  N  V  S
c      H  G  P  -  G  A  R  F  W  T  G  R  F  R  G  Q  P  T  Y  L

TCTGCCTTATTAAAATGTGTCCTGCTTCGGCATATGGGAGAGTTTATTGGTGTTCAGGAA
4981  ------+---------+---------+---------+---------+---------+  5040
      AGACGGAATAATTTTACACAGGACGAAGCCGTATACCCTCTCAAATAACCACAAGTCCTT a      S  A  L  L  K  C  V  L  L  R  H  M  G  E  F  I  G  V  Q  E
b      L  P  Y  -  N  V  S  C  F  G  I  W  E  S  L  L  V  F  R  K
c      C  L  I  K  M  C  P  A  S  A  Y  G  R  V  Y  W  C  S  G  N
```

Figure 11AB

```
5041  ACGGGTTATCTAATGAATGCGATGGAAAAAACTACTCTGAGCTGGTGAAAGAGCTTCAG
      ---------+---------+---------+---------+---------+---------+ 5100
      TGCGCAATAGATTACTTACGCTACCTTTTTTGATGAGACTCGACCACTTTCTCGAAGTC a       T  R  Y  L  M  N  A  M  E  K  N  Y  S  E  L  V  K  E  L  Q
b       R  V  I  -  M  R  W  K  K  T  T  L  S  W  -  K  S  F  S
c       A  L  S  -  N  E  C  D  G  K  K  L  L  -  A  G  E  R  A  S  A

5101  CGCCAGTTACCCATTAATAAAATCGCTGAAACTTTGCAACGGCTTGTATCAGAGCGGGTT
      ---------+---------+---------+---------+---------+---------+ 5160
      GCGGTCAATGGGTAATTATTTTAGCGACTTTGAAACGTTGCCGAACATAGTCTCGCCCAA a       R  Q  L  P  I  N  K  I  A  E  T  L  Q  R  L  V  S  E  R  V
b       A  S  Y  P  L  I  K  S  L  K  L  C  N  G  L  Y  Q  S  G  F
c       P  V  T  H  -  N  R  -  N  F  A  T  A  C  I  R  A  G  F

5161  TCTATTAGAGATTTACGTCTTATTTTCGGCACCTTAATTGACTGGGCGCCACGTGAAAAA
      ---------+---------+---------+---------+---------+---------+ 5220
      AGATAATCTCTAAATGCAGAATAAAAGCCGTGGAATTAACTGACCCGCGGTGCACTTTTT a       S  I  R  D  L  R  L  I  F  G  T  L  I  D  W  A  P  R  E  K
b       L  L  E  I  Y  V  L  F  S  A  P  -  L  T  G  R  H  V  K  K
c       Y  -  R  F  T  S  Y  F  R  H  L  N  -  L  G  A  T  -  K  R
```

Figure 11AC

```
5221        GATGTCCTGATGTTGACAGAATATGTCCGTATCGCGCTTCGTCGTCATATTCTGCGTCGT      5280
            ----+----+----+----+----+----+----+----+----+----+----+----+
            CTACAGGACTACAACTGTCTTATACAGGCATAGCGCGAAGCAGCAGTATAAGACGCAGCA a            D  V  L  M  L  T  E  Y  V  R  I  A  L  R  R  H  I  L  R  R
b            M  S  -  C  -  Q  N  M  S  V  S  R  F  V  V  I  F  C  V  V
c              C  P  D  V  D  R  I  C  P  Y  R  A  S  S  S  Y  S  A  S  S

5281        CTTAATCCGGAAGGAAAACCGCTGCCGATTTTGCGGATCGGCGAAGGTATTGAAAACCTC      5340
            ----+----+----+----+----+----+----+----+----+----+----+----+
            GAATTAGGCCTTCCTTTTGGCGACGGCTAAAACGCCTAGCCGCTTCCATAACTTTTGGAG a            L  N  P  E  G  K  P  L  P  I  L  R  I  G  E  G  I  E  N  L
b            L  I  R  K  E  N  R  C  R  F  C  G  S  A  K  V  L  K  T  S
c              -  S  G  R  K  T  A  A  D  F  A  D  R  R  R  Y  -  K  P  R

5341        GTGCGTGAATCCATTCGCCAGACGGCAATGGGGACCTATACTGCGCTGTCGTCTCGTCAT      5400
            ----+----+----+----+----+----+----+----+----+----+----+----+
            CACGCACTTAGGTAAGCGGTCTGCCGTTACCCCTGGATATGACGCGACAGCAGAGCAGTA a            V  R  E  S  I  R  Q  T  A  M  G  T  Y  T  A  L  S  S  R  H
b            C  V  N  P  F  A  R  R  Q  W  G  P  I  L  R  C  R  L  V  I
c              A  -  I  H  S  P  D  G  N  G  D  L  Y  C  A  V  V  S  S  -
```

Figure 11AD

```
5401  AAGACGCAGATCCTGCAACTTATCGAGCAGGGCGCTGAAGCAGTCAGCCAAATTATTCATT  5460
      ||||||||||||||||||||||||||||||||||||||||||||||||||||||||||||
      TTCTGCGTCTAGGACGTTGAATAGCTCGTCCGCGACTTCGTCAGTCGGTTTAATAAGTAA a      K  T  Q  I  L  Q  L  I  E  Q  A  L  K  Q  S  A  K  L  F  I
b      R  R  R  S  C  N  L  S  S  R  R  -  S  S  Q  P  N  Y  S  L
c      D  A  D  P  A  T  Y  R  A  G  A  E  A  V  S  Q  I  H  C

5461  GTCACTTCTGTCGACACCCGACGTTTCTTGCGAAAAATTACAGAAGCCACCTTGTTCGAC  5520
      ||||||||||||||||||||||||||||||||||||||||||||||||||||||||||||
      CAGTGAAGACAGCTGTGGGCTGCAAAGAACGCTTTTTAATGTCTTCGGTGGAACAAGCTG a      V  T  S  V  D  T  R  R  F  L  R  K  I  T  E  A  T  L  F  D
b      S  L  L  S  T  P  D  V  S  C  E  K  L  Q  K  P  P  C  S  T
c      H  F  C  R  H  P  T  F  F  L  A  K  N  Y  R  S  H  L  V  R  R

5521  GTACCGATTTGTCATGGCAGGAATTAGGAGAGGAGAGCCTTATACAAGTGGTAGAAAGT  5580
      ||||||||||||||||||||||||||||||||||||||||||||||||||||||||||||
      CATGGCTAAACAGTACCGTCCTTAATCCTCTCCTCTCGGAATATGTTCACCATCTTTCA a      V  P  I  L  S  W  Q  E  L  G  E  E  S  L  I  Q  V  V  E  S
b      Y  R  F  C  H  G  R  N  -  E  R  R  A  L  Y  K  W  -  K  V
c      T  D  F  F  V  M  A  G  I  R  R  G  E  P  Y  T  S  G  R  K  Y
```

Figure 11AE

```
                                                                              +5640
5581  ATTGACCTTAGCGAAGAGGAGTTGGCGGACAATGAAGAATGAATTGATGCAACGTCTGAG
      TAACTGGAATCGCTTCTCCTCAACCGCCTGTTACTTCTTACTTAACTACGTTGCAGACTC a         I  D  L  S  E  E  E  L  A   D  N  E  E  -  I  D  A  T  S  E
 b         L  T  L  A  K  R  S  W  R   T  M  K  N  E  L  M  Q  R  L  R
 c         -  P  -  R  R  G  V  G  G   Q  -  R  M  N  -  C  N  V  -  G
                              end lcrD*           start yscN*?

+5700
5641  GCTGAAATATCCGCCCCCCGATGGTTATTGTCGATGGGGCCGAATTCAGGATGTCAGCGC
      CGACTTTATAGGCGGGGGGCTACCAATAACAGCTACCCCCGGCTTAAGTCCTACAGTCGCG a         A  E  I  S  A  P  R  W  L   L  S  M  G  P  N  S  G  C  Q  R
 b         L  K  Y  P  P  P  D  G  Y   C  R  W  G  R  I  Q  D  V  S  A
 c         -  N  I  R  P  P  M  V  I   V  D  G  A  E  F  R  M  S  A  Q

+5760
5701  AACGTTGTTAAAATGCGTGGTTGCCTGGGGTATTTATGGGCGAGTTGTGCTGTATAAAGCC
      TTGCAACAATTTACGCACCAACGGACCCCATAAATACCCGCTCAACACGACATATTTCGG a         N  V  V  K  C  V  V  A  W   G  I  Y  G  R  V  V  L  Y  K  A
 b         T  L  L  N  A  W  L  P  G   V  F  M  G  E  L  C  C  I  K  P
 c         R  C  -  M  R  G  C  L  G   Y  L  W  A  S  C  A  V  -  S  L
```

Figure 11AF

```
5761  TGGAGAAGAACTTGCTGAAGTCGTGGGGATTAATGGCAGCAAAGCTTTGCTATCTCCTTT
      ----+----|----+----|----+----|----+----|----+----|----+----|  5820
      ACCTCTTCTTGAACGACTTCAGCACCCCTAATTACCGTCGTTTCGAAACGATAGAGGAAA yscN*
   a   W  R  R  T  C  -  S  R  G  D  -  W  Q  Q  S  F  A  I  S  P  F
   b   G  E  E  L  A  E  V  V  G  I  N  G  S  K  A  L  L  S  P  F
   c     E  K  N  L  L  K  S  W  G  L  M  A  A  K  L  C  Y  L  L  L 5821  TACGAGTACAATCGGGCTTCACTGCGCGGGCAGCAAGTGATGGCCTTAAGCGACGCCATCAG
      ----+----|----+----|----+----|----+----|----+----|----+----|  5880
      ATGCTCATGTTAGCCCGAAGTGACGCGCCCGTCGTTCACTACCGGAATTCGCTGCGGTAGTC a   Y  E  Y  N  R  A  S  L  R  A  A  S  D  G  L  K  R  R  H  Q
   b   T  S  T  I  G  L  H  C  G  Q  Q  V  M  A  L  S  D  A  I  R
   c     R  V  Q  S  G  F  T  A  G  S  K  -  W  P  -  A  T  P  S  G 5881  GTTCCCGTGGGCGAAGCCGTTATTAGGGCGAGTTATTGATGGCTTTGGTCGTCCCCTTGAT
      ----+----|----+----|----+----|----+----|----+----|----+----|  5940
      CAAGGGCACCCGCTTCGGCAATAATCCCGCTCAATAACTACCGAAACCAGCAGGGGAACTA a   V  P  V  G  E  A  L  L  G  R  V  I  D  G  F  G  R  P  L  D
   b   F  P  W  A  K  R  Y  -  G  E  L  L  M  A  L  V  V  P  L  M
   c     S  R  G  R  S  V  I  R  A  S  Y  -  W  L  W  S  S  P  -  W
```

Figure 11AG

```
5941  GGCCGCGAACTGCCCGACGTCTGCTGGAAAGACTATGATGCAATGCCTCCTCCCGCAATG  6000
   a  CCGGCGCTTGACGGGCTGCAGACGACCTTTCTGATACTACGTTACGGAGAGGGCGTTAC
   b   G  R  E  L  P  D  V  C  W  K  D  Y  D  A  M  P  P  P  A  M
   c   A  A  N  C  P  T  S  A  G  K  T  M  M  Q  C  L  L  P  Q  W
       P  R  T  A  R  R  L  L  E  R  L  -  C  N  A  S  S  R  N  G

6001  GTTCGACAGCCTATCACTCAACCATTAATGACGGGATTCGCGCTATTGATAGCGTTGCG  6060
   a  CAAGCTGTCGGATAGTGAGTTGGTAATTACTGCCCCTAAGCGCGATAACTATCGCAACGC
   b   V  R  Q  P  I  T  Q  P  L  M  T  G  I  R  A  L  I  D  S  V  A
   c   F  D  S  L  S  L  N  H  -  R  G  F  A  L  L  I  A  L  R
       S  T  A  Y  H  S  T  I  N  D  G  D  S  R  Y  -  R  C  D

6061  ACCTGTGGCGAAGGGCAACGAGTGGGTATTTTTCTGCTCCTGGCCGTGGGAAAAGCACG  6120
   a  TGGACACCGCTTCCCGTTGCTCACCCATAAAAAGACGAGGACCGGCACCCTTTCGTGC
   b   T  C  G  E  G  Q  R  V  G  I  F  S  A  P  G  V  G  K  S  T
   c   P  V  A  K  G  N  E  W  V  F  F  L  L  A  W  G  K  A  R
       L  W  R  R  A  T  S  G  Y  F  F  C  S  W  R  G  E  K  H  A
```

Figure 11AH

```
6121  CTTCTGGCGATGCTGTGTGTAATGCGCCAGACGCAGACAGCAATGTTCTGGTGTTAATTGGT
      ------------+---------+---------+---------+---------+---------+  6180
      GAAGACCGCTACGACACATTACGCGGTCTGCGTCTGTCGTTACAAGACCACAATTAACCA a    L   L   A   M   L   C   N   A   P   D   A   D   S   N   V   L   V   L   I   G
   b    F   W   R   C   C   V   M   R   Q   T   Q   T   A   M   F   W   C   -   L   V
   c    S   G   D   A   V   -   C   A   R   R   R   Q   Q   C   S   G   V   N   W   -

6181  GAACGTGGACGAGAAGTCCGCGGAATTCATCGATTTTACACTGTCTGAAGAGACCCGAAAA
      ------------+---------+---------+---------+---------+---------+  6240
      CTTGCACCTGCTCTTCAGGCGCTTAAGTAGCTAAAATGTGACAGACTTCTCTGGGCTTTT a    E   R   G   R   E   K   V   R   E   F   F   I   D   F   T   L   S   E   E   T   R   K
   b    N   V   D   E   K   S   A   N   S   I   L   H   C   L   K   R   P   E   N
   c    T   W   T   R   S   P   R   I   H   R   F   Y   T   V   -   R   D   P   K   T

6241  CGTTGTGTCATTGTTGTCGCAACCTCTGACAGACCCGCCTTAGAGCGCGTGAGGGCGCTG
      ------------+---------+---------+---------+---------+---------+  6300
      GCAACACAGTAACAACAGCGTTGGAGACTGTCTGGGCGGAATCTCGCGCACTCCCGCGAC a    R   C   V   I   V   V   A   T   S   D   R   P   A   L   E   R   V   R   A   L
   b    V   V   S   L   L   S   Q   P   L   T   D   P   P   -   S   A   -   G   R   C
   c    L   C   H   C   C   R   N   L   -   Q   T   R   L   R   A   R   E   G   A   V
```

Figure 11AI

```
6301  TTTGTGGCCACCACGAGATAGCAGAATTTTTTCGGATAATGGAAAGCGAGTCGTCTTGCTT  6360
      ---------+---------+---------+---------+---------+---------+
      AAACACCGGTGGTGCTATCGTCGTCTTAAAAAAGCCTATTACCTTTCGCTCAGCAGAACGAA a        F  V  A  T  T  I  A  E  F  F  R  D  N  G  K  R  V  V  L  L
b        L  W  P  P  R  -  Q  N  F  F  A  I  M  E  S  E  S  S  C  L
c        C  G  H  H  D  S  R  I  F  S  R  -  W  K  A  S  R  L  A  C

6361  GCCGACTCACTGACGCGTTATGCCAGGGCCGCACGGAAATCGCTCTGGCGCCGGAGAGAC  6420
      ---------+---------+---------+---------+---------+---------+
      CGGCTGAGTGACTGCGCAATACGGTCCCGGCGTGCCTTTAGCGAGACCGCGGCCCTCTCTG a        A  D  S  L  T  R  Y  A  R  A  A  R  K  S  L  W  R  R  E  D
b        P  T  H  -  R  V  M  P  G  P  H  G  N  R  S  G  A  G  E  T
c        R  L  T  D  A  L  C  Q  G  R  T  E  I  A  L  A  P  E  R  P

6421  CGCGGTTTCTGGAGAATATCGCCAGGCGTATTTAGTGCATTGCCACGACTTTTAGAACGT  6480
      ---------+---------+---------+---------+---------+---------+
      GCGCCAAAGACCTCTTATAGCGGTCCGCATAAATCACGTAACGGTGCTGAAAATCTTGCA a        R  G  F  W  R  I  S  P  G  V  F  S  A  L  P  R  L  L  E  R
b        A  V  S  G  E  Y  R  Q  A  Y  L  V  H  C  H  D  F  -  N  V
c        R  F  L  E  N  I  A  R  R  I  -  C  I  A  T  F  R  T  Y
```

Figure 11AJ

```
6481  ACGGGAATGGGAGAAAAGGCAGTATTACCGCATTTATACGGTACTGGTGGAAGGCGAT
      ------+---------+---------+---------+---------+---------+  6540
      TGCCCTTACCCTCTTTTTCCGTCATAATGGCGTAAATATGCCATGACCACCTTCCGCTA a        T  G  M  G  E  K  G  S  I  T  A  F  Y  T  V  L  V  E  G  D
b        R  E  W  E  K  K  A  V  L  P  H  F  I  R  Y  W  W  K  A  M
c        G  N  G  R  K  R  Q  Y  Y  R  I  L  Y  G  T  G  G  R  R  -

6541  GATATGAATGAAGCCGTTGGCGGATGAAGTCCGTTCACTGCTTGATGGACATATTGTACT
      ------+---------+---------+---------+---------+---------+  6600
      CTATACTTACTTCGGCAACCGCCTACTTCAGGCAAGTGACGAACTACCTGTATAACATGA yscN*
a        D  M  N  E  A  V  G  G  -  S  P  F  T  A  -  W  T  Y  C  T
b        I  -  M  K  P  L  A  D  E  V  R  S  L  L  D  G  H  I  V  L
c        Y  E  -  S  R  W  R  M  K  S  V  H  C  L  M  D  I  L  Y  Y 6601  ATCCCGACGGCTTGCAGAGAGGGGCATTATCCTGCCATTGACGTGTTGGCAACGCTCAG
      ------+---------+---------+---------+---------+---------+  6660
      TAGGGCTGCCGAACGTCTCTCCCCGTAATAGGACGGTAACTGCACAACCGTTGCGAGTC a        I  P  T  A  C  R  E  G  A  L  S  C  H  -  R  V  G  N  A  Q
b        S  R  R  L  A  E  R  G  H  Y  P  A  I  D  V  L  A  T  L  S
c        P  D  G  L  Q  R  G  G  I  I  L  P  L  T  C  W  Q  R  S  A
```

Figure 11AK

```
       CCGCGTTTTCCAGTCGTTACCAGCCATGAGCATCGTCAACTGGGCGGGCGATATTGCGACG
6661   ------+---------+---------+---------+---------+---------+    6720
       GGCGCAAAAGGTCAGCAATGGTCGGTACTCGTAGCAGTTGACCCGCCCGCTATAACGCTGC a        P  R  F  S  S  R  Y  Q  P  -  A  S  S  T  G  G  D  I  A  T
b        R  V  F  P  V  V  T  S  H  E  H  R  Q  L  A  A  I  L  R  R
c        A  F  F  Q  S  L  P  A  M  S  I  V  N  W  R  R  Y  C  D  G

GTGCCTGGCGCTTTACCAGGAGGTTGAACTGTTAATACGCATTGGGGAATACCAGCGAGG
6721   ------+---------+---------+---------+---------+---------+    6780
       CACGGACCGCGAAATGGTCCTCCAACTTGACAATTATGCGTAACCCCTTATGGTCGCTCC a        V  P  G  A  L  P  G  G  -  T  V  N  T  H  W  G  I  P  A  R
b        C  L  A  L  Y  Q  E  V  E  L  L  I  R  I  G  E  Y  Q  R  G
c        A  W  R  F  T  R  R  L  N  C  -  Y  A  L  G  N  T  S  E  E

AGTTGATACAGATACTGACAAAGCCATTGATACCTATCCGGATATTTGCACATTTTTGCG
6781   ------+---------+---------+---------+---------+---------+    6840
       TCAACTATGTCTATGACTGTTTCGGTAACTATGGATAGGCCTATAAACGTGTAAAAACGC a        S  -  Y  R  Y  -  Q  S  H  -  Y  L  S  G  Y  L  H  I  F  A
b        V  D  T  D  T  D  K  A  I  D  T  Y  P  D  I  C  T  F  L  R
c        L  I  Q  I  L  T  K  P  L  I  P  I  R  I  F  A  H  F  C  D
```

Figure 11AL

```
                                                                        end yscN*
6841  ACAAAGTAAGGATGAAGTATGCGGACCCGAGCTACTTATAGAAAAATTACACCAAATACT
      ----+----|----+----|----+----|----+----|----+----|----+----| 6900
      TGTTTCATTCCTACTTCATACGCCTGGGCTCGATGAATATCTTTTTAATGTGGTTTATGA a      T  K  -  G  -  S  M  R  T  R  A  T  Y  R  K  I  T  P  N  T
b         Q  S  K  D  E  V  C  G  P  E  L  L  I  E  K  L  H  Q  L  L
c         K  V  R  M  K  Y  A  D  P  S  Y  L  -  K  N  Y  T  K  Y  S 6901  CACCGAGTGATCATGGAAACTTTGCTGGAGATAATCGCGGCTGAAAAGCAATTACGCG
      ----+----|----+----|----+----|----+----|----+----|----+----| 6960
      GTGGCTCACTAGTACCTTTGAAACGACCTCTATTAGCGCCGACTTTTCGTTAATGCGC
                  yscO*
a      H  R  V  I  M  E  T  L  L  E  I  I  A  R  L  K  S  N  Y  A
b      T  E  -  S  W  K  L  C  W  R  -  S  R  G  -  K  A  I  T  R
c      P  S  D  H  G  N  F  A  G  D  N  R  A  A  E  K  Q  L  R  G 6961  GCAAGCTTACCGTACTTGATCAGCAGCAACAGGCGATTATTACGGAACAGCAGATTTGCC
      ----+----|----+----|----+----|----+----|----+----|----+----| 7020
      CGTTCGAATGGCATGAACTAGTCGTCGTTGTCCGCTAATAATGCCTTGTCGTCTAAACGG a      A  S  L  P  Y  L  I  S  S  N  R  R  L  L  R  N  S  R  F  A
b      Q  A  Y  R  T  -  S  A  A  T  G  D  Y  Y  G  T  A  D  L  P
c         K  L  T  V  L  D  Q  Q  Q  Q  A  I  I  T  E  Q  Q  I  C  Q
```

Figure 11AM

```
        AGACGCGGCGCTTTAGCAGTGTCTACCAGACTGAAAGAATTAATGGGCTGGCAAGGTACGT
7021    ------+---------+---------+---------+---------+---------+    7080
        TCTGCGCCGCGAAATCGTCACAGATGGTCTGACTTTCTTAATTACCCGACCGTTCCATGCA a         R  R  A  L  -  Q  C  L  P  D  -  K  N  -  W  A  G  K  V  R
b         D  A  R  F  S  S  V  Y  Q  T  E  R  I  N  G  L  A  R  Y  V
c         T  R  A  L  A  V  S  T  R  L  K  E  L  M  G  W  Q  G  T  L

TATCTTGTCATTTATTGTTGGATAAGAAACAACAAATGGCCGGGTTATTCACTCAGGCGC
7081    ------+---------+---------+---------+---------+---------+    7140
        ATAGAACAGTAAATAACAACCTATTCTTTGTTGTTTACCGGCCCAATAAGTGAGTCCGCG a         Y  L  V  I  Y  C  W  I  R  N  N  K  W  P  G  Y  S  L  R  R
b         I  L  S  F  I  V  G  -  E  T  T  N  G  R  V  I  H  S  G  A
c         S  C  H  L  L  D  K  K  Q  Q  M  A  G  L  F  T  Q  A  Q

AGAGCTTTTGACGCAACGGCAAGCAGTTAGAGAATCAGTATCAGCAGCTTGTCTCCCGG
7141    ------+---------+---------+---------+---------+---------+    7200
        TCTCGAAAACTGCGTTGCCGTTCGTCAATCTCTTAGTCATAGTCGTCGAACAGAGGCC a         R  A  F  -  R  N  G  K  Q  L  E  N  Q  Y  Q  Q  L  V  S  R
b         E  L  F  D  A  T  A  S  S  -  R  I  S  I  S  S  L  P  G
c         S  F  L  T  Q  R  Q  A  V  R  E  S  V  S  A  A  C  L  P  A
```

Figure 11AN

```
7201  CGAAGCGAATTACAGAAGAATTTAATGCGCTTATGAAAAAGAAAAGAAAAAATTACTATG
      ------+---------+---------+---------+---------+---------+  7260
      GCTTCGCTTAATGTCTTCTTAAATTACGCGAATACTTTTCTTTTCTTTTTTAATGATAC
                       end yscO*
a      R  S  E  L  Q  K  N  F  N  A  L  M  K  K  K  E  K  I  T  M
b              E  A  N  Y  R  R  I  L  M  R  L  -  C  A  Y  E  K  E  R  K
c                   K  R  I  T  E  E  F  -  C  A  Y  E  K  E  R  K  N  Y  Y  G 7261  GTATTAAGCGATGCGTATTACCAAAGTTGAGGGAAGTCTTGGGTTGCCATGCCAGTCTTA
      ------+---------+---------+---------+---------+---------+  7320
      CATAATTCGCTACGCATAATGGTTTCAACTCCCTTCAGAACCCAACGGTACGGTCAGAAT
                             start yscP*
a      V  L  S  D  A  Y  Y  Q  S  -  G  K  S  W  V  A  M  P  V  L
b        Y  -  A  M  R  I  T  K  V  E  G  S  L  G  L  P  C  Q  S  Y
c         I  K  R  C  V  L  P  K  L  R  E  V  L  G  C  H  A  S  L  I 7321  TCAGGATGATAACGAGGCGGAGCGTATGGACTTTGAACAACTCATGCACCAGGC
      ------+---------+---------+---------+---------+---------+  7380
      AGTCCTACTATTGCTCCGCCTCGCATACCTGAAACTTGTTGAGTACGTGGTCCG
a      S  G  -  R  G  G  G  G  T  Y  G  L  -  T  T  H  A  P  G
b       Q  D  D  N  E  A  E  A  E  R  M  D  F  E  Q  L  M  H  Q  A
c         R  M  I  T  R  R  R  R  N  V  W  T  L  N  N  S  C  T  R  H Figure 11AO
```

```
7381  ATTACCCATTGGTGAGAATAATCCTCCTGCAGCATTGAATAAGAACGTGGTTTTCACGCA  7440
      TAATGGGTAACCACTCTTATTAGGAGGACGTCGTAACTTATTCTTGCACCAAAAGTGCGT a      I  T  H  W  -  E  -  S  S  C  S  I  E  -  E  R  G  F  H  A
b       L  P  I  G  E  N  N  P  P  A  A  L  N  K  N  V  V  F  T  Q
c        Y  P  L  V  R  I  I  L  L  Q  H  -  I  R  T  W  F  S  R  N

7441  ACGTTATCGTGTTAGTGGCGGTTATCTTGACGGTGTAGAGTGTGAAGTATGTGAATCAGG  7500
      TGCAATAGCACAATCACCGCCAATAGAACTGCCACATCTCACACTTCATACACTTAGTCC a      T  L  S  C  -  W  R  L  S  -  R  C  R  V  -  S  M  -  I  R
b       R  Y  R  V  S  G  G  Y  L  D  G  V  E  C  E  V  C  E  S  G
c        V  I  V  L  V  A  V  I  L  T  V  -  S  V  K  Y  V  N  Q  G

7501  GGGGCTAATCCAGTTAAGAATCAATGTCCCTCATCATGAAATTACCGTTCGATGAAAGC  7560
      CCCCGATTAGGTCAATTCTTAGTTACAGGGAGTAGTACTTTAAATGGCAAGCTACTTTCG a      G  A  N  P  V  K  N  Q  C  P  S  S  -  N  L  P  F  D  E  S
b       G  L  I  Q  L  R  I  N  V  P  H  H  E  I  Y  R  S  M  K  A
c        G  -  S  S  -  E  S  M  S  L  I  M  K  F  T  V  R  -  K  R
```

Figure 11AP

```
7561  GCTAAAGCAGTGGCTGGAGTCTCAGTTGCTGCATATGGGGTATATAATTTCCCTGGAGAT  7620
      ----------+---------+---------+---------+---------+---------+
      CGATTTCGTCACCGACCTCAGAGTCAACGACGTATACCCCATATATTAAAGGACCTCTA a      A  K  A  A  G  V  S  V  A  A  Y  G  V  Y  N  F  P  G  D
b      L  K  Q  W  L  E  S  Q  L  H  M  G  Y  I  S  L  E  I
c       -  S  S  G  W  S  L  S  C  C  I  W  G  I  -  F  P  W  R  Y

7621  ATTCTATGTTAAGAATAGCGAATGAAGAGCGTCCGTGGGTGGAGATACTTCCAACGCAAG  7680
      ----------+---------+---------+---------+---------+---------+
      TAAGATACAATTCTTATCGCTTACTTCTCGCAGGCACCCACCTCTATGAAGGTTGCGTTC end yscP*   start yscQ*?
a      I  L  C  -  E  -  R  M  K  S  V  R  G  W  R  Y  F  Q  R  K
b      F  Y  V  K  N  S  E  -  R  A  S  V  G  G  D  T  S  N  A  R
c       S  M  L  R  I  A  N  E  E  R  P  W  V  E  I  L  P  T  Q  G 7681  GCGCTACCATTGGTGAGCTGACATTGAGTATGCAACAATATCCAGTACAGCAAGGACAT  7740
      ----------+---------+---------+---------+---------+---------+
      CGCGATGGTAACCACTCGACTGTAACTCATACGTTGTTATAGGTCATGTCGTTCCCTGTA start yscQ*?
a      A  L  P  L  V  S  -  H  -  V  C  N  N  I  Q  Y  S  K  G  H
b      R  Y  H  W  -  A  D  I  E  Y  A  T  I  S  S  T  A  R  D  I
c       A  T  I  G  E  L  T  L  S  M  Q  Q  Y  P  V  Q  Q  G  T  L
```

Figure 11AQ

```
                TATTTACCATAAATTATCATAATGAGCTGGGTAGGGTGTGTGGATTGCAGAACAATGCTGGC
7741            ----------+---------+---------+---------+---------+---------+   7800
                ATAAATGGTATTTAATAGTAGTATTACTCGACCCATCCCACACCTAACGTCTTGTTACGACCG a               Y  L  P  -  I  I  I  M  S  W  V  G  C  G  L  Q  N  N  A  G
b                  I  Y  H  K  L  S  -  -  A  G  -  G  V  D  C  R  T  M  L  A
c                     F  T  I  N  Y  H  N  E  L  G  R  V  W  I  A  E  Q  C  W  Q

AGCGCTGGTGTGAAGGGCTAATTGGCACCGCTAATCGATCGGCTATCGATCCTGAATTGC
7801            ----------+---------+---------+---------+---------+---------+   7860
                TCGCGACCACACTTCCCGATTAACCGTGGCGATTAGCTAGCCGATAGCTAGGACTTAACG a               S  A  G  V  K  G  -  L  A  P  L  I  D  R  L  S  I  L  N  C
b                  A  L  V  -  R  A  N  W  H  R  -  S  I  G  Y  R  S  -  I  A
c                     R  W  C  E  G  L  I  G  T  A  N  R  S  A  I  D  P  E  L  L

TATATGGAATAGCTGAATGGGGCTGGCCGTTATTGCAAGCCAGTGATGCAACCCTCT
7861            ----------+---------+---------+---------+---------+---------+   7920
                ATATACCTTATCGACTTACCCCGACCGGCAATAACGTTCGGTCACTACGTTGGGAGA a               Y  M  E  -  L  N  G  G  W  R  R  Y  C  K  P  V  M  Q  P  S
b                  I  W  N  S  -  M  G  A  G  A  V  I  A  S  Q  -  C  N  P  L
c                     Y  G  I  A  E  W  G  L  A  P  L  L  Q  A  S  D  A  T  L  C
```

Figure 11AR

```
7921  GTCAGAACGAGCCGCCAACATCCTGCAGTAATCTACCACATCAGCTAGCGTTGCATATTA
      ------+---------+---------+---------+---------+---------+  7980
      CAGTCTTGCTCGGCGGTTGTAGGACGTCATTAGATGGTAGTCGATCGCAACGTATAAT a       V  R  T  S  R  Q  H  P  A  V  I  Y  H  I  S  -  R  C  I  L
b       S  E  R  A  A  N  I  L  Q  -  S  T  T  S  A  S  V  A  Y  -
c       Q  N  E  P  P  T  S  C  S  N  L  P  H  Q  L  A  L  H  I  K

7981  AATGGACAGTTGAAGAGCATGAGTTCCATAGCATTATTTTTACATGGCCAACGGGTTTT
      ------+---------+---------+---------+---------+---------+  8040
      TTACCTGTCAACTTCTCGTACTCAAGGTATCGTAATAAAAATGTACCGGTTGCCCAAAAA a       N  G  Q  L  K  S  M  S  S  I  A  L  F  L  H  G  Q  R  V  F
b       M  D  S  -  R  A  -  V  P  -  H  Y  F  Y  M  A  N  G  F  F
c       W  T  V  E  E  H  E  F  H  S  I  F  T  W  P  T  G  F  L

8041  TGCGCAATATAGTCGGAGAGCTTTCTGCTGAGCGACAACAGATTTATCCTGCCCCTCCTG
      ------+---------+---------+---------+---------+---------+  8100
      ACGCGTTATATCAGCCTCTCGAAAGACGACTCGCTGTTGTCTAAATAGGACGGGGAGGAC a       C  A  I  -  S  E  S  F  L  L  S  D  N  R  F  I  L  P  L  L
b       A  Q  Y  S  R  A  F  C  -  A  T  T  D  L  S  C  P  S  C
c       R  N  I  V  G  E  L  S  A  E  R  Q  Q  I  Y  P  A  P  P  V
```

Figure 11AS

```
                 TGGTAGTCCCTGTATATTCAGGCTGGTGCCAGCTTACATTAATCGAACTTGAGTCTATCG
8100             ----------+---------+---------+---------+---------+---------+  8160
                 ACCATCAGGGACATATAAGTCCGACCACGGTCGAATGTAATTAGCTTGAACTCAGATAGC a    W  -  S  L  Y  I  Q  A  G  A  S  L  H  -  S  N  L  S  L  S
b    G  S  P  C  I  F  R  L  V  P  A  Y  I  N  R  T  -  V  Y  R
c       V  V  P  V  V  Y  S  G  W  C  Q  L  T  L  I  E  L  E  S  I  E

AAATCGGCATGGGCGTTCGGATTCATTGCTTCGGCGACATCAGACTCGGTTTTTTTGCTA
8161             ----------+---------+---------+---------+---------+---------+  8220
                 TTTAGCCGTACCCGCAAGCCTAAGTAACGAAGCCGCTGTAGTCTGAGCCAAAAAAACGAT a    K  S  A  W  A  F  G  F  I  A  S  A  T  S  D  S  V  F  F  L  L
b    N  R  H  G  R  S  D  S  L  L  R  R  H  Q  T  R  F  F  C  Y
c       I  G  M  G  V  R  I  H  C  F  G  D  I  R  L  G  F  F  A  I

TTCAACTACCTGGGGAATCTACGCAAGGGTGTTGCTGACAGAGGATAACACGATGAAAT
8221             ----------+---------+---------+---------+---------+---------+  8280
                 AAGTTGATGGACCCCCTTAGATGCGTTCCCACAACGACTGTCTCCTATTGTGCTACTTTA a    F  N  Y  L  G  E  S  T  Q  G  C  C  -  Q  R  I  T  R  -  N
b    S  T  T  W  G  N  L  R  K  G  V  A  D  R  G  -  H  D  E  I
c       Q  L  P  G  G  I  Y  A  R  V  L  L  T  E  D  N  T  M  K  F
```

Figure 11AT

```
8281  TTGACGAATTAGTCCAGGATATCGAAACGCTACTTGCGTCAGGGAGCCCAATGTCAAAGA  8340
      ---------+---------+---------+---------+---------+---------+
      AACTGCTTAATCAGGTCCTATAGCTTTGCGATGAACGCAGTCCCTCGGGTTACAGTTTCT a     L  T  N  -  S  R  I  S  K  R  Y  L  R  Q  G  A  Q  C  Q  R
   b     -  R  I  S  P  G  Y  R  N  A  T  C  V  R  E  P  N  V  K  E
   c     D  E  L  V  Q  D  I  E  T  L  L  A  S  G  S  P  M  S  K  S

8341  GTGACGGAACGTCTTCAGTCGAACTTGAGCAGATACCACAACAGGTTGCTCTTTGAGGTCG  8400
      ---------+---------+---------+---------+---------+---------+
      CACTGCCTTGCAGAAGTCAGCTTGAACTCGTCTATGGTGTTGTCCACGAGAAACTCCAGC a     V  T  E  R  L  Q  S  N  L  S  R  Y  H  N  R  C  S  L  R  S
   b     -  R  N  V  F  S  R  T  -  A  D  T  T  T  G  A  L  -  G  R
   c     D  G  T  S  S  V  E  L  E  Q  I  P  Q  Q  V  L  F  E  V  G

8401  GACGTGCCGAGTCTGGAAATTGGACAATTACGACAACTTAAAACGGGGACGTTTTGCCTG  8460
      ---------+---------+---------+---------+---------+---------+
      CTGCACGCTCAGACCTTTAACCTGTTAATGCTGTTGAATTTTGCCCCTGCAAAACGGAC a     D  V  R  V  W  K  L  D  N  Y  D  N  L  K  R  G  T  F  C  L
   b     T  C  E  S  G  N  W  T  I  T  T  T  -  N  G  G  R  F  A  C
   c     R  A  S  L  E  I  G  Q  L  R  Q  L  K  T  G  D  V  L  P  V
```

Figure 11AU

```
8461  TAGGTGGATGTTTGCGCCAGAGGTGACGATAAGAGTAAATGACCGTATTATTGGGCAAG
      ----+---------+---------+---------+---------+---------+  8520
      ATCCACCTACACAAACGCGGTCTCCACTGCTATTCTCATTTACTGGCATAATAACCCGTTC a      -  V  D  V  L  R  Q  R  -  R  -  E  -  M  T  V  L  L  G  K
b      R  W  M  F  C  A  R  G  D  D  K  S  K  -  P  Y  Y  W  A  R
c      G  G  C  F  A  P  E  V  T  I  R  V  N  D  R  I  I  G  Q  G

8521  GTGAGTTGATTGCCTGTGGCAATGAATTTATGGTGCGTATTACACGTTGGTATCTTTGCA
      ----+---------+---------+---------+---------+---------+  8580
      CACTCAACTAACGGACACCGTTACTTAAATACCACGCATAATGTGCAACCATAGAAACGT a      V  S  -  L  P  V  A  M  N  L  W  C  V  L  H  V  G  I  F  A
b      -  V  D  C  L  W  Q  -  I  Y  G  A  Y  Y  T  L  V  S  L  Q
c      E  L  I  A  C  G  N  E  F  M  V  R  I  T  R  W  Y  L  C  K

8581  AAAATACAGCGTAAACCTGATAAGAAAAATAATGCGAACAATATAATACGTTCCAGG
      ----+---------+---------+---------+---------+---------+  8640
      TTTTATGTCGCATTTGGACTATTCTTTTTATTATACGCTTGTTATATTATCGCAAGGTCC end yscQ*
a      K  I  Q  R  K  P  D  K  K  N  M  R  T  I  -  -  R  S  R
b      K  Y  S  V  N  L  I  R  K  I  C  E  Q  Y  N  S  V  P  G
c      N  T  A  -  T  -  -  E  K  -  Y  A  N  N  I  I  A  F  Q  V
```

Figure 11AV

```
8641   TCGTGTCATGAGAGATACAGTATGTCTTTACCCGATTCGCCTTTGCAACTGATTGGTATA
       ----+---------+---------+---------+---------+---------+  8700
       AGCACAGTACTCTCTATGTCATACAGAAATGGGCTAAGCGGAAACGTTGACTAACCATAT
                          start yscR*?
a         S  C  H  E  R  Y  S   M  S  L  P  D  S  P  L  Q  L  I  G  I
b         R  V  M  R  D  T  V  C  L  Y  P  I  R  L  C  N  -  L  V  Y
c         V  S  -  E  I  Q  V  V  F  T  R  F  A  F  A  T  D  W  Y  I 8701   TTGTTTCTGCTTTCAATACTGCCTCTCATTATCGTCATGGGAACTTCTTTCCTTAAACTG
       ----+---------+---------+---------+---------+---------+  8760
       AACAAAGACGAAAGTTATGACGGAGAGTAATAGCAGTACCCTTGAAGAAAGGAATTTGAC
a         L  F  L  L  S  I  L  P  L  I  I  V  M  G  T  S  F  L  K  L
b         C  F  C  F  Q  Y  C  L  S  L  S  S  W  E  L  L  S  L  N  W
c         V  S  A  F  N  T  A  S  H  Y  R  H  G  N  F  F  P  -  T  G 8761   GCGGGTGGTATTTTCGATTTTACGAAATGCTCTGGGTATTCAACAAGTCCCCCCAAATATC
       ----+---------+---------+---------+---------+---------+  8820
       CGCCCACCATAAAAGCTAAAATGCTTTACGAGACCCATAAGTTGTTCAGGGGGTTTATAG
a         A  V  V  F  S  I  L  R  N  A  L  G  I  Q  Q  V  P  P  N  I
b         R  W  Y  F  R  F  F  Y  E  M  L  W  V  F  N  K  S  P  P  K  Y  R
c         G  G  I  F  D  F  T  K  C  S  G  Y  S  T  S  P  P  K  Y  R
```

Figure 11AW

```
8821  GCACTGTATGGCCTTGCGCTTGTACTTTCCTTATTCATTATGGGCCGACGCTATTAGCT
      ------+---------+---------+---------+---------+---------+  8880
      CGTGACATACCGGAACGCGAACATGAAAGGAATAAGTAATACCCGGCTGCGATAATCGA a      A  L  Y  G  L  A  L  R  L  Y  F  P  Y  S  L  F  I  M  G  P  T  L  L  A
b      H  C  M  A  L  R  L  Y  F  P  Y  S  L  W  G  R  R  Y  -  L
c         T  V  W  P  C  A  C  T  F  L  I  H  Y  G  A  D  A  I  S  C

8881  GTAAAAGAGCGCTGGCATCCGGTTCAGGTTCGGCTCCTTTCTGGACGTCTGAGTGG
      ------+---------+---------+---------+---------+---------+  8940
      CATTTTCTCGCGACCGTAGGCCAAGTCCAGCGACGGAGGAAAGACCTGCAGACTCACC a      V  K  E  R  W  H  P  V  Q  V  A  G  A  P  F  W  T  S  E  W
b         -  K  S  A  G  I  R  F  R  S  L  A  L  L  S  G  R  L  S  G
c            K  R  A  L  A  S  G  S  G  R  W  R  S  F  L  D  V  -  V  G

8941  GACAGTAAAGCATTAGCGCCTTATCGACAGTTTTTGCAAAAAACTCTGAAGAGAAGGAA
      ------+---------+---------+---------+---------+---------+  9000
      CTGTCATTTCGTAATCGCGGAATAGCTGTCAAAAACGTTTTTTGAGACTTCTCTTCCTT a      D  S  K  A  L  A  P  Y  R  Q  F  L  Q  K  N  S  E  E  K  E
b      T  V  K  H  -  R  L  I  D  S  F  C  K  K  T  L  K  R  R  K
c      Q  -  S  I  S  A  L  S  T  V  F  A  K  K  L  -  R  E  G  S
```

Figure 11AX

```
9001  GCCAATTATTTCGGAATTTGATAAACGAACCTGGCCTGAAGACATAAAAGAAAGATA
      ----+----+----+----+----+----+----+----+----+----+----+ 9060
      CGGTTAATAAAGCCTTAAACTATTTGCTTGGACCGGACTTCTGTATTTTCTTTCTAT a      A  N  Y  F  R  N  L  I  K  R  T  W  P  E  D  I  K  R  K  I
b      P  I  I  F  G  I  -  N  E  P  G  L  K  T  -  K  E  R  -
c      Q  L  F  S  E  F  D  K  T  N  L  A  -  R  H  K  K  K  D  K

9061  AAACCTGATTCTTTGCTCATATTAATTCCGGCATTTACGGTGAGTCAGTTAACGCAGGCA
      ----+----+----+----+----+----+----+----+----+----+----+ 9120
      TTTGGACTAAGAAACGAGTATAATTAAGGCCGTAAATGCCACTCAGTCAATTGCGTCCGT a      K  P  D  S  L  L  I  L  I  P  A  F  T  V  S  Q  L  T  Q  A
b      N  L  I  L  C  S  Y  -  F  R  H  L  R  -  V  S  -  R  R  H
c      T  -  F  F  A  H  I  N  S  G  I  Y  G  E  S  V  N  A  G  I

9121  TTTCGGATTGGATTACTTATTTATCTTCCCTTTCTGGCTATTGACCTGCTTATTCAAAT
      ----+----+----+----+----+----+----+----+----+----+----+ 9180
      AAAGCCTAACCTAATGAATAAATAGAAGGGAAAGACCGATAACTGGACGAATAAAGTTTA a      F  R  I  G  L  L  I  Y  L  P  F  F  L  A  I  D  L  L  I  S  N
b      F  G  L  D  Y  L  F  I  F  P  F  W  L  L  T  C  L  F  Q  I
c      S  D  W  I  T  Y  L  S  S  L  S  G  Y  -  P  A  Y  F  K  Y
```

Figure 11AY

```
9181 ATACTGCTGGCTATGGGATGATGATGGTGTCGCCGATGACCATTTCATTACCGTTTAAG
     ----------+---------+---------+---------+---------+---------+ 9240
     TATGACGACCGATACCCCTACTACTACCACAGCGGCTACTGGTAAAGTAATGGCAAATTC a    I  L  L  A  M  G  M  M  M  V  S  P  M  T  I  S  L  P  F  K
b       Y  C  W  L  W  G  -  W  C  R  R  -  P  F  H  Y  R  L  S
c          T  A  G  Y  G  D  D  D  G  V  A  D  D  H  F  I  T  V  -  A

9241 CTGCTAATATTTTACTGGCAGGCGGTTGGGATCTGACACTGGCCCAATTGGTACAGAGC
     ----------+---------+---------+---------+---------+---------+ 9300
     GACGATTATAAAATGACCGTCCGCCAACCCTAGACTGTGACCGGGTTAACCATGTCTCG
                                                    end yscR*
a    L  L  I  F  L  L  A  G  G  W  D  L  T  L  A  Q  L  V  Q  S
b       C  -  Y  F  Y  W  Q  A  V  G  I  -  H  W  R  N  W  Y  R  A
c          A  N  I  F  T  G  R  R  L  G  S  D  T  G  A  I  G  T  E  L 9301 TTTTCATGAATGATTCTGAATTGACGCAATTGTAACGCAACTTTTATGGATCGTCCTTT
     ----------+---------+---------+---------+---------+---------+ 9360
     AAAAGTACTTACTAAGACTTAACTGCGTTAACATTGCGTTGAAAATACCTAGCAGGAAA
         start yscS*
a    F  S  -  M  I  L  N  -  R  N  L  -  R  N  F  Y  G  S  S  F
b    F  H  E  -  F  -  I  D  A  I  C  N  A  T  F  M  D  R  P  F
c       F  M  N  D  S  E  L  T  Q  F  V  T  Q  L  L  W  I  V  L  F
```

Figure 11AZ

```
9361  TTACGTCTATGCCGGTAGTGTTGGTGGCATCGGTAGTTGGTGTCATCGTAAGCCTTGTTC                9420
      ------+---------+---------+---------+---------+---------+
      AATGCAGATACGGCCATCACAACCACCGTAGCCATCAACCACAGTAGCATTCGGAACAAG a      L  R  L  C  R  -  C  W  H  R  -  L  V  S  S  -  A  L  F
b      Y  V  Y  A  G  S  V  G  G  I  G  S  W  C  H  R  K  P  C  S
c      T  S  M  P  V  V  L  V  A  S  V  V  G  V  I  V  S  L  V  Q

9421  AGGCCTTGACTCAAATACAGGACCAAACGCTACAGTTCATGATTAAATTATTGGCAATTG                9480
      ------+---------+---------+---------+---------+---------+
      TCCGGAACTGAGTTTATGTCCTGGTTTGCGATGTCAAGTACTAATTTAATAACCGTTAAC a      R  P  -  L  K  Y  R  T  K  R  Y  S  S  -  L  N  Y  W  Q  L
b      G  L  D  S  N  T  G  P  N  A  T  V  H  D  -  I  I  G  N  C
c      A  L  T  Q  I  Q  D  Q  T  L  Q  F  M  I  K  L  L  A  I  A

9481  CAATAACCTTAATGGTCAGCTACCCATGGCTTAGCGGTATCCTGTTGAATTATACCCGGC                9540
      ------+---------+---------+---------+---------+---------+
      GTTATTGGAATTACCAGTCGATGGGTACCGAATCGCCATAGGACAACTTAATATGGGCCG a      Q  -  P  -  W  S  A  T  H  G  L  A  V  S  C  -  I  I  P  G
b      N  N  L  N  G  Q  L  P  M  A  -  R  Y  P  V  E  L  Y  P  A
c      I  T  L  M  V  S  Y  P  W  L  S  G  I  L  L  N  Y  T  R  Q
```

Figure 11BA

```
                    AGATAATGTTACGAATTGGAGAGCATGGTTGAATGGCACAACAGGTAAATGAGTGGCTTA
                    ------+---------+---------+---------+---------+---------+  9600
                    TCTATTACAATGCTTAACCTCTCGTACCAACTTACCGTGTTGTCCATTTACTCACCGAAT end yscS*             start yscT*
a                R -  C  Y  E  L  E  S  M  V  E  W  H  H  N  R  -  M  S  G  L
b                  D  N  V  T  N  W  R  A  W  L  N  G  T  T  G  K  -  V  A  Y
c                     I  M  L  R  I  G  E  H  G  -  M  A  Q  Q  V  N  E  W  L  I
```

9541

```
                    TTGCATTGGCTGTGGCTTTTATTCGACCATTGAGCCTTTCTTTATTACTTCCCTTATTAA
                    ------+---------+---------+---------+---------+---------+  9660
                    AACGTAACCGACACCGAAAATAAGCTGGTAACTCGGAAAGAAATAATGAAGGGAATAATT a                L  H  W  L  W  L  L  F  D  H  -  A  F  L  Y  Y  F  P  Y  -
b                  C  I  G  C  G  F  Y  S  T  I  E  P  F  F  I  T  S  L  I  K
c                     A  L  A  V  A  F  I  R  P  L  S  L  S  L  L  L  P  L  L  K
```

9601

```
                    AAAGTGGCAGTTTAGGGGCCACTTTTACGTAATGGCGTGCTTATGTCACTTACCTTTC
                    ------+---------+---------+---------+---------+---------+  9720
                    TTTCACCGTCAAATCCCCGGTGAAAATGCATTACCGCACGAATACAGTGAATGGAAAG a                K  V  A  V  -  G  P  H  F  F  Y  V  M  A  C  L  H  L  P  F
b                  K  W  Q  F  R  G  R  T  F  T  -  W  R  A  Y  V  T  Y  L  S
c                     S  G  S  L  G  A  A  L  L  R  N  G  V  L  M  S  L  T  F  P
```

```
9721  CGATATTACCAATCATTTACCAGCAGAAGATTATGATGCATATTGGTAAAGATTACAGTT
      ---------+---------+---------+---------+---------+---------+ 9780
      GCTATAATGGTTAGTAAATGGTCGTCTTCTAATACTACGTATAACCATTTCTAATGTCAA a    R  Y  Y  Q  S  F  T  S  R  R  L  -  C  I  L  V  K  I  T  V
  b    D  I  T  N  H  L  P  A  E  D  Y  D  A  Y  W  -  R  L  Q  L
  c     I  L  P  I  Y  Q  Q  K  I  M  M  H  I  G  K  D  Y  S  W

Tn insertion P9B7
                               ⇒
9781  GGTTAGGGTTAGTCACTGGAGAGGTGATTATTGGTTTTTCAATTGGGTTTTGTGCGGCGG
      ---------+---------+---------+---------+---------+---------+ 9840
      CCAATCCCAATCAGTGACCTCTCCACTAATAACCAAAAAGTTAACCCAAAACACGCCGCC a    G  -  G  -  S  L  E  R  -  L  L  V  F  F  Q  L  G  F  V  R  R
  b    V  R  V  S  H  W  R  G  D  Y  W  F  F  N  W  V  L  C  G  G
  c    L  G  L  V  T  G  E  V  I  I  G  F  S  I  G  F  C  A  A  V 9841  TTCCCTTTTGGGCCGTTGATATGGCGGGGTTTCTGCTTGATACTTTACGTGGCGGACAA
      ---------+---------+---------+---------+---------+---------+ 9900
      AAGGGAAAACCCGGCAACTATACCGCCCCAAAGACGAACTATGAAATGCACCGCGCTGTT a    F  P  F  G  P  L  I  W  R  G  F  C  L  I  L  Y  V  A  R  Q
  b    S  L  L  G  R  -  Y  G  G  V  S  A  -  Y  F  T  W  R  D  N
  c    P  F  W  A  V  D  M  A  G  F  L  L  D  T  L  R  G  A  T  M
```

Figure 11BC

```
                                    TGGGTACGATATATTCAATTCTACAATAGAAGCTGAAACCTCACTTTTTGGCTTGCTTTTCA
9900                                ------+---------+---------+---------+---------+---------+        9960
                                    ACCCATGCTATAAGTTAAGATGTTATCTTCGACTTTGGAGTGAAAAACCGAACGAAAAGT a                                    W  V  R  Y  S  I  L  Q  -  K  L  K  P  H  F  F  L  A  C  F  S
b                                    G  Y  D  I  Q  F  Y  N  R  S  -  N  L  T  F  W  L  A  F  Q
c                                       G  T  I  F  N  S  T  I  E  A  E  T  S  L  F  G  L  L  F  S

GCCAGTTCTTGTGTGTTATTTCTTTATAAGCGGGCATGGAGTTTATATTAAACATTC
9961                                ------+---------+---------+---------+---------+---------+       10020
                                    CGGTCAAGAACACACAATAAAGAAATATTCGCCCGTACCTCAAATATAATTTGTAAG a                                    A  S  S  C  V  L  F  S  L  -  A  A  A  W  S  L  Y  -  T  F
b                                    P  V  L  V  C  Y  F  F  L  Y  K  R  R  H  G  V  F  I  K  H  S
c                                    Q  F  L  C  V  I  F  F  I  S  G  G  M  E  F  I  L  N  I  L

TGTATGAGTCATATCAATATTTACCACCAGGGCGTACTTTATTATTTGACCAGCAATTT
10021                               ------+---------+---------+---------+---------+---------+       10080
                                    ACATACTCAGTATAGTTATAAATGGTGGTCCCGCATGAAATAATAAACTGGTCGTTAAAA a                                    C  M  S  H  I  N  I  Y  H  Q  G  V  L  Y  Y  L  T  S  N  F
b                                    V  -  V  I  S  I  F  T  T  R  A  Y  F  I  I  -  P  A  I  F
c                                       Y  E  S  Y  Q  Y  L  P  P  G  R  T  L  L  F  D  Q  Q  F  L
```

Figure 11BD

```
                TAAAATATATCCAGGCAGAGTGGAGAACGCTTTATCAATTATGTATCAGCTTCTCTTC
10081           ------+---------+---------+---------+---------+---------+      10140
                ATTTTATATAGGTCCGTCTCACCTCTTGCGAAATAGTTAATACATAGTCGAAGAGAAG a                - N  I  S  R  Q  S  G  E  R  F  I  N  Y  V  S  A  S  L  F
b                  K  I  Y  P  G  R  V  E  N  A  L  S  I  M  Y  Q  L  L  S  S
c                    K  Y  I  Q  A  E  W  R  T  L  Y  Q  L  C  I  S  F  S  L  P

CTGCCATAATATGTATGGTATTAGCCGATCTGGCTTTAGGTCTTTTAAATCGGTCGGCAC
10141           ------+---------+---------+---------+---------+---------+      10200
                GACGGTATTATACATACCATAATCGGCTAGACCGAAATCCAGAAAATTTAGCCAGCCGTG a                L  P  -  Y  V  W  Y  -  P  I  W  L  -  V  F  -  I  G  R  H
b                  C  H  N  M  Y  G  I  S  R  S  G  F  R  S  F  K  S  V  G  T
c                    A  I  C  M  V  L  A  D  L  A  L  G  L  L  N  R  S  A  Q

AACAATTGAAATGTGTTTTCTTCTCAATGCCGCTCAAAAGTATATTGGTTCTACTGACGY
10201           ------+---------+---------+---------+---------+---------+      10260
                TTGTTAACTTACACAAAAGAAGAGTTACGGCGAGTTTTCATATAACCAAGATGACTGCR a                N  N  -  M  C  F  S  S  Q  C  R  S  K  V  Y  W  F  Y  -  X
b                  T  I  E  C  V  F  F  L  L  N  A  A  Q  K  Y  I  G  S  T  D  X
c                    Q  L  N  V  F  F  F  S  M  P  L  K  S  I  L  V  L  L  T  X
```

Figure 11BE

```
10261  CCTGATCTCCATTCCCTTATGCTCTCTTCATCACTATTTGGTTGAAAGGCGATAAATTTATAT  10320
       ---------+---------+---------+---------+---------+---------+
       GGACTAGAGGTAAGGGAATACGAGAGAAGTAGTGATAAACCAACTTTCGCTATTTAAAATATA a         P   D   L   I   P   L   C   S   S   S   L   F   G   -   K   R   -   I   L   Y
b         L   I   S   F   P   Y   A   L   H   H   Y   L   V   E   S   D   K   F   Y   I
c         -   S   H   S   L   M   L   F   I   T   I   W   L   K   A   I   N   F   I   F

10321  TTATCTAAAAGACTGGTTTCCATCTGTATGAGCGAGAAAACAGAACAGCCTACAGAAAAG  10380
       ---------+---------+---------+---------+---------+---------+
       AATAGATTTTCTGACCAAAGTAGACATACTCGCTCTTTTGTCTTGTCGGATGTCTTTTC
                              end yscT*   start yscU*
                                        M   S   E   K   T   E   Q   P   T   E   K
a         L   S   K   R   L   V   S   I   C
b         Y   L   K   D   W   F   P   S   V   -   A   R   K   Q   N   S   L   Q   K   R
c         I   -   K   T   G   F   H   L   Y   E   R   E   N   R   T   A   Y   R   K   E 10381  AAATTACGTGATGGCCGTAAGGAAGGGCAGGTTGTCAAAAGTATTGAAATAACATCATTA  10440
       ---------+---------+---------+---------+---------+---------+
       TTTAATGCACTACCGGCATTCCTTCCCGTCCAACAGTTTTCATAACTTTATTGTAGTAAT a         K   L   R   D   G   R   K   E   G   Q   V   V   K   S   I   E   I   T   S   L
b         N   Y   V   M   A   V   R   K   G   R   L   S   K   V   L   K   -   H   H   Y
c         I   T   -   W   P   -   G   R   A   G   C   Q   K   Y   -   N   N   I   I   I
```

Figure 11BF

```
10441  TTTCAGCTGATTGCGCTTTATTTGTATTTCATTTCTTTACTGAAAAGATGATTTGATA
       ---------+---------+---------+---------+---------+---------+ 10500
       AAAGTCGACTAACGCGAAATAAACATAAAGAAATGACTTTTCTACTAAACTAT a      F  Q  L  I  A  L  Y  L  F  I  C  I  F  F  I  S  L  L  K  R
b      F  S  -  L  R  F  I  C  I  F  F  I  S  L  L  K  R  -  F  -  Y
c      S  A  D  C  A  L  F  V  F  S  F  L  Y  -  K  D  D  F  D  T

10501  CTGATTGAGTCAATAACTTTCACATTACAATTAGTAAATAAACCATTTCTTATGCATTA
       ---------+---------+---------+---------+---------+---------+ 10560
       GACTAACTCAGTTATTGAAAGTGTAATGTTAATCATTTATTGGTAAAGAATACGTAAT a      L  I  E  S  I  T  F  T  L  Q  L  V  N  K  P  F  S  Y  A  L
b      -  L  S  Q  -  L  S  H  Y  N  -  I  N  H  F  L  M  H  -
c      D  -  V  N  N  F  H  I  T  I  S  K  -  T  I  F  L  C  I  N

10561  ACGCAATTGAGTCATGCTTTAATAGAGTCACTGACTTCTGCACTGCTGTTTCTGGGCGCT
       ---------+---------+---------+---------+---------+---------+ 10620
       TGCGTTAACTCAGTACGAAATTATCTCAGTGACTGAAGACGTGACGACAAAGACCCGCGA a      T  Q  L  S  H  A  L  I  E  S  L  T  S  A  L  L  F  L  G  A
b      R  N  -  V  M  L  -  -  S  H  -  L  L  H  C  C  F  W  A  L
c      A  I  E  S  C  F  N  R  V  T  D  F  C  T  A  V  S  G  R  W
```

Figure 11BG

```
10621  GGGTAATAGTTGCTACTGTGTGGGTAGCGTGTGTTTCTTCAGGTGTGGGGTGGTTATTGCCAGC
       ----+----+----+----+----+----+----+----+----+----+----+----+  10680
       CCCCATTATCAACGATGACACCCATCGCACAAAGAAGTCCACCCCCACCAATAACGGTCG a      G  V  I  V  A  T  V  G  S  V  F  L  Q  V  G  V  V  I  A  S
b      G  -  -  L  L  W  V  A  C  F  F  R  W  G  W  L  L  P  A
c         G  -  N     S  C  Y  C  G  -  R  V  S  S  G  G  G  Y  C  Q  Q

10681  AAGGCCATTGGTTTTAAAAGCGAGCATATAAATCCGGTAAGTAATTTTAAGCAGATATTC
       ----+----+----+----+----+----+----+----+----+----+----+----+  10740
       TTCCGGTAACCAAAATTTCGCTCGTATATTTAGGCCATTCATTAAAATTCGTCTATAAG a      K  A  I  G  F  K  S  E  H  I  N  P  V  S  N  F  K  Q  I  F
b      R  P  L  V  L  K  -  R  A  Y  K  S  G  K  -  F  -  A  D  I  L
c      G  H  W  F  -  K  R  A  Y  K  S  G  K  -  F  -  A  D  I  L

10741  TCTTTACATAGCGTAGTAGAATTATGTAAATCCAGCCTAAAAGTTATCATGCTATCTCTT
       ----+----+----+----+----+----+----+----+----+----+----+----+  10800
       AGAAATGTATCGCATCATCTTAATACATTTAGGTCGGATTTTCAATAGTACGATAGAGAA a      S  L  H  S  V  V  E  L  C  K  S  S  L  K  V  I  M  L  S  L  L
b      L  Y  I  A  -  N  Y  V  N  P  A  -  K  L  S  H  A  I  S  Y
c      F  T  -  R  S  R  I  M  -  I  Q  P  K  S  Y  H  A  I  S  Y
```

Figure 11BH

```
10801  ATCTTTGCCTTTTCTTTTATTATGCCAGTACTTTTCGGGGCTACCGTACTGTGGG
       ------+---------+---------+---------+---------+---------+ 10860
       TAGAAACGGAAAAAGAAAATAATACGGTCATGAAAAGCCCGCGATGGCATGACACCC a       I  F  A  F  F  F  Y  Y  A  S  T  F  R  A  L  P  Y  C  G
b        S  L  P  F  S  F  I  I  M  P  V  L  F  G  R  Y  R  T  V  G
c         L  C  L  F  L  L  L  C  Q  Y  F  S  G  A  T  V  L  W  V

10861  TTAGCCTGTGTGGCGTGCTTGTGGTTTCTTCTTAATAAAATGGTTATGGGGGTGATG
       ------+---------+---------+---------+---------+---------+ 10920
       AATCGGACACCGCACGAACACCAAAGAAGAAATTATTTTACCAATACCCCCACTAC a       L  A  C  G  V  L  V  V  S  S  L  I  K  W  L  W  V  G  V  M
b        -  P  V  A  C  L  W  F  L  L  -  N  G  Y  G  -  G  -  W
c         S  L  W  R  A  C  G  F  F  F  N  K  M  V  M  G  R  G  D  G

10921  GTTTTTATATCGTCGTTGGCATACTGGACTATTCTTTTCAATATTATAAGATTAGAAAA
       ------+---------+---------+---------+---------+---------+ 10980
       CAAAAAATATAGCAGCAACCGTATGACCTGATAAGAAAAGTTATAATATTCTAATCTTTT a       V  F  Y  I  V  V  G  I  L  D  Y  S  F  Q  Y  Y  K  I  R  K
b        F  F  I  S  S  L  A  Y  W  T  I  L  F  F  N  I  I  R  L  E  K
c         F  L  Y  R  R  W  H  H  T  G  L  F  F  S  I  L  -  D  -  K  S

Figure 11BI
```

```
10981 GCTATCTAAAAATGAGTAAAGATGACGTAAAACAGGAGCATAAAGATCTGGAGGGCGACC
      ---------+---------+---------+---------+---------+---------+ 11040
      CGATAGATTTTACTCATTTCTACTGCATTTTGTCCTCCGTATTTCTAGACCTCCCGCTGG a      A  I  -  K  -  V  K  M  T  -  N  R  S  I  K  I  W  R  A  T
b      L  S  K  N  E  -  R  -  R  K  T  G  A  -  R  S  G  G  R  P
c      Y  L  K  M  S  K  D  D  V  K  Q  E  H  K  D  L  E  G  D  P

Tn insertion P12F5
                                ⇒

11041 CTCAAATGAAGACGCGGCGTCGGAAATGCAGAGTGAAATACAAAGTGGGAGTTTAGCTCA
      ---------+---------+---------+---------+---------+---------+ 11100
      GAGTTTACTTCTGCGCCGCAGCCTTTACGTCTCACTTTATGTTTCACCCTCAAATCGAGT a      L  K  -  R  D  R  G  V  G  N  A  E  -  N  T  K  W  E  F  S  S
b      S  N  E  D  A  A  S  E  M  Q  S  E  I  Q  S  G  S  L  A  Q
c      Q  M  K  T  R  R  R  K  C  R  V  K  Y  K  V  G  V  -  L  N

11101 ATCTGTTAAAACAATCTGTTGCGGTAGTGCCGTAATCCAACGCCATATTGCGGTTTGTCTTGG
      ---------+---------+---------+---------+---------+---------+ 11160
      TAGACAATTTGTTAGACAACGCCATCACGGCCATTAGGTTGCGGTATAACGCCAAACAGAACC a      I  C  -  T  I  C  C  G  G  S  A  -  S  N  A  Y  C  G  L  S  W
b      S  V  K  Q  S  V  A  V  V  R  N  P  T  H  I  A  V  C  L  G
c      L  L  N  N  L  L  R  -  C  V  I  Q  R  I  L  R  F  V  L  A
```

Figure 11BJ

```
        CTATCATCCCACCGATATGCCAATACCACGCGTCCTGGAAAAGGCAGTGATGCTCAAGC
11161   ---------+---------+---------+---------+---------+---------+   11220
        GATAGTAGGGTGGCTATACGGTTATGGTGCGCAGGACCTTTTCCGTCACTACGAGTTCG a     L  S  S  H  R  Y  A  N  T  T  R  P  G  K  R  Q  -  C  S  S
    b       Y  H  P  T  D  M  P  I  P  R  V  L  E  K  K  G  S  D  A  Q  A
    c        I  I  P  P  I  C  Q  Y  H  A  S  W  K  K  A  V  M  L  K  L

TAACTATATTGTTAACATCGCTGAACGCAACTGCATCCCCGTGTTGAAAATGTTGAGCT
11221   ---------+---------+---------+---------+---------+---------+   11280
        ATTGATATAACAATTGTAGCGACTTGCGTTGACGTAGGGGCACAACTTTTACAACTCGA a     -  L  Y  C  -  H  R  -  T  Q  L  H  P  R  C  -  K  C  -  A
    b       N  Y  I  V  N  I  A  E  R  N  C  I  P  V  V  E  N  V  E  L
    c        T  I  L  L  T  S  L  N  A  T  A  S  P  L  L  K  M  L  S  W

GGCCCGCTCATTATTTTTGAAGTGGAACGCGGAGATAAAATTCCTGAAACGTTATTTGA
11281   ---------+---------+---------+---------+---------+---------+   11340
        CCGGGCGAGTAATAAAAACTTCACCTTGCGCCTCTATTTTAAGGACTTTGCAATAAACT a     G  P  L  I  F  -  S  G  T  R  R  -  N  S  -  N  V  I  -
    b       A  R  S  L  F  F  E  V  E  R  G  D  K  I  F  L  K  R  Y  L  N
    c        P  A  H  Y  F  L  K  W  N  A  E  I  K  F  L  K  R  Y  L  N
```

Figure 11BK

```
                                                                                  end yscU*
11341   ACCCGTTGCAGCCTTGTTACGTATGGTGATGAAGATATGGCATTCTACCGAAAC
        ------+---------+---------+---------+---------+---------+   11400
        TGGGCAACGTCGGAACAATGCATACCACTACTTCTATCTAATACGGTAAGATGGCTTTG a        T  R  C  S  L  V  T  Y  G  D  E  D  R  L  C  A  F  Y  R  N
b           P  V  A  A  L  L  R  M  V  M  K  I  D  Y  A  H  S  T  E  T
c              P  L  Q  P  C  Y  V  W  -  -  R  -  I  M  R  I  L  P  K  H 11401   ACCATAAATGCTTTTGGTATGCTTCTTCAGGCCACTGCGAAGGTTAAGAGGTAATAGCG
        ------+---------+---------+---------+---------+---------+   11460
        TGGTATTTACGAAAACCATACGAAGAAGTCCGGTGACGCTTCCAATTCTCCCATTATCGC a        T  I  N  A  F  G  M  C  L  L  Q  A  T  A  K  V  K  R  V  I  A
b           P  -  M  L  L  V  C  F  F  R  P  L  R  R  L  R  G  -  R
c              H  K  C  F  W  Y  A  S  S  G  H  C  E  G  -  E  G  N  S  V 11461   TATAGAGCAGTGCTTGACGATAAAGGTGAGAGACTGAAAAATAATCGCTTTTAGCCTGGCA
        ------+---------+---------+---------+---------+---------+   11520
        ATATCTCGTCACGAACTGCTATTTCCACTCTCTGACTTTTTATTAGCGAAAATCGGACCGT a        Y  R  A  V  L  D  D  K  G  E  R  L  K  I  I  A  F  S  L  A  H
b           I  E  Q  C  L  T  I  K  V  R  D  -  K  -  S  L  L  A  W  H
c              -  S  S  A  -  R  -  R  -  E  T  E  N  N  R  F  -  P  G  T Figure 11BL
```

Figure 11BM

```
11521 CAAGCACCAGATAGCGTATTATAAAATTAAACAAGATAAATGGATTGGTGCGTCTGAATGG 11580
       ----+----+----+----+----+----+----+----+----+----+----+----+
       GTTCGTGGTCTATCGCATAATATTTAATTTGTTCTATTACCTAACCACGCAGACTTACC a   Q  A  P  D  S  V  L  -  N  -  T  R  -  W  I  G  A  S  E  W
b   K  H  Q  I  A  Y  Y  K  I  K  Q  D  N  G  L  V  R  L  N  G
c   S  T  R  -  R  I  I  K  L  N  K  I  M  D  W  C  V  -  M  D

11581 ACTCGAACCACTCGACCCCCACCATGTCAAGGTGGTGCTCTAACCAACTGAGCTATGAAC 11640
       ----+----+----+----+----+----+----+----+----+----+----+----+
       TGAGCTTGGTGAGCTGGGGGTGGTACAGTTCCACCACGAGATTGGTTGACTCGATACTTG a   T  R  T  T  R  P  P  P  C  Q  G  G  A  L  T  N  -  A  M  N
b   L  E  P  L  D  P  H  H  V  K  V  V  L  -  P  T  E  L  -  T
c   S  N  H  S  T  P  T  M  S  R  W  C  S  N  Q  L  S  Y  E  R

11641 GGCAACGTTGTAGGTGACAACGGGACGAATATTAGCGTCACAACCGCAATGAGGCAAGA 11700
       ----+----+----+----+----+----+----+----+----+----+----+----+
       CCGTTGCAACATCCACTGTTGCCCCTGCTTATAATCGCAGTGTTGGCGTTACTCCGTTCT a   G  N  V  V  G  D  N  G  D  E  Y  -  R  H  N  R  N  E  A  R  E
b   A  T  L  -  V  T  T  G  T  N  I  S  V  T  T  A  M  R  Q  E
c   Q  R  C  R  -  Q  R  G  R  I  L  A  S  Q  P  Q  -  G  K  K  R
```

```
         GGGAAATGCAATTTTCTTCCTGAAATCACCTGATTGCGGTGGAAATATGCAACATGTCG
11701    ---------+---------+---------+---------+---------+---------+  11760
         CCCTTTAGCGTTAAAAGAAGGACTTTAGTGGACTAACGCCACCTTTATACGTTGTACAGC a     G   K   S   Q   F   S   S   -   N   H   L   I   A   V   E   I   C   N   M   S
    b         G   N   R   N   F   L   P   E   I   T   -   L   R   W   K   Y   A   T   C   R
    c             E   I   A   F   F   L   K   S   P   D   C   G   G   N   M   Q   H   V   E

AGAAAATAGCCGCCATGCGACGGCTATCGTCGTATTATCGGAGCGGCTGCAAAATGATG
11761    ---------+---------+---------+---------+---------+---------+  11820
         TCTTTTATCGGCGGTACGCTGCCGATAGCAGCATAATAGCCTCGCCGACGTTTTACTAC a     R   K   -   P   P   C   D   G   Y   R   R   I   I   G   A   R   C   K   M   M
    b         E   N   S   R   H   A   T   A   I   V   V   L   S   E   R   A   A   K   -   W
    c             K   I   A   A   M   R   R   L   S   S   Y   Y   R   S   A   L   Q   N   D   G

GCGGACGGGCTGACGTTGTAGATAGCCGTAGCATCATTAACACCCGCCGGGCCGAGGTC
11821    ---------+---------+---------+---------+---------+---------+  11880
         CGCCTGCCCGACTGCAACATCTATCGGCATCGTAGTAATTGTGGGCGGCCCGGCTCCAG a     A   D   G   -   R   C   R   -   R   I   R   S   I   I   N   T   A   A   E   V
    b         R   T   A   D   V   V   D   S   A   S   V   A   S   L   T   P   P   P   R   S
    c             G   R   L   T   L   -   I   A   H   P   -   H   H   -   H   H   R   R   R   G   Q
```

```
       AGGCCGATGATGAACCCCATCCAGAAGCCTGCCGGTCCCATAGATCCACCAAATCC
11881  ------+---------+---------+---------+---------+---------+  11940
       TCCGGCTACTACTTGGGGTAGGTCTTCGGACGGCCAGGGTATGCTAGGTGGTTTAGG a        R  P  M  M  N  P  I  Q  K  P  A  G  P  I  R  S  T  T  K  S
b         G  R  -  T  P  S  R  S  L  P  V  P  Y  D  P  P  P  N  P
c        A  D  D  E  P  H  P  E  A  C  R  S  H  T  I  H  H  Q  I  R

GTTAACGCCAGGATATAACCGCTGGGTAAACCTAACACCCAGTAGGCGGTAAAGGTGATA
11941  ------+---------+---------+---------+---------+---------+  12000
       CAATTGCGGTCCTATATTGGCGACCCATTTGGATTGTGGGTCATCCGCCATTTCCACTAT a        V  N  A  R  I  -  P  L  G  K  P  N  T  Q  -  A  V  K  V  I
b         L  T  P  G  Y  N  R  W  V  N  L  T  P  S  R  R  -  R  -  -
c        -  R  Q  D  I  T  A  G  -  T  -  H  P  V  G  G  K  G  D  K

AAAAAGATGGAACGCGTATCTTTATAACCGCGCCAGAATACCGCTGCCGATAACCTGTATA
12001  ------+---------+---------+---------+---------+---------+  12060
       TTTTTCTACCTTGCGCATAGAAATATTGGCGCGGTCTTATGGCGACGGCTATTGGACATAT a        K  K  M  E  R  V  S  L  -  P  R  R  E  I  P  L  P  I  T  C  I
b         K  R  W  N  A  Y  L  Y  N  R  A  E  Y  R  C  R  -  P  V  -
c        K  D  G  T  R  I  F  I  T  A  Q  N  T  A  A  D  N  L  Y  R
```

```
12061  GAGTCGGAAATCTGGTAAACCGCAGCAGCATTAATTGCGGCAAGGCGCCACGACCTC
       -------+---------+---------+---------+---------+---------+ 12120
       CTCAGCCTTTAGACCATTTGGCGTCGTCGTAATTAACGCCGTTCGCGGTGCTGGAG a       E  S  E  I  W  -  T  A  A  S  S  I  N  C  G  K  R  H  D  L
b       S  R  K  S  G  K  P  Q  R  A  A  L  I  A  A  S  A  T  T  S
c       V  G  N  L  V  N  R  S  E  Q  H  -  L  R  Q  A  P  R  P  Q

AGGGTTGTCATTGTAGAGCAAAGCAATATGCTTACGCAGAGTAACGGTAAAAATAGCGGT
       -------+---------+---------+---------+---------+---------+ 12180
       TCCCAACAGTAACATCTCGTTTCGTTATACGAATGCGTCTCATTGCCATTTTATCGCCA a       R  V  V  I  V  E  Q  S  N  M  L  T  Q  S  N  G  K  N  S  G
b       G  L  S  L  -  S  K  A  I  C  L  R  R  V  T  V  K  I  A  V
c       G  C  H  C  R  A  K  Q  Y  A  Y  A  E  -  R  -  K  -  R  -

12181  AACCACCAGCCATACAAATGCCGACGCCTAAACCGGTACGCTGCGTTTGCGCATCCAGC
       -------+---------+---------+---------+---------+---------+ 12240
       TTGGTGTCGGTATGTTTACGGCTGCGGATTTGGCCATGCGACGCAAACGCGTAGGTCG a       N  H  H  S  H  T  N  A  D  A  -  T  G  T  R  C  V  C  A  S  S
b       T  T  A  I  Q  M  P  T  P  K  P  V  R  A  A  F  A  H  P  A
c       P  Q  P  Y  K  C  R  R  L  N  R  Y  A  L  R  L  R  I  Q  R
```

Figure 11BP

```
12241 GTTGAGCCCTGGCCCCAGACCGATAACCCACTCGAATCGTTACCGCCGCAGCCAGCGACAT 12300
      ------+---------+---------+---------+---------+---------+
      CAACTCGGGACCGGGTCTGGCTATTGGGTGAGCTTAGCAATGGCGGTCGGTCGCTGTA a   V  E  P  W  P  R  P  I  T  H  S  N  R  Y  R  R  S  Q  R  H
   b   L  S  P  G  P  D  R  -  P  T  R  I  V  T  A  A  A  S  D  I
   c   -  A  L  A  Q  T  D  N  P  L  E  S  L  P  P  Q  P  A  T  S

12301 CGGCAGTACGAACATCAGCGAGCTAAAGTTAAGCGCTAATCTGATGACCGGCGACATCCAC 12360
      ------+---------+---------+---------+---------+---------+
      GCCGTCATGCTTGTAGTCGCTCGATTTCAATTCGCGTTAGACTACTGGCCGCTGTAGGTG a   R  Q  Y  E  H  Q  R  A  K  V  K  R  N  L  M  T  G  D  I  H
   b   G  S  T  N  I  S  E  L  K  L  S  A  I  -  P  A  T  S  T
   c   A  V  R  T  S  A  S  -  S  -  A  Q  S  D  D  R  R  H  P  Q

12361 AATACCTAATGGCGAAACCAGCAGCGACCGCAATAACGTCACTTCAAAGAACAG 12420
      ------+---------+---------+---------+---------+---------+
      TTATGGATTACCGCTTTGGTCGTCGCTGGCGTTATTGCAGTGAAGTTTCTTGTC a   N  T  -  W  R  N  Q  Q  R  N  D  R  K  -  R  H  F  K  E  Q
   b   I  P  N  G  E  T  S  S  A  T  T  A  N  N  V  T  S  K  N  S
   c   Y  L  M  A  K  P  A  A  Q  R  P  Q  I  T  S  L  Q  R  T  A
```

Figure 11BQ

```
12421  CCAGGCGCAATCGGCAACCCCAGTTGAATCAGGCGCTTCATGACGACGCTATCGGGTTTGC  12480
       ------+---------+---------+---------+---------+---------+
       GGTCGCGTTAGCCGTTGGGGTCAACTTAGTCCGCGAAGTACTGCTGCGATAGCCCAAACG a    P  A  Q  S  A  T  P  V  E  S  G  A  S  -  R  R  Y  R  V  C
    b    Q  R  N  R  Q  P  Q  L  N  Q  A  L  H  D  D  A  I  G  F  A
    c    S  A  I  G  N  P  S  -  I  R  R  F  M  T  T  L  S  G  L  P

12481  CAAAGCCTTTTCATTACGAATATCACGCATTGAACGCGTGTTTAATGTAAGAAAGCA  12540
       ------+---------+---------+---------+---------+---------+
       GTTTCGGAAAAGTAATGCTTATAGTGCGTAACTTGCGCACAAATTACATTCTTTCGT a    Q  S  L  F  H  Y  E  Y  H  A  L  N  A  R  V  -  C  K  K  A
    b    K  A  F  F  I  T  N  I  T  H  -  T  R  V  F  N  V  R  K  H
    c    K  P  F  S  L  R  I  S  R  I  E  R  A  C  L  M  -  E  S  M

12541  TGGGCGATAAACATCACCCAATAGACCCGCCAGTCGCAACGCCCGCGATACCGCCGA  12600
       ------+---------+---------+---------+---------+---------+
       ACCGCTATTTGTAGTGGGTTATCTGGGCGGTCAGCGTTGCGGGCGCTATGGCGGCT a    W  R  -  T  S  P  N  R  P  P  Q  S  Q  R  R  S  R  Y  R  R
    b    G  D  K  H  H  P  I  D  R  R  S  R  N  A  A  A  D  T  A  E
    c    A  I  N  I  T  Q  -  T  A  A  V  A  T  P  Q  P  I  P  P  S
```

Figure 11BR

```
12601 GTTCCGGCATACCAAAATGGCCATAGATAAAAATATAGTTCACCGGAATATTCACCAGCA
      ------+---------+---------+---------+---------+---------+ 12660
      CAAGGCCGTATGGTTTTACCGGTATCTATTTTATATCAAGTGGCCTTATAAGTGGTCGT a      V  P  A  Y  Q  N  G  H  R  -  K  Y  S  S  P  E  Y  S  P  A
b      F  R  H  T  K  M  A  I  D  K  N  I  V  H  R  N  I  H  Q  Q
c      S  G  I  P  K  W  P  -  I  K  I  -  F  T  G  I  F  T  S  R

12661 GGCCCAAAAATCCCATCACCATACCCGGTTTGGTTTTGGCCAGACCTTCGCACTGGTTTC
      ------+---------+---------+---------+---------+---------+ 12720
      CCGGGTTTTTAGGGTAGTGGTATGGGCCAAACCAAAACCGGTCTGGAAGCGTGACCAAAG a      G  P  K  I  P  S  P  Y  P  V  W  F  W  P  D  L  R  T  G  F
b      A  Q  K  S  H  H  H  T  R  F  G  F  G  Q  T  F  A  L  V  S
c      P  K  N  P  I  T  I  P  G  L  V  L  A  R  P  S  H  W  F  R

12721 GCGCTACCTGAAAGAAAAGGTATCCTGCGCCCACAGCAGCGCGAAGATAACCCACGG
      ------+---------+---------+---------+---------+---------+ 12780
      CGCGATGGACTTTCTTTTCCATAGGACGCGGGTGTCGTCGCGCTTCTATTGGGTGCC a      A  L  P  E  R  K  G  I  L  R  P  T  A  A  R  E  D  N  P  R
b      R  Y  L  K  E  K  V  S  C  A  P  Q  Q  R  A  K  I  T  H  G
c      A  T  -  K  K  R  R  Y  P  A  P  H  S  S  A  R  R  -  P  T  A
```

Figure 11BS

```
12781      CTTTATCGGCCAGCGCCGGATCAATATTATGCATAGAGCGGATAAATGTATCCGGCATTCC
           ----------+---------+---------+---------+---------+---------+ 12840
           GAAATAGCCGGTCGCGGCCTAGTTATAATACGTATCTCGCCTATTTACATAGGCCGTAAGG a           L  Y  R  P  A  P  D  Q  Y  Y  A  -  S  G  -  C  I  R  H  S
b           F  I  G  Q  R  R  I  N  I  M  H  R  A  D  N  V  S  G  I  P
c           L  S  A  S  A  G  S  I  L  C  I  E  R  I  M  Y  P  A  F  H

12841      ACAGGACGATCATCACCAGCACGGAGACAAAGCCCGCCAGCCAGAACCCTGTCGAACCT
           ----------+---------+---------+---------+---------+---------+ 12900
           TGTCCTGCTAGTAGTGGTCGTGCCTCTGTTTCGGGCGGTCGGTCTTGGGAACAGCTTGGA a           T  G  R  S  S  P  A  R  R  Q  S  P  P  A  R  T  L  V  E  P
b           Q  D  D  H  H  Q  H  G  D  K  A  R  Q  P  E  P  L  S  N  L
c           R  T  I  I  T  S  T  E  T  K  P  A  S  Q  N  P  C  R  T  -

12901      GATGCCGCGATACGCTCACGACGGCCGGAGCCATTGAGTTGCGCAATCACAGGCGTCAAGG
           ----------+---------+---------+---------+---------+---------+ 12960
           CTACGGCGCTATGCGAGTGCTGCCGGCCTCGGTAACTCAACGCGTTAGTGTCCGCAGTTCC a           D  A  R  Y  A  H  D  G  R  S  H  -  V  A  Q  S  Q  A  S  R
b           M  R  D  T  L  T  T  A  G  A  I  E  L  R  N  H  R  R  Q  G
c           C  A  I  R  S  R  R  P  E  P  L  S  C  A  I  T  G  V  K  A
```

Figure 11BT

```
12961  CCAGCAGTAAGCCGTGACCAAACAAAATGGCGGGAAGCAGATAGAGGTGCCGATAGCGAC
       ------+---------+---------+---------+---------+---------+  13020
       GGTCGTCATTCGGCACTGGTTTGTTTTACCGCCCTTCGTCTATCTCCACGGCTATCGCTG a         P  A  V  S  R  D  Q  T  K  W  R  E  A  D  R  G  A  D  S  D
b         Q  Q  -  A  V  T  K  Q  N  G  G  K  Q  I  E  V  P  I  A  T
c         S  S  K  P  -  P  N  K  M  A  G  S  R  -  R  C  R  -  R  R

13021  GGCAGCCATGTCCGTAGCGCTATAGCCTCCCGCCATGACGGTATCGACGAATCCATTGCG
       ------+---------+---------+---------+---------+---------+  13080
       CCGTCGGTACAGGCATCGCGATATCGGAGGGCGGTACTGCCATAGCTGCTTAGGTAACGC a         G  S  H  V  R  S  A  I  A  S  R  H  D  G  I  D  E  S  I  A
b         A  A  M  S  V  A  L  -  P  P  A  M  T  V  S  T  N  P  L  R
c         Q  P  C  P  -  R  Y  S  L  P  P  -  R  Y  R  R  I  H  C  G

13081  GTCTATACCACTTGCGCAAGGATCACCGGTATCTGAACGCTAATAACTGACGCGCTTCAC
       ------+---------+---------+---------+---------+---------+  13140
       CAGATATGGTGAACGCGTTCCTAGTGGCCATAGACTTGCGATTATTGACTGCGCGAAGTG a         V  Y  T  T  C  A  R  I  T  G  I  -  T  L  I  T  D  A  L  H
b         S  I  P  L  A  Q  G  S  P  V  S  E  R  -  L  T  R  F  T
c         L  Y  H  L  R  K  D  H  R  Y  L  N  A  N  N  -  R  A  S  L
```

Figure 11BU

```
13141    TGGTATACTTCTGCACGTATTCACCTTTTATTTGTTGTTATATGAAAGACTAAAAGCC
         ----+----+----+----+----+----+----+----+----+----+----+----+  13200
         ACCATATGAAGACGTGCATAAGTGGAAAATAAACAACAATATACTTTCTGATTTTTCGG a            W  Y  T  S  A  R  I  H  L  L  F  F  Y  F  V  V  I  -  K  A
b             G  I  L  H  V  F  T  F  Y  F  V  V  I  -  K  T  K  K  P
c              V  Y  F  C  T  Y  S  P  F  I  L  L  Y  E  R  L  K  S  R

13201    GCCGAAGTGGCAGCCAAAAGAAATAGCAGGGGAATTTCAGTCTATTGTAGCGGGGTATT
         ----+----+----+----+----+----+----+----+----+----+----+----+  13260
         CGGCTTCACCGTCGGTTTTCTTTATCGTCCCCTTAAAGTCAGATAACATCGCCCCATAA a            A  E  V  A  A  K  R  N  S  R  G  N  F  S  L  L  -  R  G  I
b             P  K  W  Q  P  K  E  K  -  Q  G  K  F  Q  S  I  V  A  G  Y
c              R  S  G  S  Q  K  K  -  Q  G  K  F  Q  S  I  V  A  G  Y  Y

13261    ACTATTTCTCCAGTGAAAAAACAGTTGTTAACGGCGATTGCTGGCAAGCTGTTTTTCCA
         ----+----+----+----+----+----+----+----+----+----+----+----+  13320
         TGATAAAGAGGTCACTTTTTTGTCAACAATTGCCGCTAACGACCGTTCGACAAAAAGGT a            T  I  S  P  V  K  K  Q  L  L  T  A  H  C  W  Q  A  V  F  P
b             L  F  L  Q  -  K  N  S  C  -  R  R  I  A  G  K  L  F  F  H
c              Y  F  S  S  E  K  T  V  V  N  G  A  L  L  A  S  C  F  S  T
```

Figure 11BV

```
13321                  CCTGCTATTGTGCTGAACAGTTCTGCTTTTATTTATTTCAGGAGTTGAAGATATGTTTAC                  13380
                       ----------+---------+---------+---------+---------+---------+
                       GGACGATAACACGACTTGTCAAGACGAAAATAAATAAAGTCCTCAACTTCTATACAAATG a        P  A  I  V  L  N  S  S  A  F  I  Y  F  R  S  -  R  Y  V  Y
b           L  L  C  -  T  V  L  L  F  I  S  G  V  E  D  M  F  T
c              C  Y  C  A  E  Q  F  C  F  Y  L  F  Q  E  L  K  I  C  L  R

13381                  GGGGATCGTACAGGGTACCGGCGAAACTGGTATCGATA                  13417
                       ----------+---------+---------+-------
                       CCCCTAGCATGTCCCATGGCGCTTTGACCATAGCTAT a        G  D  R  T  G  Y  R  E  T  G  I  D
b           G  I  V  Q  G  T  A  K  L  V  S  I
c              G  S  Y  R  V  P  R  N  W  Y  R
```

Figure 11BW

Figure 12A
DNA Sequence of VGC II cluster C

Tn insertion P9B4
⇒

```
      GGATCCTTTTCTTTAATGCTGCTAACGTTTCTTGCAAAATGCGTTGATGAGATTCATCC
  1   ----+----+----+----+----+----+----+----+----+----+----+----+   60
      CCTAGGAAAAGAAATTACGACGATTGCAAAGAACGTTTTACGCAACTACTCTAAGTAGG

AGTACACCACTGATAACAAAAGAGGCGNCGCATTGGCNWAMMWTKRNNMRNNSCNNNACTA
 61   ----+----+----+----+----+----+----+----+----+----+----+----+  120
      TCATGTGGTGACTATTGTTTTCTCCGCNGGCTAACCGNWTKKWAMYNNKYNNSGNNNTGAT
```

Tn insertion P7A3
⇒

```
      AACCGTTCTCTATTATCGCAGAAATAATCATCCCCCTGAGACTGATGAGAGTGACTAA
121   ----+----+----+----+----+----+----+----+----+----+----+----+  180
      TTGGCAAGAGATAATAGCGTCTTTATTATAGTAGGGGACTCTGACTACTCTCACTGATT

TCTGCCAGTGCAATAACCCGGGAATATCTGCAAGTAATGGTTGAACCTTGCGCCATTGCT
181   ----+----+----+----+----+----+----+----+----+----+----+----+  240
      AGACGGTCACGTTATTGGGCCCTTATAGACGTTCATTACCAACTTGGAACGCGGTAACGA
```

Tn insertion P964
⇒

```
      GATCCATTTGTATATCATCATGAATTAACACGCTCCCCGGCCCTTCGCTGGATACTTCAG
241   ----+----+----+----+----+----+----+----+----+----+----+----+  300
      CTAGGTAAACATATAGTAGTACTTAATTGTGCGAGGGGCCGGGAAGCGACCTATGAAGTC
```

Figure 12B

```
       CATNSSGGTAACCCATTTTTATCAAAACATCCTGCACTTCTCGTACCAATAAGTCATCAC
301    ------+---------+---------+---------+---------+---------+   360
       GTANSSCCATTGGGTAAAAATAGTTTTGTAGGACGTGAAGAGCATGGTTATTCAGTAGTG

AGATTACACCATCCCGATACATGACCCCCCATGATTCGAGAGTCGCTCTCACCTTTTGCA
361    ------+---------+---------+---------+---------+---------+   420
       TCTAATGTGGTAGGGCTATGTACTGGGGGGTACTAAGCTCTCAGCGAGAGTGGAAAACGT

TCTGTTCGCTTGACGAGCAATAACCGGACAACTGCAGGCTGCCATCTCTTTCCATTGCG
421    ------+---------+---------+---------+---------+---------+   480
       AGACAAGCGAACTGCTCGTTATTGGCCTGTTGACGTCCGACGGTAGAGAAAGGTAACGC

CCCGCACATAATGAATATTGCTTTTGTCTAATAAAAACTTAACCCGCAAAGGTAAGTCAT
481    ------+---------+---------+---------+---------+---------+   540
       GGGCGTGTATTACTTATAACGAAAAACAGATTATTTTTGAATTGGGCGTTTCCATTCAGTA

TTACCGTTTCAGGCTGACCACCAGTACTTAACAGGACACCATTCCACCGATGAAAATCA
541    ------+---------+---------+---------+---------+---------+   600
       AATGGCAAAGTCCGACTGGTGGTCATGAATTGTCCTGTGGTAAGGTGGCTACTTTTAGT

AGAATACGCCAGCCAACACCAGTACCCTGATCTGGAAACGGGTATTTGATAATCAGCAA
601    ------+---------+---------+---------+---------+---------+   660
       TCTTATGCGGTCGGTTGGTGGTCATGGGACTAGACCCTTTGCCCATAAACTATTAGTCGTT
```

Figure 12C

```
      GTTCACAATCCTGTGTTACCAAACGCGATASSCACTCCCGCAACCTGCAAAACCCCACTGG
661   ------+---------+---------+---------+---------+---------+   720
      CAAGTGTTAGGACACAAATGGTTTGCGCTATSSGTGAGGGCGTTGGACGTTTTGGGTGACC

ATGGTAGCGGCTTATTTGGATTAAATCTGCGGCCATTAACTCTGGCTTTCCCGG
721   ------+---------+---------+---------+---------+---------+   780
      TACCATCGCCGAATAAACCTAATTTAGACGCCGGTAATTGAGATTGAGACCGAAAGGGCC

CATCAACAAATAAACTATCTGCCTGTCTCTCAGAATAATTTTTCATTTATAGCCAGCG
781   ------+---------+---------+---------+---------+---------+   840
      GTAGTTGTTTATTTGATAGACGGACAAGAGAGTCTTATTAAAAAGTAAATATCGGTCGC

AATACAAATATCGCATCCCTTCTCCCCAGTGACACAGGTTACCTTCATTCAGCCATACTTC
841   ------+---------+---------+---------+---------+---------+   900
      TTATGTTTATAGCGTAGGGAAGAGGGGTCACTGTCCAATGGAAGTAAGTCGGTATGAAG

CCGGCCTTGTAAAACGTGACCTAAAAAACGTATTTTCCAGGAACTCTTTGGATTAACCAT
901   ------+---------+---------+---------+---------+---------+   960
      GGCCGGAACATTTTGCACTGGATTTTTGCATAAAAGGTCCTTGAGAAACCTAATTGGTA

GAGATATGCCATTATTACTACTGAGGCTTTAATCAAAAAAAGCCTGATTACACTATGTA
961   ------+---------+---------+---------+---------+---------+   1020
      CTCTATACGGTAATAAATGATGACTCCGAAATTAGTTTTTTTCGGACTAATGTGATACAT
```

Figure 12D

```
      CTTGAGTCGTATCATTGCGAAACAAATGACCTACACAACAGGAATATGCCCAATAAAGGA
1021  ------------------------------------------------------------  1080
      GAACTCAGCATAGTAACGCTTTGTTTACTGGATGTTGTCCTTATAGCGGGTTATTCCCT

TTTGTTTTGCGAGTGGATTTGTTTACCTTGTGTTTAAACCCTCCCAGCAATNAGACTTTGC
1081  ------------------------------------------------------------  1140
      AAACAAAACGCTCACCTAAACAAATGGAACAAATTTGGGAGGTCGTTANTCTGAAACG

CCGGCCAATAAGTGTGGCTTGCCGAANCRATTTCAGAATTTTGCACTTCGGGCAGCGGGTCT
1141  ------------------------------------------------------------  1200
      GGCCGGTTATTACACCGAACGCTTNGYTAAAGTCTTAAAACGTGAAGCCCGTCGCCCAGA

GTNTYGCYTTKGNSTATCACTTTGTTGTCCATCCTGAANTATTAAGATTAAGCATTATTT
1201  ------------------------------------------------------------  1260
      CANARCGRAAMCNSATAGTGAAACAACAGGTAGGACTTNATAATTCTAATTCGTAATAAA

TTTGCGTGCCATTGTCATTTAACAAGCGAGGTGTAACGCGWNAACAAAGAACCCGTAGTG
1261  ------------------------------------------------------------  1320
      AAACGCACGGTAACAGTAAATTGTTCGCTCCACATTGCGCWNTTGTTTCTTGGCATCAC

ATGGATTCAAGTTTAGCCACTTTTTCTCCCTGCAGTTTGGTATAGAAAGTAATATTTTA
1321  ------------------------------------------------------------  1380
      TACCTAAGTTCAAATCGGTGAAAAAGAGGACGTCAAACCATATCTTTCATTATAAAAAT
```

Figure 12E

```
       TCCAGCACAGCCTGGATATTATTTAAAGTCACCACAGATGGCTGGGAAAGTACATAAGCC
1381   ------+---------+---------+---------+---------+---------+    1440
       AGGTCGTGTCGGACCTATATAATTTCAGTGGTGTCTACCGACCCTTTCATGTATTCGG

TGAGAGCTTTTTCCAGGGCATTCAGACGCCACCATAAAGTTTGAGGTATCGCTGATTACC
1441   ------+---------+---------+---------+---------+---------+    1500
       ACTCTCGAAAAAGGTCCCGTAAGTCTGCGTGGTATTTCAAACTCCATAGCGACTAATGG

GTTGANNAACCACTAGCACCACCGTCATTCAAACCTGTATTGAACGCAATTTTCTTGCCA
1501   ------+---------+---------+---------+---------+---------+    1560
       CAACTNNTTGGTGATCGTGGTGGCAGTAAGTTTGGACATAACTTGCGTTAAAAGAACGGT

CCCAGGCGACACTGCCCGTTCCCCAGTCGATGCCTAACTGGTTAATATCTCCAGCATTAACA
1561   ------+---------+---------+---------+---------+---------+    1620
       GGGTCGCTGTGACGGCAAGGGGTCAGCTACGGATTGACCAATTATAGAGGTCGTAATTGT

TCGATAATTTCACCGAAATCTCTATCATCTGCTGGCGTTGATCTAATTCTGTGATGAGT
1621   ------+---------+---------+---------+---------+---------+    1680
       AGCTATTAAAGTGGCTTTAGAGATAGTAGACCGCAACTAGATTAAGACACTACTCA

TTCCGATACNNNGCCATATTGGNNNNCATAATCACGAACGATCACTGCCATTCTGGCGTNGG
1681   ------+---------+---------+---------+---------+---------+    1740
       AAGGCTATGNNNNCGGTATAACCNNNGTATTAGTGCTTGCTAGTGACGTAAGACCGCANCC
```

Figure 12F

```
      GTCGGCAGCAAACATNGGCAATGCCTGTGTAGCGGGTGAACCATTGTTCNTCGATGACGT
1741  ------+---------+---------+---------+---------+---------+  1800
      CAGCCGTCGTTTGTANCCGTTACGGACACATCGCCCACTTGGTAACAAGNAGCTACTGCA

CGGGACGCTGGTTTTACTCATCTCACGCAATACACTAACGACCCCTGGNNAACCACGACG
1801  ------+---------+---------+---------+---------+---------+  1860
      GCCCTGCGACCAAAATGAGTAGAGTGCGTTATGTGATTGCTGGGGACCNNTTGGTGCTGC

GACTGATCGCGATATTGGTACTGGGTATCCATCGCAGTGGCATACTTAAGCGTGTATATA
1861  ------+---------+---------+---------+---------+---------+  1920
      CTGACTAGCGCTATAACCATGACCCATAGGTAGCGTCACCGTATGAATTCGCACATATAT

CTTACACTCACCGCACTGTCTTTTCGTTTGATTAACGCATTATCCAGCACTGAAGCTAAT
1921  ------+---------+---------+---------+---------+---------+  1980
      GAATGTGAGTGGCGTGACAGAAAAGCAAACTAATTGCGTAATAGGTCGTGACTTCGATTA

TGACTAATACGAGTCAGGCAGCTGGGAACACCGCTCACCTCCACAGCTTTGGTACCGGTA
1981  ------+---------+---------+---------+---------+---------+  2040
      ACTGATTATGCTCAGTCCGTCGACCCTTGTGGCGAGTGGAGGTGTCGAAACCATGGCCAT
                                  Tn insertion P7G2
                                         ⇒
      ATTTCTTTAACCTCGCATCCCGGTGATGAAAGGATATTCTGGCTGCGTAAGTAATGAATG
2041  ------+---------+---------+---------+---------+---------+  2100
      TAAAGAAATTGGAGCGTAGGGCCACTACTTTCCTATAAGACCGACGCATTCATTACTTAC
```

Figure 12G

```
      AACCGTCCAGTAGATAAAATATTGAAAGTGATAACCTGATGTTTTAATAACGATGCAGGA
2101  ------------------------------------------------------------  2160
      TTGGCAGGTCATCTATTTTATAACTTTCACTATTGGACTACAAAATTATTGCTACGTCCT

TATACATATAACATGCTGCCATCAAACCAGGTAAGCAAATCATATTGTGCTGCCAGGTTA
2161  ------------------------------------------------------------  2220
      ATATGTATATTGTACGACGGTAGTTTGGTCCATTCGTTTAGTATAACACGACGGTCCAAT

TTCAAAATATCGACCGGTGGTCCAGGCGTAGTTTCCACTAAATGTAGCTGTTATCAAT
2221  ------------------------------------------------------------  2280
      AAGTTTATAGCTGGCCACCAGGTCCGCCTTAAAAAGGTGATTTACATGACAATAGTTA

GGGCTAATAGTAATAGCCGTATCATAGTTCTCTGAGAGCAGATGTNAAAACCTCTGCTAA
2281  ------------------------------------------------------------  2340
      CCCGATTATCATTATCGGCATAGTATCAAGAGACTCTCGTCTACANTTTGGAGACGATT

TGGCATTTGTCTGGCATAAAGGGTGAAGTCATTACCTTTCCATGATAACTCATCACTCTT
2341  ------------------------------------------------------------  2400
      ACCGTAAACAGACCGTATTTCCCACTTCAGTAATGGAAAGGTACTATTGAGTAGTGAGAA

TGCTGTATTGAGTATAAATAGTAAAATTAAGATTAAACGTTTATTTACTACCATTTTATA
2401  ------------------------------------------------------------  2460
      ACGACATAACTCATATTTATCATTTTAATTCTAATTTGCAAATAAAATGATGGTAAAATAT
```

Figure 12H

```
2461 CCCCACCCGAATAAAGTTTATGGTGATTGCGTATTACATTTTTTNAAAATGCAAGTTAAA 2520
     GGGGTGGGCTTATTTCAAATACCACTAACGCATAATGTAAAAAANTTTACGTTCAATTT

2521 GCCAGGTGTTTTCTATCTCAATAGCAATAAGCTCAGAGCTACTACTTGTGGTATAATAA 2580
     CGGTCCACAAAAGATAGAGTTATCGTTATTCGAGTCTCGATGATGAACACCATATATT

2581 CCGTTTAACCATCCCCCATCCGCTGTGAGCTGTATAGCATAATCATGGACGTTCCGGGTGT 2640
     GGCAAATTGGTAGGGGGTAGGCGACACTCGACATATCGTATTAGTACCTGCAGGCCCACA

2641 GCGCAARCRGTAGTGTCAMMTAGGCAAGACAAGGCTTAGGTAAGCTTTCCAGTCATTTA 2700
     CGCGTTYGYCATCACAGTKKATCCGTTCTGTTCCGAATCCATTCGAAAGGTCCAGTAAAT

Tn insertion P11B9
                    ⇒

2701 AGAACAAAGAAATAGAAAATGCTTCTGAGAAAATTTCTYCYBHNNNNNNNNNNNN 2760
     TCTTGTTTCTTTATCTTTTACGAAGACTCTTTTAAAGAGARGRVDNNNNNNNNNNNNN

2761 NNNNNNNNCATCAATAGTCATTATCCAGGATSSKMTWWYMNYYKSSSCYSWKATMYYSWR 2820
     NNNNNNNNGTAGTTATCAGTAATAGGTCCTASSMKAWWRKNRRMSSSGRSWMTAKRRSWY
```

Figure 12I

```
         WWTTAATGGAATGCCTTTTAAAACTGCCAGCATGAATCCCTCCTCAGACATAAATGGGAG
2821     ------+---------+---------+---------+---------+---------+      2880
         WWAATTACCTTACGGAAAATTTGACGGTCGTACTTAGGGAGGAGTCTGTATTTACCCTC

TTTCTATCAAATTCGCTCACAACCACATCCGTAAAAAGCCTGATTCACATTATTCGAC
2881     ------+---------+---------+---------+---------+---------+      2940
         AAAGATAGTTTAAGCGAGTGTTGGTGTAGGCATTTTTCGGACTAAGTGTAAATAAAGCTG

TATACTCTCTTGTACAATATCAGGATGCTGTCTACACATATACCTTGTCACAGGCGATTCT
2941     ------+---------+---------+---------+---------+---------+      3000
         ATATGAGAAGAACATGTTATAGTCCTACGACAGATGTATATGGAACAGTGTCCGCTAAGA

ATCATTCGGATTTTCCGATAAATTNMMCAATTACATTTTCAGCATTGACATAAAAACTTA
3001     ------+---------+---------+---------+---------+---------+      3060
         TAGTAAGCCTAAAAGGCTATTTAANKKGTTAATGTAAAAGTCGTAACTGTATTTTGAAT

CAATTTGNAAAATTATTTATTAAATAAACTGTTACGATGTTTTACATGCCATCTTATT
3061     ------+---------+---------+---------+---------+---------+      3120
         GTTAAACNTTTTAATAAATAATTTATTTGACAATGCTACAAAAATGTAGCGGTAGAATAA

AAAAAGTAATTGTAGTCATCGACTNGGTTATATATGAAGAAATTTATCTTCCTAATGATA
3121     ------+---------+---------+---------+---------+---------+      3180
         TTTTTCATTAACATCAGTAGCTGANCCAATATATACTTCTTTAAATAGAAGGATTACTAT
```

Figure 12J

```
       ACACCATCGATTAATCWWCTGATGAAACTATATGTACTGCCGATAGTGATCAAGTGCCAAA
3181   ------+---------+---------+---------+---------+---------+      3240
       TGTGGTAGCTAATTAGWWGACTACTTTGATATACATGACGCTATCACTAGTTCACGGTTT

GATTTTGCAACAGGCAACTGGAGGGAAGCATTATGAATTSSTCAATCTCAAGAATACSS
3241   ------+---------+---------+---------+---------+---------+      3300
       CTAAAACGTTGTCCGTTGACCTCCCTTCGTAATACTTAAASSAGTTAGAGTTCTTATGSS

YSYRNNNNNTCTTTAGTAATCAGGCTAACTTTTTATTTTTATTAACAACAATAATTWT
3301   ------+---------+---------+---------+---------+---------+      3360
       RSRYNNNNNAGAAATCATTAGTCCGATTGAAAAAATAAAAAATAATTGTTGTTATTAAWA

TTGGCTGCTATCTGTGCTTACCGCAGCTTATATATCAATGGTTCRGAAACGGCAGCATAT
3361   ------+---------+---------+---------+---------+---------+      3420
       AACCGACGATAGACACGAATGGCGTCGAATATAGTTACCAAGYCTTTGCCGTCGTATA

AATAGAGGATTTATCCGTTCTATCCGAGATGAATATTGTACTAAGCAATCAACGGTTTGA
3421   ------+---------+---------+---------+---------+---------+      3480
       TTATCTCCTAAATAGGCAAGATAGGCTCTACTTATAACATGATTCGTTAGTTGCCAAACT

AGAAGCTGAACGTGACGCTAAAAAATTTAATGTATCAATGCTCATTAGCGACTGAGATTCA
3481   ------+---------+---------+---------+---------+---------+      3540
       TCTTCGACTTGCACTGCGACTGCGATTTTTAAATTACATAGTTACGAGTAATCGCTGACTCTAAGT
```

Figure 12K

```
      TCATAACGATATTTCCCTGAGGTGAGCCGGCATCTATCTGTCGGTCCTTCAAATTGCAC
3541  ------+---------+---------+---------+---------+---------+  3600
      AGTATTGCTATAAAAGGGACTCCACTCGGCCGTAGATAGACAGCCAGGAAGTTTAACGTG

MGCCGACGCTNAACGGAGAGAAGCACCGTCTCTTTCTGCAGTCCTCCTGATATCGATGAAA
3601  ------+---------+---------+---------+---------+---------+  3660
      KCGGCTGCGANTTGCCCTCTCTTCGTGGCAGAGAAGACGTCAGGAGACTATAGCTACTTT

Tn insertion P3P4
                                    ⇒

ATAGCTTTCGTCGCGATAGTTTTATTCTTAATCATAAAAATGAGATTCGTTATTATCTA
3661  ------+---------+---------+---------+---------+---------+  3720
      TATCGAAAGCAGCGCTATCAAAATAAGAATTAGTATTTTTACTCTAAAGCAATAATAGAT

CTGATAACCCTTCAGATTATTCAACTCTACAGCCCTTTAACGGCGAAAAAGCTTTCCTTTAT
3721  ------+---------+---------+---------+---------+---------+  3780
      GACTATTGGGAAGTCTAATAAGTTGAGATGTCGGAAATTGCCGCTTTTTCGAAAGGAAATA

ACCCAACCCATGCCGATCAGGCGAAGGGCGTATTTTTTGAGGTGACGGTTAAACT
3781  ------+---------+---------+---------+---------+---------+  3840
      TGGGTTGGGTACGGCCAAAATGACCTCACTTGGTCTTATGTATTGCCGTTCCTACCG

AACGCTTCCGTTGCCGGTTGCCGATCAGGCAAGGGCGTATTTTTTGAGGTGACGGTTAAACT
3841  ------+---------+---------+---------+---------+---------+  3900
      TTGCGAAGGCAACGCCAAGGCTAGTCCGTTCCGCATAAAAAACTCCACTGCCAATTTGA
```

Figure 12L

```
3901  TCCCGATCTCATTACTAAGAGCCACCTGCCATTAGATGATAGTATTCGAGTATGGCTGGA  3960
      ----------+---------+---------+---------+---------+---------+
      AGGGCTAGAGTAATGATTCTCGGTGGACGGTAATCTACTATCATAAGCTCATACCGACCT

3960  TCAAAACAACCACTTATTGCCGTTTCATACATCCCGGCAAAAATACGTACACAGTTAG    4020
      ----------+---------+---------+---------+---------+---------+
      AGTTTTGTTGGTGAATAACGGCAAAAGTATGTAGGGCCGTTTTTATGCATGTGTCAATC

4021  AAAATGTAACGCTGCATGATGGCAGCAAATTCCCGATTTCTGATATTACGCACAA       4080
      ----------+---------+---------+---------+---------+---------+
      TTTTACATTGCGACGTACTACCGTCGTTTAAGGCCTAAAGACTATAATGCGTGTT

4081  CCTTGCATGGCCCCGGATGGAGTCTGTTACGCTGTACCCATACGGTAATCTACATAATC   4140
      ----------+---------+---------+---------+---------+---------+
      GGAACGTACCGGGCCTACCTCAGACCAATGCGACATGGGTATGCCATTAGATGTATTA

4141  GCATCTTAAAAATTATCCTTCAACAAATCCCCTTTACATTAACAGCATTGGTGTTGATGA  4200
      ----------+---------+---------+---------+---------+---------+
      CGTAGAATTTTTAATAGGAAGTTGTTTAGGGAAATGTAATTGTCGTAACCACAACTACT

4201  CGTCGGGCTTTTGCTGGTTACTACATGCTCACTGGCCAAACCGTTATGGCGTTTGTCG    4260
      ----------+---------+---------+---------+---------+---------+
      GCAGCCCGAAAAACGACCAATGATGTAGCGAGTGACCGGTTTGGCAATACCGCAAAACAGC
```

Figure 12M

```
         ATGTCATTAATAAAACCGCAACTGCACCGCTGAGCACACGTTTACCAGCACAACGACTGG
4261     ------+---------+---------+---------+---------+---------+   4320
         TACAGTAATTATTTTGGCGTTGACGTGGCGACTCGTGTGCAAATGGTCGTGTTGCTGACC

ATGAATTAGATAGTATTGCCGGTGCTTTTAACCAACTGCTTGATACTCTACAAGTCCAAT
4321     ------+---------+---------+---------+---------+---------+   4380
         TACTTAATCTATCATAACGGCCACGAAAATTGGTTGACGAACTATGAGATGTTCAGGTTA

ACGACAATCTGGAAAACAAAGTCGCAGACGCACCCAGGCGCTAAATGAAGCAAAAAACG
4381     ------+---------+---------+---------+---------+---------+   4440
         TGCTGTTAGACCTTTTGTTTCAGCCGTCTCGCGTGGGTCCGCGATTACTTCGTTTTTTGC

CGCTGAGCNAGCTAACAAACGTAAAAGCATTCATCTTACGGTAATAAGTCATGAGTTACG
4441     ------+---------+---------+---------+---------+---------+   4500
         GCGACTCGNTCGATTGTTTGCATTTTCGTAAGTAGAATGCCATTATTCAGTACTCAATGC

TACTCCGATGAATGGCGTACTCGGTGCAATTGAATTATTACAAACCACCCCTTTAAACAT
4501     ------+---------+---------+---------+---------+---------+   4560
         ATGAGGCTACTTACCGCATGAGCCACGTTAACTTAATAATGTTTGGTGGGAAATTTGTA

AGAGCAACAAGGATTAGCTGATACCGCCAGAAATTGTACACTGTCTTTGTTAGCTATTAT
4561     ------+---------+---------+---------+---------+---------+   4620
         TCTCGTTGTTCCTAATCGACTATGGCGGTCTTTAACATGTGACAGAAACAATCGATAATA
```

Figure 12N

```
       TAATAATCTGCTGGATTTTCACGCATCGAGTCTGGTCATTTCACATTACATATGGAAGA
4621   ------+---------+---------+---------+---------+---------+   4680
       ATTATTAGACGACCTAAAAAGTGCGTAGCTCAGACCAGTAAAGTGTAATGTATACCTTCT

AACAGGCGTTACTGCCGTTACTGGACCAGGCAATGCAAACCATCCAGGGGCCAGCGCNAAA
4681   ------+---------+---------+---------+---------+---------+   4740
       TTGTCGCAATGACGGCAATGACCTGGTCCGTTACGTTTGGTAGGTCCCCGGTCGCGNTTT

GCAAAAAACTGTCATTACGTACTTTTGTCGGTCAACATGTCCCTCTCTATTTCATACCG
4741   ------+---------+---------+---------+---------+---------+   4800
       CGTTTTTGACAGTAATGCATGAAAACAGCCAGTGTACAGGAGAGATAAAAGTATGGC

ACAGTATCCGTTTACNNCAAATTTGGTTAATTTACTCGGGAACGCGGTAAAATTTACCG
4801   ------+---------+---------+---------+---------+---------+   4860
       TGTCATAGGCAAATGNNGTTTAAAACCAATTAAATGAGCCCTTGCGCCATTTTAAATGGC

AAACCGGAGGATACGTCTGACGGTCAAGCGTCATGAGGAACAATTAATATTCTGGTTAG
4861   ------+---------+---------+---------+---------+---------+   4920
       TTTGGCCTCCTATGCAGACTGCCAGTTCGCAGTACTCCTTGTTAATTATAAAGACCAATC

CGATAGCGGTAAAGGGATTGAAATACAGCAGTCTCAAATCTTTACTGCTTTTATCA
4921   ------+---------+---------+---------+---------+---------+   4980
       GCTATCGCCATTTCCCTAACTTTATGTCGTCGTCAGAGTTTAGAAATGACGAAAATAGT
```

Figure 120

```
      AGCAGACACAAATTCGCAAGGTACAGGAATTGGACTGACTATTGCGTCAAGCCTGGCTAA
4981  ------+---------+---------+---------+---------+---------+   5040
      TCGTCTGTGTTTAAGCGTTCCATGTCCTTAACCTGACTGATAACGCAGTTCGGACCGATT

AATGATGGGCGGTAATCTGACACTAAAAAAGTGTCCCCGGGTTGGAACCTGTGTCTCGCT
5041  ------+---------+---------+---------+---------+---------+   5100
      TTACTACCCGCCATTAGACTGTGATTTTTCACAGGGGCCCCAACCCTTGGACACAGAGCGA

Tn insertion
                                            ⇒
      AGTATTACCCTTACAAGAATACCAGCCGCCTCAACCAATTAAAGGGACGCTGTCAGNNNC
5101  ------+---------+---------+---------+---------+---------+   5160
      TCATAATGGGAATGTTCTTATGGTCGGCGGAGTTGGTTAATTTCCCTGCGACAGTCNNNG CGTTCTGCCTGCATCGGCAACTGGCTTGCTGCTGGGGAATACGCGGTGAACCACCCCAGC
5161  ------+---------+---------+---------+---------+---------+   5220
      GCAAGACGGACGTAGCCGTTGACCGAACGACCCCTTATGCGCCACTTGGTGGGGTGGTCG AAAAATGCGCTTCTCAANNCNAGAGCTTTTGTATTTCTCCGGAAAACTCTACGACCTGGCG
5221  ------+---------+---------+---------+---------+---------+   5280
      TTTTACGCGAAGAGTTNNGNTCTCGAAAACATAAAGAGGCCTTTTGAGATGCTGGACCGC CAACAGTTAATATTGTGTACACCAAATATGCCAGTAATAAATAATTGTTACCACCCTGG
5281  ------+---------+---------+---------+---------+---------+   5340
      GTTGTCAATTATAACACATGGTTTATACGGTCATTATTATTTAAACAATGGTGGGACC
```

Figure 12P

```
5341  CAGTTGCAGATTCTTTTGGTTGATGATGCCGATATTAATCGGGATATCATCGGCAAAATG
      ----+----+----+----+----+----+----+----+----+----+----+----+ 5400
      GTCAACGTCTAAGAAAACCAACTACTACGGCTATAATTAGCCCTATAGTAGCCGTTTTAC

5401  CTTGTCAGCCTGGGCCAACACGTCACTATTGCCGCCAGTAGTAACGAGGCTCTGACTTTA
      ----+----+----+----+----+----+----+----+----+----+----+----+ 5460
      GAACAGTCGGACCCGGTTGTGCAGTGATAACGGCGGTCATCATTGCTCCGAGACTGAAAT

5461  TCACAACAGCAGCGATTCGATTAGTACTGATTGACATTAGAATGCCAGAAATAGATGGT
      ----+----+----+----+----+----+----+----+----+----+----+----+ 5520
      AGTGTTGTCGTCGCTAAGCTAAATCATGACTAACTGTAATCTTACGGTCTTTATCTACCA

5521  ATTGAATGTGTACGATTATGGCATGATGAGCCGAATAATTTAGATCCTGACTGCATGTTT
      ----+----+----+----+----+----+----+----+----+----+----+----+ 5580
      TAACTTACACATGCTAATACCGTACTACTCGGCTTATTAAATCTAGGACTGACGTACAAA

5581  GTGGCACTATCCGCTAGCGTASCVNMAGAWRWTMWTCRTYGTDDAAAAAAWRDGRKDHWT
      ----+----+----+----+----+----+----+----+----+----+----+----+ 5640
      CACCGTGATAGGCGATCGCATSGBNKTCTWYAKWAGYARCAHHTTTTTWYHCYMHDWA

5641  CATHAYANNTTACAAAACCAGTGACATTGGCTACCTTAGCTCGCTACATCAGTATTGCCG
      ----+----+----+----+----+----+----+----+----+----+----+----+ 5700
      GTADTRTNNAATGTTTTGGTCACTGTAACCGATGGAATCGAGCGATGTAGTCATAACGGC

5701  CAGAATACCAACTTTTACGAAATATAGAGCTACAGGAGCAGGATCC
      ----+----+----+----+----+----+----+----+---- 5746
      GTCTTATGGTTGAAAATGCTTTATATCTCGATGTCCTCGTCCTAGG
```

IDENTIFICATION OF GENES

This application is a 371 of PCT/GB95/02875 filed Dec. 11, 1995.

The present invention relates to methods for the identification of genes involved in the adaptation of a microorganism to its environment, particularly the identification of genes responsible for the virulence of a pathogenic microorganism.

BACKGROUND TO THE INVENTION

Antibiotic resistance in bacterial and other pathogens is becoming increasingly important. It is therefore important to find new therapeutic approaches to attack pathogenic microorganisms.

Pathogenic microorganisms have to evade the host's defence mechanisms and be able to grow in a poor nutritional environment to establish an infection. To do so a number of "virulence" genes of the microorganism are required.

Virulence genes have been detected using classical genetics and a variety of approaches have been used to exploit transposon mutagenesis for the identification of bacterial virulence genes. For example, mutants have been screened for defined physiological defects, such as the loss of iron regulated proteins (Holland et al, 1992), or in assays to study the penetration of epithelial cells (Finlay et al, 1988) and survival within macrophages (Fields et al, 1989; Miller et al, 1989a; Groisman et al, 1989). Transposon mutants have also been tested for altered virulence in live animal models of infection (Miller et al, 1989b). This approach has the advantage that genes can be identified which are important during different stages of infection, but is severely limited by the need to test a wide range of mutants individually for alterations to virulence. Miller et al (1989b) used groups of 8 to 10 mice and infected orally 95 separate groups with a different mutant thereby using between 760 and 950 mice. Because of the extremely large numbers of animals required, comprehensive screening of a bacterial genome for virulence genes has not been feasible.

Recently a genetic system (in vivo expression technology [IVET]) was described which positively selects for Salmonella genes that are specifically induced during infection (Mahan et al, 1993). The technique will identify genes that are expressed at a particular stage in the infection process. However, it will not identify virulence genes that are regulated posttranscriptionally, and more importantly, will not provide information on whether the gene(s) which have been identified are actually required for, or contribute to, the infection process.

Lee & Falkow (1994) *Methods Enzymol.* 236, 531–545 describe a method of identifying factors influencing the invasion of Salmonella into mammalian cells in vitro by isolating hyperinvasive mutants.

Walsh and Cepko (1992) *Science* 255, 434–440 describe a method of tracking the spatial location of cerebral cortical progenitor cells during the development of the cerebral cortex in the rat. The Walsh and Cepko method uses a tag that contains a unique nucleic acid sequence and the lacZ gene but there is no indication that useful mutants or genes could be detected by their method.

WO 94/26933 and Smith et al (1995) *Proc. Natl. Acad. Sci. USA* 92, 6479–6483 describe methods aimed at the identification of the functional regions of a known gene, or at least of a DNA molecule for which some sequence information is available.

Groisman et al (1993) *Proc. Natl. Acad. Sci. USA* 90, 1033–1037 describes the molecular, functional and evolutionary analysis of sequences specific to Salmonella.

Some virulence genes are already known for pathogenic microorganisms such as *Escherichia coli, Salmonella typhimurium, Salmonella typhi, Vibrio cholerae, Clostridium botulinum, Yersinia pestis, Shigella flexneri* and *Listeria monocytogenes* but in all cases only a relatively small number of the total have been identified.

The disease which *Salmonella typhimurium* causes in mice provides a good experimental model of typhoid fever (Carter & Collins, 1974). Approximately forty two genes affecting Salmonella virulence have been identified to date (Groisman & Ochman, 1994). These represent approximately one third of the total number of predicted virulence genes (Groisman and Saier, 1990).

The object of the present invention is to identify genes involved in the adaptation of a microorganism to its environment, particularly to identify further virulence genes in pathogenic microorganisms, with increased efficiency. A further object is to reduce the number of experimental animals used in identifying virulence genes. Still further objects of the invention provide vaccines, and methods for screening for drugs which reduce virulence.

SUMMARY OF THE INVENTION

A first aspect of the invention provides a method for identifying a microorganism having a reduced adaptation to a particular environment comprising the steps of:

(1) providing a plurality of microorganisms each of which is independently mutated by the insertional inactivation of a gene with a nucleic acid comprising a unique marker sequence so that each mutant contains a different marker sequence, or clones of the said microorganism;

(2) providing individually a stored sample of each mutant produced by step (1) and providing individually stored nucleic acid comprising the unique marker sequence from each individual mutant;

(3) introducing a plurality of mutants produced by step (1) into the said particular environment and allowing those microorganisms which are able to do so to grow in the said environment;

(4) retrieving microorganisms from the said environment or a selected part thereof and isolating the nucleic acid from the retrieved microorganisms;

(5) comparing any marker sequences in the nucleic acid isolated in step (4) to the unique marker sequence of each individual mutant stored as in step (2); and (6) selecting an individual mutant which does not contain any of the marker sequences as isolated in step (4).

Thus, the method uses negative selection to identify microorganisms with reduced capacity to proliferate in the environment.

A microorganism can live in a number of different environments and it is known that particular genes and their products allow the microorganism to adapt to a particular environment. For example, in order for a pathogenic microorganism, such as a pathogenic bacterium or pathogenic fungus, to survive in its host the product of one or more virulence genes is required. Thus, in a preferred embodiment of the invention a gene of a microorganism which allows the microorganism to adapt to a particular environment is a virulence gene.

Conveniently, the particular environment is a differentiated multicellular organism such as a plant or animal. Many bacteria and fungi are known to infect plants and they are able to survive within the plant and cause disease because of the presence of and expression from virulence genes. Suitable microorganisms when the particular environment is a plant include the bacteria *Agrobacterium tumefaciens* which forms tumours (galls) particularly in grape; *Erwinia amylovara; Pseudomonas solanacearuim* which causes wilt in a wide range of plants; *Rhizobium leguminosarum* which causes disease in beans; *Xanthomonas campestris* p.v. citri which causes canker in citrus fruits; and include the fungi *Magnaporthe grisea* which causes rice blast disease; *Fusarium spp.* which cause a variety of plant diseases; *Erisyphe spp.; Colletotrichum gloeosporiodes; Gaeumannomyces graminis* which causes root and crown diseases in cereals and grasses; *Glomus spp., Laccaria spp.; Leptosphaeria maculans; Phoma tracheiphila; Phytophthora spp., Pyrenophora teres; Verticillium alboatrum* and *V. dahliae*; and *Mycosphaerella musicola* and *M. fijiensis*. As described in more detail below, when the microorganism is a fungus a haploid phase to its life cycle is required.

Similarly, many microorganisms including bacteria, fungi, protozoa and trypanosomes are known to infect animals, particularly mammals including humans. Survival of the microorganism within the animal and the ability of the microorganism to cause disease is due in large part to the presence of and expression from virulence genes. Suitable bacteria include *Bordetella spp.* particularly *B. pertussis, Campylobacter spp.* particularly *C. jejuni, Clostridium spp.* particularly *C. botulinum, Enterococcus spp.* particularly *E. faecalis, Escherichia spp.* particularly *E. coli, Haemophilus spp.* particularly *H. ducreyi* and *H. influenzae, Helicobacter spp.* particularly *H. pylori, Klebsiella spp.* particularly *K. pneumoniae, Legionella spp.* particularly *L pneumophila, Listeria spp.* particularly *L. monocytogenes, Mycobacterium spp.* particularly *M. smegmatis* and *M. tuberculosis, Neisseria spp.* particularly *N. gonorrhoeae* and *N. meningitidis, Pseudomonas spp.*, particularly *Ps. aeruginosa, Salmonella spp., Shigella spp., Staphylococcus spp.* particularly *S. aureus, Streptococcus spp.* particularly *S. pyogenes* and *pneumoniae, Vibrio spp.* and *Yersinia spp.* particularly *Y. pestis*. All of these bacteria cause disease in man and also there are animal models of the disease. Thus, when these bacteria are used in the method of the invention, the particular environment is an animal which they can infect and in which they cause disease. For example, when *Salmonella typhimurium* is used to infect a mouse the mouse develops a disease which serves as a model for typhoid fever in man. *Staphylococcus aureus* causes bacteraemia and renal abscess formation in mice (Albus et al (1991) *Infect. Immun.* 59, 1008–1014) and endocarditis in rabbits (Perlman & Freedman (1971) *Yale J. Biol. Med.* 44, 206–213).

It is required that a fungus or higher eukaryotic parasite is haploid for the relevant parts of its life (such as growth in the environment). Preferably, a DNA-mediated integrative transformation system is available and, when the microorganism is a human pathogen, conveniently an animal model of the human disease is available. Suitable fungi pathogenic to humans include certain *Aspergillus spp.* (for example *A. fumigatus*), *Cryptococcus neoformans* and *Histoplasma capsulatum*. Clearly the above-mentioned fungi have a haploid phase and a DNA-mediated integrative transformation systems are available for them. Toxoplasma may also be used, being a parasite with a haploid phase during infection. Bacteria have a haploid genome.

Animal models of human disease are often available in which the animal is a mouse, rat, rabbit, dog or monkey. It is preferred if the animal is a mouse. Virulence genes detected by the method of the invention using an animal model of a human disease are clearly very likely to be genes which determine the virulence of the microorganism in man.

Particularly preferred microorganisms for use in the methods of the invention are *Salmonella typhimurium, Staphylococcus aureus, Streptococcus pneumoniae, Enterococcus faecalis, Pseudomonas aeruginosa* and *Aspergillus fumigatus*.

A preferred embodiment of the invention is now described.

A nucleic acid comprising a unique marker sequence is made as follows. A complex pool of double stranded DNA sequence "tags" is generated using oligonucleotide synthesis and a polymerase chain reaction (PCR). Each DNA "tag" has a unique sequence of between about 20 and 80 bp, preferably about 40 bp which is flanked by "arms" of about 15 to 30 bp, preferably about 20 bp, which are common to all "tags". The number of bp in the unique sequence is sufficient to allow large numbers (for example $>10^{10}$) of unique sequences to be generated by random oligonucleotide synthesis but not too large to allow the formation of secondary structures which may interfere with a PCR. Similarly, the length of the arms should be sufficient to allow efficient priming of oligonucleotides in a PCR.

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artifactual product called "primer dimer". When the 3' ends of the two primers hybridize, they form a "primed template" complex, and primer extension results in a short duplex product called "primer dimer".

Internal secondary structure should be avoided in primers. For symmetric PCR, a 40–60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37°–55° C. region, so primer extension will occur during the annealing step and the hybrid will be stabilized. The concentrations of the primers are equal in conventional (symmetric) PCR and, typically, within 0.1- to 1-$\mu$M range.

The "tags" are ligated into a transposon or transposon-like element to form the nucleic acid comprising a unique marker sequence. Conveniently, the transposon is carried on a suicide vector which is maintained as a plasmid in a "helper" organism, but which is lost after transfer to the microorganism of the method of the invention. For example, the "helper" organism may be a strain of *Eschelichia coli*, the microorganism of the method may be Salmonella and the transfer is a conjugal transfer. Although the transposon can be lost after transfer, in a proportion of cells it undergoes a transposition event through which it integrates at random, along with its unique tag, into the genome of the microorganism used in the method. It is most preferred if the transposon or transposon-like element can be selected. For example, in the case of Salmonella, a kanamycin resistance gene may be present in the transposon and exconjugants are selected on medium containing kanamycin. It is also possible to complement an auxotrophic marker in the recipient cell with a functional gene in the nucleic acid comprising the unique marker. This method is particularly convenient when fungi are used in the method.

Preferably the complementing functional gene is not derived from the same species as the recipient microorganism, otherwise non-random integration events may occur.

It is also particularly convenient if the transposon or transposon-like element is carried on a vector which is maintained episomally (ie not as part of the chromosome) in the microorganism used in the method of the first aspect of the invention when in a first given condition whereas, upon changing that condition to a second given condition, the episome cannot be maintained permitting the selection of a cell in which the transposon or transposon-like element has undergone a transposition event through which it integrates at random, along with its unique tag, into the genome of the microorganism used in the method. This particularly convenient embodiment is advantageous because, once a microorganism carrying the episomal vector is made, then each time the transposition event is selected for or induced by changing the condition of the microorganism (or a clone thereof) from a first given condition to a second given condition, the transposon can integrate at a different site in the genome of the microorganism. Thus, once a master collection of microorganisms are made, each member of which contains a unique tag sequence in the transposon or transposon-like element carried on the episomal vector (when in the first given condition), it can be used repeatedly to generate pools of random insertional mutants, each of which contains a different tag sequence (ie unique within the pool). This embodiment is particularly useful because (a) it reduces the number and complexity of manipulations required to generate the plurality ("pool") of independently mutated microorganisms in step (1) of the method; and (b) the number of different tags need only be the same as the number of microorganisms in the plurality of microorganisms in step (1) of the method. Point (a) makes the method easier to use in organisms for which transposon mutagenesis is more difficult to perform (for example, *Staphylococcus aureus*) and point (b) means that tag sequences with particularly good hybridisation characteristics can be selected therefore making quality control easier. As is described in more detail below, the "pool" size is conveniently about 100 or 200 independently-mutated microorganisms and, therefore the master collection of microorganisms is conveniently stored in one or two 96-well microtitre plates.

In a particularly preferred embodiment the first given condition is a first particular temperature or temperature range such as 25° C. to 32° C., most preferably about 30° C. and the second given condition is a second particular temperature or temperature range such as 35° C. to 45° C., most preferably 42° C. In further preferred embodiments the first given condition is the presence of an antibiotic, such as streptomycin, and the second given condition is the absence of the said antibiotic; or the first given condition is the absence of an antibiotic and the second given condition is the presence of the said antibiotic.

Transposons suitable for integration into the genome of Gram negative bacteria include Tn5, Tn10 and derivatives thereof. Transposons suitable for integration into the genome of Gram positive bacteria include Tn916 and derivatives or analogues thereof. Transposons particularly suited for use with *Staphylococcus aureus* include Tn917 (Cheung et al (1992) *Proc. Natl. Acad. Sci. USA* 89, 6462–6466) and Tn918 (Albus et al (1991) *Infect. Immun.* 59, 1008–1014).

It is particularly preferred if the transposons have the properties of the Tn917 derivatives described by Camilli et al (1990) *J. Bacteriol* 172, 3738–3744, and are carried by a temperature-sensitive vector such as pE194Ts (Villafane et al (1987) *J. Bacteriol*. 169, 4822–4829).

It will be appreciated that although transposons are convenient for insertionally inactivating a gene, any other known method, or method developed in the future may be used. A further convenient method of insertionally inactivating a gene, particularly in certain bacteria such as Streptococcus, is using insertion-duplication mutagenesis such as that described in Morrison et al (1984) *J.Bacteriol* 159, 870 with respect to *S.pneumoniae*. The general method may also be applied to other microorganisms, especially bacteria.

For fungi, insertional mutations are created by transformation using DNA fragments or plasmids carrying the "tags" and, preferably, selectable markers encoding, for example, resistance to hygromycin B or phleomycin (see Smith et al (1994) *Infect. Immunol.* 62, 5247–5254). Random, single integration of DNA fragments encoding hygromycin B resistance into the genome of filamentous fungi, using restriction enzyme mediated integration (REMI; Schiestl & Petes (1991); Lu et al (1994) *Proc. Natl. Acad. Sci. USA* 91, 12649–12653) are known.

A simple insertional mutagenesis technique for a fungus is described in Schiestl & Petes (1994) incorporated herein by reference, and include, for example, the use of Ty elements and ribosomal DNA in yeast. Random integration of the transposon or other DNA sequence allows isolation of a plurality of independently mutated microorganisms wherein a different gene is insertionally inactivated in each mutant and each mutant contains a different marker sequence.

A library of such insertion mutants is arrayed in welled microtitre dishes so that each well contains a different mutant microorganism. DNA comprising the unique marker sequence from each individual mutant microorganism (conveniently, the total DNA from the clone is used) is stored. Conveniently, this is done by removing a sample of the microorganism from the microtitre dish, spotting it onto a nucleic acid hybridisation membrane (such as nitrocellulose or nylon membranes), lysing the microorganism in alkali and fixing the nucleic acid to the membrane. Thus, a replica of the contents of the welled microtitre dishes is made.

Pools of the microorganisms from the welled microtitre dish are made and DNA is extracted. This DNA is used as a target for a PCR using primers that anneal to the common "arms" flanking the "tags" and the amplified DNA is labelled, for example with $^{32}$P. The product of the PCR is used to probe the DNA stored from each individual mutant to provide a reference hybridisation pattern for the replicas of the welled microtitre dishes. This is a check that each of the individual microorganisms does, in fact, contain a marker sequence and that the marker sequence can be amplified and labelled efficiently.

Pools of transposon mutants are made to introduce into the particular environment. Conveniently, 96-well microtitre dishes are used and the pool contains 96 transposon mutants. However, the lower limit for the pool is two mutants; there is no theoretical upper limit to the size of the pool but, as discussed below, the upper limit may be determined in relation to the environment into which the mutants are introduced.

Once the microorganisms are introduced into the said particular environment those microorganisms which are able to do so are allowed to grow in the environment. The length of time the microorganisms are left in the environment is determined by the nature of the microorganism and the environment. After a suitable length of time, the microorganisms are recovered from the environment, DNA is extracted and the DNA is used as a template for a PCR using primers that anneal to the "arms" flanking the "tags". The PCR product is labelled, for example with $^{32}$P, and is used to probe the DNA stored from each individual mutant replicated from the welled microtitre dish. Stored DNA are identified which hybridise weakly or not at all with the probe generated from the DNA isolated from the microorganisms recovered from environment. These non-hybridising DNAs correspond to mutants whose adaptation to the particular environment has been attenuated by insertion of the transposon or other DNA sequence.

In a particularly preferred embodiment the "arms" have no, or very little, label compared to the "tags". For example, the PCR primers are suitably designed to contain no, or a single, G residue, the $^{32}$P-labelled nucleotide is dCTP and, in this case, no or one radiolabelled C residue is incorporated in each "arm" but a greater number of radiolabelled C residues are incorporated in the "tag". It is preferred if the "tag" has at least ten-fold more label incorporated than the "arms"; preferably twenty-fold or more; more preferably fifty-fold or more. Conveniently the "arms" can be removed from the "tag" using a suitable restriction enzyme, a site for which may be incorporated in the primer design.

As discussed above, a particularly preferred embodiment of the invention is when the microorganism is a pathogenic microorganism and the particular environment is an animal. In this embodiment, the size of the pool of mutants introduced into the animal is determined by (a) the number of cells of each mutant that are likely to survive in the animal (assuming a virulence gene has not been inactivated) and (b) the total inoculum of the microorganism. If the number in (a) is too low then false positive results may arise and if the number in (b) is too high then the animal may die before enough mutants have had a chance to grow in the desired way. The number of cells in (a) can be determined for each microorganism used but it is preferably more than 50, more preferably more than 100.

The number of different mutants that can be introduced into a single animal is preferably between 50 and 500, conveniently about 100. It is preferred if the total inoculum does not exceed $10^6$ cells (and it is preferably $10^5$ cells) although the size of the inoculum may be varied above or below this amount depending on the microorganism and the animal.

In a particularly convenient method an inoculum of $10^5$ is used containing 1000 cells each of 100 different mutants for a single animal. It will be appreciated that in this method one animal can be used to screen 100 mutants compared to prior art methods which require at least 100 animals to screen 100 mutants.

However, it is convenient to inoculate three animals with the same pool of mutants so that at least two can be investigated (one as a replica to check the reliability of the method), whilst the third is kept as a back-up. Nevertheless, the method still provides a greater than 30-fold saving in the number of animals used.

The time between the pool of mutants being introduced into the animal and the microorganisms being recovered may vary with the microorganism and animal used. For example, when the animal is a mouse and the microorganism is *Salmonella typhimurium*, the time between inoculation and recovery is about three days.

In one embodiment of the invention microorganisms are retrieved from the environment in step (5) at a site remote from the site of introduction in step (4), so that the virulence genes being investigated include those involved in the spread of the microorganism between the two sites.

For example, in a plant the microorganism may be introduced in a lesion in the stem or at one site on a leaf and the microorganism retrieved from another site on the leaf where a disease state is indicated.

In the case of an animal, the microorganism may be introduced orally, intraperitoneally, intravenously or intranasally and is retrieved at a later time from an internal organ such as the spleen. It may be useful to compare the virulence genes identified by oral administration and those identified by intraperitoneal administration as some genes may be required to establish infection by one route but not by the other. It is preferred if Salmonella is introduced intraperitoneally.

Other preferred environments which may be used to identify virulence genes are animal cells in culture (particularly macrophages and epithelial cells) and plant cells in culture. Although using cells in culture will be useful in its own right, it will also complement the use of the whole animal or plant, as the case may be, as the environment.

It is also preferred if the environment is a part of the animal body. Within a given host-parasite interaction, a number of different environments are possible, including different organs and tissues, and parts thereof such as the Peyer's patch.

The number of individual microorganisms (ie cells) recovered from the environment should be at least twice, preferably at least ten times, more preferably 100-times the number of different mutants introduced into the environment. For example, when an animal is inoculated with 100 different mutants around 10,000 individual microorganisms should be retrieved and their marker DNA isolated.

A further preferred embodiment comprises the steps:
(1A) removing auxotrophs from the plurality of mutants produced in step (1); or (6A) determining whether the mutant selected in step (6) is an auxotroph; or both (1A) and (6A).

It is desirable to distinguish an auxotroph (that is a mutant microorganism which requires growth factors not needed by the wild type or by prototrophs) and a mutant microorganism wherein a gene allowing the microorganism to adapt to a particular environment is inactivated. Conveniently, this is done between steps (1) and (2) or after step (6).

Preferably auxotrophs are not removed when virulence genes are being identified.

A second aspect of the invention provides a method of identifying a gene which allows a microorganism to adapt to a particular environment, the method comprising the method of the first aspect of the invention, followed by the additional step:
(7) isolating the insertionally-inactivated gene or part thereof from the individual mutant selected in step (6).

Methods for isolating a gene containing a unique marker are well known in the art of molecular biology.

A further preferred embodiment comprises the further additional step:
(8) isolating from a wild-type microorganism the corresponding wild-type gene using the insertionally-inactivated gene isolated in step (7) or part thereof as a probe.

Methods for gene probing are well known in the art of molecular biology.

Molecular biological methods suitable for use in the practice of the present invention are disclosed in Sambrook et al (1989) incorporated herein by reference.

When the microorganism is a microorganism pathogenic to an animal and the gene is a virulence gene and a transposon has been used to insertionally inactivate the gene, it is convenient for the virulence genes to be cloned by digesting genomic DNA from the individual mutant selected in step (6) with a restriction enzyme which cuts outside the transposon, ligating size-fractionated DNA containing the transposon into a plasmid, and selecting plasmid recombinants on the basis of antibiotic resistance conferred by the transposon and not by the plasmid. The microorganism genomic DNA adjacent to the transposon is sequenced using two primers which anneal to the terminal regions of the transposon, and two primers which anneal close to the polylinker sequences of the plasmid. The sequences may be subjected to DNA database searches to determine if the transposon has interrupted a known virulence gene. Thus, conveniently, sequence obtained by this method is compared against the sequences present in the publicly available databases such as EMBL and GenBank. Finally, if the interrupted sequence appears to be in a new virulence gene, the mutation is transferred to a new genetic background (for example by phage P22-mediated transduction in the case of Salmonella) and the $LD_{50}$, of the mutant strain is determined to confirm that the avirulent phenotype is due to the transposition event and not a secondary mutation.

The number of individual mutants screened in order to detect all of the virulence genes in a microorganism depends on the number of genes in the genome of the microorganism. For example, it is likely that 3000–5000 mutants of *Salmonella typhimurium* need to be screened in order to detect the majority of virulence genes whereas for *Aspergillus spp.*, which has a larger genome than Salmonella, around 20 000 mutants are screened. Approximately 4% of non-essential *S. typhimurium* genes are thought to be required for virulence (Grossman & Saier, 1990) and, if so, the *S. typhimurium* genome contains approximately 150 virulence genes. However, the methods of the invention provide a faster, more convenient and much more practicable route to identifying virulence genes.

A third aspect of the invention provides a microorganism obtained using the method of the first aspect of the invention.

Such microorganisms are useful because they have the property of not being adapted to survive in a particular environment.

In a preferred embodiment, a pathogenic microorganism is not adapted to survive in a host organism (environment) and, in the case of microorganisms that are pathogenic to animals, particularly mammals, more particularly humans, the mutant obtained by the method of the invention may be used in a vaccine. The mutant is avirulent, and therefore expected to be suitable for administration to a patient, but it is expected to be antigenic and give rise to a protective immune response.

In a further preferred embodiment the pathogenic microorganism not adapted to survive in a host organism, obtained by the methods of the invention, is modified, preferably by the introduction of a suitable DNA sequence, to express an antigenic epitope from another pathogen. This modified microorganism can act as a vaccine for that other pathogen.

A fourth aspect of the invention provides a microorganism comprising a mutation in a gene identified using the method of the second aspect of the invention.

Thus, although the microorganism of the third aspect of the invention is useful, it is preferred if a mutation is specifically introduced into the identified gene. In a preferred embodiment, particularly when the microorganism is to be used in a vaccine, the mutation in the gene is a deletion or a frameshift mutation or any other mutation which is substantially incapable of reverting. Such gene-specific mutations can be made using standard procedures such as introducing into the microorganism a copy of the mutant gene on an autonomous replicon (such as a plasmid or viral genome) and relying on homologous recombination to introduce the mutation into the copy of the gene in the genome of the microorganism.

Fifth and sixth aspects of the invention provide a suitable microorganism for use in a vaccine and a vaccine comprising a suitable microorganism and a pharmaceutically-acceptable carrier.

The suitable microorganism is the aforementioned avirulent mutant.

Active immunisation of the patient is preferred. In this approach, one or more mutant microorganisms are prepared in an immunogenic formulation containing suitable adjuvants and carriers and administered to the patient in known ways. Suitable adjuvants include Freund's complete or incomplete adjuvant, muramyl dipeptide, the "Iscoms" of EP 109 942, EP 180 564 and EP 231 039, aluminium hydroxide, saponin, DEAE-dextran, neutral oils (such as miglyol), vegetable oils (such as arachis oil), liposomes, Pluronic polyols or the Ribi adjuvant system (see, for example GB-A-2 189 141). "Pluronic" is a Registered Trade Mark. The patient to be immunised is a patient requiring to be protected from the disease caused by the virulent form of the microorganism.

The aforementioned avirulent microorganisms of the invention or a formulation thereof may be administered by any conventional method including oral and parenteral (eg subcutaneous or intramuscular) injection. The treatment may consist of a single dose or a plurality of doses over a period of time.

Whilst it is possible for an avirulent microorganism of the invention to be administered alone, it is preferable to present it as a pharmaceutical formulation, together with one or more acceptable carriers. The carrier(s) must be "acceptable" in the sense of being compatible with the avirulent microorganism of the invention and not deleterious to the recipients thereof. Typically, the carriers will be water or saline which will be sterile and pyrogen free.

It will be appreciated that the vaccine of the invention, depending on its microorganism component, may be useful in the fields of human medicine and veterinary medicine.

Diseases caused by microorganisms are known in many animals, such as domestic animals. The vaccines of the invention, when containing an appropriate avirulent microorganism, particularly avirulent bacterium, are useful in man but also in, for example, cows, sheep, pigs, horses, dogs and cats, and in poultry such as chickens, turkeys, ducks and geese.

Seventh and eighth aspects of the invention provide a gene obtained by the method of the second aspect of the invention, and a polypeptide encoded thereby.

By "gene" we include not only the regions of DNA that code for a polypeptide but also regulatory regions of DNA such as regions of DNA that regulate transcription, translation and, for some microorganisms, splicing of RNA. Thus, the gene includes promoters, transcription terminators, ribosome-binding sequences and for some organisms introns and splice recognition sites.

Typically, sequence information of the inactivated gene obtained in step 7 is derived. Conveniently, sequences close to the ends of the transposon are used as the hybridisation site of a sequencing primer. The derived sequence or a DNA restriction fragment adjacent to the inactivated gene itself is used to make a hybridisation probe with which to identify, and isolate from a wild-type organism, the corresponding wild type gene.

It is preferred if the hybridisation probing is done under stringent conditions to ensure that the gene, and not a relative, is obtained. By "stringent" we mean that the gene hybridises to the probe when the gene is immobilised on a membrane and the probe (which, in this case is >200 nucleotides in length) is in solution and the immobilised gene/hybridised probe is washed in 0.1×SSC at 65° C. for 10 min. SSC is 0.15M NaCl/0.015M Na citrate.

Preferred probe sequences for cloning Salmonella virulence genes are shown in FIGS. 5 and 6 (SEQ ID Nos 39–44 and 8–36) and described in Example 2.

In a particularly preferred embodiment the Salmonella virulence genes comprise the sequence shown in FIGS. 5 and 6 and described in Example 2.

In further preference the genes are those contained within, or at least part of which is contained within, the sequences shown in FIGS. 11 and 12 (SEQ ID Nos 37 and 38) and which have been identified by the method of the second aspect of the invention. The sequences shown in FIGS. 11 and 12 are part of a gene cluster from *Salmonella typhimurium* which I have called virulence gene cluster 2 (VGC2). The position of transposon insertions are indicated within the sequence, and these transposon insertions inactivate a virulence determinant of the organism. As is discussed more fully below, and in particular in Example 4, when the method of the second aspect of the invention is used to identify virulence genes in *Salmonella typhimurium*, many of the nucleic acid insertions (and therefore genes identified) are clustered in a relatively small part of the genome. This region, VGC2, contains other virulence genes which, as described below, form part of the invention.

The gene isolated by the method of the invention can be expressed in a suitable host cell. Thus, the gene (DNA) may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued 3 Apr., 1984 to Rutter et al, U.S. Pat. No. 4,530,901 issued 23 Jul., 1985 to Weissman, U.S. Pat. No. 4,582,800 issued 15 Apr., 1986 to Crowl, U.S. Pat. No. 4,677,063 issued 30 Jun., 1987 to Mark et al, U.S. Pat. No. 4,678,751 issued 7 Jul., 1987 to Goeddel, U.S. Pat. No. 4,704,362 issued 3 Nov., 1987 to Itakura et al, U.S. Pat No. 4,710,463 issued 1 Dec., 1987 to Murray, U.S. Pat. No. 4,757,006 issued 12 Jul., 1988 to Toole, Jr. et al, U.S. Pat. No. 4,766,075 issued 23 Aug., 1988 to Goeddel et al and U.S. Pat. No. 4,810,648 issued 7Mar., 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal-cells and insect cells.

The vectors include a prokaryotic replicon, such as the Co1E1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223 3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps)

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Variants of the genes also form part of the invention. It is preferred if the variant has at least 70% sequence identity, more preferably at least 85% sequence identity, most preferably at least 95% sequence identity with the genes isolated by the method of the invention. Of course, replacements, deletions and insertions may be tolerated. The degree of similarity between one nucleic acid sequence and another can be determined using the GAP program of the University of Wisconsin Computer Group.

Similarly, variants of proteins encoded by the genes are included.

By "variants" we include insertions, deletions and substitutions, either conservative or non-conservative, where such changes do not substantially alter the normal function of the protein.

By "conservative substitutions" is intended combinations such as Gly, Ala; Val, Ile, Leu; Asp, Glu; Asn, Gln; Ser, Thr; Lys, Arg; and Phe, Tyr.

Such variants may be made using the well known methods of protein engineering and site-directed mutagenesis.

A ninth aspect of the invention provides a method of identifying a compound which reduces the ability of a microorganism to adapt to a particular environment comprising the steps of selecting a compound which interferes with the function of (1) a gene obtained by the method of the second aspect of the invention or of (2) a polypeptide encoded by such a gene.

Pairwise screens for compounds which affect the wild type cell but not a cell overproducing a gene isolated by the methods of the invention form part of this aspect of the invention.

For example, in one embodiment one cell is a wild type cell and a second cell is the Salmonella which is made to overexpress the gene isolated by the method of the invention. The viability and/or growth of each cell in the particular environment is determined in the presence of a compound to be tested to identify which compound reduces the viability or growth of the wild type cell but not the cell overexpressing the said gene.

It is preferred if the gene is a virulence gene.

For example, in one embodiment the microorganism (such as *S. typhimurium*) is made to over-express the virulence gene identified by the method of the first aspect of the invention. Each of (a) the "over-expressing" microorganism and (b) an equivalent microorganism (which does not over-express the virulence gene) are used to infect cells in culture. Whether a particular test compound will selectively inhibit the virulence gene function is determined by assessing the amount of the test compound which is required to prevent infection of the host cells by (a) the over-expressing microorganism and (b) the equivalent microorganism (at least for some virulence gene products it is envisaged that the test compound will inactivate them, and itself be inactivated, by binding to the virulence gene product). If more of the compound is required to prevent infection by the (a) than (b) then this suggests that the compound is selective. It is preferred if the microorganisms (such as Salmonella) are destroyed extracellularly by a mild antibiotic such as gentamicin (which does not penetrate host cells) and that the effect of the test compound in preventing infection of the cell by the microorganism is by lysing the said cell and determining how many microorganisms are present (for example by plating on agar).

Pairwise screens and other screens for compounds are generally disclosed in Kirsch & Di Domenico (1993) in "The Discovery of Natural Products with a Therapeutic Potential" (Ed, V. P. Gallo), Chapter 6, pages 177–221, Butterworths, V. K. (incorporated herein by reference).

Pairwise screens can be designed in a number of related formats in which the relative sensitivity to a compound is compared using two genetically related strains. If the strains differ at a single locus, then a compound specific for that target can be identified by comparing each strain's sensitivity to the inhibitor. For example, inhibitors specific to the target will be more active against a super-sensitive test strain when compared to an otherwise isogenic sister strain. In an agar diffusion format, this is determined by measuring the size of the zone of inhibition surrounding the disc or well carrying the compound. Because of diffusion, a continuous concentration gradient of compound is set up, and the strain's sensitivity to inhibitors is proportional to the distance from the disc or well to the edge of the zone. General antimicrobials, or antimicrobials with modes of action other than the desired one are generally observed as having similar activities against the two strains.

Another type of molecular genetic screen, involving pairs of strains where a cloned gene product is overexpressed in one strain compared to a control strain. The rationale behind this type of assay is that the strain containing an elevated quantity of the target protein should be more resistant to inhibitors specific to the cloned gene product than an isogenic strain, containing normal amounts of the target protein. In an agar diffusion assay, the zone size surrounding a specific compound is expected to be smaller in the strain overexpressing the target protein compared to an otherwise isogenic strain.

Additionally or alternatively selection of a compound is achieved in the following steps:

1. A mutant microorganism obtained using the method of the first aspect of the invention is used as a control (it has a given phenotype, for example, avirulence).

2. A compound to be tested is mixed with the wild-type microorganism.

3. The wild-type microorganism is introduced into the environment (with or without the test compound).

4. If the wild-type microorganism is unable to adapt to the environment (following treatment by, or in the presence of, the compound), the compound is one which reduces the ability of the microorganism to adapt to, or survive in, the particular environment.

When the environment is an animal body and the microorganism is a pathogenic microorganism, the compound identified by this method can be used in a medicament to prevent or ameliorate infection with the microorganism.

A tenth aspect of the invention therefore provides a compound identifiable by the method of the ninth aspect.

It will be appreciated that uses of the compound of the tenth aspect are related to the method by which it can be identified, and in particular in relation to the host of a pathogenic microorganism. For example, if the compound is identifiable by a method which uses a virulence gene, or polypeptide encoded thereby, from a bacterium which infects a mammal, the compound may be useful in treating infection of a mammal by that bacterium.

Similarly, if the compound is identifiable by a method which uses a virulence gene, or polypeptide encoded thereby, from a fungus which infects a plant, the compound may be useful in treating infection of a plant by that fungus.

An eleventh aspect of the invention provides a molecule which selectively interacts with, and substantially inhibits the function of, a gene of the seventh aspect of the invention or a nucleic acid product thereof.

By "nucleic acid product thereof" we include any RNA, especially mRNA, transcribed from the gene.

Preferably a molecule which selectively interacts with, and substantially inhibits the function of, said gene or said nucleic acid product is an antisense nucleic acid or nucleic acid derivative.

More preferably, said molecule is an antisense oligonucleotide.

Antisense oligonucleotides are single-stranded nucleic acid, which can specifically bind to a complementary nucleic acid sequence. By binding to the appropriate target sequence, an RNA—RNA, a DNA—DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise sequence-specific molecules which specifically bind double-stranded DNA via recognition of major groove hydrogen binding sites.

Clearly, the sequence of the antisense nucleic acid or oligonucleotide can readily be determined by reference to the nucleotide sequence of the gene in question. For example, antisense nucleic acid or oligonucleotides can be designed which are complementary to a part of the sequence shown in FIGS. 11 or 12, especially to sequences which form a part of a virulence gene.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079–7083 showed increased inhibition in tissue culture of HIV-1 using oligonucleotide phosphoramidates and phosphorothioates. Sarin et al (1988) *Proc. Natl. Acad. Sci. USA* 85, 7448–7451 demonstrated increased inhibition of HIV-1 using oligonucleotide methylphosphonates. Agrawal et al (1989) *Proc. Natl. Acad. Sci. USA* 86, 7790–7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430–3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res.* 19, 747–750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesizing oligonucleoside phosphorothioates is provided in Agrawal and Tang (1990) *Tetrahedron Letters* 31, 7541–7544, the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 291 1; Jager et al (1988) *Biochemistry* 27, 7237; Uznanski et al (1987) *Tetrahedron Letters* 28, 3401; Bannwarth (1988) Helv. Chim. Acta. 71, 1517; Crosstick and Vyle (1989) *Tetrahedron Letters* 30, 4693; Agrawal et al (1990) *Proc. Natl. Acad. Sci. USA* 87, 1401–1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesized and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747–750 and Agrawal et al (1991)

*Proc. Natl. Acad. Sci. USA* 88(17), 7595–7599, the teachings of which are hereby incorporated herein by reference.

A further method of making oligonucleotides resistant to nuclease attack is for them to be "self-stabilized" as described by Tang et al (1993) *Nucl. Acids Res.* 21, 2729–2735 incorporated herein by reference. Self-stabilized oligonucleotides have hairpin loop structures at their 3' ends, and show increased resistance to degradation by snake venom phosphodiesterase, DNA polymerase I and fetal bovine serum. The self-stabilized region of the oligonucleotide does not interfere in hybridization with complementary nucleic acids, and pharmacokinetic and stability studies in mice have shown increased in vivo persistence of self-stabilized oligonucleotides with respect to their linear counterparts.

In accordance with the invention, the inherent binding specificity of antisense oligonucleotides characteristic of base pairing is enhanced by limiting the availability of the antisense compound to its intend locus in vivo, permitting lower dosages to be used and minimizing systemic effects. Thus, oligonucleotides are applied locally to achieve the desired effect. The concentration of the oligonucleotides at the desired locus is much higher than if the oligonucleotides were administered systemically, and the therapeutic effect can be achieved using a significantly lower total amount. The local high concentration of oligonucleotides enhances penetration of the targeted cells and effectively blocks translation of the target nucleic acid sequences.

The oligonucleotides can be delivered to the locus by any means appropriate for localized administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus.

The oligonucleotides are most preferably administered via a hydrogel material. The hydrogel is noninflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10 to about 80% by weight ethylene oxide and from about 20 to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warms, it solidifies to form a gel, and the oligonucleotides diffuse out of the gel into the surrounding cells over a period of time defined by the exact composition of the gel.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerized or solidified, using melt or solvent evaporation techniques, or mechanically mixed with the material. In one embodiment, the oligonucleotides are mixed into or applied onto coatings for implantable devices such as dextran coated silica beads, stents, or catheters.

The dose of oligonucleotides is dependent on the size of the oligonucleotides and the purpose for which is it administered. In general, the range is calculated based on the surface area of tissue to be treated. The effective dose of oligonucleotide is somewhat dependent on the length and chemical composition of the oligonucleotide but is generally in the range of about 30 to 3000 $\mu$g per square centimetre of tissue surface area.

The oligonucleotides may be administered to the patient systemically for both therapeutic and prophylactic purposes. The oligonucleotides may be administered by any effective method, for example, parenterally (eg intravenously, subcutaneously, intramuscularly) or by oral, nasal or other means which permit the oligonucleotides to access and circulate in the patient's bloodstream. Oligonucleotides administered systemically preferably are given in addition to locally administered oligonucleotides, but also have utility in the absence of local administration. A dosage in the range of from about 0.1 to about 10 grams per administration to an adult human generally will be effective for this purpose.

It will be appreciated that the molecules of this aspect of the invention are useful in treating or preventing any infection caused by the microorganism from which the said gene has been isolated, or a close relative of said microorganism. Thus, the said molecule is an antibiotic.

Thus, a twelfth aspect of the invention provides a molecule of the eleventh aspect of the invention for use in medicine.

A thirteenth aspect of the invention provides a method of treating a host which has, or is susceptible to, an infection with a microorganism, the method comprising administering an effective amount of a molecule according to the eleventh aspect of the invention wherein said gene is present in said microorganisms, or a close relative of said microorganism.

By "effective amount" we mean an amount which substantially prevents or ameliorates the infection. By "host" we include any animal or plant which may be infected by a microorganism.

It will be appreciated that pharmaceutical formulations of the molecule of the eleventh aspect of the invention form part of the invention. Such pharmaceutical formulations comprise the said molecule together with one or more acceptable carriers. The carrier(s) must be "acceptable" in the sense of being compatible with the said molecule of the invention and not deleterious to the recipients thereof. Typically, the carriers will be water or saline which will be sterile and pyrogen free.

As mentioned above, and as described in more detail in Example 4 below, I have found that certain virulence genes are clustered in *Salmonella typhimurium* in a region of the chromosome that I have called VGC2. DNA—DNA hybridisation experiments have determined that sequences homologous to at least part of VGC2 are found in many species and strains of Salmonella but are not present in the *E. coli* and Shigella strains tested (see Example 4). These sequences almost certainly correspond to conserved genes, at least in Salmonella, and at least some of which are virulence genes. It is believed that equivalent genes in other Salmonella species and, if present, equivalent genes in other enteric or other bacteria will also be virulence genes.

Whether a gene within the VGC2 region is a virulence gene is readily determined. For example, those genes within VGC2 which have been identified by the method of the second aspect of the invention (when applied to *Salmonella typhimurium* and wherein the environment is an animal such as a mouse) are virulence genes. Virulence genes are also identified by making a mutation in the gene (preferably a non-polar mutation) and determining whether the mutant strain is avirulent. Methods of making mutations in a selected gene are well known and are described below.

A fourteenth aspect of the invention provides the VGC2 DNA of *Salmonella typhimurium* or a part thereof, or a variant of said DNA or a variant of a part thereof.

The VGC2 DNA of *Salmonella typhimurium* is depicted diagrammatically in FIG. 8 and is readily obtainable from *Salmonella typhimurium* ATCC 14028 (available from the American Type Culture Collection, 10801 University Boulevard, Manassas, Va. 20110-689 2209,. USA; also deposited at the NCTC, Public Health Laboratory Service, Colindale, UK under accession no. NCTC 12021) using the information provided in Example 4. For example, probes derived from the sequences shown in FIGS. 11 and 12 may be used to identify λ clones from a *Salmonella typhimurium* genomic library. Standard genome walking methods can be employed to obtain all of the VGC2 DNA. The restriction map shown in FIG. 8 can be used to identify and locate DNA fragments from VGC2.

By "part of the VGC2 DNA of *Salmonella typhimurium*" we mean any DNA sequence which comprises at least 10 nucleotides, preferably at least 20 nucleotides, more preferably at least 50 nucleotides, still more preferably at least 100 nucleotides, and most preferably at least 500 nucleotides of VGC2. A particularly preferred part of the VGC2 DNA is the sequence shown in FIG. 11, or a part thereof. Another particularly preferred part of the VGC2 DNA is the sequence shown in FIG. 12, or a part thereof.

Advantageously, the part of the VGC2 DNA is a gene, or part thereof.

Genes can be identified within the VGC2 region by statistical analysis of the open reading frames using computer programs known in the art. If an open reading frame is greater than about 100 codons it is likely to be a gene (although genes smaller than this are known). Whether an open reading frame corresponds to the polypeptide coding region of a gene can be determined experimentally. For example, a part of the DNA corresponding to the open reading frame may be used as a probe in a northern (RNA) blot to determine whether mRNA is expressed which hybridises to the said DNA; alternatively or additionally a mutation may be introduced into the open reading frame and the effect of the mutation on the phenotype of the microorganism can be determined. If the phenotype is changed then the open reading frame corresponds to a gene. Methods of identifying genes within a DNA sequence are known in the art.

By "variant of said DNA or a variant of a part thereof" we include any variant as defined by the term "variant" in the seventh aspect of the invention.

Thus, variants of VGC2 DNA of *Salmonella typhimurium* include equivalent genes, or parts thereof, from other Salmonella species, such as *Salmonella typhi* and *Salmonella enterica*, as well as equivalent genes, or parts thereof, from other bacteria such as other enteric bacteria.

By "equivalent gene" we include genes which are functionally equivalent and those in which a mutation leads to a similar phenotype (such as avirulence). It will be appreciated that before the present invention VGC2 or the genes contained therein had not been identified and certainly not implicated in virulence determination.

Thus, further aspects of the invention provide a mutant bacterium wherein if the bacterium normally contains a gene that is the same as or equivalent to a gene in VGC2, said gene is mutated or absent in said mutant bacterium; methods of making a mutant bacterium wherein if the bacterium normally contains a gene that is the same as or equivalent to a gene in VGC2, said gene is mutated or absent in said mutant bacterium. The following is a preferred method to inactivate a VGC2 gene. One first subclones the gene on a DNA fragment from a Salmonella λ DNA library or other DNA library using a fragment of VGC2 as a probe in hybridisation experiments, and map the gene with respect to restriction enzyme sites and characterise the gene by DNA sequencing in *Escherichia coli*. Using restriction enzymes, one then introduces into the coding region of the gene a segment of DNA encoding resistance to an antibiotic (for example, kanamycin), possibly after deleting a portion of the coding region of the cloned gene by restriction enzymes. Methods and DNA constructs containing an antibiotic resistance marker are available to ensure that the inactivation of the gene of interest is preferably non-polar, that is to say, does not affect the expression of genes downstream from the gene of interest. The mutant version of the gene is then transferred from *E. coli* to *Salmonella typhimurium* using phage P22 transduction and transductants checked by Southern hybridisation for homologous recombination of the mutant gene into the chromosome.

This approach is commonly used in Salmonella (and can be used in *S. typhi*), and further details can be found in many papers, including Galan et al (1992) 174, 4338–4349.

Still further aspects provide a use of said mutant mutant bacterium in a vaccine; pharmaceutical compositions comprising said bacterium and a pharmaceutically acceptable carrier; a polypeptide encoded by VGC2 DNA of *Salmonella typhimurium* or a part thereof, or a variant of a part thereof; a method of identifying a compound which reduces the ability of a bacterium to infect or cause disease in a host; a compound identifiable by said method; a molecule which selectively interacts with, and substantially inhibits the function of, a gene in VGC2 or a nucleic product thereof; and medical uses and pharmaceutical compositions thereof.

The VGC2 DNA contains genes which have been identified by the methods of the first and second aspects of the invention as well as genes which have been identified by their location (although identifiable by the methods of the first and second aspects of the invention). These further aspects of the invention relate closely to the fourth, fifth, sixth, seventh, eighth, ninth, tenth, eleventh, twelfth and thirteenth aspects of the invention and, accordingly, the information given in relation to those aspects, and preferences expressed in relation to those aspects, applies to these further aspects.

It is preferred if the gene is from VGC2 or is an equivalent gene from another species of Salmonella such as *S. typhi*. It is preferred if the mutant bacterium is a *S. typhimurium* mutant or a mutant of another species of Salmonella such as *S. typhi*.

It is believed that at least some of the genes in VGC2 confer the ability for the bacterium, such as *S. typhimurium*, to enter cells.

The invention will now be described with reference to the following Examples and Figures wherein.

FIG. 4 shows a DNA colony blot hybridisation analysis of 95 S. typhimurium exconjugants of a microtitre dish (A1–H11), which were injected into a mouse. Replicate filters were hybridised with labelled amplified tags from the pool (inoculum pattern), or with labelled amplified tags from DNA isolated from over 10,000 pooled colonies that were recovered from the spleen of the infected animal (spleen pattern). Colonies B6, A11 and C8 gave rise to weak hybridisation signals on both sets of filters. Hybridisation signals from colonies A3, C5, G3 (aroA), and F10 are present on the inoculum pattern but not on the spleen pattern.

FIG. 5 shows the sequence of a Salmonella gene isolated using the method of the invention and a comparison to the Escheiichia coli clp protease genome (SEQ ID NOS: 39 and 40).

FIG. 6 shows partial sequences of further Salmonella gene isolated using the method of the invention (SEQ ID Nos. 8 to 36).

FIGS. 7A and 7B show the mapping of VGC2 on the S. typhimurium chromosome. (A) DNA probes from three regions of VGC2 were used in Southern hybridisation analysis of lysates from a set of S. typhimurium strains harboring locked in Mud-P22 prophages. Lysates which hybridised to a 7.5 kb PstI fragment (probe A in FIG. 8) are shown. The other two probes used hybridised to the same lysates. (B) The insertion points and packaging directions of the phage are shown along with the map position in minutes (edition VIII, ref 22 in Example 4). The phage designations correspond to the following strains: 18P, TT15242; 18Q, 15241; 19P, TT15244; 19Q, TT15243; 20P, TT15246 and 20Q, TT15245 (Ref in Example 4). The locations of mapped genes are shown by horizontal bars and the approximate locations of other genes are indicated.

Figures 8A, 8B, 8C:
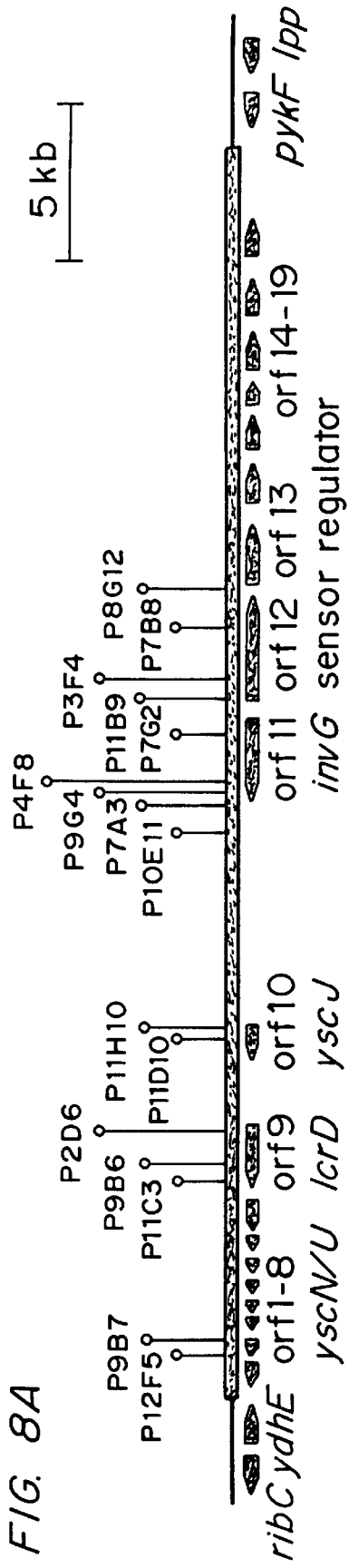

FIGS. 8A, 8B, and 8C show a physical and genetic map of VGC2. (A) The positions of 16 transposon insertions are shown above the line. The extent of VGC2 is indicated by the thicker line. The position and direction of transcription of ORFs described in the text of Example 4 are shown by arrows below the line, together with the names of similar genes, with the exception of ORFs 12 and 13 whose products are similar to the sensor and regulatory components respectively, of a variety of two component regulatory systems. (B) The location of overlapping clones and an EcoRI/XbaI restriction fragment from Mud-P22 prophage strain TF15244 are shown as filled bars. Only the portions of the λ clones which have been mapped are shown and the clones may extend beyond these limits.

(C) The positions of restriction sites are marked: B, BamHI; E, EcoRI; V, EcoRV; H, HindIII; P, PstI and X, XbaI. The positions of the 7.5 kb PstI fragment (probe A) used as a probe in FIG. 7 and that of the 2.2 kb PstI/HindIII fragment (probe B) used as a probe in FIG. 10 are shown below the restriction map. The positions of Sequence 1 (described in FIG. 11) and Sequence 2 (described in FIG. 12) are shown by the thin arrows (labelled Sequence 1 and Sequence 2).

Figure 9:
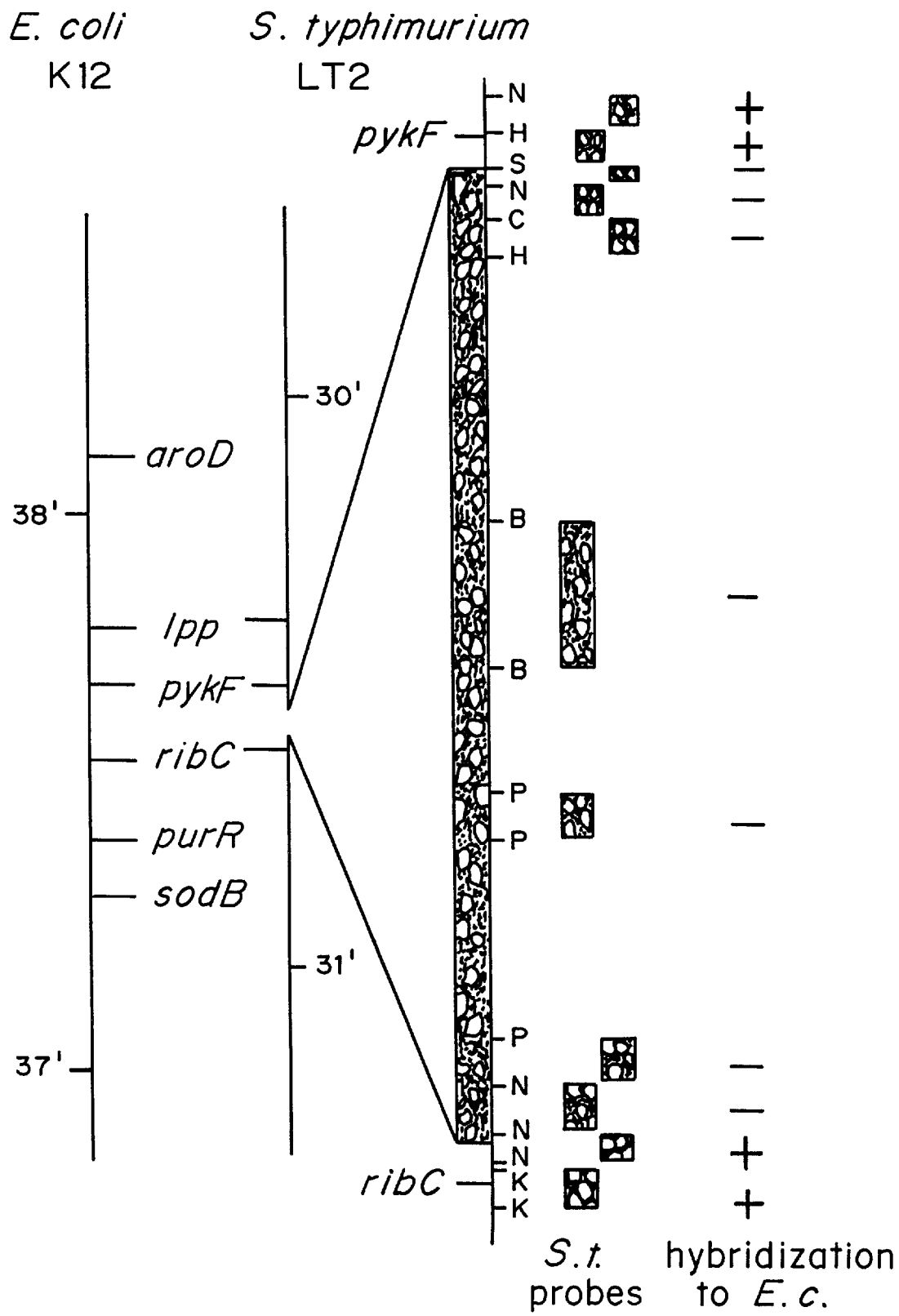

FIG. 9 describes mapping the boundaries of VGC2. (A) The positions of mapped genes at minutes 37 to 38 on the E. coli K12 chromosome are aligned with the corresponding region of the S. typhimurium LT2 chromosome (minutes 30 to 31). An expanded map of the VGC2 region is shown with 11 S. typhimurium (S. t.) DNA fragments used as probes (thick bars) and the restriction sites used to generate them: B, BamHI; C, ClaI; H, HindII; K, KpnI; P, PstI; N, NsiI and S. SalI. Probes that hybridised to E. coil K12 (E. c.) genomic DNA are indicated by +; those which failed to hybridise are indicated by.

FIGS. 10A and 10B shows that VGC2 is conserved among and specific to the Saimonellae. Genomic DNA from Salmonella serovars and other pathogenic bacteria was restricted with PstI (A), HindIII or EcoRV (B) and subjected to Southern hybridisation analysis, using a 2.2 kb PstI/HindIII fragment from λ clone 7 as a probe (probe B FIG. 2). The filters were hybridised and washed under stringent (A) or non-stringent (B) conditions.

FIG. 11 shows the DNA sequence of "Sequence 1" of VGC2 from the center to the left-hand end (see the arrow labelled Sequence 1 in FIG. 8). The DNA is translated in all six reading frames (SEQ ID NOS: 45–501) and the start and stop positions of putative genes, and the transposon insertion positions for various mutants identified by STM are indicated (SEQ ID No 37).

As is conventional a * indicates a stop codon and standard nucleotide ambiguity codes are used where necessary.

FIG. 12 shows the DNA sequence of "Sequence 2" of VGC2 (cluster C) (see the arrow labelled Sequence 2 in FIG. 8). The transposon insertion positions for various mutants identified by STM are indicated (SEQ ID No 38).

As is conventional a * indicates a stop codon and standard nucleotide ambiguity codes are used where necessary.

FIGS. 7 to 12 are most relevant to Example 4.

EXAMPLE 1

Identification of Virulence Genes in *Salmonella typhimurium*

Materials and Methods

Bacterial Strains and Plasmids

*Salmonella typhimurium* strain 12023 (equivalent to American Type Culture Collection (ATCC) strain 14028) was obtained from the National Collection of Type Cultures (NCTC), Public Health Laboratory Service, Colindale, London, UK. A spontaneous nalidixic acid resistant mutant of this strain (12023 Nal$^r$) was selected in our laboratory. Another derivative of strain 12023, CL1509 (aroA::Tn10) was a gift from Fred Heffron. *Escherichia coli* strains CC118 λpir (Δ[ara-leu], araD, ΔlacX74, galE, galK, phoA20, thi-1, rpsE, rpoB, argE(Am), recA1, λpir phage lysogen) and S17-1 λpir(Tp$^r$, Sm$^r$, recA, thi, pro, hsdRM$^+$, RP4:2-Tc:Mu:KmTn7, λpir) were gifts from Kenneth Timmis. *E. coli* DH5α was used for propagating pUC18 (Gibco-BRL) and Bluescript (Stratagene) plasmids containing *S. typhimurium* DNA. Plasmid pUTmini-Tn5Km2 (de Lorenzo et al, 1990) was a gift from Kenneth Timmis.

Construction of semi-random Sequence Tags and Ligations

The oligonucleotide pool RT1(5'-CTAGGTACCTACAACCTCAAGCTT-[NK]$_{20}$-AAGCTTGGTTAGAATGGGTACCATG-3') (SEQ ID No 1), and primers P2 (5'-TACCTACAACCTCAAGCT-3') (SEQ ID No 2), P3 (5'-CATGGTACCCATTCTAAC-3')

(SEQ ID No 3), P4 (5'-TACCCATTCTAACCAAGC-3') (SEQ ID No 4) and P5 (5'-CTAGGTACCTACAACCTC-3') (SEQ ID No 5) were synthesized on a oligonucleotide synthesizer (Applied Biosystems, model 380B). Double stranded DNA tags were prepared from RT1 in a 100 µl volume PCR containing 1.5 mM $MgCl_2$, 50 mM KCl, and 10 mM Tris-Cl (pH 8.0) with 200 pg of RT1 as target; 250 µM each dATP, dCTP, dGTP, dTTP; 100 pM of primers P3 and P5; and 2.5 U of Amplitaq (Perkin-Elmer Cetus). Thermal cycling conditions were 30 cycles of 95° C. for 30 s, 50° C. for 45 s, and 72° C. for 10 s. The PCR product was gel purified (Sambrook et al, 1989), passed through an elutipD column (available from Schleicher and Schull) and digested with KpnI prior to ligation into pUC18 or pUTmini-Tn5Km2. For ligations, plasmids were digested with KpnI and dephosphorylated with calf intestinal alkaline phosphatase (Gibco-BRL). Linearized plasmid molecules were gel- purified (Sambrook et al, 1989) prior to ligation to remove any residual uncut plasmid DNA from the digestion. Ligation reactions contained approximately 50 ng each of plasmid and double stranded tag DNA in a 25 µl volume with 1 unit T4 DNA ligase (Gibco-BRL) in a buffer supplied with the enzyme.

Ligations were carried out for 2 h at 24° C. To determine the proportion of bacterial colonies arising from either self ligation of the plasmid DNA or uncut plasmid DNA, a control reaction was carried out in which the double stranded tag DNA was omitted from the ligation reaction. This yielded no ampicillin resistant bacterial colonies following transformation of E. coli CC118 (Sambrook et al, 1989), compared with 185 colonies arising from a ligation reaction containing the double stranded tag DNA.

Bactetial Transformation and Matings

The products of several ligations between pUT mini-Tn5Km2 and the double stranded tag DNA were used to transform E. coli CC118 (Sambrook et al, 1989). A total of approximately 10,300 transformants were pooled and plasmid DNA extracted from the pool was used to transform E. coli S-17 λpir (de Lorenzo & Timmis, 1994). For mating experiments, a pool of approximately 40,000 ampicillin resistant E. coli S-17 λpir transformants, and S. typhimurium 12023 Nal$^r$ were cultured separately to an optical density $(OD)_{580}$ of 1.0. Aliquots of each culture (0.4 ml) were mixed in 5 ml 10 mM $MgSO_4$, and filtered through a Millipore membrane (0.45 µm diameter). The filters were placed on the surface of agar containing M9 salts (de Lorenzo & Timmis, 1994) and incubated at 37° C. for 16 h. The bacteria were recovered by shaking the filters in liquid LB medium for 40 min at 37° C. and exconjugants were selected by plating the suspension onto LB medium containing 100 µg ml$^{-1}$ nalidixic acid (to select against the donor strain) and 50 µg ml$^{-1}$ kanamycin (to select for the recipient strain). Each exconjugant was checked by transferring nalidixic acid resistant (nal$^r$), kanamycin resistant (kan$^r$) colonies to MacConkey Lactose indicator medium (to distinguish between E. coli and S. typhimurium), and to LB medium containing ampicillin. Approximately 90% of the nal$^r$, kan$^r$ colonies were sensitive to ampicillin, indicating that these resulted from authentic transposition events (de Lorenzo & Timmis, 1994). Individual ampicillin-sensitive exconjugants were stored in 96 well microtitre dishes containing LB medium. For long term storage at −80° C., either 7% DMSO or 15% glycerol was included in the medium.

Phenotypic Characterisation of Mutants

Mutants were replica plated from microtitre dishes onto solid medium containing M9 salts and 0.4% glucose (Sambrook et al, 1989) to identify auxotrophs. Mutants with rough colony morphology were detected by low magnification microscopy of colonies on agar plates.

Colony Blots, DNA Extractions, PCRS, DNA Labelings and Hybridisations

For colony blot hybridizations, a 48-well metal replicator (Sigma) was used to transfer exconjugants from microtitre dishes to Hybond N nylon filters (Amersham, UK) that had been placed on the surface of LB agar containing 50 µg ml$^{-1}$ kanamycin. After overnight incubation at 37° C., the filters supporting the bacterial colonies were removed and dried at room temperature for 10 min. The bacteria were lysed with 0.4N NaOH and the filters washed with 0.5N Tris-Cl pH 7.0 according to the filter manufacturer's instructions. The bacterial DNA was fixed to the filters by exposure to UV light from a Stratalinker (Stratagene). Hybridisations to $^{32}$P-labelled probes were carried out under stringent conditions as previously described (Holden et al, 1989). For DNA extractions, S. typhimurium transposon mutant strains were grown in liquid LB medium in microtitre dishes or resuspended in LB medium following growth on solid media. Total DNA was prepared by the hexadecyltrimethylammoniumbromide (CTAB) method according to Ausubel et al (1987). Briefly, cells from 150 to 1000 µl volumes were precipitated by centrifugation and resuspended in 576 µl TE. To this was added 15 µl of 20% SDS and 3 µl of 20 mg ml$^{-1}$ proteinase K. After incubating at 37° C. for 1 hour, 166 µl of 3M NaCl was added and mixed thoroughly, followed by 80 µl of 10% (w/v) CTAB and 0.7M NaCl. After thorough mixing, the solution was incubated at 65° C. for 10 min. Following extraction with phenol and phenol-chloroform, the DNA was precipitated by addition of isopropanol, washed with 70% ethanol and resuspended in TE at a concentration of approximately 1 µg µl$^{-1}$.

The DNA samples were subjected to two rounds of PCR to generate labelled probes. The first PCR was performed in 100 µl reactions containing 20 mM Tris-Cl pH 8.3; 50 mM KCl; 2 mM $MgCl_2$; 0.01% Tween 80; 200 µM each dATP, dCTP, dGTP, dTTP; 2.5 units of Amplitaq polymerase (Perkin-Elmer Cetus); 770 ng each primer P2 and P4; and 5 µg target DNA. After an initial denaturation of 4 min at 95° C., thermal cycling consisted of 20 cycles of 45 s at 50° C., 10 s at 72° C., and 30 s at 95° C. PCR products were extracted with chloroform/isoamyl alcohol (24/1) and precipitated with ethanol. DNA was resuspended in 10 µl TE and the PCR products were purified by electrophoresis through a 1.6% Seaplaque (FMC Bioproducts) gel in TAE buffer. Gel slices containing fragments of about 80 bp were excised and used for the second PCR. This reaction was carried out in a 20 µl total volume, and contained 20 mM Tris-Cl pH 8.3; 50 mM KCl; 2 mM $MgCl_2$; 0.01% Tween 80; 50 M each dATP, dTTP, dGTP; 10 µl $^{32}$P-dCTP (3000 Ci/mmol, Amersham); 150 ng each primer P2 and P4; approximately 10 ng of target DNA (1–2 µl of 1.6% Seaplaque agarose containing the first round PCR product); 0.5 units of Amplitaq polymerase. The reaction was overlayed with 20 µl mineral oil and thermal cycling was performed as described above. Incorporation of the radioactive label was quantitated by absorbance to Whatman DE81paper (Sambrook et al, 1989).

Infection Studies

Individual Salmonella exconjugants containing tagged transposons were grown in 2% tryptone, 1% yeast extract, 0.92% v/v glycerol, 0.5% $Na_2PO_4$, 1% $KNO_3$ (TYGPN medium) (Ausubel et al, 1987) in microtitre plates overnight at 37° C. A metal replicator was used to transfer a small volume of the overnight cultures to a fresh microtitre plate and the cultures were incubated at 37° C. until the $OD_{580}$ (measured using a Titertek Multiscan microtitre plate reader) was approximately 0.2 in each well. Cultures from individual wells were then pooled and the $OD_{550}$ determined using a spectrophotometer. The culture was diluted in sterile saline to approximately $5 \times 10^5$ cfu ml$^{-1}$. Further dilutions were plated out onto TYGPN containing nalidixic acid (100 mg ml$^{-1}$) and kanamycin (50 mg ml$^{-1}$) to confirm the cfu present in the inoculum.

Groups of three female BALB/c mice (20–25g) were injected intraperitoneally with 0.2 ml of bacterial suspension containing approximately $1 \times 10^5$ cfu ml$^{-1}$. Mice were sacrificed three days post-inoculation and their spleens were removed to recover bacteria. Half of each spleen was homogenized in 1 ml of sterile saline in a microfuge tube. Cellular debris was allowed to settle and 1 ml of saline containing cells still in suspension was removed to a fresh tube and centrifuged for two minutes in a microfuge. The supernatant was aspirated and the pellet resuspended in 1 ml of sterile distilled water. A dilution series was made in sterile distilled water and 100 ml of each dilution was plated onto TYGPN agar containing nalidixic acid (100 ug ml$^{-1}$) and kanamycin (50 ug ml$^{-1}$). Bacteria were recovered from plates containing between 1000 and 4000 colonies, and a total of over 10,000 colonies recovered from each spleen were pooled and used to prepare DNA for PCR generation of probes to screen colony blots.

Virulence Gene Cloning and DNA Sequencing

Total DNA was isolated from *S typhimurium* exconjugants and digested separately with SstI, SalI, PstI and SphI. Digests were fractionated through agarose gels, transferred to Hybond N$^+$ membranes (Amersham) and subjected to Southern hybridisation analysis using the kanamycin resistance gene of pUT mini-Tn5Km2 as a probe. The probe was labelled with digoxygenin (Boehringer-Mannheim) and chemiluminescence detection was carried out according to the manufacturer's instructions. The hybridisation and washing conditions were as described above. Restriction enzymes which gave rise to hybridising fragments in the 3–5 kb range were used to digest DNA for a preparative agarose gel, and DNA fragments corresponding to the sizes of the hybridisation signals were excised from this, purified and ligated into pUC18. Ligation reactions were used to transform *E. coli* DH5a to kanamycin resistance. Plasmids from kanamycin-resistant transformants were purified by passage through an elutipD column and checked by restriction enzyme digestion. Plasmid inserts were partially sequenced by the di-deoxy method (Sanger et al, 1977) using the −40 primer and reverse sequencing primer (United States Biochemical Corporation) and the primers P6 (5'-CCTAGGCGGCCAGATCTGAT-3') (SEQ ID No 6) and P7 (5'GCACTTGTGTATAAGAGTCAG-3') (SEQ ID No 7) which anneal to the I and O termini of Tn5, respectively. Nucleotide sequences and deduced amino acid sequences were assembled using the Macvector 3.5 software package run on a Macintosh SE/30 computer. Sequences were compared with the EMBL and Genbank DNA databases using the UNIX/SUN computer system at the Human Genome Mapping Project Resource Center, Harrow, UK.

Results

Tag Design

Figure 1A:
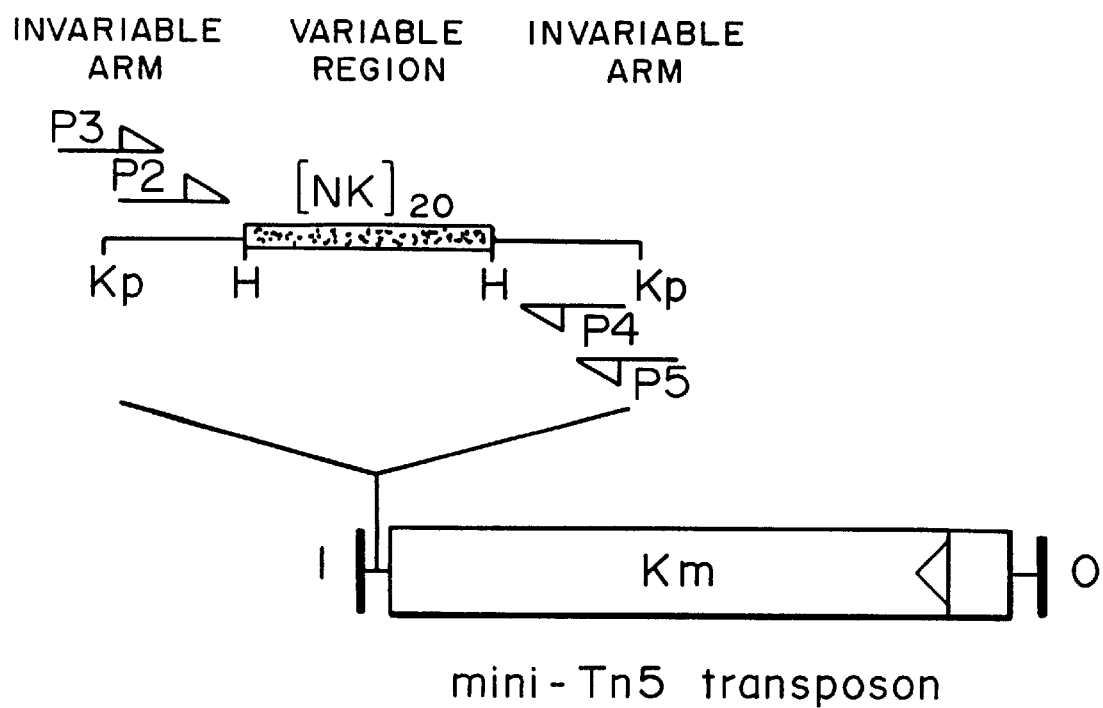
FIGS. 1A and 1B illustrate diagrammatically one particularly preferred method of the invention.
Figure 1B:
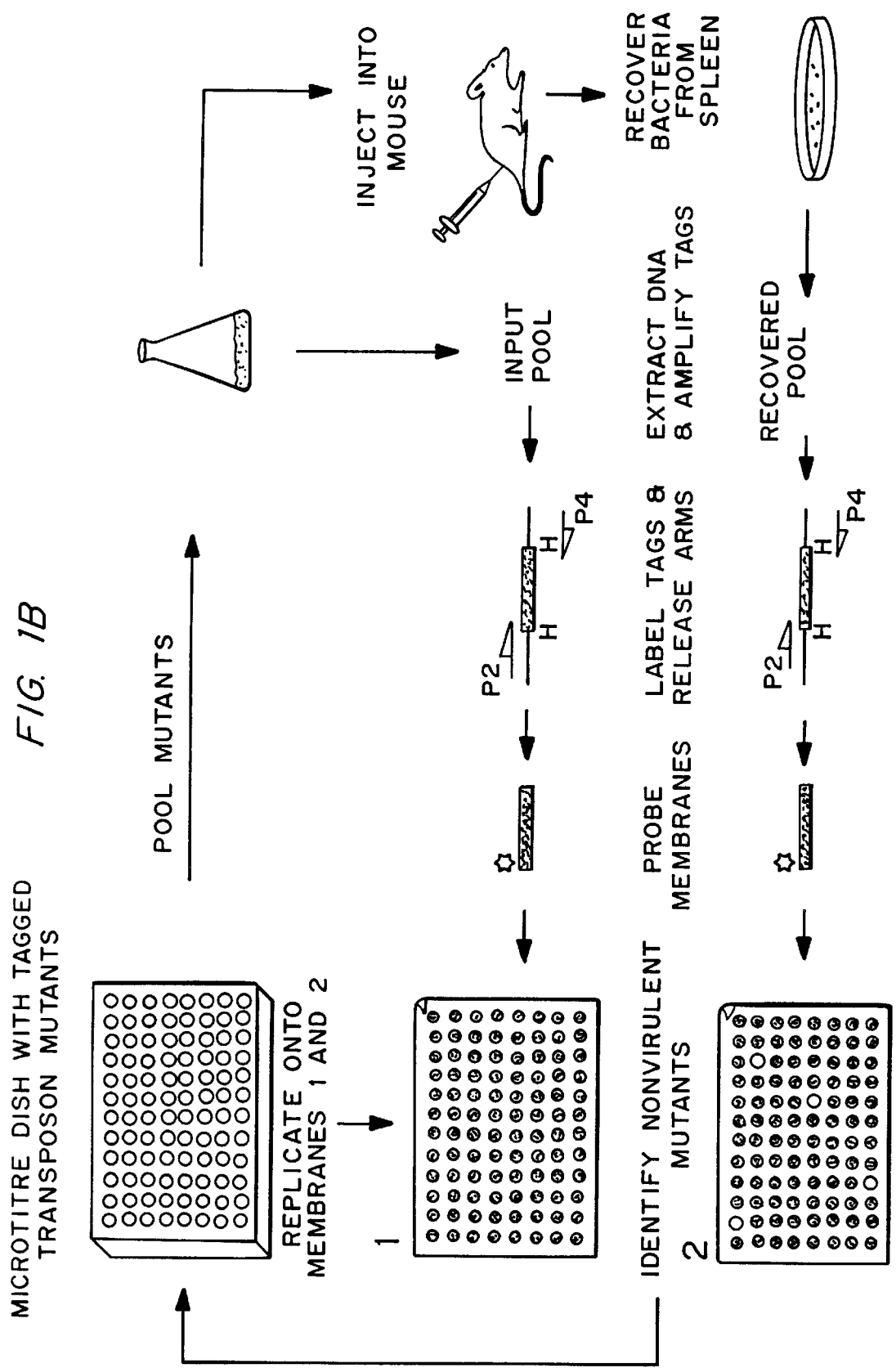
Figure 2:
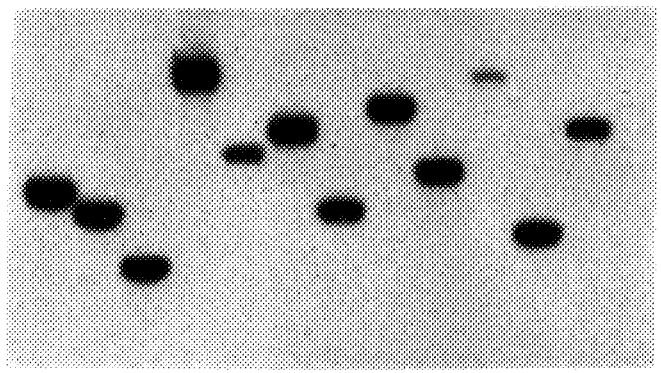
FIG. 2 shows a Southern hybridisation analysis of DNA from 12 S. typhimurium exconjugants following digestion with EcoRV. The filter was probed with the kanamycin resistance gene of the mini-Tn5 transposon.

The structure of the DNA tags is shown in FIG. 1a. Each tag consists of a variable central region flanked by "arms", of invariant sequence. The central region sequence ($[NK]_{20}$) was designed to prevent the occurrence of sites for the commonly used 6 bp-recognition restriction enzymes, but is sufficiently variable to ensure that statistically, the same sequence should only occur once in $2 \times 10^{11}$ molecules (DNA sequencing of 12 randomly selected tags showed that none shared more than 50% identity over the variable region). (N means any base (A, G, C or T) and K means G or T.) The arms contain KpnI sites close to the ends to facilitate the initial cloning step, and the HindIII sites bordering the variable region were used to release radiolabelled variable regions from the arms prior to hybridisation analysis. The arms were also designed such that primers P2 and P4 each contain only one guanine residue. Therefore during a PCR using these primers, only one cytosine will be incorporated into each newly synthesised arm, compared to an average of ten in the unique sequence. When radiolabelled dCTP is included in the PCR, an average of ten-fold more label will be present in the unique sequence compared with each arm. This is intended to minimise background hybridisation signals from the arms, after they have been released from the unique sequences by digestion with HindIII. Double stranded tags were ligated into the KpnI site of the mini-Tn5 transposon Km2, carried on plasmid pUT (de Lorenzo & Timmis, 1994). Replication of this plasmid is dependent on the R6K-specified π product of the pir gene. It carries the oriT sequence of the RP4 plasmid, permitting transfer to a variety of bacterial species (Miller & Mekalanos, 1988), and the trp* gene needed for transposition of the mini-Tn5 element. The tagged mini-Tn5 transposons were transferred to *S. typhimurium* by conjugation, and 288 exconjugants resulting from transposition events were stored in the wells of microtitre dishes. Total DNA isolated from 12 of these was digested with EcoRV, and subjected to Southern hybridisation analysis using the kanamycin resistance gene of the mini-Tn5 transposon as a probe. In each case, the exconjugant had arisen as a result a single integration of the transposon into a different site of the bacterial genome (FIG. 2).

Specificity and Sensitivity Studies

We next determined the efficiency and uniformity of amplification of the DNA tags in PCRs involving pools of exconjugant DNAs as targets for the reactions. In an attempt to minimise unequal amplification of tags in the PCR, we determined the maximum quantity of DNA target that could be used in a 100 μl reaction, and the minimum number of PCR cycles, that resulted in products which could be visualised by ethidium bromide staining of an agarose gel (5 μg DNA and 20 cycles, respectively).

*S. typhimurium* exconjugants which had reached stationary growth phase in microtitre dishes were combined, and used to extract DNA. This was subjected to a PCR using primers P2 and P4. PCR products of 80 bp were gel-purified and used as targets for a second PCR, using the same primers but with $^{32}$P-labelled CTP. This resulted in over 60% of the radiolabelled dCTP being incorporated into the PCR products. The radiolabelled products were digested with HindIII and used to probe colony blotted DNA from their corresponding microtitre dishes. Of the 1510 mutants tested in this way, 358 failed to yield a clear signal on an autoradiogram following an overnight exposure of the colony blot. There are three potential explanations for this. Firstly, it is possible that a proportion of the transposons did not carry tags. However, by comparing the transformation frequencies resulting from ligation reactions involving the transposon in the presence or absence of tags, it seems unlikely that untagged transposons could account for more than approximately 0.5% of the total (see Materials and Methods). More probable causes are that the variable sequence was truncated in some of the tags, and/or that some of the sequences formed secondary structures, both of which might have prevented amplification. Mutants which failed to give clear signals were not included in further studies. The specificity of the efficiently amplifiable tags was demonstrated by generating a probe from 24 colonies of a microtitre dish, and using it to probe a colony blot of 48 colonies, which included the 24 used to generate the probe. The lack of any hybridisation signal from the 24 colonies not used to generate the probe (FIG. 3) shows that the hybridisation conditions employed were sufficiently stringent to prevent cross-hybridisation among labelled tags, and suggests that each exconjugant is not reiterated within a microtitre dish.

There are further considerations in determining the maximum pool size that can be used as an inoculum in animal experiments. As the quantity of labelled tag for each transposon is inversely proportional to the complexity of the tag pool, there is a limit to the pool size above which hybridisation signals become too weak to be detected after overnight exposure of an autoradiogram. More importantly, as the complexity of the pool increases, so must the likelihood of failure of a virulent representative of the pool to be present in sufficient numbers, in the spleen of an infected animal, to produce enough labelled probe. We have not determined the upper limit for pool size in the murine model of salmonellosis that we have employed, but it must be in excess of 96.

Virulence Tests of the Transposon Mutants

Figure 3:
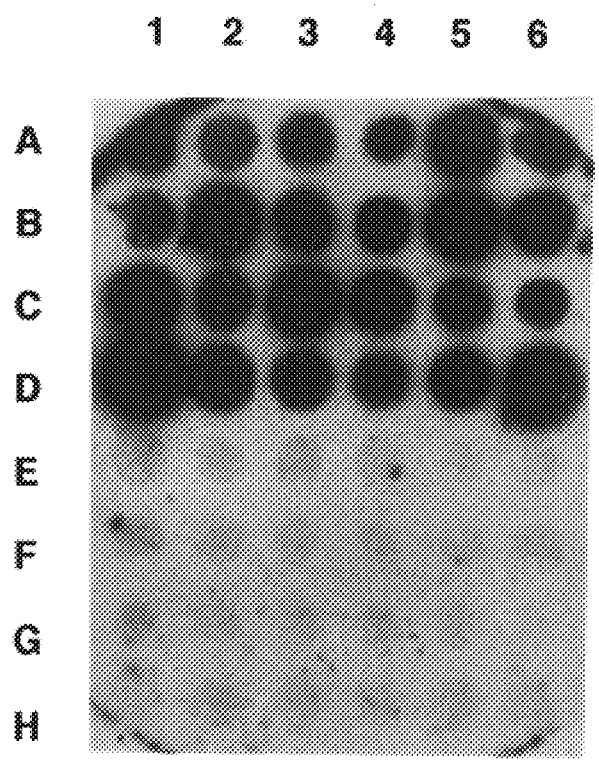
FIG. 3 shows a colony blot hybridisation analysis of DNA from 48 S. typhimurium exconjugants from a half of a microtitre dish (A1–H6). The filter was hybridised with a probe comprising labelled amplified tags from DNA isolated from a pool of the first 24 colonies (A1–D6).
Figure 4A:
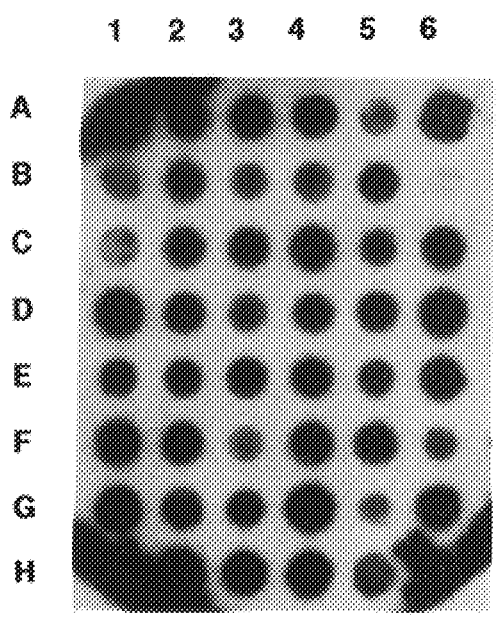
Figure 4B:
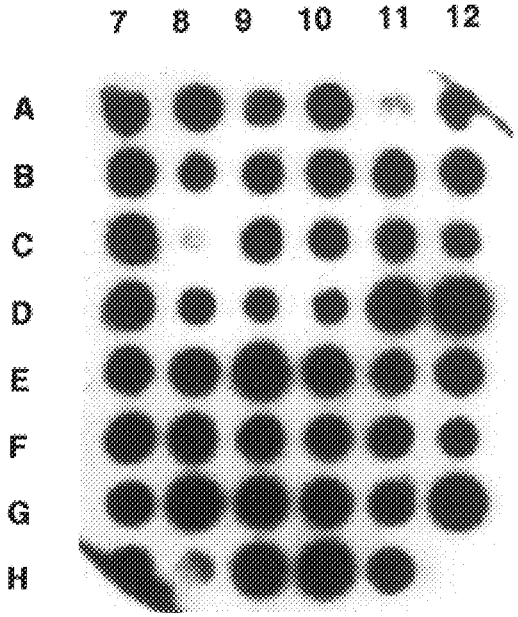
Figure 4C:
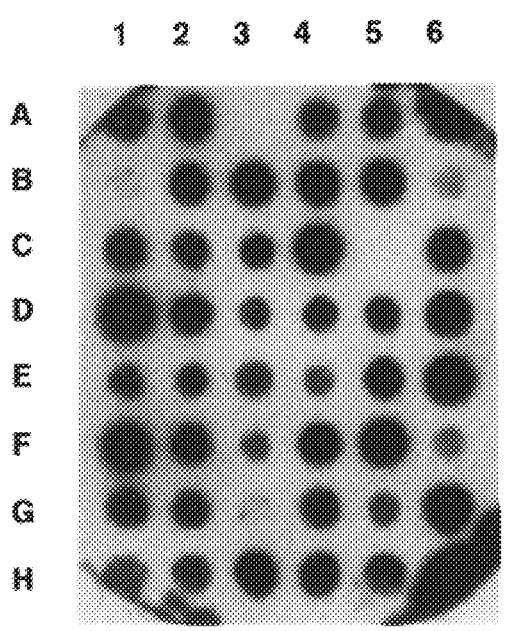
Figure 4D:
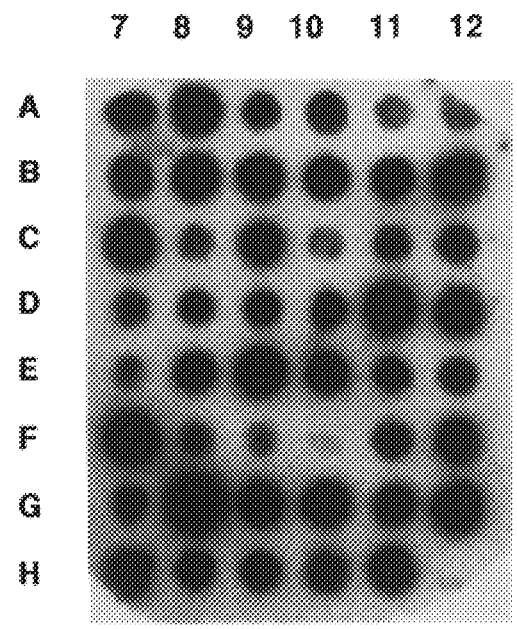

A total of 1152 uniquely tagged insertion mutants (from two microtitre dishes) were tested for virulence in BALB/c mice in twelve pools, each representing a 96-well microtitre dish. Animals received an intraperitoneal injection of approximately $10^3$ cells of each of 96 transposon mutants of a microtitre dish ($10^5$ organisms in total). Three days after injection mice were sacrificed, and bacteria were recovered by plating spleen homogenates onto laboratory medium. Approximately 10,000 colonies recovered from each mouse were pooled and DNA was extracted. The tags present in this DNA sample were amplified and labelled by the PCR, and colony blots probed and compared with the hybridisation pattern obtained using tags amplified from the inoculum (FIG. 3). As a control, an aroA mutant of *S. typhimrium* was tagged and employed as one of the 96 mutants in the inoculum. This strain would not be expected to be recovered in the spleen because its virulence is severely attenuated (Buchmeier et al, 1993). Forty-one mutants were identified whose DNA hybridized to labelled tags from the inoculum but not from labelled tags from bacteria recovered from the spleen. The experiment was repeated and the same forty-one mutants were again identified. Two of these were the aroA mutant (one per pool), as expected. Another was an auxotrophic mutant (it failed to grow on minimal medium). All of the mutants had normal colony morphology.

EXAMPLE 2

Cloning and Partial Characterisation of Sequences Flanking the Transposon

DNA was extracted from one of the mutants described in Example 1 (Pool 1, F10), digested with SstI, and subcloned on the basis of kanamycin resistance. The sequence of 450 bp flanking one end of the transposon was determined using primer P7. This sequence shows 80% identity to the *E. coli* clp (lon) gene, which encodes a heat-regulated protease (FIG. 5; SEQ ID Nos 39 and 40). To our knowledge, this gene has not previously been implicated as a virulence determinant.

Partial sequences of thirteen further *Salmonella typhimurium* virulence genes are shown in FIG. 6 (sequences A2 to A9 and B1 to B5; SEQ ID Nos 8–36). Deduced amino acid sequences of P2D6, S4C3, P3F4, P7G2 and P9B7 bear similarities to a family of secretion-associated proteins that have been conserved throughout bacterial pathogens of animals and plants, and which are known in Salmonella as the inv family. In *S. typhimurium* the inv genes are required for bacterial invasion into intestinal tissue. The virulence of inv mutants is attenuated when they are inoculated by the oral route, but not when they are administered intraperitoneally. The discovery of inv-related genes that are required for virulence following intraperitoneal inoculation suggests a new secretion apparatus which might be required for invasion of non-phagocytic cells of the spleen and other organs. The products of these new genes might represent better drug targets than the inv proteins in the treatment of established infections.

Further characterisation of the genes identified in this example is described in Example 4.

EXAMPLE 3

$LD_{50}$ Determinations and Mouse Vaccination Study

Mutations identified by the method of the invention attenuate virulence.

Five of the mutations in genes not previously implicated in virulence were transferred by P22-mediated transduction to the nalidixic acid-sensitive parent strain of *S. typhimurium* 12028. Transductants were checked by restriction mapping then injected by the intraperitoneal route into groups of BALB/c mice to determine their 50% lethal dose ($LD_{50}$). The $LD_{50}$ values for mutants S4C3, P7G2, P3F4 and P9B7 were all several orders of magnitude higher than that of the wild-type strain. No difference in the $LD_{50}$ was detected for mutant P1F10; however, there was a statistically significant decrease in the proportion of P1F10 cells recovered from the spleens of mice injected with an inoculum consisting of an equal proportion of this strain and the wild-type strain. This implies that this mutation does attenuate virulence, but to a degree that is not detectable by $LD_{50}$.

Mutants P3F4 and P9B7 were also administered by the oral route at an inoculum level of $10^7$ cells/mouse. None of the mice became ill, indicating that the oral $LD_{50}$ levels of these mutants are at least an order of magnitude higher than that of the wild-type strain.

In the mouse vaccination study groups of five female BALB/c mice of 20–25 g in mass were initially inoculated orally (p.o.) or intraperitoneally (i.p.) with serial ten fold dilutions of *Salmonella typhimurium* mutant strains P3F4 and P9B7. After four weeks the mice were then inoculated with 500 c.f.u. of the parental wild type strain. Deaths were then recorded over four weeks.

A group of two mice of the same age and batch as the mice inoculated with the mutant strains were also inoculated i.p. with 500 c.f.u. of the wild type strain as a positive control. Both non-immunised mice died as expected within four weeks. Results are tabulated below:

| initial inoculum in c.f.u. | no. mice surviving first challenge | no. mice surviving wild type challenge |
|---|---|---|
| 1) p.o. initial inoculation with mutant strain P3F4 | | |
| $5 \times 10^9$ | 5 | 2 (40%) |
| $5 \times 10^8$ | 5 | 2 (40%) |
| $5 \times 10^7$ | 5 | 0 (0%) |

-continued

| initial inoculum in c.f.u. | no. mice surviving first challenge | no. mice surviving wild type challenge |
|---|---|---|
| 2) i.p. initial inoculum with mutant strain P3F4 | | |
| $5 \times 10^6$ | 3 | 3 (100%) |
| $5 \times 10^5$ | 5 | 4 (80%) |
| $5 \times 10^4$ | 6 | 5 (83%) |
| $5 \times 10^3$ | 5 | 4 (80%) |
| 3)p.o. initial inoculum with mutant strain P9B7 | | |
| $5 \times 10^9$ | 5 | 0 (0%) |
| 4) i.p. initial inoculum with mutant P9B7 | | |
| $5 \times 10^6$ | 4 | 2 (50%) |

From these experiments I conclude that mutant P3P4 appears to give some protection against subsequent wild type challenge. This protection appears greater in mice that were immunised i.p.

EXAMPLE 4

Identification of a Virulence Locus Encoding a Second Type III Secretion System in Salmonella typhimurium Abbreviations used in this Example are VGC1, virulence gene cluster 1; VGC2, virulence gene cluster 2.

Background to the Experiments Described

Salmonella typhimurium is a principal agent of gastroenteritis in humans and produces a systemic illness in mice which serves as a model for human typhoid fever (1). Following oral inoculation of mice with S. typhimurium, the bacteria pass from the lumen of the small intestine through the intestinal mucosa, via enterocytes or M cells of the Peyer's patch follicles (2). The bacteria then invade macrophages and neutrophils, enter the reticuloendothelial system and disseminate to other organs, including the spleen and liver, where further reproduction results in an overwhelming and fatal bacteremia (3). To invade host cells, to survive and replicate in a variety of physiologically stressful intracellular and extracellular environments and to circumvent the specific antibacterial activities of the immune system, S. typhimurium employs a sophisticated repertoire of virulence factors (4).

To gain a more comprehensive understanding of virulence mechanisms of S. typhimurium and other pathogens the transposon mutagenesis system described in Example 1, which is conveniently called 'signature-tagged mutagenesis' (STM), which combines the strength of mutational analysis with the ability to follow simultaneously the fate of a large number of different mutants within a single animal (5 and Example 1; Reference 5 was published after the priority date for this invention). Using this approach we identified 43 mutants with attenuated virulence from a total of 1152 mutants that were screened. The nucleotide sequences of DNA flanking the insertion points of transposons in 5 of these mutants showed that they were related to genes encoding type III secretion systems of a variety of bacterial pathogens (6, 7). The products of the inv/spa gene cluster of S. typhimurium (8, 9) are proteins that form a type III secretion system required for the assembly of surface appendages mediating entry into epithelial cells (10). Hence the virulence of strains carrying mutations in the inv/spa cluster is attenuated only if the inoculum is administered orally and not when given intraperitoneally (8). In contrast the 5 mutants identified by STM are avirulent following intraperitoneal inoculation (5).

In this example we show that the transposon insertion points of these 5 mutants and an additional 11 mutants identified by STM all map to the same region of the S. typhimurium chromosome. Further analysis of this region reveals additional genes whose deduced products have sequence similarity to other components of type III secretion systems. This chromosomal region which we refer to as virulence gene cluster 2 (VGC2) is not present in a number of other enteric bacteria, and represents an important locus for S. typhimurium virulence.

Materials and Methods

Bacterial Strains, Transduction and Growth Media. Salmonella enterica serotypes 5791 (aberdeen), 423180 (gallinarum), 7101 (cubana) and 12416 (typhimurium LT2) were obtained from the National Collections of Type Cultures, Public Health Laboratory Service, UK. Salmonella typhi BRD123 genomic DNA was a gift from G. Dougan, enteropathogenic Escherichia coli (EPEC), enterohemorrhagic E. coli (EHEC), Vibrio cholera biotype El Tor, Shigella fiexneri serotype 2 and Staphylococcus aureus were clinical isolates obtained from the Department of Infectious Diseases and Bacteriology, Royal Postgraduate Medical School, UK. Genomic DNA from Yersinia pestis was a gift from J. Heesemann. However, genomic DNA can be isolated using standard methods. The bacterial strains and the methods used to generate signature-tagged mini-Tn5 transposon mutants of S. typhimurium NCTC strain 12023 have been described previously (5, 11). Routine propagation of plasmids was in E. coli DH5α. Bacteria were grown in LB broth (12) supplemented with the appropriate antibiotics. Before virulence levels of individual mutant strains were assessed, the mutations were first transferred by phage P22 mediated transduction (12) to the nalidixic acid sensitive parental strain of S. typhimurium 12023. Transductants were analysed by restriction digestion and Southern hybridisation before use as inoculum.

Lambda Library Screening. Lambda (λ) clones with overlapping insert DNAs covering VGC2 were obtained by standard methods (13) from a λ1059 library (14) containing inserts from a partial Sau3A digest of S. typhimurium LT2 genomic DNA. The library was obtained via K. Sanderson, from the Salmonella Genetic Stock Center (SGSC), Calgary, Canada.

Mud-P22 Lysogens. Radiolabelled DNA probes were hybridised to Hybond N (Amersham) filters bearing DNA prepared from lysates of a set of S. typhimurium strains harboring Mud-P22 prophages at known positions in the S. typhimurium genome. Preparation of mitomycin-induced Mud-P22 lysates was as described (12, 15). The set of Mud-P22 prophages was originally assembled by Benson and Goldman (16) and was obtained from the SGSC.

Gel Electrophoresis and Southern Hybridisation. Gel electrophoresis was performed in 1% or 0.6% agarose gels run in 0.5×TBE. Gel fractionated DNA was transferred to Hybond N or N+ membranes (Amersham) and stringent hybridisation and washing procedures (permitting hybridisation between nucleotide sequences with 10% or less mismatches) were as described by Holden et al, (17). For non-stringent conditions (permitting hybridisation between sequences with 50% mismatches) filters were hybridised overnight at 42° C. in 10% formamide/0.25M $Na_2HPO_4$/7% SDS and the most stringent step was with 20 mM $Na_2HPO_4$/ 1% SDS at 42° C. DNA fragments used as probes were labelled with [$^{32}$P]dCTP using the 'Radprime' system (Gibco-BRL) or with [digoxigenin-11]dUTP and detected using the Digoxigenin system (Boehringer Mannheim) according to the manufacturers' instructions, except that hybridisation was performed in the same solution as that used for radioactively labelled probes. Genomic DNA was prepared for Southern hybridisation as described previously (13).

Molecular Cloning and Nucleotide Sequencing. Restriction endonucleases and T4 DNA ligase were obtained from Gibco-BRL. General molecular biology techniques were as described in Sambrook et al, (18). Nucleotide sequencing was performed by the dideoxy chain termination method (19) using a T7 sequencing kit (Pharmacia). Sequences were assembled with the MacVector 3.5 software or AssemblyLIGN packages. Nucleotide and derived amino acid sequences were compared with those in the European Molecular Biology Laboratory (EMBL) and SwissProt databases using the BLAST and FASTA programs of the GCG package from the University of Wisconsin (version 8) (20) on the network service at the Human Genome Mapping Project Resource Center, Hinxton, UK.

Virulence Tests. Groups of five female BALB/c mice (20–25g) were inoculated orally (p.o.) or intraperitoneally (i.p.) with 10-fold dilutions of bacteria suspended in physiological saline. For preparation of the inoculum, bacteria were grown overnight at 37° C. in LB broth with shaking (50 rpm) and then used to inoculate fresh medium for various lengths of time until an optical density (OD) at 560 nm of 0.4 to 0.6 had been reached. For cell densities of $5 \times 10^8$ colony forming units (cfu) per ml and above, cultures were concentrated by centrifugation and resuspended in saline. The concentration of cfu/ml was checked by plating a dilution series of the inoculum onto LB agar plates. Mice were inoculated i.p. with 0.2 ml volumes and p.o. by gavage with the same volume of inoculum. The $LD_{50}$ values were calculated after 28 days by the method of Reed and Meunch (21).

Results

Localisation of Transposon Insertions. The generation of a bank of *Salmonella typhimurium* mini Tn5 transposon mutants and the screen used to identify 43 mutants with attenuated virulence have been described previously (5). Transposons and flanking DNA regions were cloned from exconjugants by selection for kanamycin resistance or by inverse PCR. Nucleotide sequences of 300–600 bp of DNA flanking the transposons were obtained for 33 mutants. Comparison of these sequences with those in the DNA and protein databases indicated that 14 mutants resulted from transposon insertions into previously known virulence genes, 7 arose from insertions into new genes with similarity to known genes of the enterobacteria and 12 resulted from insertions into sequences without similarity to entries in the DNA and protein databases (ref. 5, Example 1 and this Example).

Three lines of evidence suggested that 16 of 19 transposon insertions into new sequences were clustered in three regions of the genome, initially designated A, B and C. First, comparing nucleotide sequences from regions flanking transposon insertion points with each other and with those in the databases showed that some sequences overlapped with one another or had strong similarity to different regions of the same gene. Second, Southern analysis of genomic DNA digested with several restriction enzymes and probed with restriction fragments flanking transposon insertion points indicated that some transposon insertions were located on the same restriction fragments. Third, when the same DNA probes were hybridised to plaques from a *S. typhimurium* λ DNA library, the probes from mutants which the previous two steps had suggested might be linked were found to hybridise to the same λ DNA clones. Thus two mutants (P9B7 and P12F5) were assigned to cluster A, five mutants (P2D6, P9B6, P11C3, P11 D10 and P11H10) to cluster B and nine mutants (P3F4, P4F8, P7A3, P7B8, P7G2, P8G12, P9G4, P10E11 and P11B9) to cluster C (FIG. 8).

Hybridisation of DNA probes from these three clusters to lysates from a set of *S. typhimurium* strains harboring locked-in Mud-P22 prophages (15, 16) showed that the three loci were all located in the minute 30 to 31 region (edition VIII, ref. 22) (FIG. 7), indicating that the three loci were closely linked or constituted one large virulence locus. To determine if any of the λ clones covering clusters A, B and C contained overlapping DNA inserts, DNA fragments from the terminal regions of each clone were used as probes in Southern hybridisation analysis of the other λ clones. Hybridising DNA fragments showed that several λ clones overlap and that clusters A, B and C comprise one contiguous region (FIG. 8). DNA fragments from the ends of this region were then used to probe the λ library to identify further clones containing inserts representing the adjacent regions. No λ clones were identified that covered the extreme right hand terminus of the locus so this region was obtained by cloning a 6.5 kb EcoRI/XbaI fragment from a lysate of the Mud-P22 prophage strain T[15244 (16).

Restriction mapping and Southern hybridisation analysis were then used to construct a physical map of this locus (FIG. 8). To distinguish this locus from the well characterised inv/spa gene cluster at minute 63 (edition VIII, ref. 22) (8, 9, 23, 24, 25, 26), we refer to the latter as virulence gene cluster 1 (VGC 1) and have termed the new virulence locus VGC2. FIG. 2 shows the position of two portions of DNA whose nucleotide sequence has been determined ("Sequence 1"and "Sequence 2"). The nucleotide sequence is shown in FIGS. 11 and 12.

Mapping the boundaries of VGC2 on the *S. typhimurium* chromosome. Nucleotide sequencing of λ clone 7 at the left hand side of VGC2 revealed the presence of an open reading frame (ORF) whose deduced amino acid sequence is over 90% identical to the derived product of a segment of the ydhE‡ gene of *E. coli* and sequencing of the 6.5 kb EcoRI/XbaI cloned fragment on the right hand side of VGC2 revealed the presence of an ORF whose predicted amino acid sequence is over 90% identical to pyruvate kinase I of *E. coli* encoded by the pykF gene (27). On the *E. coli* chromosome ydhE and pykF are located close to one another, at minute 37 to 38 (28). Eleven non-overlapping DNA fragments distributed along the length of VGC2 were used as probes in non-stringent Southern hybridisation analysis of *E coli* and *S. typhimurium* genomic DNA. Hybridising DNA fragments showed that a region of approximately 40 kb comprising VGC2 was absent from the *E. coli* genome and localised the boundaries of VGC2 to within 1 kb (FIG. 9). Comparison of the location of the XbaI site close to the right hand end of VGC2 (FIG. 8) with a map of known XbaI sites (29) at the minute 30 region of the chromosome (22) enables a map position of 30.7 minutes to be deduced for VGC2.

Structure of VGC2. Nucleotide sequencing of portions of VGC2 has revealed the presence of 19 ORFs (FIG. 8). The G+C content of approximately 26 kb of nucleotide sequence within VGC2 is 44.6%, compared to 47% for VGC1 (9) and 51–53% estimated for the entire Salmonella genome (30).

The complete deduced amino acid sequences of ORFs 1–11 are similar to those of proteins of type III secretion systems (6, 7), which are known to be required for the export of virulence determinants in a variety of bacterial pathogens of plants and animals (7). The predicted proteins of ORFs 1 –8 (FIG. 8) are similar in organisation and sequence to the products of the yscN-U genes of *Yersinia pseudotuberculosis* (31), to invC/spaS of the inv/spa cluster in VGC 1 of *Salmonella typhimurium* (8, 9) and to spa47/spa40 of the spa/mxi cluster of *Shigella flexneri* (32, 33, 34, 35,). For example the predicted amino acid sequence of ORF 3 (FIG. 8) is 50% identical to YscS of *Y. pseudotuberculosis* (31), 34% identical to Spa9 from *S. flexneri* (35) and 37% identical to SpaQ of VGC1 of *S. typhimurium* (9). The predicted protein product of ORF9 is closely related to the LcrD family of proteins with 43% identity to, LcrD of *Y. enterocolitica* (36), 39% identity to MxiA of *S. fiexneri* (32) and 40% identity to InvA of VGC1 (23). Partial nucleotide sequences for the remaining ORFs shown in FIG. 8 indicate that the predicted protein from ORF10 is most similar to *Y. enterocolitica* YscJ (37) a lipoprotein located in the bacterial outer membrane, with ORF11similar to *S. typhimurium* InvG, a member of the PulD family of translocases (38). ORF12 and ORF13 show significant similarity to the sensor and regulatory subunits respectively, from a variety of proteins comprising two component regulatory systems (39). There is ample coding capacity for further genes between ORFs 9 and 10, ORFs 10 and 11, and between ORF 19 and the right hand end of VGC2.

VGC2 is conserved among and is specific to the Salmonellae. A 2.2 kb PstI/HindIII fragment located at the center of VGC2 (probe B, FIG. 8) lacking sequence similarity to entries in the DNA and protein databases was used as a probe in Southern hybridisation analysis of genomic DNA from Salmonella serovars and other pathogenic bacteria (FIG. 10A). DNA fragments hybridising under non-stringent conditions showed that VGC2 is present in *S. aberdeen, S. gallinarum, S. cubana, S. typhi* and is absent from EPEC, EHEC, *Y. pestis, S. flexneri, V cholera* and *S. aureus*. Thus VGC2 is conserved among and is likely to be specific to the Salmonellae.

To determine if the organisation of the locus is conserved among the Salmonella serovars tested, stringent Southern hybridisations with genomic DNA digested with two further restriction enzymes were carried out. Hybridising DNA fragments showed that there is some heterogeneity in the arrangement of restriction sites between *S. typhimurium* LT2 and *S. gallinarum, S. cubana* and *S. typhi* (FIG. 10B). Furthermore, *S. gallinarum* and *S. typhi* contain additional hybridising fragments to those present in the other Salmonellae examined, suggesting that regions of VGC2 have been duplicated in these species.

VGC2 is required for virulence in mice. Previous experiments showed that the $LD_{50}$ values for i.p. inoculation of transposon mutants P3F4, P7G2, P9B7 and P11C3 were at least 100-fold greater than the wild type strain (5). In order to clarify the importance of VGC2 in the process of infection, the p.o. and i.p. $LD_{50}$ values for mutants P3F4 and P9B7 were determined (Table 1). Both mutants showed a reduction in virulence of at least five orders of magnitude by either route of inoculation in comparison with the parental strain. This profound attenuation of virulence by both routes of inoculation demonstrates that VGC2 is required for events in the infective process after epithelial cell penetration in BALB/c mice.

TABLE 1

$LD_{50}$ values of *S. typhimurium* strains.

| Strain | $LD_{50}$ (cfu) i.p. | $LD_{50}$ (cfu) p.o. |
|---|---|---|
| 12023 wild type | 4.2 | $6.2 \times 10^4$ |
| P3F4 | $1.5 \times 10^6$ | $>5 \times 10^9$ |
| P9B7 | $>1.5 \times 10^6$ | $>5 \times 10^9$ | cfu, colony forming units

Discussion A hitherto unknown virulence locus in *S. typhimurium* of approximately 40 kb located at minute 30.7 on the chromosome by mapping the insertion points of a group of signature-tagged transposon mutants with attenuated virulence has been identified (5). This locus is referred to as virulence gene cluster 2 (VGC2) to distinguish it from the inv/spa virulence genes at 63 minutes (edition VIII, ref. 22) which we suggest be renamed VGC1. VGC1 and VGC2 both encode components of type III secretion systems. However, these secretion systems-are functionally distinct. cfu, colony forming units Of 19 mutants that arose from insertions into new genes (ref. 5 and this example) 16 mapped to the same region of the chromosome. It is possible that mini-Tn5 insertion occurs preferentially in VGC2. Alternatively, as the negative selection used to identify mutants with attenuated virulence (5) was very stringent (reflected by the high LD50 values for VGC2 mutants) it is possible that, among the previously unknown genes, only mutations in those of VGC2 result in a degree of attenuation sufficient to be recovered in the screen. The failure of previous searches for *S. typhimurium* virulence determinants to identify VGC2 might stem from reliance on cell culture assays rather than a live animal model of infection. A previous study which identified regions of the *S. typhimurium* LT2 chromosome unique to Salmonellae (40) located one such region (RF333) to minutes 30.5–32. Therefore, RF333 may correspond to VGC2, although it was not known that RF333 was involved in virulence determination.

Comparisons with the type III secretion systems encoded by the virulence plasmids of Yersinia and Shigella as well as with VGC1 of Salmonella indicates that VGC2 encodes the basic structural components of the secretory apparatus. Furthermore, the order of ORFs 1–8 in VGC2 is the same as the gene order in homologues in Yersinia, Shigella and VGC1 of *S. typhimurium*. The fact that the organisation and structure of the VGC2 secretion system is no more closely related to VGC1 than to the corresponding genes of Yersinia, together with the low G+C content of VGC2 suggests that VGC2, like VGC1 (40, 41, 42) was acquired independently by *S. typhimurium* via horizontal transmission. The proteins encoded by ORFs 12 and 13 show strong similarity to bacterial two component regulators (39) and could regulate either ORFs 1–11 and/or the secreted proteins of this system.

Many genes in VGC1 have been-shown to be important for entry of *S. typhimurium* into epithelial cells. This process requires bacterial contact (2) and results in cytoskeletal rearrangements leading to localised membrane ruffling (43, 44). The role of VGC1 and its restriction to this stage of the infection is reflected in the approximately 50-fold attenuation of virulence in BALB/c mice inoculated p.o. with VGC1 mutants and by the fact that VGC1 mutants show no loss of virulence when administered i.p. (8). The second observation also explains why no VGC1 mutants were obtained in our screen (5). In contrast, mutants in VGC2 are profoundly attenuated following both p.o. and i.p. inoculation. This shows that, unlike VGC1, VGC2 is required for virulence in mice after epithelial cell penetration, but these findings do not exclude a role for VGC1 in this early stage of infection.

Thus in summary mapping the insertion points of 16 signature-tagged transposon mutants on the *Salmonella typhimurium* chromosome led to the identification of a 40 kb virulence gene cluster at minute 30.7. This locus is conserved among all other Salmonella species examined, but not present in a variety of other pathogenic bacteria or in *Escherichia coli* K12. Nucleotide sequencing of a portion of this locus revealed 11 open reading frames whose predicted proteins encode components of a type III secretion system. To distinguish between this and the type III secretion system encoded by the inv/spa invasion locus we refer to the inv/spa locus as virulence gene cluster 1 (VGC1) and the new locus as VGC2. VGC2 has a lower G+C content than that of the Salmonella genome and is flanked by genes whose products share greater than 90% identity with those of the *E. coil* ydhE and pykF genes. Thus VGC2 was probably acquired horizontally by insertion into a region corresponding to that between the ydhE and pykF genes of *E. coli*. Virulence studies of VGC2 mutants have shown them to be attenuated by at least five orders of magnitude compared with the wild type strain following oral or intraperitoneal inoculation.

References for This Example

1. Carter, P. B. & Collins, F. M. (1974) *J. Exp. Med.* 139, 1189–1203.
2. Takeuchi, A. (1967) *Am. J. Pathol.* 50, 109–136.
3. Finlay, B. B. (1994) *Curr. Top. Microbiol. Immunol.* 192, 163–185.
4. Groisman, E. A. & Ochman, H. (1994) *Trends Microbiol.* 2, 289–293.
5. Hensel, M., Shea, J. E., Gleeson, C., Jones, M. D., Dalton, E. & Holden, D. W. (1995) *Science* 269, 400–403.
6. Salmond, G. P. C. & Reeves, P. J. (1993) *Trends Biochem. Sci.* 18, 7–12.
7. Van Gijsegem, F., Genin., S. & Boucher, C. (1993) *Trends Microbiol.* 1, 175–180.
8. Galan, J. E. & Curtiss, R. (1989) *Proc. Natl. Acad. Sci. U.S.A.* 86, 6383–6387.
9. Groisman, E. A. & Ochman, H. (1993) *EMBO J.* 12, 3779–3787.
10. Ginocchio, C. C., Olmsted, S. B., Wells, C. L. & Galan, J. E. (1994) *Cell* 76, 717–724.
11. de Lorenzo, V. & Timmis, K. N. (1994) *Methods Enzymol.* 264, 386–405.
12. Davis, R. H., Botstein, D. & Roth, J. R. (1980) *Advanced Bacterial Genetics*, Cold Spring Harbor Laboratory, Cold Spring Harbor, N.Y.
13. Ausubel, F. M., Brent, R., Kingston, R. E., Moore, D. D., Seidman, J. G., Smith, J. A. and Struhl, K. (1987) *Current Protocols in Molecular Biology* Vol 4 John Wiley and Sons, Inc, New York.
14. Maurer, R., Osmond, B. C., Shekhtman, E., Wong, A. & Botstein, D. (1984) *Genetics* 108, 1–23.
15. Youderain, P., Sugiono, P., Brewer, K. L., Higgins, N. P. & Elliott, T. (1988) *Genetics* 118, 581–592.
16. Benson, N. R. & Goldman, B. S. (1992) *J. Bacteriol.* 174, 1673–1681.
17. Holden, D. W., Kronstad, J. W. & Leong, S. (1989) *EMBO J.* 8, 1927–1934.
18. Sambrook, J., Fritsch, E. F. & Maniatis, T. (1989) *Molecular cloning: a laboratory manual* (Cold Spring Harbor Laboratory, Cold Spring Harbor, N.Y.).
19. Sanger, F., Nicklen, S. & Coulson, A. R. (1977) *Proc. Natl. Acad. Sci. U.S.A.* 74, 5463–5467.
20. Devereux, J., Hearberli, P. & Smithies, O. (1984) *Nucl. Acids Res.* 12, 387–399.
21. Reed, L. J. & Muench, H. (1938) *Am. J. Hyg.* 27, 493–497.
22. Sanderson, K. E., Hessel, A. & Rudd, K. E. (1995) *Microbiol. Rev.* 59, 241–303.
23. Galan, J. E., Ginocchio, C. & Costeas, P. (1992) *J. Bacteiol.* 174, 4338–4349.
24. Ginocchio, C., Pace, J. & Galan, J. E. (1992) *Proc. Natl. Acad. Sci. U.S.A.* 89, 5976–5980.
25. Eichelberg, K., Ginocchio, C. C. & Galan, J. E. (1994) *J. Bacterol.* 176, 4501–4510.
26. Collazo, C. M., Zierler, M. K. & Galan, J. E. (1995) *MoL Microbiol.* 15, 25–38.
27. Ohara, O., Dorit, R. L. & Gilbert, W. (1989) *Proc. Natl. Acad. Sci. USA* 86, 6883–6887.
28. Bachman, B. (1990) *Micro. Rev.* 54, 130–197.
29. Liu, S. L., Hessel, A. & Sanderson, K. E. (1993) *J. Bacteriol.* 175, 4104–4120.
30. Fasman, G. D. (1976) *CRC Handbook of Biochemistry and Molecular Biology*, CRC Press, Cleveland.
31. Bergman, T., Erickson, K., Galyov, E., Persson, C. & Wolf Watz, H. (1994) *J. Bacteriol.* 176, 2619–2626.
32. Andrews, G. P. & Maurelli, A. T. (1992) *Infect. Immun.* 60, 3287–3295.
33. Allaoui, A., Sansonetti, P. J. & Parsot, C. (1993) *Mol. Microbiol.* 7, 59–68.
34. Venkatesan, M., Buysse, J. M. & Oaks, E. V. (1992) *J. Bacteriol.* 174, 1990–2001.
35. Sasakawa, C., Komatsu, K., Tobe, T., Suzuki, T. & Yoshikawa, M. (1993) *J. Bacteriol.* 175, 2334–2346.
36. Plano, G. V., Barve, S. S. & Straley, S. C. (1991) *J. Bacteriol.* 173, 7293–7303.
37. Michiels, T., Vanooteghem, J. C., Lambert de Rouvroit, C., China, B., Gustin, A., Boudry, P. & Cornelis, G. R. (1991) *J. Bacteriol.* 173, 4994–5009.
38. Kaniga, K., Bossio, J. C. & Galan, J. E. (1994) *Mol. Microbiol.* 13, 555–568.
39. Ronson, C. W., Nixon, B. T. & Ausubel, F. M. (1987) *Cell* 49, 579–581.
40. Groisman, E. A., Sturmoski, M. A., Solomon, F. R., Lin, R. & Ochman, H. (1993) *Proc. Natl. Acad. Sci. U.S.A.* 90, 1033–1037.
41. Altmeyer, R. M., McNern, J. K., Bossio, J. C., Rosenshine, I., Finlay, B. B. & Galan, J. E. (1993) *Mol. Microbiol.* 7, 89–98.
42. Li, J., Ochman, H., Groisman, E. A., Boyd, E. F., Soloman, F., Nelson, K. & Selander, R. K. (1995) *Proc. Natl. Acad. Sci. USA* 92, 7252–7256.
43. Finlay, B. B. & Rauschkowski, S. (1991) *J. Cell Sci.* 99, 283–296.
44. Francis, C. L., Starnbach, M. N. & Falkow, S. (1992) *Mol. Microbiol.* 6, 3077–3087.

EXAMPLE 5

Identification of Virulence Genes in Streptococcus Pneumoniae (a) Mutagenesis

In the absence of a convenient transposon system, the most efficient way of creating tagged mutants of *Streptococcus pneumoniae* is to use insertion-duplication mutagenesis (Morrison et al (1984) *J. Bacteriol.* 159, 870). Random *S. pneumoniae* DNA fragments of 200–400 bp will be generated by genomic DNA digestion with a restriction enzyme or by physical shearing by sonication followed by gel fractionation and DNA end-repair using T4 DNA polymerase. The fragments are ligated into plasmid pJDC9

(Pearce et al (1993) *Mol. Microbiol.* 9, 1037 which carries the erm gene for erythromycin selection in *E. coli* and *S. pneumoniae*), previously modified by incorporation of DNA sequence tags into one of the polylinker cloning sites. The size of cloned *S. pneumoniae* DNA is sufficient to ensure homologous recombination, and reduces the possibility of generating an unrepresentative library in *E. coli* (expression of *S. pneumoniae* proteins can be toxic to *E. coli*). Alternative vectors carrying different selectable markers are available and can be used in place of pJDC9. Tagged plasmids carrying DNA fragments are introduced to an appropriate *S. pneumoniae* strain selected on the basis of serotype and virulence in a murine model of pneumococcal pneumonia. Regulation of competence for genetic transformation in *S. pneumoniae* is governed by competence factor, a peptide of 17 amino acids which has been characterized recently by Don Morrison's group at the University of Illinois at Chicago and which is described Havarstein, Coomaraswamy and Morrison (1995) *Proc. Natl. Acad. Sci. USA* 92, 11140–11144. Incorporation of minute quantities of this peptide in transformation experiments leads to very efficient transformation frequencies in some encapsulated clinical isolates of *S. pneumoniae*. This overcomes a major hurdle in pneumococcal molecular genetics and the availability of the peptide greatly facilitates the construction of *S. pneumoniae* mutant banks and allows flexibility in choosing the strain(s) to be mutated. A proportion of transformants are analysed to verify homologous integration of the plasmid sequences, and checked for stability. The very low level of reversion associated with mutants generated by insertion-duplication is minimized by the fact that the duplicated regions will be short (200–400 bp); however if the level of reversion is unacceptably high, antibiotic selection is maintained during growth of the transformants in culture and during growth in the animal.

(b) Animal model

The *S. pneumoniae* mutant bank is organized into pools for inoculation into Swiss and/or C57B1/6 mice. Preliminary experiments are conducted to determine the optimum complexity of the pools and the optimum inoculum level. One attractive model utilises inocula of $10^5$ cfu, delivered by mouth to the trachea (Veber et al (1993) *J. Antimicrobial Chemotherapy* 32, 473). Swiss mice develop acute pneumonia within 3–4 days, and C57B1/6 mice develop subacute pneumonia within 8–10 days. These pulmonary models of infection yield 108 cfu/lung (Veber et al (1993) *J. Antimicrobial Chemotherapy* 32, 473) at the time of death. If required, mice are also injected intraperitoneally for the identification of genes required for bloodstream infection (Sullivan et al (1993) *Antimicrobial Agents and Chemotherapy* 37, 234).

(c) Virulence Gene Identification

Once the parameters of the infection model are optimized, a mutant bank consisting of several thousand strains is subjected to virulence tests. Mutants with attenuated virulence are identified by hybridisation analysis, using labelled tags from the 'input' and 'recovered' pools as probes. If *S. pneumoniae* DNA cannot be colony blotted easily, chromosomal DNA is liberated chemically or enzymatically in the wells of microtitre dishes prior to transfer onto nylon membranes using a dot-blot apparatus. DNA flanking the integrated plasmid is cloned by plasmid rescue in *E. coli* (Morrison et al (1984) *J. Bacteriol.* 159, 870), and sequenced. Genomic DNA libraries are constructed in appropriate vectors maintained in either *E. coli* or a Gram-positive host strain, and are probed with restriction fragments flanking the integrated plasmid to isolate cloned virulence genes which is then fully sequenced and subjected to detailed functional analysis.

EXAMPLE 6

Identification of Virulence Genes in Enterococcus Faecalis (a) Mutagenesis Mutagenesis of *E. faecalis* is accomplished using plasmid pAT112 or a derivative, developed for this purpose. pAT112 carries genes for selection in both Gram-negative and Gram-positive bacteria, and the att site of Tn1545. It therefore requires the presence in the host strain of the integrase for transposition, and stable, single copy insertions are obtained if the host does not contain an excisionase gene (Trieu-Cuot et al (1991) *Gene* 106, 21). Recovery of DNA flanking the integrated plasmid is accomplished by restriction digestion of genomic DNA, intramolecular ligation and transformation of *E. coli*. The presence of single sites for restriction enzymes in pAT 112 and its derivatives will (Trieu-Cuot et al (1991) *Gene* 106, 21) allows the incorporation of DNA sequence tags prior to transfer to a virulent strain of *E. faecalis* carrying plasmid pAT145 (to provide the integrase function) by either conjugation, electroporation or transformation (Trieu-Cuot et al (1991) Gene 106, 21; Wirth et al (1986) *J. Bacteriol.* 165, 831).

(b) Animal model

A large number of insertion mutants are analysed for random integration of the plasmid by isolating DNA from transcipients, restriction enzyme digestion and Southern hybridisation. Individual mutants are stored in the wells of microtitre dishes, and complexity and size of pooled inocula are optimised prior to screening of the mutant bank. Two different models of infection caused by *E. faecalis* are employed. The first is a well established rat model of endocarditis, involving tail vein injection of up to $10^8$ cfu of *E. faecalis* into animals that have a catheter inserted across the aortic valve (Whitman et al (1993) *Antimicrobial Agents and Chemotherapy* 37, 1069). Animals are sacrificed at various times after inoculation, and bacterial vegetations on the aortic valve are excised, homogenized and plated to culture medium to recover bacterial colonies. Virulent bacteria are also recovered from the blood at various times after inoculation. The second model is of peritonitis in mice, following intraperitoneal injection of up to $10^9$ cfu of *E. faecalis* (Chenoweth et al (1990) *Antimicrobial Agents and Chemotherapy* 34, 1800). As with the *S. pneumoniae* model, preliminary experiments are done to establish the optimum complexity of the pools and the optimum inoculum level, prior to screening the mutant bank.

(c) Virulence gene identification

Isolation of DNA flanking the site of integration of pAT112 using its *E. coli* origin of replication is simplified by the lack of sites for most of the commonly used 6 bp recognition restriction enzymes in the vector. Therefore DNA from the strains of interest are digested with one of these enzymes, self-ligated, transformed into *E. coli* and sequenced using primers based on the sequences adjacent to the att sites on the plasmid. A genomic DNA library of *E. faecalis* are probed with sequences of interest to identify intact copies of virulence genes which are then sequenced.

EXAMPLE 7

Identification of Virulence Genes in *Pseudomonas aerulinosa*

(a) Mutagenesis

Since transposon Tn5 has been used by others to mutagenise *Pseudomonas aeruginosa*, and the mini-Tn5 derivative that was used for the identification of *Salmonella typhimurium* virulence genes (Example 1) is reported to have broad utilisation among Gram-negative bacteria, including several pseudomonads (DeLorenzo and Timaris (1994) *Methods Enzymol.* 264, 386), a *P. aeruginosa* mutant bank is constructed using our existing pool of signature tagged mini-Tn5 transposons by conjugal transfer of the suicide vector to one or more virulent (and possibly mucoid) recipient strains. This approach represents a significant time saving. Other derivatives of Tn5 designed specifically for *P. aeruginosa* mutagenesis (Rella et al (1985) *Gene* 33, 293), may alternatively be employed with the mini Tn5 transposon.

(b) Animal model and virulence gene identification

The bank of *P. aeruginosa* insertion mutants is screened for attenuated virulence in a chronic pulmonary infection model in rats. Suspensions of *P. aeruginosa* cells are introduced into a bronchus following tracheotomy, and disease develops over a 30 day period (Woods et al (1982) *Infect. Immun.* 36, 1223). Bacteria are recovered by plating lung homogenates to laboratory medium and sequence tags from these are used to probe DNA colony blots of bacteria used as the inoculum. It is also possible to subject the mutant bank to virulence tests in a model of endogenous bacteremia (Hirakata et al (1992) *Antimicrobial Agents and Chemotherapy* 36, 1198), and cystic fibrosis (Davidson et al (1995) *Nature Genetics* 9, 351) in mice. Cloning and sequencing of DNA flanking the transposons is done as described in Example 1. Genomic DNA libraries for the isolation and sequencing of intact copies of the genes are constructed in the laboratory by standard methods.

EXAMPLE 8

Identification of Virulence Genes in *Aspergillus fumigatus*

(a) Mutagenesis

The functional eqiuvalent of transposon mutagenesis in fungi is restriction enzyme mediated integration (REMI) of transforming DNA (Schiestl and Petes (1991) *Proc. Natl. Acad. Sci.* 88, 7585). In this process, fungal cells are transformed with DNA fragments carrying a selectable marker in the presence of a restriction enzyme, and single copy integrations occur at different genomic sites, defined by the target sequence of the restriction enzyme. REMI has already been used successfully to isolate virulence genes of Cochliobolus (Lu et al (1994) *Proc. Natl. Acad. Sci. USA* 91, 12649) and Ustilago (Bolker et al (1995) *Mol. Gen. Genet.* 248, 547), and have shown that incorporation of active restriction enzyme with a plasmid encoding hygromycin resistance leads to single and apparently random integration of the linear plasmid into the *A. fumigatus* genome. Sequence tags are introduced into a convenient site in one of two vectors for hygromycin resistance, and used to transform a clinical isolate of *A. fumigatus*.

(b) Animal Model and Virulence Gene Identification

The low-dose model of aspergillosis in neutropenic mice in particular closely matches the course of pulmonary disease in humans (Smith et al (1994) *Infect. Immun.* 62, 5247). Mice are inoculated intranasally with up to 1,000,000 conidiospores/mouse, and virulent fungal mutants are recovered 7–10 days later by using lung homogenates to inoculate liquid medium. Hyphae are collected after a few hours, from which DNA is extracted for amplification and labelling of tags to probe colony blots of DNA from the pool of transformants comprising the inoculum. DNA from the regions flanking the REMI insertion points are cloned by digesting the transformant DNA with a restriction enzyme that cuts outside the REMI vector, self ligation and transformation of *E. coli*. Primers based on the known sequence of the plasmid are used to determine the adjacent *A. fumigatus* DNA sequences. To prove that the insertion of the vector was the cause of the avirulent phenotype, the recovered plasmid is recut with the same restriction enzyme used for cloning, and transformed back into the wild-type *A. fumigatus* parent strain. Transformants that have arisen by homologous recombination are then subjected to virulence tests.

REFERENCES (other than for Example 4)

Ausubel, F. M., Brent, R., Kingston, R. E., Moore, D. D., Seidman, J. G., Smith, J. A. and Struhl, K. (1987) *Current Protocols in Molecular Biology*, New York: John Wiley and Sons.

Buchmeier, N. A., Lipps, C. J., So, M. Y. and Heffron, F. (1993) Recombination-deficient mutants of *Salmonella typhimurium* are avirulent and sensitive to the oxidative burst of macrophages. *Mol. Microbiol.* 7, 933–936.

Carter, P. B. and Collins, F. M. (1974) The route of enteric infection in normal mice. *J. Exp. Med.* 139, 1189–1203.

de Lorenzo, V. and Timmis, K. N. (1994) Analysis and construction of stable phenotypes in Gram-negative bacteria with Tn5- and Tn10-derived minitransposons. *Meth ods Enzymol.* 264, 386–405.

de Lorenzo, V., Herrero, M., Jakubzik, U. and Timmis, K. N. (1990) Mini-Tn5 transposon derivatives for insertion mutagenesis, promoter probing, and chromosomal insertion of cloned DNA in gram-negative eubacteria. *J. Bacteriol.* 172, 6568–6572.

Fields, P. I., Groisman, E. A. and Heffron, F. (1989) A Salmonella locus that controls resistance to microbicidal proteins from phagocytic cells. *Science* 243, 1059–1062.

Finlay, B. B., Starnbach, M. N., Francis, C. L., Stocker, B. A., Chatfield, S., Dougan, G. and Falkow, S. (1988) Identification and characterization of TnphoA mutants of Salmonella that are unable to pass through a polarized MDCK epithelial cell monolayer. *Mol. Microbiol.* 2, 757–766.

Groisman, E. A., Chiao, E., Lipps, C. J., Heffron, F. (1989) *Salmonella typhimurium* phoP virulence gene is a transcriptional regulator. *Proc. Natl. Acad. Sci. USA.* 86, 7077–7081.

Groisman, E. A. and Ochman, H. (1994) How to become a pathogen. *Trends Microbiol.* 2, 289–293.

Groisman, E. A. and Saier, M. H., Jr. (1990) Salmonella virulence: new clues to intramacrophage survival. *Trends Biochem. Sci.* 15, 30–33.

Herrero, M., de Lorenzo, V. and Timmis, K. N. (1990) Transposon vectors containing non-antibiotic resistance selection markers for cloning and stable chromosomal insertion of foreign genes in Gram-negative bacteria. *J. Bacteriol.* 172, 6557–6567.

Holden D. W., Kronstad J. W., Leong S. A. (1989) Mutation in a heat-regulated hsp70 gene of *Ustilago maydis. EMBO J.* 8, 1927–1934.

Holland J., Towner K. J., Williams P. (1992) Tn916 insertion mutagenesis in *Eschefichia coli* and *Haemophilus influenzae* type b following conjugative transfer. *J. Gen. Microbiol.* 138, 509–515.

Mahan, M. J., Slauch, J. M., Mekalanos, J. J. (1993) Selection of bacterial virulence genes that are specifically induced in host tissues. *Science* 259, 686–688.

Miller, S. I., Kukral, A. M. and Mekalanos, J. J. (1989a) A two-component regulatory system (phoP phoQ) controls *Salmonella typhimurium* virulence. *Proc. Natl. Acad. Sci. USA.* 86, 5054–5058.

Miller, I., Maskell, D., Hormaeche, C., Johnson, K., Pickard, D. and Dougan, G. (1989b) Isolation of orally attenuated *Salmonella typhimurium* following TnphoA mutagenesis. *Infect. Immun.* 57, 2758–2763.

Miller, V. L. and Mekalanos, J. J. (1988) A novel suicide vector and its use in construction of invertion mutations: osmoregulation of outer membrane proteins and virulence determinants in *Vibrio cholerae* requires toxR. *J. Bacteriol.* 170, 2575–2583.

Sambrook, J., Fritsch, E. F. and Maniatis, T. (1989) *Molecular cloning: a laboratory manual*, Cold Spring Harbor, N.Y.: Cold Spring Harbor Laboratory.

Sanger, F., Nicklen, S. and Coulson, A. R. (1977) DNA sequencing with chain terminating inhibitors. *Proc. Natl. Acad. Sci. USA.* 74, 5463–5467.

Schiestl R. H., and Petes T. D. (1991) Integration of DNA fragments by illegitimate recombination in *Saccharomyces cerevisiae. Proc. Natl. Acad. Sci USA.* 88, 7585–7589.

---

I claim:

1. A method for identifying a microorganism having a reduced adaptation to a particular environment comprising the steps of:

(a) providing a plurality of microorganisms each of which is independently mutated by the insertional inactivation of a gene with a nucleic acid comprising a unique marker sequence so that each mutant contains a different marker sequence, or clones of the microorganism;

(b) providing individually a stored sample of each mutant produced by step (a) and providing individually stored nucleic acid comprising the unique marker sequence from each individual mutant;

(c) introducing a plurality of mutants produced by step (a) into the said particular environment and allowing those microorganisms which are able to do so to grow in the said environment;

(d) retrieving microorganisms from the said environment or a selected part thereof and isolating the nucleic acid from the retrieved microorganisms;

(e) comparing any marker sequences in the nucleic acid isolated in step (d) to the unique marker sequence of each individual mutant stored in step (b); and (f) selecting an individual mutant which does not contain any of the marker sequences isolated in step (d), wherein the microorganism is a pathogenic microorganism and wherein the environment is a differentiated multicellular organism or an animal or plant cell in culture.

2. The method of claim 1 wherein the plurality of microorganisms as defined in step (a) is produced from a plurality of microorganisms, each of which comprises a nucleic acid comprising a unique marker sequence, by changing their condition from a first given condition to a second given condition wherein (a) in the first given condition the nucleic acid comprising a unique marker is maintained episomally and (b) in the second given condition the nucleic acid comprising a unique marker sequence insertionally inactivates a gene.

3. The method of claim 1 further comprising after step (a), removing auxotrophs from the plurality of mutants produced in step (a).

4. The method of claim 1 further comprising the step:

(g) isolating the insertionally-inactivated gene from the individual mutant selected in step (f).

5. The method of claim 1 wherein the multicellular organism is a plant.

6. The method of claim 1 wherein the multicellular organism is a non-human animal.

7. The method of claim 1 wherein the environment is a differentiated multicellular organism and wherein in step (d)

the microorganisms are retrieved from the said environment at a site remote from the site of introduction in step (c).

8. The method of claim 1 wherein the microorganism is a bacterium.

9. The method of claim 1 wherein the microorganism is a fungus.

10. The method of claim 1 wherein in step (a) the gene is insertionally inactivated using a transposon or transposon like element or other DNA sequence carrying a unique marker sequence.

11. The method of claim 1 wherein in step (a) each unique marker sequence is flanked on either side by sequences common to each said nucleic acid.

12. The method of claim 1 further comprising after step (f), determining whether the mutant selected in step (f) is an auxotroph.

13. A microorganism obtained using the method of claim 1, 2, or 3.

14. The method of claim 4 further comprising the step: (h) isolating from a wild-type microorganism the corresponding wild-type gene using the insertionally-inactivated gene isolated in step (g) as a probe.

15. The method of claim 4 wherein the insertionally-inactivated gene is a virulence gene.

16. The method of claim 5 wherein the microorganism is a bacterium pathogenic to plants.

17. The method of claim 5 wherein the microorganism is a fungus pathogenic to plants.

18. The method of claim 6 wherein the animal is selected from the group consisting of a mouse, rat, rabbit, dog and monkey.

19. The method of claim 6 wherein in step (c) the microorganism is introduced orally or intraperitoneally.

20. The method of claim 6 wherein the microorganism is a bacterium pathogenic to animals.

21. The method of claim 6 wherein the microorganism is a fungus pathogenic to animals.

22. The method of claim 6 wherein the microorganism is Salmonella.

23. The method of claim 11 wherein in step (b) the nucleic acid comprising the unique marker sequence is isolated using DNA amplification techniques and oligonucleotide primers which hybridize to the said common sequences.

24. The method of claim 11 wherein in step (d) the nucleic acid is isolated using DNA amplification techniques and oligonucleotide primers which hybridize to the common sequences.

25. A gene obtained using the method of claim 4 or 14 which is isolated from *Salmonella typhimurium* genome and hybridizes to SEQ ID No 39 or 40 under stringent conditions.

26. A gene obtained using the method of claim 4 or 14 which is isolated from the *Salmonella typhimurium* genome and hybridizes to any one of SEQ ID Nos 8–36 under stringent conditions.

27. The method of claim 18 wherein the animal is a mouse.

28. The method of claim 19 wherein in step (d) the microorganisms are retrieved from the spleen.

29. The method of claim 20 wherein the bacterium is selected from the group consisting of *Bordetella pertussis, Campylobacter jejuni, Clostridium botulinum, Escherichia coli, Haemophilus ducreyi, Haemophilus influenzae, Helicobacter pylori, Klebsiella pneumoniae, Legionella pneumophila, Listeria spp., Neisseria gonorrhoeae, Neisseria meningitidis, Pseudomonas spp., Salmonella spp., Shigella spp., Staphylococcus aureus, Streptococcus pyogenes, Streptococcus pneumoniae, Vibrio spp.*, and *Yersinia pestis*.

30. The method of claim 21 wherein the fungus is selected from the group consisting of *Aspergillus spp., Cryptococcus neoformans* and *Histoplasma capsulatum*.

31. The method of claim 29 wherein the bacterium is Salmonella.

* * * * *

UNITED STATES PATENT AND TRADEMARK OFFICE
Certificate

Patent No. 5,876,931                                          Patented: March 2, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: David William Holden, London, United Kingdom; Jacqueline Elizabeth Shea, High Wycombe, United Kingdom; and Michael Hensel, Munich, Germany.

Signed and Sealed this Fourteenth Day of December, 1999.

GEORGE C. ELLIOTT, Ph. D.
*Supervisory Patent Examiner*
Technology Center 1600

UNITED STATES PATENT AND TRADEMARK OFFICE
CERTIFICATE OF CORRECTION

PATENT NO.    : 5,876,931
DATED         : March 2, 1999
INVENTOR(S)   : David William Holden, Jacqueline Elizabeth Shea and Michael Hensel It is certified that error appears in the above-identified patent and that said Letters Patent is hereby corrected as shown below:

<u>Title page,</u>
Items [86] and [87], should read as follows:

-- [86]  PCT No.:              PCT/GB95/02875
         Section 371 Date:     Jul. 19, 1996
         Section 102(e) Date:  Jul. 19, 1996

[87]  PCT Pub. No.:         WO96/17951
         PCT Pub. Date:        Jun. 13, 1996 --

Signed and Sealed this

Fourth Day of May, 2004

JON W. DUDAS
*Acting Director of the United States Patent and Trademark Office*

SEQUENCE LISTING ( 1 ) GENERAL INFORMATION:

( i i i ) NUMBER OF SEQUENCES: 501

( 2 ) INFORMATION FOR SEQ ID NO: 1:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Synthetic oligonucleotide ( x i ) SEQUENCE DESCRIPTION: SEQ ID NO: 1:

```
CTAGGTACCT ACAACCTCAA GCTTNKNKNK NKNKNKNKNK NKNKNKNKNK NKNKNKNKNK        60
NKNKAAGCTT GGTTAGAATG GGTACCATG                                         89
```

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Synthetic oligonucleotide ( x i ) SEQUENCE DESCRIPTION: SEQ ID NO: 2:

```
TACCTACAAC CTCAAGCT                                                     18
```

( 2 ) INFORMATION FOR SEQ ID NO: 3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: Synthetic oligonucleotide ( x i ) SEQUENCE DESCRIPTION: SEQ ID NO: 3:

CATGGTACCC ATTCTAAC                                                                          18

( 2 ) INFORMATION FOR SEQ ID NO: 4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Synthetic oligonucleotide ( x i ) SEQUENCE DESCRIPTION: SEQ ID NO: 4:

TACCCATTCT AACCAAGC                                                                          18

( 2 ) INFORMATION FOR SEQ ID NO: 5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Synthetic oligonucleotide ( x i ) SEQUENCE DESCRIPTION: SEQ ID NO: 5:

CTAGGTACCT ACAACCTC                                                                          18

( 2 ) INFORMATION FOR SEQ ID NO: 6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Synthetic oligonucleotide ( x i ) SEQUENCE DESCRIPTION: SEQ ID NO: 6:

CCTAGGCGGC CAGATCTGAT                                                                        20

( 2 ) INFORMATION FOR SEQ ID NO: 7:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (ii) MOLECULE TYPE: cDNA (iii) HYPOTHETICAL: NO (iii) ANTI-SENSE: NO (vi) ORIGINAL SOURCE:
  (A) ORGANISM: Synthetic oligonucleotide (xi) SEQUENCE DESCRIPTION: SEQ ID NO: 7:

GCACTTGTGT ATAAGAGTCA G                                                                                      21

(2) INFORMATION FOR SEQ ID NO: 8:

(i) SEQUENCE CHARACTERISTICS:
    (A) LENGTH: 300 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Partial sequence of Salmonella typhimurium
        virulence gene (xi) SEQUENCE DESCRIPTION: SEQ ID NO: 8:

GGTCTTAATG TACGGGCATG GTCTGCATCG ATAACTCCGG CACGCAAATC GCCATCGATA        60
CTCATTTGTT TGGCTGGCAT CCCATCAAGC GAGAAACGTG CGCTAACTTC CGCCACCCTC       120
TCGATACCTT TTGTAATGAC AATAAATTGC ACGATAGTAA TGATGGTAAA TACGACCAAC       180
CCAACGGTGA GATTTCCTCC TACGACAAAC TTACCGAAAG CATCCACAAA TATTACCGGC       240
ATTATGTTGT AACAGTACCC AGCCGTGATG TGCTGATTGG GGAGTTAACA ACCGATTTAT       300

(2) INFORMATION FOR SEQ ID NO: 9:

(i) SEQUENCE CHARACTERISTICS:
    (A) LENGTH: 300 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Partial sequence of Salmonella typhimurium
        virulence gene (xi) SEQUENCE DESCRIPTION: SEQ ID NO: 9:

GCGCGGACGC TAGTGTGGTG GGTGACAGCC AGACGTTACC GAACGGGATG GGGCAGATCT        60
GTTGGCTTAC AAAAGACATG GCCCATAAGG CGCAAGGTTT TGGGACTGGA CGTTTTCGCG       120
GGCAGACAAC GTATCTCTGT CTTATTAAAA TGTGTCCTGC TTCGGCATAT GTATCGAACC       180
CTCGGAGCAA AGTCGTTTGG GCGCAGAATT AGTACGTTTG GGTCGGTTGC TGTTATTCCT       240
TGGGCTCGGA AAAAGAGTGC CAGCGTGAAG GAGTGGGATT TGGCAGACTG GCCGCCTAAT       300

(2) INFORMATION FOR SEQ ID NO: 10:

(i) SEQUENCE CHARACTERISTICS:
    (A) LENGTH: 300 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Partial sequence of Salmonella typhimurium virulence gene (xi) SEQUENCE DESCRIPTION: SEQ ID NO: 10:

```
CACTATAGGG AAAGCTTGCA TGCCTGCAGG TCGACTCTAG AGGATCTACT AGTCATATGG      60
ATTGCACTTG TGTATAAGAG TCAGGATTAG AGGACATGCG CCGGGAACCA TACTATCTTT     120
TTCCGGTGCT TCGACGCCAT TTGCGGAAAC CACAGACTTT TTGCGGCGAA TGAGGATAAT     180
TGGCAATGCT AACAACGCTG AAAAGAAAGC GAGAGTGATA AAAGGAAAGC CAGGAATTAA     240
AGCGAGGAGC ATTAAAACCA CAGCGGCTAA TATGAGCGAC TGAGGTTGTC TGGCAATTTG     300
```

(2) INFORMATION FOR SEQ ID NO: 11:

(i) SEQUENCE CHARACTERISTICS:
    (A) LENGTH: 300 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Partial sequence of Salmonella typhimurium virulence gene (xi) SEQUENCE DESCRIPTION: SEQ ID NO: 11:

```
TGCAGGCCGA CTCTAGAGGA TCCCCGGGTA CCGGTAATTT CTTTAACCTC GCATCCCGGT      60
GGATGAAAGG ATATTCTGGC TGCGTAAGTA ATGAATGAAC CGCCCAGTAG ATAAATATT      120
GAAAGTGATA ACCTGATGTT TTAATAACGA TGCAGGATAT ACATATAACA TGCTGGCATC     180
AAACCAGGTA AGCAAATCAT ATTGTGCTGC CAGGTTATTC AAACTATCGA CCGGTGGTCC     240
AGGCGGGAAT TTTTCCACTA AATGTAGGTG GGATCAATGG GCTAATTGGT ATAGGCGGAT     300
```

(2) INFORMATION FOR SEQ ID NO: 12:

(i) SEQUENCE CHARACTERISTICS:
    (A) LENGTH: 324 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Partial sequence of Salmonella typhimurium virulence gene (xi) SEQUENCE DESCRIPTION: SEQ ID NO: 12:

```
CCTGTGATTC    CGGATGAAAT    AGCTTTTACG    AAAGCTGTCA    GACNTGCTGA    AGAATACGCT         60

GCAAATGGTA    AGCTTGTAAC    TTTTGGGTAT    TGTTCCAACG    CATGCTGAAA    CGGGTTATGG        120

ATATATTCGT    CGCGGTGAGT    TGATAGGAAA    TGACGCTTAT    GCAGTGGCTG    AATTTGTGGA        180

GAAACCGGAT    ATCGATACCG    CCCGTGACTA    TTTCAAATCA    GGGGAAATAT    TACTGGCCTA        240

GCGGCGATGT    TTTTATTTCG    CGCAAAGCCC    TTATTTAAAC    GAATTAAACG    TATCTATCAC        300

CCCCAAATTC    ATACAGCTTG    TGAA                                                       324
```

( 2 ) INFORMATION FOR SEQ ID NO: 13:

( i ) SEQUENCE CHARACTERISTICS:
        ( A ) LENGTH: 292 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium
            virulence gene ( x i ) SEQUENCE DESCRIPTION: SEQ ID NO: 13:

```
TTACTAAACA    GGGCCCCGGA    CCATGTAAAC    ACCACGCTTG    CCAACACTAA    AAAACGATGC         60

TTGCCGTAAA    AAAATTGAAC    GTTATTTACT    TAATACGCCT    ATTTTATTTA    CATTATGCAC        120

GGACAGAGGG    TGAGGATTAA    ATGGATAATA    TTGATAATAA    GTATACTCCA    CAGCTATGTA        180

AAATTTTGGG    GGCTATATCG    GATTGGTTG     TTTTTAATTT    AGCCTTATGG    CTTTCACTAG        240

GATGTGTCTA    TTTTTTTTGT    GGTCAAGCAC    AGAGATTTAT    TCCCCAACCA    CC                292
```

( 2 ) INFORMATION FOR SEQ ID NO: 14:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium
            virulence gene ( x i ) SEQUENCE DESCRIPTION: SEQ ID NO: 14:

```
TTTCCTTGCC    GTGACAGTCC    GGGATGCGAG    GTTAACGAAA    TTACCGGCAC    CAAAGCTGTG         60

GAGGTGAGCG    GTGTCCCCAG    CTGCCTGACT    CGTATTAGTC    AATTAGCTTC    AGTGCTGGAT        120

AATGCGTTAA    TCAAACGAAA    AGACAGTGCG    GTGAGTGTAA    GTATATACAC    GCTTAAGTAT        180

GCCACTGCGA    TGGATACCCA    GTACCATTAT    CGCGATCAGT    CCGTCGTGGT    TCCAGGGGTC        240

GCCTAGTGTA    TTGCGTGAGA    TGAGTAACAC    CAGCGTCCCG    ACGTCATCGA    CGAACAATGG        300
```

( 2 ) INFORMATION FOR SEQ ID NO: 15:

( i ) SEQUENCE CHARACTERISTICS:
        ( A ) LENGTH: 297 base pairs
        ( B ) TYPE: nucleic acid (C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Partial sequence of Salmonella typhimurium virulence gene (xi) SEQUENCE DESCRIPTION: SEQ ID NO: 15:

| | | | | | | |
|---|---|---|---|---|---|---|
| CATGAGTAAC | CTACCCAACT | GTAATCTTTA | CCAATATGCA | TCATAATCTT | CTGCTGGTAA | 60 |
| ATGATTGGTA | ATATCGGAAA | GGTAAGTGAC | ATAAGCACGC | CATTACGTAA | AAGTGCGGCC | 120 |
| CCTAAACTGC | CACTTTTTAA | TAAGGGAAGT | AATAAAGAAA | GGCTCAATGG | TCGAATAAAA | 180 |
| GCCACAGCCA | ATGCAATAAG | CCACTCATTT | ACCTGTTGTG | CCATTCAACC | ATGCTCTCCA | 240 |
| ATTCGTAACA | TTATCTGCCG | GGTATAATTC | AACAGGATAC | CGCTAAGCCA | TGGGTAG | 297 |

(2) INFORMATION FOR SEQ ID NO: 16:

(i) SEQUENCE CHARACTERISTICS:
(A) LENGTH: 184 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Partial sequence of Salmonella typhimurium virulence gene (xi) SEQUENCE DESCRIPTION: SEQ ID NO: 16:

| | | | | | | |
|---|---|---|---|---|---|---|
| ATTCCAGCCC | CCGGGCCATC | TAACCACTAT | GAACAATCAT | CTTCTGGGTG | GACAATCATT | 60 |
| GGTACCATCG | GCCAGGCTTG | TGCAATATGT | ATGTCATCAC | GTAAAAGCGC | GGCCCCTTAA | 120 |
| TCTCCCCATT | CTTCCTTAAG | GGCAGTTATC | ACGGCTGGCT | CAATGGCCGG | CTTAACAGCC | 180 |
| ACAG | | | | | | 184 |

(2) INFORMATION FOR SEQ ID NO: 17:

(i) SEQUENCE CHARACTERISTICS:
(A) LENGTH: 306 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Partial sequence of Salmonella typhimurium virulence gene (xi) SEQUENCE DESCRIPTION: SEQ ID NO: 17:

| | | | | | | |
|---|---|---|---|---|---|---|
| GAGGCGCGTC | TTCGGTTGAG | GGTCGCCCTC | CAGATCTTTA | TGCTCCTGTT | TTACGTCATC | 60 |
| TTTACTCATT | TTAAGATCTT | TTCTAATCTT | ATAATATTGA | AAAGAATAGT | CCAGTATGCC | 120 |
| AACGACGAAA | TAAAGAAACA | TCACCCCAAC | CCATAACCAT | TTTTTCAATG | ATGAAAGCAC | 180 |

-continued

| | | | | | |
|---|---|---|---|---|---|
| AAGCACGCCA | CAGGCTACAC | CACAGCCCGG | AGGGGGCCGG | AAAGTGCTGG | GATCTTGATT | 240
| AATGAAAAAG | GCAAAGGGAA | GAGATAGGAT | GATGCATGCT | GGTTGGAGGC | AGATTATTCA | 300
| TCTTCG | | | | | | 306

( 2 ) INFORMATION FOR SEQ ID NO: 18:

( i ) SEQUENCE CHARACTERISTICS:
        ( A ) LENGTH: 297 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium
             virulence gene ( x i ) SEQUENCE DESCRIPTION: SEQ ID NO: 18:

| | | | | | |
|---|---|---|---|---|---|
| AGTTGCCGTA | TTTATTAAAT | ATTCACCTCA | GGTCAATATG | GAGGTCTTCC | CGGCTAAAAA | 60
| TCATTGCTTT | ACTAGAGATA | TCACTCCCTG | GGTTGCAATA | CAGTACGATT | AGTTATCTTG | 120
| ATGCAGCCTG | CTGATTTCAG | AATGGCAGCT | GACGTACCCG | CGAGACAAAC | ATTCTGGATT | 180
| ATGGACGTTA | TCAACGCCAA | TATAGGGAAG | GTGGTGAAGT | GGTTGATGAA | ATACCCCTAT | 240
| CCCTTGCATG | TTATCGCTGA | CAGGACTGTT | ATCAGGAGCG | GGCATCCTCG | ATCGGCT | 297

( 2 ) INFORMATION FOR SEQ ID NO: 19:

( i ) SEQUENCE CHARACTERISTICS:
        ( A ) LENGTH: 297 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium
             virulence gene ( x i ) SEQUENCE DESCRIPTION: SEQ ID NO: 19:

| | | | | | |
|---|---|---|---|---|---|
| CAAGAGACAG | ATCCAACTCG | GGCCGATCGC | CATAACGCCA | GCAGTTTGAA | AGATGAAAGC | 60
| CCAGCTTATC | CAGCCATTCC | GGTACAGCGT | AACGAGCAGG | TTGCCAGAAA | TAACGATAAA | 120
| GTTGCAACAC | CTCGGGATCA | GGTCGGCTCA | AAAACGGGGT | CTCAGGCAAA | AATAGCCGAT | 180
| CAGGATGCCC | ACTCCTAATA | ACAGTCCTGT | CAACGATAAC | ATCAACGGAT | AAGGGTATTT | 240
| CATCAACCAC | TTCACCACCT | TCCCTTTATT | GGCGTTGGAT | AACGTCCATA | ATCCAGA | 297

( 2 ) INFORMATION FOR SEQ ID NO: 20:

( i ) SEQUENCE CHARACTERISTICS:
        ( A ) LENGTH: 298 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: Partial sequence of Salmonella typhimurium virulence gene ( x i ) SEQUENCE DESCRIPTION: SEQ ID NO: 20:

| | | | | | | |
|---|---|---|---|---|---|---|
| AGGGCTTTAT | TGATTCCATT | TTTACACTGA | TGAATGTTCC | GTTGCGCTGC | CCGGATTACA | 60 |
| GCCGGATCCT | CTAGAGTCGA | CCTGCAGAAC | CGAGCCAGGA | GCAAATTAAT | TTTTTGGGC | 120 |
| AATTGCTGAA | AGATGAAGCA | TCCACCAGTA | ACGCCAGTGC | TTTATTACCG | CAGGTTATGT | 180 |
| TGACCAGACA | AATAGATTAT | ATGCAGTTAA | CGGTAGGCGT | CGATTATCTT | GTCAGAATAT | 240 |
| CAGGCGCAGC | ATCGCAAGCG | CTTAATAAGC | TGGGTAACAT | GGCATGAAGG | GGCAACCC | 298 |

( 2 ) INFORMATION FOR SEQ ID NO: 21:

( i ) SEQUENCE CHARACTERISTICS:
        ( A ) LENGTH: 298 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium virulence gene ( x i ) SEQUENCE DESCRIPTION: SEQ ID NO: 21:

| | | | | | | |
|---|---|---|---|---|---|---|
| CACTATAGGG | AAAGCTTGCA | TGCCTGCAGG | TCGACTCTAG | AGGATCTACT | AGTCATATGG | 60 |
| ATTCCTAGGC | GGCCAGATCT | GATCAAGAGA | CAGATCCAAC | TCGGGCCGAT | CGCCATAACG | 120 |
| CCAGCAGTTT | GAAAGATGAA | AGCCCAGCTT | ATCCAGCCAT | TCCGGTACAG | CGTAACGAGC | 180 |
| AGGTTGCCAG | AAATAACGAT | AAAGTTGCAA | CACCTCGGGA | TCAGGTCGGC | TCAAAAACGG | 240 |
| GGTCTCAGGC | AAAAATAGCC | GATCAGGATG | CCCACTCCTA | ATAACAGTCC | TGTCAACG | 298 |

( 2 ) INFORMATION FOR SEQ ID NO: 22:

( i ) SEQUENCE CHARACTERISTICS:
        ( A ) LENGTH: 301 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium virulence gene ( x i ) SEQUENCE DESCRIPTION: SEQ ID NO: 22:

| | | | | | | |
|---|---|---|---|---|---|---|
| CCCCCCCCCT | TCTCCTGGCT | TACACAGCCC | CAGACCGGCG | CTGGAAAAGG | CCATTCCCGC | 60 |
| CATACAGGAG | GCCAGCAACA | TATTTTCACG | CGCCGCCAGA | TCGTGGCCGT | AACCCACGGC | 120 |
| TTTCGGCAGC | GATTTGCCAA | TCATCGCTAT | CGCGCCAATC | GCCAGGCTGT | CGGTAAACGG | 180 |
| CGTGGCGTTG | AGCGCGCTGT | AGGCCTCAAT | CGCATGCGTC | AACGCATCGA | TACCGGTCAT | 240 |

| | | | | | |
|---|---|---|---|---|---|
|CGCCGTCACG|TTTGGCGGAA|CGCCTTCGGT|CACGGAAGCA|TCAAGAATCG|CCACGTCCGG|300|
|C|||||| 301|

(2) INFORMATION FOR SEQ ID NO: 23:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 23:

| | | | | | |
|---|---|---|---|---|---|
|CGCGAACGTG|CGCCGCAACT|GCTTGTGGAC|GGTGAATTGC|AGTTTGACGC|CGCTTTCGTG|60|
|CCGGAGGTCG|CCGCGCAAAA|AGCGCCTGAC|AGCCCGCTGC|AAGGCCGCGC|CAACGTGATG|120|
|ATTTTCCCGT|CGCTGGAGGC|GGGCAATATT|GGCTACAAAA|TCACTCAGCG|TCTGGGAGGC|180|
|TATCGCGCTG|TTGGGCCGCT|AATTCAGGGG|CTTGGCGCGC|CGCTTCACGA|CCTCTCCCGA|240|
|GGCTGTAGCG|TGCAGGAAAT|TATCGAACTG|CGGTTGGTGA|GAAAACCAA||289|

(2) INFORMATION FOR SEQ ID NO: 24:

(i) SEQUENCE CHARACTERISTICS:
        (A) LENGTH: 303 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence od Salmonella typhimurium
            virulence gene (xi) SEQUENCE DESCRIPTION: SEQ ID NO: 24:

| | | | | | |
|---|---|---|---|---|---|
|CGCCCTAGCA|TGCCTGGCGT|TGTCCGGTTA|TTGCTCGTCA|AGCGAACAGA|TGCAAAAGGT|60|
|GAGAGCGACT|CTCGAATCAT|GGGGGGTCAT|GTATCGGGAT|GGTGTAATCT|GTGATGACTT|120|
|ATTGGTACGA|GAAGTGCAGG|ATGTTTTGGA|TAAAAATGGG|TTACCCGCAT|GCTGAAGTAT|180|
|CCAGCGAAGG|GCCGGGGAGC|GTGTTAATTC|ATGATGATAT|ACAAATGGAT|CAGCAATGGC|240|
|GCAAGGTTCA|ACCATTACTT|GCAGATATTC|CCGGGTTATT|GCACTGGCAG|ATTAGTCACT|300|
|CTC|||||| 303|

(2) INFORMATION FOR SEQ ID NO: 25:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Partial sequence of Salmonella typhimurium virulence gene (xi) SEQUENCE DESCRIPTION: SEQ ID NO: 25:

| | | | | | | |
|---|---|---|---|---|---|---|
| CCCTTCCCAG | GCTCGACAGG | TACACAGCCA | GCCACTGGTG | CAGGCAGTTA | CTTGCTTTCA | 60 |
| TCATGGGAAG | GAGCAATATC | CTGATATATT | AAAGAAAGAG | CGGGATCCCC | TTTCTTTACT | 120 |
| GCTGCTAACG | TTTCTTGCAA | AATGCGTTGA | TGAGATTCAT | CCAGCACACC | ACTGATAACA | 180 |
| AAAGAGCGCC | GCATTGGCGT | AACATTGACA | AGCCCACTA | AACCGCTCTC | TATTATCGCA | 240 |
| GAAATAATAT | CATCCCCCTG | AGACTGATGA | GAGTGACTAT | TCTGCCAGCG | CAAATAACCC | 300 |

(2) INFORMATION FOR SEQ ID NO: 26:

(i) SEQUENCE CHARACTERISTICS:
(A) LENGTH: 303 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Partial sequence of Salmonella typhimurium virulence gene (xi) SEQUENCE DESCRIPTION: SEQ ID NO: 26:

| | | | | | | |
|---|---|---|---|---|---|---|
| ATACCGAGTA | TTAAGCGGCT | GTGTAACATC | GTCATCCAAC | AACATACGCA | GCGAGCCGCC | 60 |
| ACGCCGGAAA | AACCGCATCG | TGTCATGTGC | CTGTTGTAGG | GTCGGGTCTT | TTTTCATGAG | 120 |
| TACGTTTTCT | GCGCTATCAT | ACTGGAAATT | TCCCCCCACT | TACTGATAAG | CCCTGTCAGT | 180 |
| TGGGTAAGGA | CAGAGTTAAG | CTCCTGAGAC | ATTTTTTGGA | ATGGTTATCT | TTCCCCGACT | 240 |
| CATAAAATCG | GTATTCCCGC | TGGGGGCAAT | ATCCAAAGAC | GCTTTGGTCG | CCCGTAGGGC | 300 |
| ACC | | | | | | 303 |

(2) INFORMATION FOR SEQ ID NO: 27:

(i) SEQUENCE CHARACTERISTICS:
(A) LENGTH: 300 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Partial sequence of Salmonella typhimurium virulence gene (xi) SEQUENCE DESCRIPTION: SEQ ID NO: 27:

| | | | | | | |
|---|---|---|---|---|---|---|
| GCCGTATGCC | TGCAGTTGCC | CGGTTATTGC | TCGTCAAGCG | AACCGATGCC | AAAGGTGAGA | 60 |
| GCGACTCTCG | AATCATGGGG | GGTCATGTAT | CGGGATGGTG | TAATCTGTGA | TGACTTATTG | 120 |
| GTACGAGAAG | TGCAGGATGT | TTTGGTAAAA | ATGGGTTACC | CCCATGCTGA | AGTATCCAGC | 180 |
| GAAGGGGCGG | GGAGCGTGTT | AATTCACGAT | GATATTCAAA | TGGGTCAGCA | ATGGGGCAAG | 240 |

GTTCAACCCC CACTTGCAGA TATTCCCCCC CCTATTGGAC TGGCAGATTA GTCACTCTCA    300

( 2 ) INFORMATION FOR SEQ ID NO: 28:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium
            virulence gene ( x i ) SEQUENCE DESCRIPTION: SEQ ID NO: 28:

GGGCGACCTG CCCGCGGCGC AACTTTCCCC GAAGCGTTTT CCATTTCCTT GTTCTTAAAT    60
GACCTGGAAA GCTTACCTAA GCCTTGTCTT GCCTATGTGA CAATACTGCT TGGAGAACAC    120
CCGGACGTCC ATGATTATGC TATACAGATC ACAGCGGATG GGGGATGGTG AATCGGTTAT    180
TATACCACAA GTCGCAGCTC TGAGCTTATT GCTATTGAGA TAGAAAAACA CCCCGCTTCA    240
ACTTGGATTT TGAATAATGT AATACGCAAT CACCATACAC TATATTCGGG TGGCGTATAA    300

( 2 ) INFORMATION FOR SEQ ID NO: 29:

( i ) SEQUENCE CHARACTERISTICS:
        ( A ) LENGTH: 266 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Partial sequence of Salmonella typhimurium
            virulence gene ( x i ) SEQUENCE DESCRIPTION: SEQ ID NO: 29:

TTCGAGCTGG GGCACCGCTA ATATCTTTAA CCTCGCATCC CGGTGATGAA AGGATATTCT    60
GGCTGCGTAA GTAATGAATG AACCGCCCAG CAGATAAAAT ATTGACAGTG ATAACCCGAT    120
GTTTTTTTAA CGATGCAGGC TATACATATA ACATAGCTGG CCACCAACAC AGCTGAAGTA    180
AATCATATTG TTGCTGCCAG GCTACTTCAC ACTATTGTCC GGCGGGCCAG CGGGGATTTT    240
CCCCCTAAAT CTCGCTGGTT CTCAAA    266

( 2 ) INFORMATION FOR SEQ ID NO: 30:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO

-continued (vi) ORIGINAL SOURCE:
    (A) ORGANISM: Partial sequence of Salmonella typhimurium
        virulence gene (xi) SEQUENCE DESCRIPTION: SEQ ID NO: 30:

| | | | | | | |
|---|---|---|---|---|---|---|
| AGTCTACGAT | TTCGCTATAT | CTTCTCTTAA | TCATGGCCGC | CATTTGTGGA | TGCGATTTTA | 60 |
| AAATATCCGG | GCGATCTTTC | ATTAAAAAAT | AAAGATTCCC | CATGACTTCA | CAGATAAAGG | 120 |
| TATCGGTATT | TTGAGTGATA | CGTAACAATT | CGTTCTCTTC | GTGTGGGTCC | ATGATGCGAA | 180 |
| GAATAATGGT | GGCATCATTT | TCATGAGGAT | TATGAACCCG | AAATCTTTCT | CTTTGCGATG | 240 |
| CGCAGGCTAA | CTCTTTCAAC | TCAAAAAAA | TCTCTGTAAG | CCGCTCTCGT | GTGGGGCGC | 300 |

(2) INFORMATION FOR SEQ ID NO: 31:

(i) SEQUENCE CHARACTERISTICS:
        (A) LENGTH: 299 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
        virulence gene (xi) SEQUENCE DESCRIPTION: SEQ ID NO: 31:

| | | | | | | |
|---|---|---|---|---|---|---|
| GCGCCCTTT | AATTGGTTGA | GGCGGCTGGT | ATTCTTGTAA | GGGTAATACT | AGCGAGACCC | 60 |
| AGGTTCCACC | CCCGGGGACA | CTTTTTAGTG | TCAGATTACC | GCCCATCATT | TTAGCCAGGC | 120 |
| TTGACGCAAT | AGTCAGTCCA | ATTCCTGTAC | CTTGCGAATT | TGTGTCTGCT | TGATAAAAAG | 180 |
| CAGAAAAGAT | TTGAGACTGC | TGCTGTTTTT | CAATCCCCCC | ACCGCTATCG | CTAACCAGAA | 240 |
| ATATTAATTG | TTCCTCACCA | AGATTGAGCG | CCAGACGTAT | CCCTCCCCCC | TCGGGAAAT | 299 |

(2) INFORMATION FOR SEQ ID NO: 32:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
        virulence gene (xi) SEQUENCE DESCRIPTION: SEQ ID NO: 32:

| | | | | | | |
|---|---|---|---|---|---|---|
| GGATAAGATC | CCGGATAAGT | ATGTCAGGCT | CGTATGCACA | ACAGGCATTA | TAAACCTCTA | 60 |
| GACCATTTTT | AACATGCTCT | ACTATTTTAA | AATGAGGCCA | GGGTAATAAG | GCATTCATAA | 120 |
| TGCCGTTAAT | GATGATTTCA | TGATCGTCTA | CTAATAAGAT | CTTATATTCT | TTCATTTGGC | 180 |
| TGCCCTCGCG | AAAATTAAGA | TAATATTAAG | TAATGGTGTA | GGTTGTGGAG | ATCATACGTA | 240 |
| TTTTCTGGCG | TAAGTCGGTT | AGTTCCTCCA | GCGCGATGAT | TTTCCCATT | TTTACGCGAT | 300 |

(2) INFORMATION FOR SEQ ID NO: 33:

(  i  ) SEQUENCE CHARACTERISTICS:
            ( A ) LENGTH: 278 base pairs
            ( B ) TYPE: nucleic acid
            ( C ) STRANDEDNESS: double
            ( D ) TOPOLOGY: linear (  i i  ) MOLECULE TYPE: DNA (genomic)

(  i i i  ) HYPOTHETICAL: NO (  i i i  ) ANTI-SENSE: NO (  v i  ) ORIGINAL SOURCE:
            ( A ) ORGANISM: Partial sequence of Salmonella typhimurium
                    virulence gene (  x i  ) SEQUENCE DESCRIPTION: SEQ ID NO: 33:

```
TTCCATATTG  CTCGTCCGGG  GAGCGTGTTA  ATTCTTGATG  ATATACCAAT  GGATCTGCAA       60
TGGCGCAAGG  TTCAACCATT  ACTTGGAGAT  ATTCCCGGGT  TATTGTACTG  GGAGATTAGT      120
CACTCTCATC  AGTCTCAGGG  GGGTGATGTT  ATTTCTGGGA  TAATAGAGCA  ACGGCGTTAG      180
CAGGGGTCGG  TCAGTAGTCA  CGGCCAACTT  CGGTGCACTT  TTGCGTATCA  CTGGGGTATC      240
ATAACTGAAT  CTCATCCCCC  CCACTTTGGT  AATCACAC                                278
```

( 2 ) INFORMATION FOR SEQ ID NO: 34:

(  i  ) SEQUENCE CHARACTERISTICS:
            ( A ) LENGTH: 301 base pairs
            ( B ) TYPE: nucleic acid
            ( C ) STRANDEDNESS: double
            ( D ) TOPOLOGY: linear (  i i  ) MOLECULE TYPE: DNA (genomic)

(  i i i  ) HYPOTHETICAL: NO (  i i i  ) ANTI-SENSE: NO (  v i  ) ORIGINAL SOURCE:
            ( A ) ORGANISM: Partial sequence of Salmonella typhimurium
                    virulence gene (  x i  ) SEQUENCE DESCRIPTION: SEQ ID NO: 34:

```
AATTCTTTTA  CCTCCATAAG  CTGCGTGGCA  TAGCGATACA  GAGTATTAAG  CGGGTGTGTT       60
ACATCGTCAT  CCAACAACAT  ACGCAGCGAG  CCGCCACGCC  GGAAAAACCG  CATCGTGTCA      120
TGTGCCTGTT  GTAGGGTCGG  GTCTTTTTTT  CATGAGTACG  TGTTCTGCGC  TATCATACTG      180
GAAATTTCCC  CCCACTTACT  GATAAGCCCT  GTCAGTTGGG  TAAGGACAGC  GTTAAGCTCC      240
TGAGACATTT  TTTGAGTTGT  TATCTGCCCC  CCGACTCATA  AGATCGGGTA  TTCCGCGGTG      300
G                                                                          301
```

( 2 ) INFORMATION FOR SEQ ID NO: 35:

(  i  ) SEQUENCE CHARACTERISTICS:
            ( A ) LENGTH: 297 base pairs
            ( B ) TYPE: nucleic acid
            ( C ) STRANDEDNESS: double
            ( D ) TOPOLOGY: linear (  i i  ) MOLECULE TYPE: DNA (genomic)

(  i i i  ) HYPOTHETICAL: NO (  i i i  ) ANTI-SENSE: NO (  v i  ) ORIGINAL SOURCE:
            ( A ) ORGANISM: Partial sequence of Salmonella typhimurium
                    virulence gene ( x i ) SEQUENCE DESCRIPTION: SEQ ID NO: 35:

| | | | | | |
|---|---|---|---|---|---|
| ATATCCCTAA | TGCTTTTCCT | TAAAATAAAT | ACCACGGAAG | GATACTGGCC | ACCTAGCCAA | 60
| ATTTAGAAAG | CAATGAACAT | CCGGTTTATT | CCTGAAAACG | ATTACTCCGG | CGCACGTTGT | 120
| TCTGGCGTTA | CCTGAGCCAG | CAAACGATAT | AATGGGGTGG | TGACCCGCAT | ACCGGTCATT | 180
| GGCATCCCAT | CCACACCGGA | GGGAGTAAAA | CTCATTAGGC | CATAGGTAAT | ATCATTAAGA | 240
| CGCTCTAATA | AATGAGGGTG | GGGGGCCCAA | ACTACCACTC | CAGTATGTAT | TGAGTCA | 297

( 2 ) INFORMATION FOR SEQ ID NO: 36:

( i ) SEQUENCE CHARACTERISTICS:
        ( A ) LENGTH: 291 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v ) ORIGINAL SOURCE:
        ( A ) ORGANISM: Partial sequence of Salmonella typhimurium
            virulence gene ( x i ) SEQUENCE DESCRIPTION: SEQ ID NO: 36:

| | | | | | |
|---|---|---|---|---|---|
| CCCATGGGCG | CAATTTGTTG | CGCAGCGTTT | ACCCGACCAT | CGCGTTTATG | AGCTGTAATT | 60
| CATGGGGGT | AAAAACGGGC | GTGACGACCC | CAACGGAAGA | TAAGGCCGGG | CTTAAACAGG | 120
| AGATTATTGC | TAATGCGCAG | CGCAAAGTGT | TGCTGGCGGA | CAGCAGTAAG | TATGGCGCGC | 180
| ATTCGCTCTT | TAATGTGGTG | CCGCTTGAGC | GCTTTAATGA | CGTGATTACC | GACGTCAATC | 240
| TGCCGCCGTC | AGCGCAGGTT | GAACTGAAAG | GGCGCGCTTT | TTGCGCTAAC | G | 291

( 2 ) INFORMATION FOR SEQ ID NO: 37:

( i ) SEQUENCE CHARACTERISTICS:
        ( A ) LENGTH: 13417 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: DNA sequence of VGC II from centre to left
            hand end ( x i ) SEQUENCE DESCRIPTION: SEQ ID NO: 37:

| | | | | | |
|---|---|---|---|---|---|
| CTGCAGAACC | GAGCCAGGAG | CAAATTAATT | TTTTTGAACA | ATTGCTGAAA | GATGAAGCAT | 60
| CCACCAGTAA | CGCCAGTGCT | TTATTACCGC | AGGTTATGTT | GACCAGACAA | ATGGATTATA | 120
| TGCAGTTAAC | GGTAGGCGTC | GATTATCTTG | CCAGAATATC | ACGGCGAGC | ATGCCAAGCG | 180
| CTTAATAAGC | TGGATAACAT | GGCATGAAGG | TTCATCGTAT | AGTATTTCTT | ACTGTCCTTA | 240
| CGTTCTTTCT | TACGGCATGT | GATGTGGATC | TTTATCGCTC | ATTGCCAGAA | GATGAAGCGA | 300
| ATCAAATGCT | GGCATTACTT | ATGCAGCATC | ATATTGATGC | GAAAAAAAC | AGGAAGAGGA | 360
| TGGTGTAACC | TTACGTGTCG | AGCAGTCGGC | AGTTTATTAA | TGCGGTTGAG | GCTACTTAGA | 420
| CTTAACGGTT | ATCCGCATAG | GGCAGTTTAC | AACGGCGGAT | AAGATGTTTC | CGGCTAATCA | 480

```
GTTAGTGGTA  TCACCCCAGG  AAGAACAGGC  AGAAGATTAA  TTTTTTAAAA  GAACAAAGAA   540
TTGAAGGAAT  GCTGAGTCAG  ATGGAGGGGC  GTGATTAATG  GCAAAAGTGA  CCATTGCGCT   600
ACCGACTTAT  GATGAGGGAA  GTAACGCTTC  TCCGAGCTCA  GTTGCCGTAT  TTATAAAATA   660
TTCACCTCAG  GTCAATATGG  AGGCCTTTCG  GGTAAAAATT  AAAGATTTAA  TAGAGATGTC   720
AATCCCTGGG  TTGCAATACA  GTAAGATTAG  TATCTTGATG  CAGCCTGCTG  AATTCAGAAT   780
GGTAGCTGAC  GTACCCGCGA  GACAAACATT  CTGGATTATG  GACGTTATCA  ACGCCAATAA   840
AGGGAAGGTG  GTGAAGTGGT  TGATGAAATA  CCCTTATCCG  TTGATGTTAT  CGTTGACAGG   900
ACTGTTATTA  GGAGTGGGCA  TCCTGATCGG  CTATTTTGC   CTGAGACGCC  GTTTTGAGC    960
CGACCTGATC  CCGAGGTGTT  GCAACTTAT   CGTTATTTCT  GGCAACCTGC  TCGTTACGCT  1020
GTACCGGAAT  GGCTGGATAA  GCTGGGCTTT  CATCTTCAAA  CTGCTGGCGT  TATGGCGATC  1080
GGCCCGAGTT  GGATCGTCTT  CTTGACAGAG  CGTTAAATAG  ACTAAGAGGA  AGCTCTGTTA  1140
TTCCAGCCTG  TTTAAATGAC  AGGCAAAAAC  GGCAGGTTCG  TCTTGCGCCG  CGTATATCGG  1200
CATTTGCCTT  TGGGCTGGGA  TTATTCAAAC  TCAGGTGTAG  TGACTATTTT  ATGCTACCAG  1260
AGTATCGGCA  ATTGCTTCTA  CAGTGGTTTA  GCGAGGATGA  GATCTGGCAG  CTATATGGTT  1320
GGTTGGGGCA  AAGAGATGGC  AAATTACTTC  CTCCGCAAGT  GATGCAACAA  ACTGCATTGC  1380
AGATCGGTAC  CGCCATTCTT  AATCGGGAAG  CGCATGACGA  TGCGGGTTTT  ACATGCGCTA  1440
TTAGTATTAT  TACCCCCTCC  GCAGCGTATA  CTTTGGCCGA  AGACTTCTCT  TACCGAGATT  1500
ATCTTCATGG  AGCATTTGCT  ATGAGTTTTA  CTTCACTTCC  TCTGACGGAA  ATTAACCATA  1560
AGCTACCCGC  TCGAAATATT  ATTGAGTCAC  AGTGGATAAC  ATTACAATTA  ACTTTATTTG  1620
CGCAAGAGCA  ACAAGCTAAG  AGAGTTTCAC  ATGCTATTGT  GAGCTCCGCT  TACCGTAAGG  1680
CTGAAAAAAT  CATCCGAGAC  GCCTATCGTT  ATCAGCGTGA  ACAGAAAGTT  GAGCAGCAAC  1740
AAGAACTAGC  GTGCTTGCGT  AAAAATACGC  TGGAAAAAAT  GGAAGTGGAA  TGGCTGGAAC  1800
AGCATGTAAA  ACATTTACAA  GACGATGAAA  ATCAATTTCG  TTCATTGGTC  GATCACGCAG  1860
CGCATCATAT  TAAAAATAGT  ATAGAACAGG  TTCTGTTGGC  CTGGTTCGAC  CAACAGTCGG  1920
TAGACAGTGT  TATGTGCCAT  CGTCTGGCAC  GCCAGGCCAC  GGCTATGGCG  AAGAGGGAG   1980
CGCTTTATTT  GCGTATTCAT  CCTGAAAAAG  AGGCATTGAT  GCGAGAAACT  TTTGGCAAGC  2040
GGTTTACGTT  GATTATCGAG  CCTGGTTTCT  CTCCCGATCA  GGCTGAACTT  TCCTCAACAC  2100
GATATGCCGT  TGAATTTTCA  CTTTCTCGTC  ATTTCAACGC  GTTACTGAAA  TGGTTACGTA  2160
ATGGTGAAGA  TAAAAGAGGT  AGCGATGAAT  ATTAAAATTA  ATGAGATAAA  AATGACGCCC  2220
CCTACAGCAT  TTACCCCTGG  CCAGGTTATA  GAGGAACAAG  AGGTTATTTC  GCCTTCAATG  2280
TTAGCTCTCC  AGGAGTTACA  GGAAACGACG  GGGGCAGCGC  TCTATGAGAC  GATGGAAGAA  2340
ATAGGAATGG  CGCTGAGTGG  TAAACTGCGC  GAAAATTATA  AATTCACTGA  TGCTGAGAAA  2400
CTGGAGCGCA  GACAGCAGGC  TTTGCTGCGT  TTGATAAAAC  AAATACAGGA  GGATAATGGG  2460
GCAACGTTGC  GTCCGCTTAC  CGAAGAGAAT  AGTGATCCTG  ATTTACAGAA  TGCGTATCAA  2520
ATTATCGCTC  TTGCAATGGC  GCTTACTGCC  GGCGGGTTGT  CAAAAAAGAA  AAAACGCGAT  2580
TTGCAATCGC  AACTGGATAC  GTTACAGCGG  AGGAGGGATG  GGAACTTGCC  GTTTTTAGTT  2640
TACTGGAACT  TGGCGAAGTG  GATACCGTAC  GCTGTCCTCT  CTGAAGCGTT  TTATGCAACA  2700
GGCGATAGAC  AACGATGAAA  TGCCCTTATC  GCAGTGGTTC  AGACGCGTGG  CAGACTGGCC  2760
GGATCGCTGT  GAACGGGTCC  GTATTTTGCT  AAGAGCAGTA  GCCTTTGAAC  TTAGCATATG  2820
CATCGAACCC  TCGGAGCAAA  GTCGTTTGGC  CGCAGCATTA  GTACGTTTGC  GTCGTTTGCT  2880
```

```
GTTATTCCTT GGCCTTGAAA AAGAGTGCCA GCGTGAGGAG TGGATTTGCC AGTTGCCGCC   2940
TAATACATTA CTGCCGCTAC TACTCGATAT TATTTGTGAG CGCTGGCTTT TCAGTGATTG   3000
GTTGCTTGAT AGACTTACCG CTATAGTTTC TTCATCGAAG ATGTTCAATC GGTTACTCCA   3060
ACAACTTGAT GCGCAGTTTA TGCTGATACC CGATAACTGT TTTAACGACG AAGATCAACG   3120
TGAACAAATT CTCGAAACGC TTCGTGAAGT AAAGATAAAT CAGGTTTTAT TCTGATACCT   3180
GGCTTTCAAT ATTTAGGTAA ATTGGCTTTC TGGCTCATCA TGAGGCGTCA GGATGGATTG   3240
GGATCTCATT ACTGAACGTA ATATTCAGCT TTTTATTCAA TTAGCAGGAT TAGCTGAACG   3300
GCCTTTAGCA ACCAATATGT TCTGGCGGCA AGGACAATAT GAAACTATCA TAACGGTCGT   3360
ATTCTCTTAT GTCAGATACT CAAGCAAACC TTCTTAGACG AAGAACTGCT TTTTAAAGCG   3420
TTGGCTAACT GGAAACCCGC AGCGTTCCAG GGTATTCCTC AACGATTATT TTGTTGCGC    3480
GATGGGCTTG CAATGAGTTG TTCTCCACCT CTTTCCAGCT CCGCCGAGCT CTGGTTACGA   3540
TTACATCATC GACAAATAAA ATTTCNTGGA GTCGCAATGC GTTCATGGTT AGGTGAGGGA   3600
GTCAGGGCGC AACAGTGGCT CAGTGTATGC GCGGGTCGGC AGGATATGGT TCTGGCGACG   3660
GTGTTATTAA TCGCTATTGT GATGATGCTG TTACCCTTGC CGACCTGGAT GGTTGATATC   3720
CTGATTACTA TCAACCTTAT GTTTTCAGTG ATCCTGCTCT TAATTGCTAT TTATCTTAGT   3780
GACCCTCTCG ATTTATCGGT ATTTCCGTCT TTATTACTTA TTACTACATT ATATCGTTTG   3840
TCACTCACAA TCAGCACATC ACGGCTGGTA CTGTTACAAC ATAATGCCGG TAATATTGTG   3900
GATGCTTTCG GTAAGTTTGT CGTAGGAGGA AATCTCACCG TTGGGTTGGT CGTATTTACC   3960
ATCATTACTA TCGTGCAATT TATTGTCATT ACAAAAGGTA TCGAGAGGGT GGCGGAAGTT   4020
AGCGCACGTT TCTCGCTTGA TGGGATGCCA GGCAAACAAA TGAGTATCGA TGGCGATTTG   4080
CGTGCCGGAG TTATCGATGC AGACCATGCC CGTACATTAA GACAGCATGT CCAGCAGGAA   4140
AGCCGCTTTC TCGGTGCGAT GGACGGTGCG ATGAAATTTG TTAAAGGCGA TACGATTGCC   4200
GGTATTATTG TTGTTCTGGT GAACATTATC GGCGGTATCA TTATCGCTAT CGTACAATAT   4260
GATATGTCGA TGAGTGAGGC TGTTCACACT TATAGCGTAC TGTCAATCGG AGATGGTTTA   4320
TGTGGGCAAA TTCCATCGCT GCTGATTTCC CTTAGCGCGG GAATTATTGT CACCCGTGTC   4380
CCGGGTGAGA AACGCCAGAA CCTGGCGACA GAGTTGAGTT CTCAAATTGC CAGACAACCT   4440
CAGTCGCTCA TATTAACCGC TGTGGTTTTA ATGCTCCTCG CTTTAATTCC TGGCTTTCCT   4500
TTTATCACTC TCGCTTTCTT TTCAGCGTTG TTAGCATTGC CAATTATCCT CATTCGCCGC   4560
AAAAAGTCTG TGGTTTCCGC AAATGGCGTC GAAGCACCGG AAAAAGATAG TATGGTTCCC   4620
GGCGCATGTC CTCTAATCTT ACGTCTTAGC CCGACGTTAC ATTCTGCCGA CCTGATTCGT   4680
GATATTGACG CCATGAGATG GTTTTTATTT GAGGATACCG GCGTCCCTCT CCCTGAGGTG   4740
AATATTGAGG TTTTGCCTGA ACCCACCGAA AAATTGACGG TACTGCTATA TCAGGAACCC   4800
GTATTTAGTT TATCTATTCC CGCTCAGGCG GATTATTTAT TGATAGGCGC GGACGCTAGT   4860
GTGGTGGGTG ACAGCCAGAC GTTACCGAAC GGGATGGGGC AGATCTGTTG GCTTACAAAA   4920
GACATGGCCC ATAAGGCGCA AGGTTTTGGA CTGGACGTTT TCGCGGGCAG CCAACGTATC   4980
TCTGCCTTAT TAAAATGTGT CCTGCTTCGG CATATGGGAG AGTTTATTGG TGTTCAGGAA   5040
ACGCGTTATC TAATGAATGC GATGGAAAAA AACTACTCTG AGCTGGTGAA AGAGCTTCAG   5100
CGCCAGTTAC CCATTAATAA AATCGCTGAA ACTTTGCAAC GGCTTGTATC AGAGCGGGTT   5160
TCTATTAGAG ATTTACGTCT TATTTTCGGC ACCTTAATTG ACTGGGCGCC ACGTGAAAAA   5220
GATGTCCTGA TGTTGACAGA ATATGTCCGT ATCGCGCTTC GTCGTCATAT TCTGCGTCGT   5280
```

```
CTTAATCCGG  AAGGAAAACC  GCTGCCGATT  TTGCGGATCG  GCGAAGGTAT  TGAAAACCTC    5340
GTGCGTGAAT  CCATTCGCCA  GACGGCAATG  GGGACCTATA  CTGCGCTGTC  GTCTCGTCAT    5400
AAGACGCAGA  TCCTGCAACT  TATCGAGCAG  GCGCTGAAGC  AGTCAGCCAA  ATTATTCATT    5460
GTCACTTCTG  TCGACACCCG  ACGTTTCTTG  CGAAAAATTA  CAGAAGCCAC  CTTGTTCGAC    5520
GTACCGATTT  TGTCATGGCA  GGAATTAGGA  GAGGAGAGCC  TTATACAAGT  GGTAGAAAGT    5580
ATTGACCTTA  GCGAAGAGGA  GTTGGCGGAC  AATGAAGAAT  GAATTGATGC  AACGTCTGAG    5640
GCTGAAATAT  CCGCCCCCCG  ATGGTTATTG  TCGATGGGGC  CGAATTCAGG  ATGTCAGCGC    5700
AACGTTGTTA  AATGCGTGGT  TGCCTGGGGT  ATTTATGGGC  GAGTTGTGCT  GTATAAAGCC    5760
TGGAGAAGAA  CTTGCTGAAG  TCGTGGGGAT  TAATGGCAGC  AAAGCTTTGC  TATCTCCTTT    5820
TACGAGTACA  ATCGGGCTTC  ACTGCGGGCA  GCAAGTGATG  GCCTTAAGCG  ACGCCATCAG    5880
GTTCCCGTGG  GCGAAGCGTT  ATTAGGGCGA  GTTATTGATG  GCTTTGGTCG  TCCCCTTGAT    5940
GGCCGCGAAC  TGCCCGACGT  CTGCTGGAAA  GACTATGATG  CAATGCCTCC  TCCCGCAATG    6000
GTTCGACAGC  CTATCACTCA  ACCATTAATG  ACGGGATTC  GCGCTATTGA  TAGCGTTGCG    6060
ACCTGTGGCG  AAGGGCAACG  AGTGGGTATT  TTTTCTGCTC  CTGGCGTGGG  GAAAAGCACG    6120
CTTCTGGCGA  TGCTGTGTAA  TGCGCCAGAC  GCAGACAGCA  ATGTTCTGGT  GTTAATTGGT    6180
GAACGTGGAC  GAGAAGTCCG  CGAATTCATC  GATTTTACAC  TGTCTGAAGA  GACCCGAAAA    6240
CGTTGTGTCA  TTGTTGTCGC  AACCTCTGAC  AGACCCGCCT  TAGAGCGCGT  GAGGGCGCTG    6300
TTTGTGGCCA  CCACGATAGC  AGAATTTTTT  CGCGATAATG  GAAAGCGAGT  CGTCTTGCTT    6360
GCCGACTCAC  TGACGCGTTA  TGCCAGGGCC  GCACGGAAAT  CGCTCTGGCG  CCGGAGAGAC    6420
CGCGGTTTCT  GGAGAATATC  GCCAGGCGTA  TTTAGTGCAT  TGCCACGACT  TTTAGAACGT    6480
ACGGGAATGG  GAGAAAAAGG  CAGTATTACC  GCATTTTATA  CGGTACTGGT  GGAAGGCGAT    6540
GATATGAATG  AAGCCGTTGG  CGGATGAAGT  CCGTTCACTG  CTTGATGGAC  ATATTGTACT    6600
ATCCCGACGG  CTTGCAGAGA  GGGGGCATTA  TCCTGCCATT  GACGTGTTGG  CAACGCTCAG    6660
CCGCGTTTTT  CCAGTCGTTA  CCAGCCATGA  GCATCGTCAA  CTGGCGGCGA  TATTGCGACG    6720
GTGCCTGGCG  CTTTACCAGG  AGGTTGAACT  GTTAATACGC  ATTGGGGAAT  ACCAGCGAGG    6780
AGTTGATACA  GATACTGACA  AAGCCATTGA  TACCTATCCG  GATATTTGCA  CATTTTTGCG    6840
ACAAAGTAAG  GATGAAGTAT  GCGGACCCGA  GCTACTTATA  GAAAAATTAC  ACCAAATACT    6900
CACCGAGTGA  TCATGGAAAC  TTTGCTGGAG  ATAATCGCGC  GGCTGAAAAG  CAATTACGCG    6960
GCAAGCTTAC  CGTACTTGAT  CAGCAGCAAC  AGGCGATTAT  TACGGAACAG  CAGATTTGCC    7020
AGACGCGCGC  TTTAGCAGTG  TCTACCAGAC  TGAAAGAATT  AATGGGCTGG  CAAGGTACGT    7080
TATCTTGTCA  TTTATTGTTG  GATAAGAAAC  AACAAATGGC  CGGGTTATTC  ACTCAGGCGC    7140
AGAGCTTTTT  GACGCAACGG  CAAGCAGTTA  GAGAATCAGT  ATCAGCAGCT  TGTCTCCCGG    7200
CGAAGCGAAT  TACAGAAGAA  TTTTAATGCG  CTTATGAAAA  AGAAAGAAAA  AATTACTATG    7260
GTATTAAGCG  ATGCGTATTA  CCAAAGTTGA  GGGAAGTCTT  GGGTTGCCAT  GCCAGTCTTA    7320
TCAGGATGAT  AACGAGGCGG  AGGCGGAACG  TATGGACTTT  GAACAACTCA  TGCACCAGGC    7380
ATTACCCATT  GGTGAGAATA  ATCCTCCTGC  AGCATTGAAT  AAGAACGTGG  TTTTCACGCA    7440
ACGTTATCGT  GTTAGTGGCG  GTTATCTTGA  CGGTGTAGAG  TGTGAAGTAT  GTGAATCAGG    7500
GGGGCTAATC  CAGTTAAGAA  TCAATGTCCC  TCATCATGAA  ATTTACCGTT  CGATGAAAGC    7560
GCTAAAGCAG  TGGCTGGAGT  CTCAGTTGCT  GCATATGGGG  TATATAATTT  CCCTGGAGAT    7620
ATTCTATGTT  AAGAATAGCG  AATGAAGAGC  GTCCGTGGGT  GGAGATACTT  CCAACGCAAG    7680
```

```
GCGCTACCAT  TGGTGAGCTG  ACATTGAGTA  TGCAACAATA  TCCAGTACAG  CAAGGGACAT   7740
TATTTACCAT  AAATTATCAT  AATGAGCTGG  GTAGGGTGTG  GATTGCAGAA  CAATGCTGGC   7800
AGCGCTGGTG  TGAAGGGCTA  ATTGGCACCG  CTAATCGATC  GGCTATCGAT  CCTGAATTGC   7860
TATATGGAAT  AGCTGAATGG  GGGCTGGCGC  CGTTATTGCA  AGCCAGTGAT  GCAACCCTCT   7920
GTCAGAACGA  GCCGCCAACA  TCCTGCAGTA  ATCTACCACA  TCAGCTAGCG  TTGCATATTA   7980
AATGGACAGT  TGAAGAGCAT  GAGTTCCATA  GCATTATTTT  TACATGGCCA  ACGGGTTTTT   8040
TGCGCAATAT  AGTCGGAGAG  CTTTCTGCTG  AGCGACAACA  GATTTATCCT  GCCCCTCCTG   8100
TGGTAGTCCC  TGTATATTCA  GGCTGGTGCC  AGCTTACATT  AATCGAACTT  GAGTCTATCG   8160
AAATCGGCAT  GGGCGTTCGG  ATTCATTGCT  TCGGCGACAT  CAGACTCGGT  TTTTTTGCTA   8220
TTCAACTACC  TGGGGGAATC  TACGCAAGGG  TGTTGCTGAC  AGAGGATAAC  ACGATGAAAT   8280
TTGACGAATT  AGTCCAGGAT  ATCGAAACGC  TACTTGCGTC  AGGGAGCCCA  ATGTCAAAGA   8340
GTGACGGAAC  GTCTTCAGTC  GAACTTGAGC  AGATACCACA  ACAGGTGCTC  TTTGAGGTCG   8400
GACGTGCGAG  TCTGGAAATT  GGACAATTAC  GACAACTTAA  AACGGGGAC   GTTTTGCCTG   8460
TAGGTGGATG  TTTTGCGCCA  GAGGTGACGA  TAAGAGTAAA  TGACCGTATT  ATTGGGCAAG   8520
GTGAGTTGAT  TGCCTGTGGC  AATGAATTTA  TGGTGCGTAT  TACACGTTGG  TATCTTTGCA   8580
AAAATACAGC  GTAAACCTGA  TAAGAAAAAT  AATATGCGAA  CAATATAATA  GCGTTCCAGG   8640
TCGTGTCATG  AGAGATACAG  TATGTCTTTA  CCCGATTCGC  CTTTGCAACT  GATTGGTATA   8700
TTGTTTCTGC  TTTCAATACT  GCCTCTCATT  ATCGTCATGG  GAACTTCTTT  CCTTAAACTG   8760
GCGGTGGTAT  TTTCGATTTT  ACGAAATGCT  CTGGGTATTC  AACAAGTCCC  CCCAAATATC   8820
GCACTGTATG  GCCTTGCGCT  TGTACTTTCC  TTATTCATTA  TGGGGCCGAC  GCTATTAGCT   8880
GTAAAGAGC   GCTGGCATCC  GGTTCAGGTC  GCTGGCGCTC  CTTTCTGGAC  GTCTGAGTGG   8940
GACAGTAAAG  CATTAGCGCC  TTATCGACAG  TTTTTGCAAA  AAAACTCTGA  AGAGAAGGAA   9000
GCCAATTATT  TTCGGAATTT  GATAAAACGA  ACCTGGCCTG  AAGACATAAA  AGAAAGATA    9060
AAACCTGATT  CTTTGCTCAT  ATTAATTCCG  GCATTTACGG  TGAGTCAGTT  AACGCAGGCA   9120
TTTCGGATTG  GATTACTTAT  TTATCTTCCC  TTTCTGGCTA  TTGACCTGCT  TATTTCAAAT   9180
ATACTGCTGG  CTATGGGGAT  GATGATGGTG  TCGCCGATGA  CCATTTCATT  ACCGTTTAAG   9240
CTGCTAATAT  TTTTACTGGC  AGGCGGTTGG  GATCTGACAC  TGGCGCAATT  GGTACAGAGC   9300
TTTTCATGAA  TGATTCTGAA  TTGACGCAAT  TTGTAACGCA  ACTTTTATGG  ATCGTCCTTT   9360
TTACGTCTAT  GCCGGTAGTG  TTGGTGGCAT  CGGTAGTTGG  TGTCATCGTA  AGCCTTGTTC   9420
AGGCCTTGAC  TCAAATACAG  GACCAAACGC  TACAGTTCAT  GATTAAATTA  TTGGCAATTG   9480
CAATAACCTT  AATGGTCAGC  TACCCATGGC  TTAGCGGTAT  CCTGTTGAAT  TATACCCGGC   9540
AGATAATGTT  ACGAATTGGA  GAGCATGGTT  GAATGGCACA  ACAGGTAAAT  GAGTGGCTTA   9600
TTGCATTGGC  TGTGGCTTTT  ATTCGACCAT  TGAGCCTTTC  TTTATTACTT  CCCTTATTAA   9660
AAAGTGGCAG  TTTAGGGGCC  GCACTTTAC   GTAATGGCGT  GCTTATGTCA  CTTACCTTTC   9720
CGATATTACC  AATCATTTAC  CAGCAGAAGA  TTATGATGCA  TATTGGTAAA  GATTACAGTT   9780
GGTTAGGGTT  AGTCACTGGA  GAGGTGATTA  TTGGTTTTTC  AATTGGGTTT  TGTGCGGCGG   9840
TTCCCTTTTG  GGCCGTTGAT  ATGGCGGGGT  TTCTGCTTGA  TACTTTACGT  GGCGCGACAA   9900
TGGGTACGAT  ATTCAATTCT  ACAATAGAAG  CTGAAACCTC  ACTTTTGGC   TTGCTTTTCA   9960
GCCAGTTCTT  GTGTGTTATT  TTCTTTATAA  GCGGCGGCAT  GGAGTTTATA  TTAAACATTC  10020
TGTATGAGTC  ATATCAATAT  TTACCACCAG  GGCGTACTTT  ATTATTTGAC  CAGCAATTTT  10080
```

```
TAAAATATAT  CCAGGCAGAG  TGGAGAACGC  TTTATCAATT  ATGTATCAGC  TTCTCTCTTC  10140
CTGCCATAAT  ATGTATGGTA  TTAGCCGATC  TGGCTTTAGG  TCTTTTAAAT  CGGTCGGCAC  10200
AACAATTGAA  TGTGTTTTTC  TTCTCAATGC  CGCTCAAAAG  TATATTGGTT  CTACTGACG Y 10260
CCTGATCTCA  TTCCCTTATG  CTCTTCATCA  CTATTTGGTT  GAAAGCGATA  AATTTTATAT  10320
TTATCTAAAA  GACTGGTTTC  CATCTGTATG  AGCGAGAAAA  CAGAACAGCC  TACAGAAAAG  10380
AAATTACGTG  ATGGCCGTAA  GGAAGGGCAG  GTTGTCAAAA  GTATTGAAAT  AACATCATTA  10440
TTTCAGCTGA  TTGCGCTTTA  TTTGTATTTT  CATTTCTTTA  CTGAAAAGAT  GATTTTGATA  10500
CTGATTGAGT  CAATAACTTT  CACATTACAA  TTAGTAAATA  AACCATTTTC  TTATGCATTA  10560
ACGCAATTGA  GTCATGCTTT  AATAGAGTCA  CTGACTTCTG  CACTGCTGTT  TCTGGGCGCT  10620
GGGGTAATAG  TTGCTACTGT  GGGTAGCGTG  TTTCTTCAGG  TGGGGGTGGT  TATTGCCAGC  10680
AAGGCCATTG  GTTTAAAAG   CGAGCATATA  AATCCGGTAA  GTAATTTTAA  GCAGATATTC  10740
TCTTTACATA  GCGTAGTAGA  ATTATGTAAA  TCCAGCCTAA  AAGTTATCAT  GCTATCTCTT  10800
ATCTTTGCCT  TTTTCTTTTA  TTATTATGCC  AGTACTTTTC  GGGCGCTACC  GTACTGTGGG  10860
TTAGCCTGTG  GCGTGCTTGT  GGTTTCTTCT  TTAATAAAAT  GGTTATGGGT  AGGGGTGATG  10920
GTTTTTTATA  TCGTCGTTGG  CATACTGGAC  TATTCTTTTC  AATATTATAA  GATTAGAAAA  10980
GCTATCTAAA  AATGAGTAAA  GATGACGTAA  AACAGGAGCA  TAAAGATCTG  GAGGGCGACC  11040
CTCAAATGAA  GACGCGGCGT  CGGAAATGCA  GAGTGAAATA  CAAAGTGGGA  GTTTAGCTCA  11100
ATCTGTTAAA  CAATCTGTTG  CGGTAGTGCG  TAATCCAACG  CATATTGCGG  TTTGTCTTGG  11160
CTATCATCCC  ACCGATATGC  CAATACCACG  CGTCCTGGAA  AAAGGCAGTG  ATGCTCAAGC  11220
TAACTATATT  GTTAACATCG  CTGAACGCAA  CTGCATCCCC  GTTGTTGAAA  ATGTTGAGCT  11280
GGCCCGCTCA  TTATTTTTTG  AAGTGGAACG  CGGAGATAAA  ATTCCTGAAA  CGTTATTTGA  11340
ACCCGTTGCA  GCCTTGTTAC  GTATGGTGAT  GAAGATAGAT  TATGCGCATT  CTACCGAAAC  11400
ACCATAAATG  CTTTTGGTAT  GCTTCTTCAG  GCCACTGCGA  AGGTTAAGAG  GGTAATAGCG  11460
TATAGAGCAG  TGCTTGACGA  TAAAGGTGAG  AGACTGAAAA  TAATCGCTTT  TAGCCTGGCA  11520
CAAGCACCAG  ATAGCGTATT  ATAAAATTAA  ACAAGATAAT  GGATTGGTGC  GTCTGAATGG  11580
ACTCGAACCA  CTCGACCCCC  ACCATGTCAA  GGTGGTGCTC  TAACCAACTG  AGCTATGAAC  11640
GGCAACGTTG  TAGGTGACAA  CGGGGACGAA  TATTAGCGTC  ACAACCGCAA  TGAGGCAAGA  11700
GGGAAATCGC  AATTTTCTTC  CTGAAATCAC  CTGATTGCGG  TGGAAATATG  CAACATGTCG  11760
AGAAAATAGC  CGCCATGCGA  CGGCTATCGT  CGTATTATCG  GAGCGCGCTG  CAAAATGATG  11820
GCGGACGGCT  GACGTTGTAG  ATAGCGCATC  CGTAGCATCA  TTAACACCGC  CGCCGAGGTC  11880
AGGCCGATGA  TGAACCCCAT  CCAGAAGCCT  GCCGGTCCCA  TACGATCCAC  CACCAAATCC  11940
GTTAACGCCA  GGATATAACC  GCTGGGTAAA  CCTAACACCC  AGTAGGCGGT  AAAGGTGATA  12000
AAAAGATGG   AACGCGTATC  TTTATAACCG  CGCAGAATAC  CGCTGCCGAT  AACCTGTATA  12060
GAGTCGGAAA  TCTGGTAAAC  CGCAGCGAGC  AGCATTAATT  GCGGCAAGCG  CCACGACCTC  12120
AGGGTTGTCA  TTGTAGAGCA  AAGCAATATG  CTTACGCAGA  GTAACGGTAA  AAATAGCGGT  12180
AACCACAGCC  ATACAAATGC  CGACGCCTAA  ACCGGTACGC  GCTGCGTTTG  CGCATCCAGC  12240
GTTGAGCCCT  GGCCCAGACC  GATAACCCAC  TCGAATCGTT  ACCGCCGCAG  CCAGCGACAT  12300
CGGCAGTACG  AACATCAGCG  AGCTAAAGTT  AAGCGCAATC  TGATGACCGG  CGACATCCAC  12360
AATACCTAAT  GGCGAAACCA  GCAGCGCAAC  GACCGCAAAT  AACGTCACTT  CAAAGAACAG  12420
CCAGCGCAAT  CGGCAACCCC  AGTTGAATCA  GGCGCTTCAT  GACGACGCTA  TCGGGTTTGC  12480
```

| | | | | | | |
|---|---|---|---|---|---|---|
|CAAAGCCTTT|TTCATTACGA|ATATCACGCA|TTGAACGCGC|GTGTTTAATG|TAAGAAAGCA|12540|
|TGGCGATAAA|CATCACCCAA|TAGACCGCCG|CAGTCGCAAC|GCCGCAGCCG|ATACCGCGA|12600|
|GTTCCGGCAT|ACCAAAATGG|CCATAGATAA|AAATATAGTT|CACCGGAATA|TTCACCAGCA|12660|
|GGCCCAAAAA|TCCCATCACC|ATACCCGGTT|TGGTTTTGGC|CAGACCTTCG|CACTGGTTTC|12720|
|GCGCTACCTG|AAAGAAAAGG|TATCCTGCGC|CCCACAGCAG|CGCGCGAAGA|TAACCCACGG|12780|
|CTTTATCGGC|CAGCGCCGGA|TCAATATTAT|GCATAGAGCG|GATAATGTAT|CCGGCATTCC|12840|
|ACAGGACGAT|CATCACCAGC|ACGGAGACAA|AGCCCGCCAG|CCAGAACCCT|TGTCGAACCT|12900|
|GATGCGCGAT|ACGCTCACGA|CGGCCGGAGC|CATTGAGTTG|CGCAATCACA|GGCGTCAAGG|12960|
|CCAGCAGTAA|GCCGTGACCA|AACAAAATGG|CGGGAAGCAG|ATAGAGGTGC|CGATAGCGAC|13020|
|GGCAGCCATG|TCCGTAGCGC|TATAGCCTCC|CGCCATGACG|GTATCGACGA|ATCCATTGCG|13080|
|GTCTATACCA|CTTGCGCAAG|GATCACCGGT|ATCTGAACGC|TAATAACTGA|CGCGCTTCAC|13140|
|TGGTATACTT|CTGCACGTAT|TCACCTTTTA|TTTTGTTGTT|ATATGAAAGA|CTAAAAGCC|13200|
|GCCGAAGTGG|CAGCCAAAAG|AAATAGCAGG|GGAAATTTCA|GTCTATTGTA|GCGGGGTATT|13260|
|ACTATTTCTC|CAGTGAAAAA|ACAGTTGTTA|ACGGCGCATT|GCTGGCAAGC|TGTTTTTCCA|13320|
|CCTGCTATTG|TGCTGAACAG|TTCTGCTTTT|ATTTATTTCA|GGAGTTGAAG|ATATGTTTAC|13380|
|GGGGATCGTA|CAGGGTACCG|CGAAACTGGT|ATCGATA| | |13417|

(2) INFORMATION FOR SEQ ID NO: 38:

(i) SEQUENCE CHARACTERISTICS:
        (A) LENGTH: 5746 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: DNA sequence of VGC II cluster C (xi) SEQUENCE DESCRIPTION: SEQ ID NO: 38:

| | | | | | | |
|---|---|---|---|---|---|---|
|GGATCCTTTT|TCTTTAATGC|TGCTAACGTT|TCTTGCAAAA|TGCGTTGATG|AGATTCATCC|60|
|AGTACACCAC|TGATAACAAA|AGAGCGNCGC|ATTGGCNWAM|MWTKRNNMRN|NSCNNNACTA|120|
|AACCGTTCTC|TATTATCGCA|GAAATAATAT|CATCCCCTG|AGACTGATGA|GAGTGACTAA|180|
|TCTGCCAGTG|CAATAACCCG|GGAATATCTG|CAAGTAATGG|TTGAACCTTG|CGCCATTGCT|240|
|GATCCATTTG|TATATCATCA|TGAATTAACA|CGCTCCCCGG|CCCTTCGCTG|GATACTTCAG|300|
|CATNSSGGTA|ACCCATTTTT|ATCAAACAT|CCTGCACTTC|TCGTACCAAT|AAGTCATCAC|360|
|AGATTACACC|ATCCCGATAC|ATGACCCCC|ATGATTCGAG|AGTCGCTCTC|ACCTTTTGCA|420|
|TCTGTTCGCT|TGACGAGCAA|TAACCGGACA|ACTGCAGGCT|GCCATCTTCT|TTCCATTGCG|480|
|CCCGCACATA|ATGAATATTG|CTTTTGTCTA|ATAAAAACTT|AACCCGCAAA|GGTAAGTCAT|540|
|TTACCGTTTC|AGGCTGACCA|CTAATACTTA|ACAGGACACC|CATTCCACCG|ATGAAAATCA|600|
|AGAATACGCC|AGCCAACCAC|CAGTACCCTG|ATCTGGAAAC|GGGTATTTGA|TAATCAGCAA|660|
|GTTCACAATC|CTGTTTACCA|AACGCGATAS|SCACTCCCGC|AACCTGCAAA|ACCCCACTGG|720|
|ATGGTAGCGG|CTTATTTGGA|TTAAATCTGC|GGCCATTAAC|TCTAACTCTG|GCTTTCCCGG|780|
|CATCAACAAA|TAAACTATCT|GCCTGTTCTC|TCAGAATAAT|TTTTTCATTT|ATAGCCAGCG|840|

```
AATACAAATA  TCGCATCCCT  TCTCCCCCAG  TGACAGGTTA  CCTTCATTCA  GCCATACTTC      900

CCGGCCTTGT  AAAACGTGAC  CTAAAAAACG  TATTTTCCAG  GAACTCTTTG  GATTAACCAT      960

GAGATATGCC  ATTATTTACT  ACTGAGGCTT  TAATCAAAAA  AGCCTGATT   ACACTATGTA     1020

CTTGAGTCGT  ATCATTGCGA  AACAAATGAC  CTACAACAGG  AATATCGCCC  AATAAAGGGA     1080

TTTTGTTTTG  CGAGTGGATT  TGTTTACCTT  GTTTAAACCC  TCCCAGCAAT  NAGACTTTGC    1140

CCGGCCAATA  ATGTGGCTTG  CGAANCRATT  TCAGAATTTT  GCACTTCGGG  CAGCGGGTCT    1200

GTNT Y GCY TT  KGNSTATCAC  TTTGTTGTCC  ATCCTGAANT  ATTAAGATTA  AGCATTATTT   1260

TTTGCGTGCC  ATTGTCATTT  AACAAGCGAG  GTGTAACGCG  WNAACAAAGA  ACCCGTAGTG    1320

ATGGATTCAA  GTTTAGCCAC  TTTTTCTCCC  TGCAGTTTGG  TATAGAAAGT  AATATTTTA     1380

TCCAGCACAG  CCTGGATATT  ATTTAAAGTC  ACCACAGATG  GCTGGGAAAG  TACATAAGCC   1440

TGAGAGCTTT  TTTCCAGGGC  ATTCAGACGC  ACCATAAAGT  TTGAGGTATC  GCTGATTACC   1500

GTTGANNAAC  CACTAGCACC  ACCGTCATTC  AAACCTGTAT  TGAACGCAAT  TTTCTTGCCA   1560

CCCAGCGACA  CTGCCGTTCC  CCAGTCGATG  CCTAACTGGT  TAATATCTCC  AGCATTAACA   1620

TCGATAATTT  TCACCGAAAT  CTCTATCATC  TGCTGGCGTT  GATCTAATTC  TGTGATGAGT   1680

TTCCGATACN  NNGCCATATT  GGNNNCATAA  TCACGAACGA  TCACTGCATT  CTGGCGTNGG   1740

GTCGGCAGCA  AACATNGGCA  ATGCCTGTGT  AGCGGGTGAA  CCATTGTTCN  TCGATGACGT   1800

CGGGACGCTG  GTTTTACTCA  TCTCACGCAA  TACACTAACG  ACCCCTGGNN  AACCACGACG   1860

GACTGATCGC  GATATTGGTA  CTGGGTATCC  ATCGCAGTGG  CATACTTAAG  CGTGTATATA   1920

CTTACACTCA  CCGCACTGTC  TTTTCGTTTG  ATTAACGCAT  TATCCAGCAC  TGAAGCTAAT   1980

TGACTAATAC  GAGTCAGGCA  GCTGGGAACA  CCGCTCACCT  CCACAGCTTT  GGTACCGGTA   2040

ATTTCTTTAA  CCTCGCATCC  CGGTGATGAA  AGGATATTCT  GGCTGCGTAA  GTAATGAATG   2100

AACCGTCCAG  TAGATAAAAT  ATTGAAAGTG  ATAACCTGAT  GTTTTAATAA  CGATGCAGGA   2160

TATACATATA  ACATGCTGCC  ATCAAACCAG  GTAAGCAAAT  CATATTGTGC  TGCCAGGTTA   2220

TTCAAAATAT  CGACCGGTGG  TCCAGGCGGA  ATTTTTCCAC  TAAATGTAGC  TGTTATCAAT   2280

GGGCTAATAG  TAATAGCCGT  ATCATAGTTC  TCTGAGAGCA  GATGTNAAAA  CCTCTGCTAA   2340

TGGCATTTGT  CTGGCATAAA  GGGTGAAGTC  ATTACCTTTC  CATGATAACT  CATCACTCTT   2400

TGCTGTATTG  AGTATAAATA  GTAAAATTAA  GATTAAACGT  TTATTTACTA  CCATTTTATA   2460

CCCCACCCGA  ATAAAGTTTA  TGGTGATTGC  GTATTACATT  TTTNAAAAT   GCAAGTTAAA   2520

GCCAGGTGTT  TTTCTATCTC  AATAGCAATA  AGCTCAGAGC  TACTACTTGT  GGTATAATAA   2580

CCGTTTAACC  ATCCCCCATC  CGCTGTGAGC  TGTATAGCAT  AATCATGGAC  GTCCGGGTGT   2640

GCGCAARCRG  TAGTGTCAMM  TAGGCAAGAC  AAGGCTTAGG  TAAGCTTTCC  AGGTCATTTA   2700

AGAACAAAGA  AATAGAAAAT  GCTTCTGAGA  AAATTTCT Y C   Y BHNNNNNNN  NNNNNNNNN   2760

NNNNNNNCA TCAATAGTCA TTATCCAG-
GA  TSSKMTWWYM  N Y  Y KSSSCY S  WKATM Y  Y SWR     2820

WWTTAATGGA  ATGCCTTTTA  AAACTGCCAG  CATGAATCCC  TCCTCAGACA  TAAATGGGAG   2880

TTTCTATCAA  ATTCGCTCAC  AACCACATCC  GTAAAAAGCC  TGATTCACAT  TTATTTCGAC   2940

TATACTCTTC  TTGTACAATA  TCAGGATGCT  GTCTACATAT  ACCTTGTCAC  AGGCGATTCT   3000

ATCATTCGGA  TTTTCCGATA  AATTNMMCAA  TTACATTTTC  AGCATTGACA  TAAAAACTTA   3060

CAATTTGNAA  AATTATTTAT  TAAATAAACT  GTTACGATGT  TTTTACATCG  CCATCTTATT   3120

AAAAAGTAAT  TGTAGTCATC  GACTNGGTTA  TATATGAAGA  AATTTATCTT  CCTAATGATA   3180
```

| | | | | | | |
|---|---|---|---|---|---|---|
| ACACCATCGA | TTAATCWWCT | GATGAAACTA | TATGTACTGC | GATAGTGATC | AAGTGCCAAA | 3240 |
| GATTTTGCAA | CAGGCAACTG | GAGGGAAGCA | TTATGAATTT | SSTCAATCTC | AAGAATACSS | 3300 |
| YSYRNNNNNN | TCTTTAGTAA | TCAGGCTAAC | TTTTTTATTT | TTATTAACAA | CAATAATTWT | 3360 |
| TTGGCTGCTA | TCTGTGCTTA | CCGCAGCTTA | TATATCAATG | GTTCRGAAAC | GGCAGCATAT | 3420 |
| AATAGAGGAT | TTATCCGTTC | TATCCGAGAT | GAATATTGTA | CTAAGCAATC | AACGGTTTGA | 3480 |
| AGAAGCTGAA | CGTGACGCTA | AAAATTTAAT | GTATCAATGC | TCATTAGCGA | CTGAGATTCA | 3540 |
| TCATAACGAT | ATTTTCCCTG | AGGTGAGCCG | GCATCTATCT | GTCGGTCCTT | CAAATTGCAC | 3600 |
| MGCCGACGCT | NAACGGAGAG | AAGCACCGTC | TCTTTCTGCA | GTCCTCTGAT | ATCGATGAAA | 3660 |
| ATAGCTTTCG | TCGCGATAGT | TTTATTCTTA | ATCATAAAAA | TGAGATTTCG | TTATTATCTA | 3720 |
| CTGATAACCC | TTCAGATTAT | TCAACTCTAC | AGCCTTTAAC | GCGAAAAAGC | TTTCCTTTAT | 3780 |
| ACCCAACCCA | TGCCGGGTTT | TACTGGAGTG | AACCAGAATA | CATAAACGGC | AAAGGATGGC | 3840 |
| AACGCTTCCG | TTGCGGTTGC | CGATCAGGCA | AGGCGTATTT | TTTGAGGTGA | CGGTTAAACT | 3900 |
| TCCCGATCTC | ATTACTAAGA | GCCACCTGCC | ATTAGATGAT | AGTATTCGAG | TATGGCTGGA | 3960 |
| TCAAAACAAC | CACTTATTGC | CGTTTTCATA | CATCCCGGCA | AAAAATACGT | ACACAGTTAG | 4020 |
| AAAATGTAAC | GCTGCATGAT | GGATGGCAGC | AAATTCCCGG | ATTTCTGATA | TTACGCACAA | 4080 |
| CCTTGCATGG | CCCCGGATGG | AGTCTGGTTA | CGCTGTACCC | ATACGGTAAT | CTACATAATC | 4140 |
| GCATCTTAAA | AATTATCCTT | CAACAAATCC | CCTTTACATT | AACAGCATTG | GTGTTGATGA | 4200 |
| CGTCGGCTTT | TTGCTGGTTA | CTACATCGCT | CACTGGCCAA | ACCGTTATGG | CGTTTTGTCG | 4260 |
| ATGTCATTAA | TAAAACCGCA | ACTGCACCGC | TGAGCACACG | TTTACCAGCA | CAACGACTGG | 4320 |
| ATGAATTAGA | TAGTATTGCC | GGTGCTTTTA | ACCAACTGCT | TGATACTCTA | CAAGTCCAAT | 4380 |
| ACGACAATCT | GGAAAACAAA | GTCGCAGACG | CACCCAGGCG | CTAAATGAAG | CAAAAAAACG | 4440 |
| CGCTGAGCNA | GCTAACAAAC | GTAAAAGCAT | TCATCTTACG | GTAATAAGTC | ATGAGTTACG | 4500 |
| TACTCCGATG | AATGGCGTAC | TCGGTGCAAT | TGAATTATTA | CAAACCACCC | CTTTAAACAT | 4560 |
| AGAGCAACAA | GGATTAGCTG | ATACCGCCAG | AAATTGTACA | CTGTCTTTGT | TAGCTATTAT | 4620 |
| TAATAATCTG | CTGGATTTTT | CACGCATCGA | GTCTGGTCAT | TTCACATTAC | ATATGGAAGA | 4680 |
| AACAGCGTTA | CTGCCGTTAC | TGGACCAGGC | AATGCAAACC | ATCCAGGGGC | CAGCGCNAAA | 4740 |
| GCAAAAAACT | GTCATTACGT | ACTTTTGTCG | GTCAACATGT | CCCTCTCTAT | TTTCATACCG | 4800 |
| ACAGTATCCG | TTTACNNCAA | ATTTTGGTTA | ATTTACTCGG | GAACGCGGTA | AAATTTACCG | 4860 |
| AAACCGGAGG | ATACGTCTGA | CGGTCAAGCG | TCATGAGGAA | CAATTAATAT | TTCTGGTTAG | 4920 |
| CGATAGCGGT | AAAGGGATTG | AAATACAGCA | GCAGTCTCAA | ATCTTTACTG | CTTTTTATCA | 4980 |
| AGCAGACACA | AATTCGCAAG | GTACAGGAAT | TGGACTGACT | ATTGCGTCAA | GCCTGGCTAA | 5040 |
| AATGATGGGC | GGTAATCTGA | CACTAAAAAG | TGTCCCCGGG | GTTGGAACCT | GTGTCTCGCT | 5100 |
| AGTATTACCC | TTACAAGAAT | ACCAGCCGCC | TCAACCAATT | AAAGGGACGC | TGTCAGNNNC | 5160 |
| CGTTCTGCCT | GCATCGGCAA | CTGGCTTGCT | GGGGAATACG | CGGTGAACCA | CCCCACCAGC | 5220 |
| AAAATGCGCT | TCTCAANNCN | AGAGCTTTTG | TATTTCTCCG | GAAAACTCTA | CGACCTGGCG | 5280 |
| CAACAGTTAA | TATTGTGTAC | ACCAAATATG | CCAGTAATAA | ATAATTTGTT | ACCACCCTGG | 5340 |
| CAGTTGCAGA | TTCTTTTGGT | TGATGATGCC | GATATTAATC | GGGATATCAT | CGGCAAAATG | 5400 |
| CTTGTCAGCC | TGGGCCAACA | CGTCACTATT | GCCGCCAGTA | GTAACGAGGC | TCTGACTTTA | 5460 |
| TCACAACAGC | AGCGATTCGA | TTTAGTACTG | ATTGACATTA | GAATGCCAGA | AATAGATGGT | 5520 |
| ATTGAATGTG | TACGATTATG | GCATGATGAG | CCGAATAATT | TAGATCCTGA | CTGCATGTTT | 5580 |

| | | | | | |
|---|---|---|---|---|---|
|GTGGCACTAT|CCGCTAGCGT|ASCVNMAGAW|RWTMWTCRTY|GTDDAAAAAA|WRDGRKDHWT 5640|
|CATHAYANNT|TACAAAACCA|GTGACATTGG|CTACCTTAGC|TCGCTACATC|AGTATTGCCG 5700|
|CAGAATACCA|ACTTTTACGA|AATATAGAGC|TACAGGAGCA|GGATCC| 5746|

( 2 ) INFORMATION FOR SEQ ID NO: 39:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 39:

| | | | | | |
|---|---|---|---|---|---|
|CCACCAGCCG|CTGGGGTACC|AGGGCCAGGC|GACGGATATT|GAAATTCACG|CCCGCGAAAT 60|
|TTTGAAAGTA|AAAGGGCGCA|TGAATGAACT|TATGRMKYKM|MATACGGGTC|ANTCTCTTGA 120|
|GCAGATTGAA|SGTGATACTG|A| | | 141|

( 2 ) INFORMATION FOR SEQ ID NO: 40:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 40:

| | | | | | |
|---|---|---|---|---|---|
|TGAAGCGGTA|GAGTACGGTT|TGGTTGACTC|AATTTTGACC|CATCGTAATT|GATGCCCTGG 60|
|ACGCAA| | | | | 66|

( 2 ) INFORMATION FOR SEQ ID NO: 41:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 41:

| | | | | | |
|---|---|---|---|---|---|
|CCAACCGTTG|GGCGGCTACC|AGGGCCAGGC|GACCGATATC|GAAATTCATG|CCCGTGAAAT 60|
|TCTGAAAGTT|AAAGGGCGCA|TGAATGAACT|TATGGCGCTT|CATACGGGTC|AATCATTAGA 120|
|ACAGATTGAA|CGTGATACCG|A| | | 141|

( 2 ) INFORMATION FOR SEQ ID NO: 42:

( i ) SEQUENCE CHARACTERISTICS:
        ( A ) LENGTH: 66 base pairs
        ( B ) TYPE: nucleic acid
        ( C ) STRANDEDNESS: double (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO: 42:

TGAAGCGGTG GAATACGGTC TGGTCGATTC GATTCTGACC CATCGTAATT GATGCCAGAG 60

GCGCAA 66

(2) INFORMATION FOR SEQ ID NO: 43:

(i) SEQUENCE CHARACTERISTICS:
(A) LENGTH: 107 base pairs
(B) TYPE: nucleic acid
(C) STRANDEDNESS: double
(D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO: 43:

GATATCGAAA TTCATGCCCG TGAAATTCTG AAAGTTAAAG GGCGCATGAA TGAACTTATG 60

GCGCTTCATA CGGGTCAATC ATTAGAACAG ATTGAACGTG ATACCGA 107

(2) INFORMATION FOR SEQ ID NO: 44:

(i) SEQUENCE CHARACTERISTICS:
(A) LENGTH: 66 base pairs
(B) TYPE: nucleic acid
(C) STRANDEDNESS: double
(D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO: 44:

TGAAGCGGTG GAATACGGTC TGGTCGATTC GATTCTGACC CATCGTAATT GATGCCAGAG 60

GCGCAA 66

(2) INFORMATION FOR SEQ ID NO:45:

(i) SEQUENCE CHARACTERISTICS:
(A) LENGTH: 15 amino acids
(B) TYPE: amino acid
(C) STRANDEDNESS: single
(D) TOPOLOGY: linear (i i) MOLECULE TYPE: protein (i i i) HYPOTHETICAL: NO (x i) SEQUENCE DESCRIPTION: SEQ ID NO:45:

Leu Gln Asn Arg Ala Arg Ser Lys Leu Ile Phe Leu Asn Asn Cys
1               5                   10                  15

(2) INFORMATION FOR SEQ ID NO:46:

(i) SEQUENCE CHARACTERISTICS:
(A) LENGTH: 17 amino acids
(B) TYPE: amino acid ( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:46:

Lys Met Lys His Pro Pro Val Thr Pro Val Leu Tyr Tyr Arg Arg Leu
1               5                   1 0                  1 5
Cys ( 2 ) INFORMATION FOR SEQ ID NO:47:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:47:

Pro Asp Lys Trp Ile Ile Cys Ser
1               5

( 2 ) INFORMATION FOR SEQ ID NO:48:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:48:

Ala Ser Ile Ile Leu Pro Glu Tyr His Gly Ala Ala Cys Gln Ala Leu
1               5                   1 0                  1 5
Asn Lys Leu Asp Asn Met Ala
            2 0

( 2 ) INFORMATION FOR SEQ ID NO:49:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:49:

Arg Phe Ile Val
1

( 2 ) INFORMATION FOR SEQ ID NO:50:

( i ) SEQUENCE CHARACTERISTICS:
( A ) LENGTH: 79 amino acids
( B ) TYPE: amino acid
( C ) STRANDEDNESS: single
( D ) TOPOLOGY: linear (i i) MOLECULE TYPE: protein (i i i) HYPOTHETICAL: NO (x i) SEQUENCE DESCRIPTION: SEQ ID NO:50:

Tyr Phe Leu Leu Ser Leu Arg Ser Phe Leu Arg His Val Met Trp Ile
1               5                   10                  15

Phe Ile Ala His Cys Gln Lys Met Lys Arg Ile Lys Cys Trp His Tyr
            20                  25                  30

Leu Cys Ser Ile Ile Leu Met Arg Lys Lys Thr Gly Arg Gly Trp Cys
            35              40                  45

Asn Leu Thr Cys Arg Ala Val Gly Ser Leu Leu Met Arg Leu Arg Leu
        50              55                  60

Leu Arg Leu Asn Gly Tyr Pro His Arg Ala Val Tyr Asn Gly Gly
65              70                  75

(2) INFORMATION FOR SEQ ID NO:51:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: protein (i i i) HYPOTHETICAL: NO (x i) SEQUENCE DESCRIPTION: SEQ ID NO:51:

Asp Val Ser Gly
1

(2) INFORMATION FOR SEQ ID NO:52:

(i) SEQUENCE CHARACTERISTICS:
(A) LENGTH: 16 amino acids
(B) TYPE: amino acid
(C) STRANDEDNESS: single
(D) TOPOLOGY: linear (i i) MOLECULE TYPE: protein (i i i) HYPOTHETICAL: NO (x i) SEQUENCE DESCRIPTION: SEQ ID NO:52:

Ser Val Ser Gly Ile Thr Pro Gly Arg Thr Gly Arg Arg Leu Ile Phe
1               5                   10                  15

(2) INFORMATION FOR SEQ ID NO:53:

(i) SEQUENCE CHARACTERISTICS:
(A) LENGTH: 8 amino acids
(B) TYPE: amino acid
(C) STRANDEDNESS: single
(D) TOPOLOGY: linear (i i) MOLECULE TYPE: protein (i i i) HYPOTHETICAL: NO (x i) SEQUENCE DESCRIPTION: SEQ ID NO:53:

Lys Asn Lys Glu Leu Lys Glu Cys
1               5

(2) INFORMATION FOR SEQ ID NO:54:

(i) SEQUENCE CHARACTERISTICS:
(A) LENGTH: 18 amino acids (B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:54:

Val Arg Trp Arg Gly Val Ile Asn Gly Lys Ser Asp His Cys Ala Thr
1               5                   10                  15
Asp Leu (2) INFORMATION FOR SEQ ID NO:55:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:55:

Arg Phe Ser Glu Leu Ser Cys Arg Ile Tyr Lys Ile Phe Thr Ser Gly
1               5                   10                  15
Gln Tyr Gly Gly Leu Ser Gly Lys Asn
            20                  25

(2) INFORMATION FOR SEQ ID NO:56:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:56:

Arg Phe Asn Arg Asp Val Asn Pro Trp Val Ala Ile Gln
1               5                   10

(2) INFORMATION FOR SEQ ID NO:57:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:57:

Tyr Leu Asp Ala Ala Cys
1               5

(2) INFORMATION FOR SEQ ID NO:58:

(i) SEQUENCE CHARACTERISTICS:
(A) LENGTH: 5 amino acids
(B) TYPE: amino acid
(C) STRANDEDNESS: single
(D) TOPOLOGY: linear ( i i ) MOLECULE TYPE: protein ( i i i ) HYPOTHETICAL: NO ( x i ) SEQUENCE DESCRIPTION: SEQ ID NO:58:

Ile Gln Asn Gly Ser
1               5

( 2 ) INFORMATION FOR SEQ ID NO:59:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:59:

Arg Thr Arg Glu Thr Asn Ile Leu Asp Tyr Gly Arg Tyr Gln Arg Gln
1               5                   10                  15

( 2 ) INFORMATION FOR SEQ ID NO:60:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:60:

Arg Glu Gly Gly Glu Val Val Asp Glu Ile Pro Leu Ser Val Asp Val
1               5                   10                  15

Ile Val Asp Arg Thr Val Ile Arg Ser Gly His Pro Asp Arg Leu Phe
                20                  25                  30

Leu Pro Glu Thr Pro Phe Leu Ser Arg Pro Asp Pro Glu Val Leu Gln
                35              40                  45

Leu Tyr Arg Tyr Phe Trp Gln Pro Ala Arg Tyr Ala Val Pro Glu Trp
        50                  55                  60

Leu Asp Lys Leu Gly Phe His Leu Gln Thr Ala Gly Val Met Ala Ile
65                      70                  75                  80

Gly Pro Ser Trp Ile Val Phe Leu Thr Glu Arg
                85                  90

( 2 ) INFORMATION FOR SEQ ID NO:61:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:61:

Glu Glu Ala Leu Leu Phe Gln Pro Val
1               5

(2) INFORMATION FOR SEQ ID NO:62:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:62:

```
Met Thr Gly Lys Asn Gly Arg Phe Val Leu Arg Arg Val Tyr Arg His
 1               5                  10                  15
Leu Pro Leu Gly Trp Asp Tyr Ser Asn Ser Gly Val Val Thr Ile Leu
            20                  25                  30
Cys Tyr Gln Ser Ile Gly Asn Cys Phe Tyr Ser Gly Leu Ala Arg Met
             35              40                  45
Arg Ser Gly Ser Tyr Met Val Gly Trp Gly Lys Glu Met Ala Asn Tyr
        50                  55                  60
Phe Leu Arg Lys
65
```

(2) INFORMATION FOR SEQ ID NO:63:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:63:

```
Cys Asn Lys Leu His Cys Arg Ser Val Pro Pro Phe Leu Ile Gly Lys
 1               5                  10                  15
Arg Met Thr Met Arg Val Leu His Ala Leu Leu Val Leu Leu Pro Pro
            20                  25                  30
Pro Gln Arg Ile Leu Trp Pro Lys Thr Ser Leu Thr Glu Ile Ile Phe
             35              40                  45
Met Glu His Leu Leu
        50
```

(2) INFORMATION FOR SEQ ID NO:64:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:64:

```
Val Leu Leu His Phe Leu
 1               5
```

(2) INFORMATION FOR SEQ ID NO:65:

(i) SEQUENCE CHARACTERISTICS:
        (A) LENGTH: 17 amino acids
        (B) TYPE: amino acid ( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:65:

Arg Lys Leu Thr Ile Ser Tyr Pro Leu Glu Ile Leu Leu Ser His Ser
 1               5                  10                 15
Gly ( 2 ) INFORMATION FOR SEQ ID NO:66:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:66:

Leu Tyr Leu Arg Lys Ser Asn Lys Leu Arg Glu Phe His Met Leu Leu
 1               5                  10                 15

( 2 ) INFORMATION FOR SEQ ID NO:67:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:67:

Ala Pro Leu Thr Val Arg Leu Lys Lys Ser Ser Glu Thr Pro Ile Val
 1               5                  10                 15
Ile Ser Val Asn Arg Lys Leu Ser Ser Asn Lys Asn
                20                  25

( 2 ) INFORMATION FOR SEQ ID NO:68:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:68:

Arg Ala Cys Val Lys Ile Arg Trp Lys Lys Trp Lys Trp Asn Gly Trp
 1               5                  10                 15
Asn Ser Met ( 2 ) INFORMATION FOR SEQ ID NO:69:

( i ) SEQUENCE CHARACTERISTICS:
( A ) LENGTH: 24 amino acids
( B ) TYPE: amino acid
( C ) STRANDEDNESS: single (D) TOPOLOGY: linear (ii) MOLECULE TYPE: protein (iii) HYPOTHETICAL: NO (xi) SEQUENCE DESCRIPTION: SEQ ID NO:69:

Asn Ile Tyr Lys Thr Met Lys Ile Asn Phe Val His Trp Ser Ile Thr
1               5                   10                  15
Gln Arg Ile Ile Leu Lys Ile Val
            20

(2) INFORMATION FOR SEQ ID NO:70:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:70:

Asn Arg Phe Cys Trp Pro Gly Ser Thr Asn Ser Arg
1               5                   10

(2) INFORMATION FOR SEQ ID NO:71:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:71:

Thr Val Leu Cys Ala Ile Val Trp His Ala Arg Pro Arg Leu Trp Arg
1               5                   10                  15
Lys Arg Glu Arg Phe Ile Cys Val Phe Ile Leu Lys Lys Arg His
            20                  25                  30

(2) INFORMATION FOR SEQ ID NO:72:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:72:

Cys Glu Lys Leu Leu Ala Ser Gly Leu Arg
1               5                   10

(2) INFORMATION FOR SEQ ID NO:73:

(i) SEQUENCE CHARACTERISTICS:
    (A) LENGTH: 31 amino acids
    (B) TYPE: amino acid
    (C) STRANDEDNESS: single
    (D) TOPOLOGY: linear (  i  i  ) MOLECULE TYPE: protein (  i  i  i  ) HYPOTHETICAL: NO (  x  i  ) SEQUENCE DESCRIPTION: SEQ ID NO:73:

| Leu | Ser | Ser | Leu | Val | Ser | Leu | Pro | Ile | Arg | Leu | Asn | Phe | Pro | Gln | His |
|---|---|---|---|---|---|---|---|---|---|---|---|---|---|---|---|
| 1 | | | | 5 | | | | | 10 | | | | | 15 | |
| Asp | Met | Pro | Leu | Asn | Phe | His | Phe | Leu | Val | Ile | Ser | Thr | Arg | Tyr | |
| | | | | 20 | | | | 25 | | | | | 30 | | |

( 2 ) INFORMATION FOR SEQ ID NO:74:

(  i  ) SEQUENCE CHARACTERISTICS:
( A ) LENGTH: 189 amino acids
( B ) TYPE: amino acid
( C ) STRANDEDNESS: single
( D ) TOPOLOGY: linear (  i  i  ) MOLECULE TYPE: protein (  i  i  i  ) HYPOTHETICAL: NO (  x  i  ) SEQUENCE DESCRIPTION: SEQ ID NO:74:

| Asn | Gly | Tyr | Val | Met | Val | Lys | Ile | Lys | Glu | Val | Ala | Met | Asn | Ile | Lys |
|---|---|---|---|---|---|---|---|---|---|---|---|---|---|---|---|
| 1 | | | | 5 | | | | | 10 | | | | | 15 | |
| Ile | Asn | Glu | Ile | Lys | Met | Thr | Pro | Pro | Thr | Ala | Phe | Thr | Pro | Gly | Gln |
| | | | 20 | | | | | 25 | | | | | 30 | | |
| Val | Ile | Glu | Glu | Gln | Glu | Val | Ile | Ser | Pro | Ser | Met | Leu | Ala | Leu | Gln |
| | | | 35 | | | | | 40 | | | | | 45 | | |
| Glu | Leu | Gln | Glu | Thr | Thr | Gly | Ala | Ala | Leu | Tyr | Glu | Thr | Met | Glu | Glu |
| | | | 50 | | | | | 55 | | | | | 60 | | |
| Ile | Gly | Met | Ala | Leu | Ser | Gly | Lys | Leu | Arg | Glu | Asn | Tyr | Lys | Phe | Thr |
| 65 | | | | | 70 | | | | | 75 | | | | | 80 |
| Asp | Ala | Glu | Lys | Leu | Glu | Arg | Arg | Gln | Gln | Ala | Leu | Leu | Arg | Leu | Ile |
| | | | | 85 | | | | | 90 | | | | | 95 | |
| Lys | Gln | Ile | Gln | Glu | Asp | Asn | Gly | Ala | Thr | Leu | Arg | Pro | Leu | Thr | Glu |
| | | | | 100 | | | | | 105 | | | | | 110 | |
| Glu | Asn | Ser | Asp | Pro | Asp | Leu | Gln | Asn | Ala | Tyr | Gln | Ile | Ile | Ala | Leu |
| | | | | 115 | | | | | 120 | | | | | 125 | |
| Ala | Met | Ala | Leu | Thr | Ala | Gly | Gly | Leu | Ser | Lys | Lys | Lys | Lys | Arg | Asp |
| | | | | 130 | | | | | 135 | | | | | 140 | |
| Leu | Gln | Ser | Gln | Leu | Asp | Thr | Leu | Gln | Arg | Arg | Arg | Asp | Gly | Asn | Leu |
| 145 | | | | | 150 | | | | | 155 | | | | | 160 |
| Pro | Phe | Leu | Val | Tyr | Trp | Asn | Leu | Ala | Lys | Trp | Ile | Pro | Tyr | Ala | Val |
| | | | | 165 | | | | | 170 | | | | | 175 | |
| Leu | Ser | Glu | Ala | Phe | Tyr | Ala | Thr | Gly | Asp | Arg | Gln | Arg | | | |
| | | | 180 | | | | | 185 | | | | | | | |

( 2 ) INFORMATION FOR SEQ ID NO:75:

(  i  ) SEQUENCE CHARACTERISTICS:
( A ) LENGTH: 17 amino acids
( B ) TYPE: amino acid
( C ) STRANDEDNESS: single
( D ) TOPOLOGY: linear (  i  i  ) MOLECULE TYPE: protein (  i  i  i  ) HYPOTHETICAL: NO (  x  i  ) SEQUENCE DESCRIPTION: SEQ ID NO:75:

| Asn | Ala | Leu | Ile | Ala | Val | Val | Gln | Thr | Arg | Gly | Arg | Leu | Ala | Gly | Ser |
|---|---|---|---|---|---|---|---|---|---|---|---|---|---|---|---|
| 1 | | | | 5 | | | | | 10 | | | | | 15 | |

Leu ( 2 ) INFORMATION FOR SEQ ID NO:76:

( i ) SEQUENCE CHARACTERISTICS:
　　　　( A ) LENGTH: 11 amino acids
　　　　( B ) TYPE: amino acid
　　　　( C ) STRANDEDNESS: single
　　　　( D ) TOPOLOGY: linear ( i i ) MOLECULE TYPE: protein ( i i i ) HYPOTHETICAL: NO ( x i ) SEQUENCE DESCRIPTION: SEQ ID NO:76:

```
Thr  Gly  Pro  Tyr  Phe  Ala  Lys  Ser  Ser  Ser  Leu
 1                  5                        10
```

( 2 ) INFORMATION FOR SEQ ID NO:77:

( i ) SEQUENCE CHARACTERISTICS:
　　　　( A ) LENGTH: 27 amino acids
　　　　( B ) TYPE: amino acid
　　　　( C ) STRANDEDNESS: single
　　　　( D ) TOPOLOGY: linear ( i i ) MOLECULE TYPE: protein ( i i i ) HYPOTHETICAL: NO ( x i ) SEQUENCE DESCRIPTION: SEQ ID NO:77:

```
His  Met  His  Arg  Thr  Leu  Gly  Ala  Lys  Ser  Phe  Gly  Arg  Ser  Ile  Ser
 1                  5                        10                       15
Thr  Phe  Ala  Ser  Phe  Ala  Val  Ile  Pro  Trp  Pro
                 20                      25
```

( 2 ) INFORMATION FOR SEQ ID NO:78:

( i ) SEQUENCE CHARACTERISTICS:
　　　　( A ) LENGTH: 5 amino acids
　　　　( B ) TYPE: amino acid
　　　　( C ) STRANDEDNESS: single
　　　　( D ) TOPOLOGY: linear ( i i ) MOLECULE TYPE: protein ( i i i ) HYPOTHETICAL: NO ( x i ) SEQUENCE DESCRIPTION: SEQ ID NO:78:

```
Lys  Arg  Val  Pro  Ala
 1                  5
```

( 2 ) INFORMATION FOR SEQ ID NO:79:

( i ) SEQUENCE CHARACTERISTICS:
　　　　( A ) LENGTH: 8 amino acids
　　　　( B ) TYPE: amino acid
　　　　( C ) STRANDEDNESS: single
　　　　( D ) TOPOLOGY: linear ( i i ) MOLECULE TYPE: protein ( i i i ) HYPOTHETICAL: NO ( x i ) SEQUENCE DESCRIPTION: SEQ ID NO:79:

```
Gly  Val  Asp  Leu  Pro  Val  Ala  Ala
 1                  5
```

( 2 ) INFORMATION FOR SEQ ID NO:80:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:80:

```
Tyr  Ile  Thr  Ala  Ala  Thr  Thr  Arg  Tyr  Tyr  Leu
 1              5                        10
```

( 2 ) INFORMATION FOR SEQ ID NO:81:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:81:

```
Ala  Leu  Ala  Phe  Gln
 1              5
```

( 2 ) INFORMATION FOR SEQ ID NO:82:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:82:

```
Thr  Tyr  Arg  Tyr  Ser  Phe  Phe  Ile  Glu  Asp  Val  Gln  Ser  Val  Thr  Pro
 1              5                        10                       15
Thr  Thr
```

( 2 ) INFORMATION FOR SEQ ID NO:83:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:83:

```
Cys  Ala  Val  Tyr  Ala  Asp  Thr  Arg
 1              5
```

( 2 ) INFORMATION FOR SEQ ID NO:84:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:84:

Arg Arg Arg Ser Thr
 1               5

( 2 ) INFORMATION FOR SEQ ID NO:85:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:85:

Thr Asn Ser Arg Asn Ala Ser
 1               5

( 2 ) INFORMATION FOR SEQ ID NO:86:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:86:

Ser Lys Asp Lys Ser Gly Phe Ile Leu Ile Pro Gly Phe Gln Tyr Leu
 1               5                  10                  15

Gly Lys Leu Ala Phe Trp Leu Ile Met Arg Arg Gln Asp Gly Leu Gly
            20                  25                  30

Ser His Tyr
        35

( 2 ) INFORMATION FOR SEQ ID NO:87:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:87:

Tyr Ser Ala Phe Tyr Ser Ile Ser Arg Ile Ser
 1               5                  10

( 2 ) INFORMATION FOR SEQ ID NO:88:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:88:

| Thr | Ala | Phe | Ser | Asn | Gln | Tyr | Val | Leu | Ala | Ala | Arg | Thr | Ile |
|-----|-----|-----|-----|-----|-----|-----|-----|-----|-----|-----|-----|-----|-----|
| 1   |     |     |     | 5   |     |     |     |     | 10  |     |     |     |     |

( 2 ) INFORMATION FOR SEQ ID NO:89:

( i ) SEQUENCE CHARACTERISTICS:
    ( A ) LENGTH: 759 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:89:

| Asn | Tyr | His | Asn | Gly | Arg | Ile | Leu | Leu | Cys | Gln | Ile | Leu | Lys | Gln | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Leu | Asp | Glu | Glu | Leu | Leu | Phe | Lys | Ala | Leu | Ala | Asn | Trp | Lys | Pro |
|     |     |     | 20  |     |     |     |     | 25  |     |     |     |     | 30  |     |     |
| Ala | Ala | Phe | Gln | Gly | Ile | Pro | Gln | Arg | Leu | Phe | Leu | Leu | Arg | Asp | Gly |
|     |     |     | 35  |     |     |     | 40  |     |     |     |     |     | 45  |     |     |
| Leu | Ala | Met | Ser | Cys | Ser | Pro | Pro | Leu | Ser | Ser | Ser | Ala | Glu | Leu | Trp |
|     | 50  |     |     |     |     | 55  |     |     |     |     | 60  |     |     |     |     |
| Leu | Arg | Leu | His | His | Arg | Gln | Ile | Lys | Phe | Xaa | Gly | Val | Ala | Met | Arg |
| 65  |     |     |     |     | 70  |     |     |     |     | 75  |     |     |     |     | 80  |
| Ser | Trp | Leu | Gly | Glu | Gly | Val | Arg | Ala | Gln | Gln | Trp | Leu | Ser | Val | Cys |
|     |     |     |     | 85  |     |     |     |     | 90  |     |     |     |     | 95  |     |
| Ala | Gly | Arg | Gln | Asp | Met | Val | Leu | Ala | Thr | Val | Leu | Leu | Ile | Ala | Ile |
|     |     |     | 100 |     |     |     |     | 105 |     |     |     |     | 110 |     |     |
| Val | Met | Met | Leu | Leu | Pro | Leu | Pro | Thr | Trp | Met | Val | Asp | Ile | Leu | Ile |
|     |     |     | 115 |     |     |     | 120 |     |     |     |     |     | 125 |     |     |
| Thr | Ile | Asn | Leu | Met | Phe | Ser | Val | Ile | Leu | Leu | Leu | Ile | Ala | Ile | Tyr |
|     | 130 |     |     |     |     | 135 |     |     |     |     | 140 |     |     |     |     |
| Leu | Ser | Asp | Pro | Leu | Asp | Leu | Ser | Val | Phe | Pro | Ser | Leu | Leu | Leu | Ile |
| 145 |     |     |     |     | 150 |     |     |     |     | 155 |     |     |     |     | 160 |
| Thr | Thr | Leu | Tyr | Arg | Leu | Ser | Leu | Thr | Ile | Ser | Thr | Ser | Arg | Leu | Val |
|     |     |     |     | 165 |     |     |     |     | 170 |     |     |     |     | 175 |     |
| Leu | Leu | Gln | His | Asn | Ala | Gly | Asn | Ile | Val | Asp | Ala | Phe | Gly | Lys | Phe |
|     |     |     | 180 |     |     |     |     | 185 |     |     |     |     | 190 |     |     |
| Val | Val | Gly | Gly | Asn | Leu | Thr | Val | Gly | Leu | Val | Val | Phe | Thr | Ile | Ile |
|     |     |     | 195 |     |     |     |     | 200 |     |     |     |     | 205 |     |     |
| Thr | Ile | Val | Gln | Phe | Ile | Val | Ile | Thr | Lys | Gly | Ile | Glu | Arg | Val | Ala |
|     | 210 |     |     |     |     | 215 |     |     |     |     | 220 |     |     |     |     |
| Glu | Val | Ser | Ala | Arg | Phe | Ser | Leu | Asp | Gly | Met | Pro | Gly | Lys | Gln | Met |
| 225 |     |     |     |     | 230 |     |     |     |     | 235 |     |     |     |     | 240 |
| Ser | Ile | Asp | Gly | Asp | Leu | Arg | Ala | Gly | Val | Ile | Asp | Ala | Asp | His | Ala |
|     |     |     |     | 245 |     |     |     |     | 250 |     |     |     |     | 255 |     |
| Arg | Thr | Leu | Arg | Gln | His | Val | Gln | Gln | Glu | Ser | Arg | Phe | Leu | Gly | Ala |
|     |     |     | 260 |     |     |     |     | 265 |     |     |     |     | 270 |     |     |
| Met | Asp | Gly | Ala | Met | Lys | Phe | Val | Lys | Gly | Asp | Thr | Ile | Ala | Gly | Ile |
|     |     |     | 275 |     |     |     |     | 280 |     |     |     |     | 285 |     |     |
| Ile | Val | Val | Leu | Val | Asn | Ile | Ile | Gly | Gly | Ile | Ile | Ile | Ala | Ile | Val |
|     |     |     | 290 |     |     |     |     | 295 |     |     |     |     | 300 |     |     |

| Gln | Tyr | Asp | Met | Ser | Met | Ser | Glu | Ala | Val | His | Thr | Tyr | Ser | Val | Leu |
| 305 | | | | | 310 | | | | | 315 | | | | | 320 |
| Ser | Ile | Gly | Asp | Gly | Leu | Cys | Gly | Gln | Ile | Pro | Ser | Leu | Leu | Ile | Ser |
| | | | | 325 | | | | | 330 | | | | | 335 | |
| Leu | Ser | Ala | Gly | Ile | Ile | Val | Thr | Arg | Val | Pro | Gly | Glu | Lys | Arg | Gln |
| | | | 340 | | | | | 345 | | | | | 350 | | |
| Asn | Leu | Ala | Thr | Glu | Leu | Ser | Ser | Gln | Ile | Ala | Arg | Gln | Pro | Gln | Ser |
| | | | 355 | | | | | 360 | | | | | 365 | | |
| Leu | Ile | Leu | Thr | Ala | Val | Val | Leu | Met | Leu | Leu | Ala | Leu | Ile | Pro | Gly |
| | | | 370 | | | | | 375 | | | | | 380 | | |
| Phe | Pro | Phe | Ile | Thr | Leu | Ala | Phe | Phe | Ser | Ala | Leu | Leu | Ala | Leu | Pro |
| 385 | | | | | 390 | | | | | 395 | | | | | 400 |
| Ile | Ile | Leu | Ile | Arg | Arg | Lys | Ser | Val | Val | Ser | Ala | Asn | Gly | Val | |
| | | | | 405 | | | | | 410 | | | | | 415 | |
| Glu | Ala | Pro | Glu | Lys | Asp | Ser | Met | Val | Pro | Gly | Ala | Cys | Pro | Leu | Ile |
| | | | | 420 | | | | | 425 | | | | | 430 | |
| Leu | Arg | Leu | Ser | Pro | Thr | Leu | His | Ser | Ala | Asp | Leu | Ile | Arg | Asp | Ile |
| | | | 435 | | | | | 440 | | | | | 445 | | |
| Asp | Ala | Met | Arg | Trp | Phe | Leu | Phe | Glu | Asp | Thr | Gly | Val | Pro | Leu | Pro |
| | | 450 | | | | | 455 | | | | | 460 | | | |
| Glu | Val | Asn | Ile | Glu | Val | Leu | Pro | Glu | Pro | Thr | Glu | Lys | Leu | Thr | Val |
| 465 | | | | | 470 | | | | | 475 | | | | | 480 |
| Leu | Leu | Tyr | Gln | Glu | Pro | Val | Phe | Ser | Leu | Ser | Ile | Pro | Ala | Gln | Ala |
| | | | | 485 | | | | | 490 | | | | | 495 | |
| Asp | Tyr | Leu | Leu | Ile | Gly | Ala | Asp | Ala | Ser | Val | Val | Gly | Asp | Ser | Gln |
| | | | 500 | | | | | 505 | | | | | 510 | | |
| Thr | Leu | Pro | Asn | Gly | Met | Gly | Gln | Ile | Cys | Trp | Leu | Thr | Lys | Asp | Met |
| | | | 515 | | | | | 520 | | | | | 525 | | |
| Ala | His | Lys | Ala | Gln | Gly | Phe | Gly | Leu | Asp | Val | Phe | Ala | Gly | Ser | Gln |
| | | 530 | | | | | 535 | | | | | 540 | | | |
| Arg | Ile | Ser | Ala | Leu | Leu | Lys | Cys | Val | Leu | Leu | Arg | His | Met | Gly | Glu |
| 545 | | | | | 550 | | | | | 555 | | | | | 560 |
| Phe | Ile | Gly | Val | Gln | Glu | Thr | Arg | Tyr | Leu | Met | Asn | Ala | Met | Glu | Lys |
| | | | | 565 | | | | | 570 | | | | | 575 | |
| Asn | Tyr | Ser | Glu | Leu | Val | Lys | Glu | Leu | Gln | Arg | Gln | Leu | Pro | Ile | Asn |
| | | | 580 | | | | | 585 | | | | | 590 | | |
| Lys | Ile | Ala | Glu | Thr | Leu | Gln | Arg | Leu | Val | Ser | Glu | Arg | Val | Ser | Ile |
| | | | 595 | | | | | 600 | | | | | 605 | | |
| Arg | Asp | Leu | Arg | Leu | Ile | Phe | Gly | Thr | Leu | Ile | Asp | Trp | Ala | Pro | Arg |
| | | 610 | | | | | 615 | | | | | 620 | | | |
| Glu | Lys | Asp | Val | Leu | Met | Leu | Thr | Glu | Tyr | Val | Arg | Ile | Ala | Leu | Arg |
| 625 | | | | | 630 | | | | | 635 | | | | | 640 |
| Arg | His | Ile | Leu | Arg | Arg | Leu | Asn | Pro | Glu | Gly | Lys | Pro | Leu | Pro | Ile |
| | | | | 645 | | | | | 650 | | | | | 655 | |
| Leu | Arg | Ile | Gly | Glu | Gly | Ile | Glu | Asn | Leu | Val | Arg | Glu | Ser | Ile | Arg |
| | | | 660 | | | | | 665 | | | | | 670 | | |
| Gln | Thr | Ala | Met | Gly | Thr | Tyr | Thr | Ala | Leu | Ser | Ser | Arg | His | Lys | Thr |
| | | | 675 | | | | | 680 | | | | | 685 | | |
| Gln | Ile | Leu | Gln | Leu | Ile | Glu | Gln | Ala | Leu | Lys | Gln | Ser | Ala | Lys | Leu |
| | | | 690 | | | | | 695 | | | | | 700 | | |
| Phe | Ile | Val | Thr | Ser | Val | Asp | Thr | Arg | Arg | Phe | Leu | Arg | Lys | Ile | Thr |
| 705 | | | | | 710 | | | | | 715 | | | | | 720 |
| Glu | Ala | Thr | Leu | Phe | Asp | Val | Pro | Ile | Leu | Ser | Trp | Gln | Glu | Leu | Gly |
| | | | | 725 | | | | | 730 | | | | | 735 | |

Glu Glu Ser Leu Ile Gln Val Val Glu Ser Ile Asp Leu Ser Glu Glu
            740                 745                 750

Glu Leu Ala Asp Asn Glu Glu
            755

( 2 ) INFORMATION FOR SEQ ID NO:90:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:90:

Ile Asp Ala Thr Ser Glu Ala Glu Ile Ser Ala Pro Arg Trp Leu Leu
 1               5                  10                  15

Ser Met Gly Pro Asn Ser Gly Cys Gln Arg Asn Val Val Lys Cys Val
                20                  25                  30

Val Ala Trp Gly Ile Tyr Gly Arg Val Val Leu Tyr Lys Ala Trp Arg
            35                  40                  45

Arg Thr Cys
        50

( 2 ) INFORMATION FOR SEQ ID NO:91:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:91:

Ser Arg Gly Asp
 1

( 2 ) INFORMATION FOR SEQ ID NO:92:

( i ) SEQUENCE CHARACTERISTICS:
        ( A ) LENGTH: 257 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:92:

Trp Gln Gln Ser Phe Ala Ile Ser Phe Tyr Glu Tyr Asn Arg Ala Ser
 1               5                  10                  15

Leu Arg Ala Ala Ser Asp Gly Leu Lys Arg Arg His Gln Val Pro Val
                20                  25                  30

Gly Glu Ala Leu Leu Gly Arg Val Ile Asp Gly Phe Gly Arg Pro Leu
            35                  40                  45

Asp Gly Arg Glu Leu Pro Asp Val Cys Trp Lys Asp Tyr Asp Ala Met
        50                  55                  60

Pro Pro Pro Ala Met Val Arg Gln Pro Ile Thr Gln Pro Leu Met Thr

-continued

```
                65                          70                          75                          80
Gly  Ile  Arg  Ala  Ile  Asp  Ser  Val  Ala  Thr  Cys  Gly  Glu  Gly  Gln  Arg
                    85                          90                          95
Val  Gly  Ile  Phe  Ser  Ala  Pro  Gly  Val  Gly  Lys  Ser  Thr  Leu  Leu  Ala
               100                         105                         110
Met  Leu  Cys  Asn  Ala  Pro  Asp  Ala  Asp  Ser  Asn  Val  Leu  Val  Leu  Ile
          115                         120                         125
Gly  Glu  Arg  Gly  Arg  Glu  Val  Arg  Glu  Phe  Ile  Asp  Phe  Thr  Leu  Ser
     130                         135                         140
Glu  Glu  Thr  Arg  Lys  Arg  Cys  Val  Ile  Val  Ala  Thr  Ser  Asp  Arg
145                         150                         155                    160
Pro  Ala  Leu  Glu  Arg  Val  Arg  Ala  Leu  Phe  Val  Ala  Thr  Thr  Ile  Ala
               165                         170                         175
Glu  Phe  Phe  Arg  Asp  Asn  Gly  Lys  Arg  Val  Val  Leu  Leu  Ala  Asp  Ser
               180                         185                         190
Leu  Thr  Arg  Tyr  Ala  Arg  Ala  Ala  Arg  Lys  Ser  Leu  Trp  Arg  Arg  Arg
          195                         200                         205
Asp  Arg  Gly  Phe  Trp  Arg  Ile  Ser  Pro  Gly  Val  Phe  Ser  Ala  Leu  Pro
     210                         215                         220
Arg  Leu  Leu  Glu  Arg  Thr  Gly  Met  Gly  Glu  Lys  Gly  Ser  Ile  Thr  Ala
225                         230                         235                    240
Phe  Tyr  Thr  Val  Leu  Val  Glu  Gly  Asp  Asp  Met  Asn  Glu  Ala  Val  Gly
                    245                         250                         255
Gly
```

( 2 ) INFORMATION FOR SEQ ID NO:93:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:93:

```
Ser  Pro  Phe  Thr  Ala
  1                    5
```

( 2 ) INFORMATION FOR SEQ ID NO:94:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:94:

```
Trp  Thr  Tyr  Cys  Thr  Ile  Pro  Thr  Ala  Cys  Arg  Glu  Gly  Ala  Leu  Ser
  1                    5                         10                         15
Cys  His
```

( 2 ) INFORMATION FOR SEQ ID NO:95:

( i ) SEQUENCE CHARACTERISTICS:
        ( A ) LENGTH: 15 amino acids ( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:95:

```
Arg  Val  Gly  Asn  Ala  Gln  Pro  Arg  Phe  Ser  Ser  Arg  Tyr  Gln  Pro
 1                    5                        10                       15
```

( 2 ) INFORMATION FOR SEQ ID NO:96:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:96:

```
Ala  Ser  Ser  Thr  Gly  Gly  Asp  Ile  Ala  Thr  Val  Pro  Gly  Ala  Leu  Pro
 1                    5                        10                       15
Gly  Gly
```

( 2 ) INFORMATION FOR SEQ ID NO:97:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:97:

```
Thr  Val  Asn  Thr  His  Trp  Gly  Ile  Pro  Ala  Arg  Ser
 1                    5                        10
```

( 2 ) INFORMATION FOR SEQ ID NO:98:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:98:

```
Tyr  Leu  Ser  Gly  Tyr  Leu  His  Ile  Phe  Ala  Thr  Lys
 1                    5                        10
```

( 2 ) INFORMATION FOR SEQ ID NO:99:

( i ) SEQUENCE CHARACTERISTICS:
( A ) LENGTH: 59 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:99:

Ser Met Arg Thr Arg Ala Thr Tyr Arg Lys Ile Thr Pro Asn Thr His
1               5                   10                  15

Arg Val Ile Met Glu Thr Leu Leu Glu Ile Ile Ala Arg Leu Lys Ser
            20                  25                  30

Asn Tyr Ala Ala Ser Leu Pro Tyr Leu Ile Ser Ser Asn Arg Arg Leu
        35                  40                  45

Leu Arg Asn Ser Arg Phe Ala Arg Arg Ala Leu
    50                  55

( 2 ) INFORMATION FOR SEQ ID NO:100:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:100:

Gln Cys Leu Pro Asp
1               5

( 2 ) INFORMATION FOR SEQ ID NO:101:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:101:

Trp Ala Gly Lys Val Arg Tyr Leu Val Ile Tyr Cys Trp Ile Arg Asn
1               5                   10                  15

Asn Lys Trp Pro Gly Tyr Ser Leu Arg Arg Arg Ala Phe
            20                  25

( 2 ) INFORMATION FOR SEQ ID NO:102:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:102:

Arg Asn Gly Lys Gln Leu Glu Asn Gln Tyr Gln Gln Leu Val Ser Arg
1               5                   10                  15

Arg Ser Glu Leu Gln Lys Asn Phe Asn Ala Leu Met Lys Lys Lys Glu
            20                  25                  30

Lys Ile Thr Met Val Leu Ser Asp Ala Tyr Tyr Gln Ser
        35                  40                  45

(2) INFORMATION FOR SEQ ID NO:103:

(i) SEQUENCE CHARACTERISTICS:
  (A) LENGTH: 12 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:103:

```
Gly Lys Ser Trp Val Ala Met Pro Val Leu Ser Gly
 1               5                  10
```

(2) INFORMATION FOR SEQ ID NO:104:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:104:

```
Arg Gly Gly Gly Gly Thr Tyr Gly Leu
 1               5
```

(2) INFORMATION FOR SEQ ID NO:105:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:105:

```
Thr Thr His Ala Pro Gly Ile Thr His Trp
 1               5                  10
```

(2) INFORMATION FOR SEQ ID NO:106:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:106:

```
Ser Ser Cys Ser Ile Glu
 1               5
```

(2) INFORMATION FOR SEQ ID NO:107:

(i) SEQUENCE CHARACTERISTICS:
  (A) LENGTH: 10 amino acids
  (B) TYPE: amino acid
  (C) STRANDEDNESS: single
  (D) TOPOLOGY: linear (i i) MOLECULE TYPE: protein (i i i) HYPOTHETICAL: NO (x i) SEQUENCE DESCRIPTION: SEQ ID NO:107:

Glu Arg Gly Phe His Ala Thr Leu Ser Cys
1               5                   10

(2) INFORMATION FOR SEQ ID NO:108:

(i) SEQUENCE CHARACTERISTICS:
 (A) LENGTH: 4 amino acids
 (B) TYPE: amino acid
 (C) STRANDEDNESS: single
 (D) TOPOLOGY: linear (i i) MOLECULE TYPE: protein (i i i) HYPOTHETICAL: NO (x i) SEQUENCE DESCRIPTION: SEQ ID NO:108:

Trp Arg Leu Ser
1

(2) INFORMATION FOR SEQ ID NO:109:

(i) SEQUENCE CHARACTERISTICS:
 (A) LENGTH: 4 amino acids
 (B) TYPE: amino acid
 (C) STRANDEDNESS: single
 (D) TOPOLOGY: linear (i i) MOLECULE TYPE: protein (i i i) HYPOTHETICAL: NO (x i) SEQUENCE DESCRIPTION: SEQ ID NO:109:

Arg Cys Arg Val
1

(2) INFORMATION FOR SEQ ID NO:110:

(i) SEQUENCE CHARACTERISTICS:
 (A) LENGTH: 14 amino acids
 (B) TYPE: amino acid
 (C) STRANDEDNESS: single
 (D) TOPOLOGY: linear (i i) MOLECULE TYPE: protein (i i i) HYPOTHETICAL: NO (x i) SEQUENCE DESCRIPTION: SEQ ID NO:110:

Ile Arg Gly Ala Asn Pro Val Lys Asn Gln Cys Pro Ser Ser
1               5                   10

(2) INFORMATION FOR SEQ ID NO:111:

(i) SEQUENCE CHARACTERISTICS:
 (A) LENGTH: 30 amino acids
 (B) TYPE: amino acid
 (C) STRANDEDNESS: single
 (D) TOPOLOGY: linear (i i) MOLECULE TYPE: protein (i i i) HYPOTHETICAL: NO (x i) SEQUENCE DESCRIPTION: SEQ ID NO:111:

Asn Leu Pro Phe Asp Glu Ser Ala Lys Ala Val Ala Gly Val Ser Val
1               5                   10                  15

Ala Ala Tyr Gly Val Tyr Asn Phe Pro Gly Asp Ile Leu Cys
                    20                  25                  30

(2) INFORMATION FOR SEQ ID NO:112:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:112:

Arg Met Lys Ser Val Arg Gly Trp Arg Tyr Phe Gln Arg Lys Ala Leu
 1               5                  10                  15
Pro Leu Val Ser
             20

(2) INFORMATION FOR SEQ ID NO:113:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:113:

Val Cys Asn Asn Ile Gln Tyr Ser Lys Gly His Tyr Leu Pro
 1               5                  10

(2) INFORMATION FOR SEQ ID NO:114:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:114:

Ile Ile Ile Met Ser Trp Val Gly Cys Gly Leu Gln Asn Asn Ala Gly
 1               5                  10                  15
Ser Ala Gly Val Lys Gly
             20

(2) INFORMATION FOR SEQ ID NO:115:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:115:

Leu Ala Pro Leu Ile Asp Arg Leu Ser Ile Leu Asn Cys Tyr Met Glu (2) INFORMATION FOR SEQ ID NO:116:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:116:

```
Leu Asn Gly Gly Trp Arg Arg Tyr Cys Lys Pro Val Met Gln Pro Ser
 1               5                  10                  15
Val Arg Thr Ser Arg Gln His Pro Ala Val Ile Tyr His Ile Ser
             20                  25                  30
```

(2) INFORMATION FOR SEQ ID NO:117:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:117:

```
Arg Cys Ile Leu Asn Gly Gln Leu Lys Ser Met Ser Ser Ile Ala Leu
 1               5                  10                  15
Phe Leu His Gly Gln Arg Val Phe Cys Ala Ile
             20                  25
```

(2) INFORMATION FOR SEQ ID NO:118:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:118:

```
Ser Glu Ser Phe Leu Leu Ser Asp Asn Arg Phe Ile Leu Pro Leu Leu
 1               5                  10                  15
Trp
```

(2) INFORMATION FOR SEQ ID NO:119:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:119:

```
Ser Leu Tyr Ile Gln Ala Gly Ala Ser Leu His
```

( 2 ) INFORMATION FOR SEQ ID NO:120:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:120:

```
Ser  Asn  Leu  Ser  Leu  Ser  Lys  Ser  Ala  Trp  Ala  Phe  Gly  Phe  Ile  Ala
 1                  5                        10                       15
Ser  Ala  Thr  Ser  Asp  Ser  Val  Phe  Leu  Leu  Phe  Asn  Tyr  Leu  Gly  Glu
               20                       25                       30
Ser  Thr  Gln  Gly  Cys  Cys
               35
```

( 2 ) INFORMATION FOR SEQ ID NO:121:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:121:

```
Gln  Arg  Ile  Thr  Arg
 1                  5
```

( 2 ) INFORMATION FOR SEQ ID NO:122:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:122:

```
Asn  Leu  Thr  Asn
 1
```

( 2 ) INFORMATION FOR SEQ ID NO:123:

( i ) SEQUENCE CHARACTERISTICS:
    ( A ) LENGTH: 56 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:123:

```
Ser  Arg  Ile  Ser  Lys  Arg  Tyr  Leu  Arg  Gln  Gly  Ala  Gln  Cys  Gln  Arg
 1                  5                        10                       15
```

```
Val Thr Glu Arg Leu Gln Ser Asn Leu Ser Arg Tyr His Asn Arg Cys
            20                  25                  30

Ser Leu Arg Ser Asp Val Arg Val Trp Lys Leu Asp Asn Tyr Asp Asn
            35                  40                  45

Leu Lys Arg Gly Thr Phe Cys Leu
            50                  55
```

( 2 ) INFORMATION FOR SEQ ID NO:124:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:124:

```
Val Asp Val Leu Arg Gln Arg
 1               5
```

( 2 ) INFORMATION FOR SEQ ID NO:125:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:125:

```
Met Thr Val Leu Leu Gly Lys Val Ser
 1               5
```

( 2 ) INFORMATION FOR SEQ ID NO:126:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:126:

```
Leu Pro Val Ala Met Asn Leu Trp Cys Val Leu His Val Gly Ile Phe
 1               5                  10                  15

Ala Lys Ile Gln Arg Lys Pro Asp Lys Lys Asn Asn Met Arg Thr Ile
            20                  25                  30
```

( 2 ) INFORMATION FOR SEQ ID NO:127:

( i ) SEQUENCE CHARACTERISTICS:
        ( A ) LENGTH: 225 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:127:

| Arg | Ser | Arg | Ser | Cys | His | Glu | Arg | Tyr | Ser | Met | Ser | Leu | Pro | Asp | Ser |
|---|---|---|---|---|---|---|---|---|---|---|---|---|---|---|---|
| 1 | | | | 5 | | | | | 10 | | | | | 15 | |
| Pro | Leu | Gln | Leu | Ile | Gly | Ile | Leu | Phe | Leu | Leu | Ser | Ile | Leu | Pro | Leu |
| | | | 20 | | | | 25 | | | | | 30 | | | |
| Ile | Ile | Val | Met | Gly | Thr | Ser | Phe | Leu | Lys | Leu | Ala | Val | Val | Phe | Ser |
| | | | 35 | | | | 40 | | | | | 45 | | | |
| Ile | Leu | Arg | Asn | Ala | Leu | Gly | Ile | Gln | Gln | Val | Pro | Pro | Asn | Ile | Ala |
| | 50 | | | | | 55 | | | | | | 60 | | | |
| Leu | Tyr | Gly | Leu | Ala | Leu | Val | Leu | Ser | Leu | Phe | Ile | Met | Gly | Pro | Thr |
| 65 | | | | | 70 | | | | | 75 | | | | | 80 |
| Leu | Leu | Ala | Val | Lys | Glu | Arg | Trp | His | Pro | Val | Gln | Val | Ala | Gly | Ala |
| | | | | 85 | | | | | 90 | | | | | 95 | |
| Pro | Phe | Trp | Thr | Ser | Glu | Trp | Asp | Ser | Lys | Ala | Leu | Ala | Pro | Tyr | Arg |
| | | | 100 | | | | | 105 | | | | | 110 | | |
| Gln | Phe | Leu | Gln | Lys | Asn | Ser | Glu | Glu | Lys | Glu | Ala | Asn | Tyr | Phe | Arg |
| | | | 115 | | | | | 120 | | | | | 125 | | |
| Asn | Leu | Ile | Lys | Arg | Thr | Trp | Pro | Glu | Asp | Ile | Lys | Arg | Lys | Ile | Lys |
| | | 130 | | | | | 135 | | | | | 140 | | | |
| Pro | Asp | Ser | Leu | Leu | Ile | Leu | Ile | Pro | Ala | Phe | Thr | Val | Ser | Gln | Leu |
| 145 | | | | | 150 | | | | | 155 | | | | | 160 |
| Thr | Gln | Ala | Phe | Arg | Ile | Gly | Leu | Leu | Ile | Tyr | Leu | Pro | Phe | Leu | Ala |
| | | | | 165 | | | | | 170 | | | | | 175 | |
| Ile | Asp | Leu | Leu | Ile | Ser | Asn | Ile | Leu | Leu | Ala | Met | Gly | Met | Met | Met |
| | | | 180 | | | | | 185 | | | | | 190 | | |
| Val | Ser | Pro | Met | Thr | Ile | Ser | Leu | Pro | Phe | Lys | Leu | Leu | Ile | Phe | Leu |
| | | 195 | | | | | 200 | | | | | 205 | | | |
| Leu | Ala | Gly | Gly | Trp | Asp | Leu | Thr | Leu | Ala | Gln | Leu | Val | Gln | Ser | Phe |
| | 210 | | | | | 215 | | | | | 220 | | | | |
| Ser | | | | | | | | | | | | | | | |
| 225 | | | | | | | | | | | | | | | |

( 2 ) INFORMATION FOR SEQ ID NO:128:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:128:

Met  Ile  Leu  Asn
  1

( 2 ) INFORMATION FOR SEQ ID NO:129:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:129:

Arg  Asn  Phe  Tyr  Gly  Ser  Ser  Phe  Leu  Arg  Leu  Cys  Arg ( 2 ) INFORMATION FOR SEQ ID NO:130:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:130:

Cys Trp Trp His Arg
1               5

( 2 ) INFORMATION FOR SEQ ID NO:131:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:131:

Leu Val Ser Ser
1

( 2 ) INFORMATION FOR SEQ ID NO:132:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:132:

Ala Leu Phe Arg Pro
1               5

( 2 ) INFORMATION FOR SEQ ID NO:133:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:133:

Leu Lys Tyr Arg Thr Lys Arg Tyr Ser Ser
1               5                   10

( 2 ) INFORMATION FOR SEQ ID NO:134:

( i ) SEQUENCE CHARACTERISTICS:
        ( A ) LENGTH: 7 amino acids
        ( B ) TYPE: amino acid ( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:134:

Leu Asn Tyr Trp Gln Leu Gln
1               5

( 2 ) INFORMATION FOR SEQ ID NO:135:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:135:

Trp Ser Ala Thr His Gly Leu Ala Val Ser Cys
1               5                   10

( 2 ) INFORMATION FOR SEQ ID NO:136:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:136:

Ile Ile Pro Gly Arg
1               5

( 2 ) INFORMATION FOR SEQ ID NO:137:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:137:

Cys Tyr Glu Leu Glu Ser Met Val Glu Trp His Asn Arg
1               5                   10

( 2 ) INFORMATION FOR SEQ ID NO:138:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:138:

Met Ser Gly Leu Leu His Trp Leu Trp Leu Leu Phe Asp His
1               5                   10

( 2 ) INFORMATION FOR SEQ ID NO:139:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:139:

Ala Phe Leu Tyr Tyr Phe Pro Tyr
1                   5

( 2 ) INFORMATION FOR SEQ ID NO:140:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:140:

Lys Val Ala Val
1

( 2 ) INFORMATION FOR SEQ ID NO:141:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:141:

Gly Pro His Phe Tyr Val Met Ala Cys Leu Cys His Leu Pro Phe Arg
1               5                   10                  15
Tyr Tyr Gln Ser Phe Thr Ser Arg Arg Leu
            20                  25

( 2 ) INFORMATION FOR SEQ ID NO:142:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:142:

Cys Ile Leu Val Lys Ile Thr Val Gly
1               5

(2) INFORMATION FOR SEQ ID NO:143:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:143:

Ser Leu Glu Arg
1

(2) INFORMATION FOR SEQ ID NO:144:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:144:

Leu Leu Val Phe Gln Leu Gly Phe Val Arg Arg Phe Pro Phe Gly Pro
1               5                   10                  15
Leu Ile Trp Arg Gly Phe Cys Leu Ile Leu Tyr Val Ala Arg Gln Trp
                20                  25                  30
Val Arg Tyr Ser Ile Leu Gln
                35

(2) INFORMATION FOR SEQ ID NO:145:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:145:

Lys Leu Lys Pro His Phe Leu Ala Cys Phe Ser Ala Ser Ser Cys Val
1               5                   10                  15
Leu Phe Ser Leu
                20

(2) INFORMATION FOR SEQ ID NO:146:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:146:

Ala Ala Ala Trp Ser Leu Tyr
1               5

( 2 ) INFORMATION FOR SEQ ID NO:147:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:147:

```
Thr Phe Cys Met Ser His Ile Asn Ile Tyr His Gln Gly Val Leu Tyr
 1               5                  10                  15
Tyr Leu Thr Ser Asn Phe
            20
```

( 2 ) INFORMATION FOR SEQ ID NO:148:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:148:

```
Asn Ile Ser Arg Gln Ser Gly Glu Arg Phe Ile Asn Tyr Val Ser Ala
 1               5                  10                  15
Ser Leu Phe Leu Pro
            20
```

( 2 ) INFORMATION FOR SEQ ID NO:149:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:149:

```
Tyr Val Trp Tyr
 1
```

( 2 ) INFORMATION FOR SEQ ID NO:150:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:150:

```
Pro Ile Trp Leu
 1
```

( 2 ) INFORMATION FOR SEQ ID NO:151:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:151:

Ile Gly Arg His Asn Asn
 1               5

( 2 ) INFORMATION FOR SEQ ID NO:152:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:152:

Met Cys Phe Ser Ser Gln Cys Arg Ser Lys Val Tyr Trp Phe Tyr
 1               5                  10                  15

( 2 ) INFORMATION FOR SEQ ID NO:153:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:153:

Xaa Pro Asp Leu Ile Pro Leu Cys Ser Ser Ser Leu Phe Gly
 1               5                  10

( 2 ) INFORMATION FOR SEQ ID NO:154:

( i ) SEQUENCE CHARACTERISTICS:
    ( A ) LENGTH: 225 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:154:

Ile Leu Tyr Leu Ser Lys Arg Leu Val Ser Ile Cys Met Ser Glu Lys
 1               5                  10                  15

Thr Glu Gln Pro Thr Glu Lys Lys Leu Arg Asp Gly Arg Lys Glu Gly
                20                  25                  30

Gln Val Val Lys Ser Ile Glu Ile Thr Ser Leu Phe Gln Leu Ile Ala
                35                  40                  45

Leu Tyr Leu Tyr Phe His Phe Phe Thr Glu Lys Met Ile Leu Ile Leu
                50                  55                  60

Ile Glu Ser Ile Thr Phe Thr Leu Gln Leu Val Asn Lys Pro Phe Ser

-continued

```
65                          70                          75                          80
Tyr Ala Leu Thr Gln Leu Ser His Ala Leu Ile Glu Ser Leu Thr Ser
                    85                          90                          95
Ala Leu Leu Phe Leu Gly Ala Gly Val Ile Val Ala Thr Val Gly Ser
                100                         105                         110
Val Phe Leu Gln Val Gly Val Val Ile Ala Ser Lys Ala Ile Gly Phe
                115                         120                         125
Lys Ser Glu His Ile Asn Pro Val Ser Asn Phe Lys Gln Ile Phe Ser
        130                         135                         140
Leu His Ser Val Val Glu Leu Cys Lys Ser Ser Leu Lys Val Ile Met
145                         150                         155                         160
Leu Ser Leu Ile Phe Ala Phe Phe Tyr Tyr Tyr Ala Ser Thr Phe
                165                         170                         175
Arg Ala Leu Pro Tyr Cys Gly Leu Ala Cys Gly Val Leu Val Val Ser
                180                         185                         190
Ser Leu Ile Lys Trp Leu Trp Val Gly Val Met Val Phe Tyr Ile Val
            195                         200                         205
Val Gly Ile Leu Asp Tyr Ser Phe Gln Tyr Tyr Lys Ile Arg Lys Ala
        210                         215                         220
Ile
225
```

( 2 ) INFORMATION FOR SEQ ID NO:155:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:155:

```
Val Lys Met Thr
 1
```

( 2 ) INFORMATION FOR SEQ ID NO:156:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:156:

```
Asn Arg Ser Ile Lys Ile Trp Arg Ala Thr Leu Lys
 1               5                  10
```

( 2 ) INFORMATION FOR SEQ ID NO:157:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:157:

Arg Arg Gly Val Gly Asn Ala Glu
 1               5

( 2 ) INFORMATION FOR SEQ ID NO:158:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:158:

Asn Thr Lys Trp Glu Phe Ser Ser Ile Cys
 1               5                   10

( 2 ) INFORMATION FOR SEQ ID NO:159:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:159:

Thr Ile Cys Cys Gly Ser Ala
 1               5

( 2 ) INFORMATION FOR SEQ ID NO:160:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:160:

Ser Asn Ala Tyr Cys Gly Leu Ser Trp Leu Ser Ser His Arg Tyr Ala
 1               5                   10                  15
Asn Thr Thr Arg Pro Gly Lys Arg Gln
             20                  25

( 2 ) INFORMATION FOR SEQ ID NO:161:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:161:

Thr Gln Leu His Pro Arg Cys
 1               5

( 2 ) INFORMATION FOR SEQ ID NO:162:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:162:

```
Ala Gly Pro Leu Ile Ile Phe
 1               5
```

( 2 ) INFORMATION FOR SEQ ID NO:163:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:163:

```
Ser Gly Thr Arg Arg
 1               5
```

( 2 ) INFORMATION FOR SEQ ID NO:164:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:164:

```
Thr Arg Cys Ser Leu Val Thr Tyr Gly Asp Glu Asp Arg Leu Cys Ala
 1               5                  10                  15
Phe Tyr Arg Asn Thr Ile Asn Ala Phe Gly Met Leu Leu Gln Ala Thr
                20                  25                  30
Ala Lys Val Lys Arg Val Ile Ala Tyr Arg Ala Val Leu Asp Asp Lys
                35                  40                  45
Gly Glu Arg Leu Lys Ile Ile Ala Phe Ser Leu Ala Gln Ala Pro Asp
                50                  55                  60
Ser Val Leu
 65
```

( 2 ) INFORMATION FOR SEQ ID NO:165:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:165:

Trp Ile Gly Ala Ser Glu Trp Thr Arg Thr Thr Arg Pro Pro Pro Cys
1               5                   10                  15
Gln Gly Gly Ala Leu Thr Asn
            20

( 2 ) INFORMATION FOR SEQ ID NO:166:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:166:

Ala Met Asn Gly Asn Val Val Gly Asp Asn Gly Asp Glu Tyr
1               5                   10

( 2 ) INFORMATION FOR SEQ ID NO:167:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:167:

Arg His Asn Arg Asn Glu Ala Arg Gly Lys Ser Gln Phe Ser Ser
1               5                   10                  15

( 2 ) INFORMATION FOR SEQ ID NO:168:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:168:

Asn His Leu Ile Ala Val Glu Ile Cys Asn Met Ser Arg Lys
1               5                   10

( 2 ) INFORMATION FOR SEQ ID NO:169:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:169:

Pro Pro Cys Asp Gly Tyr Arg Arg Ile Ile Gly Ala Arg Cys Lys Met
1               5                   10                  15

```
Met Ala Asp Gly
          20
```

( 2 ) INFORMATION FOR SEQ ID NO:170:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:170:

```
Arg Ile Arg Ser Ile Ile Asn Thr Ala Ala Glu Val Arg Pro Met Met
 1               5                  10                  15
Asn Pro Ile Gln Lys Pro Ala Gly Pro Ile Arg Ser Thr Thr Lys Ser
            20                  25                  30
Val Asn Ala Arg Ile
            35
```

( 2 ) INFORMATION FOR SEQ ID NO:171:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:171:

```
Pro Leu Gly Lys Pro Asn Thr Gln
 1               5
```

( 2 ) INFORMATION FOR SEQ ID NO:172:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:172:

```
Ala Val Lys Val Ile Lys Lys Met Glu Arg Val Ser Leu
 1               5                  10
```

( 2 ) INFORMATION FOR SEQ ID NO:173:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:173:

```
Pro Arg Arg Ile Pro Leu Pro Ile Thr Cys Ile Glu Ser Glu Ile Trp
 1               5                  10                  15
```

( 2 ) INFORMATION FOR SEQ ID NO:174:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:174:

Thr Ala Ala Ser Ser Ile Asn Cys Gly Lys Arg His Asp Leu Arg Val
1               5                   10                  15

Val Ile Val Glu Gln Ser Asn Met Leu Thr Gln Ser Asn Gly Lys Asn
            20                  25                  30

Ser Gly Asn His Ser His Thr Asn Ala Asp Ala
            35              40

( 2 ) INFORMATION FOR SEQ ID NO:175:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:175:

Thr Gly Thr Arg Cys Val Cys Ala Ser Ser Val Glu Pro Trp Pro Arg
1               5                   10                  15

Pro Ile Thr His Ser Asn Arg Tyr Arg Arg Ser Gln Arg His Arg Gln
            20                  25                  30

Tyr Glu His Gln Arg Ala Lys Val Lys Arg Asn Leu Met Thr Gly Asp
            35                  40                  45

Ile His Asn Thr
        50

( 2 ) INFORMATION FOR SEQ ID NO:176:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:176:

Trp Arg Asn Gln Gln Arg Asn Asp Arg Lys
1               5                   10

( 2 ) INFORMATION FOR SEQ ID NO:177:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:177:

Arg His Phe Lys Glu Gln Pro Ala Gln Ser Ala Thr Pro Val Glu Ser
1               5                   10                  15

Gly Ala Ser ( 2 ) INFORMATION FOR SEQ ID NO:178:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:178:

Arg Arg Tyr Arg Val Cys Gln Ser Leu Phe His Tyr Glu Tyr His Ala
1               5                   10                  15

Leu Asn Ala Arg Val
                20

( 2 ) INFORMATION FOR SEQ ID NO:179:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:179:

Cys Lys Lys Ala Trp Arg
1               5

( 2 ) INFORMATION FOR SEQ ID NO:180:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:180:

Thr Ser Pro Asn Arg Pro Pro Gln Ser Gln Arg Arg Ser Arg Tyr Arg
1               5                   10                  15

Arg Val Pro Ala Tyr Gln Asn Gly His Arg
                20                  25

( 2 ) INFORMATION FOR SEQ ID NO:181:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:181:

```
Lys Tyr Ser Ser Pro Glu Tyr Ser Pro Ala Gly Pro Lys Ile Pro Ser
 1               5                  10                 15
Pro Tyr Pro Val Trp Phe Trp Pro Asp Leu Arg Thr Gly Phe Ala Leu
                20              25                  30
Pro Glu Arg Lys Gly Ile Leu Arg Pro Thr Ala Ala Arg Glu Asp Asn
            35              40              45
Pro Arg Leu Tyr Arg Pro Ala Pro Asp Gln Tyr Tyr Ala
        50              55              60
```

( 2 ) INFORMATION FOR SEQ ID NO:182:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:182:

```
Cys Ile Arg His Ser Thr Gly Arg Ser Ser Pro Ala Arg Arg Gln Ser
 1               5                  10                 15
Pro Pro Ala Arg Thr Leu Val Glu Pro Asp Ala Arg Tyr Ala His Asp
                20              25                  30
Gly Arg Ser His
            35
```

( 2 ) INFORMATION FOR SEQ ID NO:183:

( i ) SEQUENCE CHARACTERISTICS:
    ( A ) LENGTH: 59 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:183:

```
Val Ala Gln Ser Gln Ala Ser Arg Pro Ala Val Ser Arg Asp Gln Thr
 1               5                  10                 15
Lys Trp Arg Glu Ala Asp Arg Gly Ala Asp Ser Asp Gly Ser His Val
                20              25                  30
Arg Ser Ala Ile Ala Ser Arg His Asp Gly Ile Asp Glu Ser Ile Ala
            35              40              45
Val Tyr Thr Thr Cys Ala Arg Ile Thr Gly Ile
        50              55
```

( 2 ) INFORMATION FOR SEQ ID NO:184:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:184:

Thr Leu Ile Thr Asp Ala Leu His Trp Tyr Thr Ser Ala Arg Ile His
1               5                   1 0                 1 5

Leu Leu Phe Cys Cys Tyr Met Lys Asp
            2 0             2 5

( 2 ) INFORMATION FOR SEQ ID NO:185:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:185:

Lys Ala Ala Glu Val Ala Ala Lys Arg Asn Ser Arg Gly Asn Phe Ser
1               5                   1 0                 1 5

Leu Leu ( 2 ) INFORMATION FOR SEQ ID NO:186:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:186:

Arg Gly Ile Thr Ile Ser Pro Val Lys Lys Gln Leu Leu Thr Ala His
1               5                   1 0                 1 5

Cys Trp Gln Ala Val Phe Pro Pro Ala Ile Val Leu Asn Ser Ser Ala
            2 0                 2 5                 3 0

Phe Ile Tyr Phe Arg Ser
            3 5

( 2 ) INFORMATION FOR SEQ ID NO:187:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:187:

Arg Tyr Val Tyr Gly Asp Arg Thr Gly Tyr Arg Glu Thr Gly Ile Asp
1               5                   1 0                 1 5

( 2 ) INFORMATION FOR SEQ ID NO:188:

( i ) SEQUENCE CHARACTERISTICS:
( A ) LENGTH: 8 amino acids
( B ) TYPE: amino acid
( C ) STRANDEDNESS: single
( D ) TOPOLOGY: linear (i i) MOLECULE TYPE: protein (i i i) HYPOTHETICAL: NO (x i) SEQUENCE DESCRIPTION: SEQ ID NO:188:

Cys Arg Thr Glu Pro Gly Ala Asn
 1               5

(2) INFORMATION FOR SEQ ID NO:189:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:189:

Thr Ile Ala Glu Arg
 1               5

(2) INFORMATION FOR SEQ ID NO:190:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:190:

Ser Ile His Gln
 1

(2) INFORMATION FOR SEQ ID NO:191:

(i) SEQUENCE CHARACTERISTICS:
        (A) LENGTH: 63 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:191:

Arg Gln Cys Phe Ile Thr Ala Gly Tyr Val Asp Gln Thr Asn Gly Leu
 1               5                   10                  15

Tyr Ala Val Asn Gly Arg Arg Arg Leu Ser Cys Gln Asn Ile Thr Ala
                 20                  25                  30

Gln His Ala Lys Arg Leu Ile Ser Trp Ile Thr Trp His Glu Gly Ser
                 35                  40                  45

Ser Tyr Ser Ile Ser Tyr Cys Pro Tyr Val Leu Ser Tyr Gly Met
         50                  55                  60

(2) INFORMATION FOR SEQ ID NO:192:

(i) SEQUENCE CHARACTERISTICS:
        (A) LENGTH: 10 amino acids
        (B) TYPE: amino acid
        (C) STRANDEDNESS: single
        (D) TOPOLOGY: linear ( i i ) MOLECULE TYPE: protein ( i i i ) HYPOTHETICAL: NO ( x i ) SEQUENCE DESCRIPTION: SEQ ID NO:192:

Cys  Gly  Ser  Leu  Ser  Leu  Ile  Ala  Arg  Arg
1                   5                        10

( 2 ) INFORMATION FOR SEQ ID NO:193:

( i ) SEQUENCE CHARACTERISTICS:
                ( A ) LENGTH: 13 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL: NO ( x i ) SEQUENCE DESCRIPTION: SEQ ID NO:193:

Ser  Glu  Ser  Asn  Ala  Gly  Ile  Thr  Tyr  Ala  Ala  Ser  Tyr
1                   5                        10

( 2 ) INFORMATION FOR SEQ ID NO:194:

( i ) SEQUENCE CHARACTERISTICS:
                ( A ) LENGTH: 20 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL: NO ( x i ) SEQUENCE DESCRIPTION: SEQ ID NO:194:

Cys  Glu  Lys  Lys  Gln  Glu  Glu  Asp  Gly  Val  Thr  Leu  Arg  Val  Glu  Gln
1                   5                        10                       15

Ser  Ala  Val  Tyr
                20

( 2 ) INFORMATION FOR SEQ ID NO:195:

( i ) SEQUENCE CHARACTERISTICS:
                ( A ) LENGTH: 36 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL: NO ( x i ) SEQUENCE DESCRIPTION: SEQ ID NO:195:

Gly  Tyr  Leu  Asp  Leu  Thr  Val  Ile  Arg  Ile  Gly  Gln  Phe  Thr  Thr  Ala
1                   5                        10                       15

Asp  Lys  Met  Phe  Pro  Ala  Asn  Gln  Leu  Val  Val  Ser  Pro  Gln  Glu  Glu
                20                       25                       30

Gln  Ala  Glu  Asp
                35

( 2 ) INFORMATION FOR SEQ ID NO:196:

( i ) SEQUENCE CHARACTERISTICS:
                ( A ) LENGTH: 7 amino acids
                ( B ) TYPE: amino acid
                ( C ) STRANDEDNESS: single (D) TOPOLOGY: linear (ii) MOLECULE TYPE: protein (iii) HYPOTHETICAL: NO (xi) SEQUENCE DESCRIPTION: SEQ ID NO:196:

Phe Phe Lys Arg Thr Lys Asn
1               5

(2) INFORMATION FOR SEQ ID NO:197:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:197:

Arg Asn Ala Glu Ser Asp Gly Gly Ala
1               5

(2) INFORMATION FOR SEQ ID NO:198:

(i) SEQUENCE CHARACTERISTICS:
(A) LENGTH: 127 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:198:

Leu Met Ala Lys Val Thr Ile Ala Leu Pro Thr Tyr Asp Glu Gly Ser
1               5                   10                  15
Asn Ala Ser Pro Ser Ser Val Ala Val Phe Ile Lys Tyr Ser Pro Gln
            20                  25                  30
Val Asn Met Glu Ala Phe Arg Val Lys Ile Lys Asp Leu Ile Glu Met
        35                  40                  45
Ser Ile Pro Gly Leu Gln Tyr Ser Lys Ile Ser Ile Leu Met Gln Pro
    50                  55                  60
Ala Glu Phe Arg Met Val Ala Asp Val Pro Ala Arg Gln Thr Phe Trp
65                  70                  75                  80
Ile Met Asp Val Ile Asn Ala Asn Lys Gly Lys Val Val Lys Trp Leu
                85                  90                  95
Met Lys Tyr Pro Tyr Pro Leu Met Leu Ser Leu Thr Gly Leu Leu Leu
            100                 105                 110
Gly Val Gly Ile Leu Ile Gly Tyr Phe Cys Leu Arg Arg Arg Phe
            115                 120                 125

(2) INFORMATION FOR SEQ ID NO:199:

(i) SEQUENCE CHARACTERISTICS:
(A) LENGTH: 48 amino acids
(B) TYPE: amino acid
(C) STRANDEDNESS: single
(D) TOPOLOGY: linear (ii) MOLECULE TYPE: protein (iii) HYPOTHETICAL: NO ( x i ) SEQUENCE DESCRIPTION: SEQ ID NO:199:

Ala Asp Leu Ile Pro Arg Cys Cys Asn Phe Ile Val Ile Ser Gly Asn
1               5                   10                  15

Leu Leu Val Thr Leu Tyr Arg Asn Gly Trp Ile Ser Trp Ala Phe Ile
            20                  25                  30

Phe Lys Leu Leu Ala Leu Trp Arg Ser Ala Arg Val Gly Ser Ser Ser
        35                  40                  45

( 2 ) INFORMATION FOR SEQ ID NO:200:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:200:

Gln Ser Val Lys
1

( 2 ) INFORMATION FOR SEQ ID NO:201:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:201:

Thr Lys Arg Lys Leu Cys Tyr Ser Ser Leu Phe Lys
1               5                   10

( 2 ) INFORMATION FOR SEQ ID NO:202:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:202:

Gln Ala Lys Thr Ala Gly Ser Ser Cys Ala Ala Tyr Ile Gly Ile Cys
1               5                   10                  15

Leu Trp Ala Gly Ile Ile Gln Thr Gln Val
            20                  25

( 2 ) INFORMATION FOR SEQ ID NO:203:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:203:

Leu Phe Tyr Ala Thr Arg Val Ser Ala Ile Ala Ser Thr Val Val
1               5                   10                  15

( 2 ) INFORMATION FOR SEQ ID NO:204:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:204:

Asp Leu Ala Ala Ile Trp Leu Val Gly Ala Lys Arg Trp Gln Ile Thr
1               5                   10                  15
Ser Ser Ala Ser Asp Ala Thr Asn Cys Ile Ala Asp Arg Tyr Arg His
            20                  25                  30
Ser ( 2 ) INFORMATION FOR SEQ ID NO:205:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:205:

Ser Gly Ser Ala
1

( 2 ) INFORMATION FOR SEQ ID NO:206:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:206:

Arg Cys Gly Phe Tyr Met Arg Tyr
1               5

( 2 ) INFORMATION FOR SEQ ID NO:207:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:207:

```
Tyr  Tyr  Tyr  Pro  Leu  Arg  Ser  Val  Tyr  Phe  Gly  Arg  Arg  Leu  Leu  Leu
 1              5                   10                            15

Pro  Arg  Leu  Ser  Ser  Trp  Ser  Ile  Cys  Tyr  Glu  Phe  Tyr  Phe  Thr  Ser
                20                  25                       30

Ser  Asp  Gly  Asn
          35
```

(2) INFORMATION FOR SEQ ID NO:208:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:208:

```
Ala  Thr  Arg  Ser  Lys  Tyr  Tyr
 1              5
```

(2) INFORMATION FOR SEQ ID NO:209:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:209:

```
Val  Thr  Val  Asp  Asn  Ile  Thr  Ile  Asn  Phe  Ile  Cys  Ala  Arg  Ala  Thr
 1              5                   10                            15
Ser
```

(2) INFORMATION FOR SEQ ID NO:210:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:210:

```
Glu  Ser  Phe  Thr  Cys  Tyr  Cys  Glu  Leu  Arg  Leu  Pro
 1              5                   10
```

(2) INFORMATION FOR SEQ ID NO:211:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:211:

```
Lys  Asn  His  Pro  Arg  Arg  Leu  Ser  Leu  Ser  Ala
 1              5                   10
```

( 2 ) INFORMATION FOR SEQ ID NO:212:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:212:

```
Ala  Ala  Thr  Arg  Thr  Ser  Val  Leu  Ala
 1              5
```

( 2 ) INFORMATION FOR SEQ ID NO:213:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:213:

```
Lys  Tyr  Ala  Gly  Lys  Asn  Gly  Ser  Gly  Met  Ala  Gly  Thr  Ala  Cys  Lys
 1              5                   10                            15
Thr  Phe  Thr  Arg  Arg
                20
```

( 2 ) INFORMATION FOR SEQ ID NO:214:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:214:

```
Lys  Ser  Ile  Ser  Phe  Ile  Gly  Arg  Ser  Arg  Ser  Ala  Ser  Tyr
 1              5                   10
```

( 2 ) INFORMATION FOR SEQ ID NO:215:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:215:

```
Tyr  Arg  Thr  Gly  Ser  Val  Gly  Leu  Val  Arg  Pro  Thr  Val  Gly  Arg  Gln
 1              5                   10                            15
Cys  Tyr  Val  Pro  Ser  Ser  Gly  Thr  Pro  Gly  His  Gly  Tyr  Gly  Gly  Arg
```

```
                         20                          25                         30
Gly  Ser  Ala  Leu  Phe  Ala  Tyr  Ser  Ser
                         35                      40
```

( 2 ) INFORMATION FOR SEQ ID NO:216:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:216:

```
Lys  Arg  Gly  Ile  Asp  Ala  Arg  Asn  Phe  Trp  Gln  Ala  Val  Tyr  Val  Asp
 1                   5                             10                      15
Tyr  Arg  Ala  Trp  Phe  Leu  Ser  Arg  Ser  Gly
                    20                       25
```

( 2 ) INFORMATION FOR SEQ ID NO:217:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:217:

```
Thr  Phe  Leu  Asn  Thr  Ile  Cys  Arg
 1                   5
```

( 2 ) INFORMATION FOR SEQ ID NO:218:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:218:

```
Ile  Phe  Thr  Phe  Ser  Ser  Phe  Gln  Arg  Val  Thr  Glu  Met  Val  Thr
 1                   5                             10                      15
```

( 2 ) INFORMATION FOR SEQ ID NO:219:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:219:

```
Ile  Leu  Lys  Leu  Met  Arg
 1                   5
```

( 2 ) INFORMATION FOR SEQ ID NO:220:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:220:

Arg Pro Leu Gln His Leu Pro Leu Ala Arg Leu
 1               5                  10

( 2 ) INFORMATION FOR SEQ ID NO:221:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:221:

Arg Asn Lys Arg Leu Phe Arg Leu Gln Cys
 1               5                  10

( 2 ) INFORMATION FOR SEQ ID NO:222:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:222:

Leu Ser Arg Ser Tyr Arg Lys Arg Arg Gly Gln Arg Ser Met Arg Arg
 1               5                  10                  15

Trp Lys Lys ( 2 ) INFORMATION FOR SEQ ID NO:223:

( i ) SEQUENCE CHARACTERISTICS:
  ( A ) LENGTH: 25 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:223:

Val Val Asn Cys Ala Lys Ile Ile Asn Ser Leu Met Leu Arg Asn Trp
 1               5                  10                  15

Ser Ala Asp Ser Arg Leu Cys Cys Val
             20                  25

( 2 ) INFORMATION FOR SEQ ID NO:224:

( i ) SEQUENCE CHARACTERISTICS:
    ( A ) LENGTH: 66 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:224:

```
Asn Lys Tyr Arg Arg Ile Met Gly Gln Arg Cys Val Arg Leu Pro Lys
 1               5                  10                  15
Arg Ile Val Ile Leu Ile Tyr Arg Met Arg Ile Lys Leu Ser Leu Leu
            20                  25                  30
Gln Trp Arg Leu Leu Pro Ala Gly Cys Gln Lys Arg Lys Asn Ala Ile
        35                  40                  45
Cys Asn Arg Asn Trp Ile Arg Tyr Ser Gly Gly Met Gly Thr Cys
    50                  55                  60
Arg Phe
65
```

( 2 ) INFORMATION FOR SEQ ID NO:225:

( i ) SEQUENCE CHARACTERISTICS:
        ( A ) LENGTH: 178 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:225:

```
Phe Thr Gly Thr Trp Arg Ser Gly Tyr Arg Thr Leu Ser Ser Leu Lys
 1               5                  10                  15
Arg Phe Met Gln Gln Ala Ile Asp Asn Asp Glu Met Pro Leu Ser Gln
            20                  25                  30
Trp Phe Arg Arg Val Ala Asp Trp Pro Asp Arg Cys Glu Arg Val Arg
        35                  40                  45
Ile Leu Leu Arg Ala Val Ala Phe Glu Leu Ser Ile Cys Ile Glu Pro
    50                  55                  60
Ser Glu Gln Ser Arg Leu Ala Ala Ala Leu Val Arg Leu Arg Arg Leu
65                  70                  75                  80
Leu Leu Phe Leu Gly Leu Glu Lys Glu Cys Gln Arg Glu Glu Trp Ile
            85                  90                  95
Cys Gln Leu Pro Pro Asn Thr Leu Leu Pro Leu Leu Leu Asp Ile Ile
           100                 105                 110
Cys Glu Arg Trp Leu Phe Ser Asp Trp Leu Leu Asp Arg Leu Thr Ala
       115                 120                 125
Ile Val Ser Ser Ser Lys Met Phe Asn Arg Leu Leu Gln Gln Leu Asp
   130                 135                 140
Ala Gln Phe Met Leu Ile Pro Asp Asn Cys Phe Asn Asp Glu Asp Gln
145                 150                 155                 160
Arg Glu Gln Ile Leu Glu Thr Leu Arg Glu Val Lys Ile Asn Gln Val
                165                 170                 175
Leu Phe
```

( 2 ) INFORMATION FOR SEQ ID NO:226:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:226:

Tyr Leu Ala Phe Asn Ile
 1                   5

( 2 ) INFORMATION FOR SEQ ID NO:227:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:227:

Val Asn Trp Leu Ser Gly Ser Ser
 1               5

( 2 ) INFORMATION FOR SEQ ID NO:228:

( i ) SEQUENCE CHARACTERISTICS:
    ( A ) LENGTH: 57 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:228:

Gly Val Arg Met Asp Trp Asp Leu Ile Thr Glu Arg Asn Ile Gln Leu
 1               5                  10                  15

Phe Ile Gln Leu Ala Gly Leu Ala Glu Arg Pro Leu Ala Thr Asn Met
                20                  25                  30

Phe Trp Arg Gln Gly Gln Tyr Glu Thr Ile Ile Thr Val Val Phe Ser
                35                  40                  45

Tyr Val Arg Tyr Ser Ser Lys Pro Ser
                50              55

( 2 ) INFORMATION FOR SEQ ID NO:229:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:229:

Thr Lys Asn Cys Phe Leu Lys Arg Trp Leu Thr Gly Asn Pro Gln Arg
 1               5                  10                  15

Ser Arg Val Phe Leu Asn Asp Tyr Phe Cys Cys Ala Met Gly Leu Gln
                20                  25                  30

( 2 ) INFORMATION FOR SEQ ID NO:230:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:230:

```
Val  Val  Leu  His  Leu  Phe  Pro  Ala  Pro  Pro  Ser  Ser  Gly  Tyr  Asp  Tyr
 1              5                        10                       15
Ile  Ile  Asp  Lys
              20
```

( 2 ) INFORMATION FOR SEQ ID NO:231:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:231:

```
Asn  Phe  Xaa  Glu  Ser  Gln  Cys  Val  His  Gly
 1              5                        10
```

( 2 ) INFORMATION FOR SEQ ID NO:232:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:232:

```
Val  Arg  Glu  Ser  Gly  Arg  Asn  Ser  Gly  Ser  Val  Tyr  Ala  Arg  Val  Gly
 1              5                        10                       15
Arg  Ile  Trp  Phe  Trp  Arg  Arg  Cys  Tyr
              20                        25
```

( 2 ) INFORMATION FOR SEQ ID NO:233:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:233:

```
Cys  Cys  Tyr  Pro  Cys  Arg  Pro  Gly  Trp  Leu  Ile  Ser
 1              5                        10
```

( 2 ) INFORMATION FOR SEQ ID NO:234:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:234:

```
Leu  Leu  Ser  Thr  Leu  Cys  Phe  Gln
 1                    5
```

( 2 ) INFORMATION FOR SEQ ID NO:235:

( i ) SEQUENCE CHARACTERISTICS:
    ( A ) LENGTH: 53 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:235:

```
Leu  Leu  Phe  Ile  Leu  Val  Thr  Leu  Ser  Ile  Tyr  Arg  Tyr  Phe  Arg  Leu
 1                    5                        10                          15
Tyr  Tyr  Leu  Leu  Leu  His  Tyr  Ile  Val  Cys  His  Ser  Gln  Ser  Ala  His
                 20                           25                    30
His  Gly  Trp  Tyr  Cys  Tyr  Asn  Ile  Met  Pro  Val  Ile  Leu  Trp  Met  Leu
                 35                           40                    45
Ser  Val  Ser  Leu  Ser
      50
```

( 2 ) INFORMATION FOR SEQ ID NO:236:

( i ) SEQUENCE CHARACTERISTICS:
    ( A ) LENGTH: 45 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:236:

```
Glu  Glu  Ile  Ser  Pro  Leu  Gly  Trp  Ser  Tyr  Leu  Pro  Ser  Leu  Leu  Ser
 1                    5                        10                          15
Cys  Asn  Leu  Leu  Ser  Leu  Gln  Lys  Val  Ser  Arg  Gly  Trp  Arg  Lys  Leu
                 20                           25                    30
Ala  His  Val  Ser  Arg  Leu  Met  Gly  Cys  Gln  Ala  Asn  Lys
                 35                     40                    45
```

( 2 ) INFORMATION FOR SEQ ID NO:237:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:237:

Val Ser Met Ala Ile Cys Val Pro Glu Leu Ser Met Gln Thr Met Pro
1               5                   10                  15
Val His ( 2 ) INFORMATION FOR SEQ ID NO:238:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:238:

Asp Ser Met Ser Ser Arg Lys Ala Ala Phe Ser Val Arg Trp Thr Val
1               5                   10                  15
Arg ( 2 ) INFORMATION FOR SEQ ID NO:239:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:239:

Asn Leu Leu Lys Ala Ile Arg Leu Pro Val Leu Leu Leu Phe Trp
1               5                   10                  15

( 2 ) INFORMATION FOR SEQ ID NO:240:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:240:

Thr Leu Ser Ala Val Ser Leu Ser Leu Ser Tyr Asn Met Ile Cys Arg
1               5                   10                  15

( 2 ) INFORMATION FOR SEQ ID NO:241:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:241:

Val Arg Leu Phe Thr Leu Ile Ala Tyr Cys Gln Ser Glu Met Val Tyr

```
              1               5                 10                  15
Val Gly Lys Phe His Arg Cys
              20
```

( 2 ) INFORMATION FOR SEQ ID NO:242:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:242:

```
Phe Pro Leu Ala Arg Glu Leu Leu Ser Pro Val Ser Arg Val Arg Asn
 1                 5                      10                  15
Ala Arg Thr Trp Arg Gln Ser
              20
```

( 2 ) INFORMATION FOR SEQ ID NO:243:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:243:

```
Val Leu Lys Leu Pro Asp Asn Leu Ser Arg Ser Tyr
 1                 5                      10
```

( 2 ) INFORMATION FOR SEQ ID NO:244:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:244:

```
Pro Leu Trp Phe
 1
```

( 2 ) INFORMATION FOR SEQ ID NO:245:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:245:

```
Cys Ser Ser Leu
 1
```

( 2 ) INFORMATION FOR SEQ ID NO:246:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:246:

```
Phe Leu Ala Phe Leu Leu Ser Leu Ser Leu Ser Phe Gln Arg Cys
 1               5                  10                  15
```

( 2 ) INFORMATION FOR SEQ ID NO:247:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:247:

```
His Cys Gln Leu Ser Ser Phe Ala Ala Lys Ser Leu Trp Phe Pro Gln
 1               5                  10                  15
Met Ala Ser Lys His Arg Lys Lys Ile Val Trp Phe Pro Ala His Val
            20                  25                  30
Leu
```

( 2 ) INFORMATION FOR SEQ ID NO:248:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:248:

```
Ser Tyr Val Leu Ala Arg Arg Tyr Ile Leu Pro Thr
 1               5                  10
```

( 2 ) INFORMATION FOR SEQ ID NO:249:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:249:

```
Phe Val Ile Leu Thr Pro
 1               5
```

( 2 ) INFORMATION FOR SEQ ID NO:250:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:250:

Asp Gly Phe Tyr Leu Arg Ile Pro Ala Ser Leu Ser Leu Arg
 1               5                  10

( 2 ) INFORMATION FOR SEQ ID NO:251:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:251:

Ile Leu Arg Phe Cys Leu Asn Pro Pro Lys Asn
 1               5                  10

( 2 ) INFORMATION FOR SEQ ID NO:252:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:252:

Arg Tyr Cys Tyr Ile Arg Asn Pro Tyr Leu Val Tyr Leu Phe Pro Leu
 1               5                  10                  15
Arg Arg Ile Ile Tyr
            20

( 2 ) INFORMATION FOR SEQ ID NO:253:

( i ) SEQUENCE CHARACTERISTICS:
    ( A ) LENGTH: 48 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:253:

Ala Arg Thr Leu Val Trp Trp Val Thr Ala Arg Arg Tyr Arg Thr Gly
 1               5                  10                  15
Trp Gly Arg Ser Val Gly Leu Gln Lys Thr Trp Pro Ile Arg Arg Lys
                20                  25                  30
Val Leu Asp Trp Thr Phe Ser Arg Ala Ala Asn Val Ser Leu Pro Tyr
                35                  40                  45

( 2 ) INFORMATION FOR SEQ ID NO:254:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:254:

Asn Val Ser Cys Phe Gly Ile Trp Glu Ser Leu Leu Val Phe Arg Lys
 1               5                  10                  15
Arg Val Ile ( 2 ) INFORMATION FOR SEQ ID NO:255:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:255:

Met Arg Trp Lys Lys Thr Thr Leu Ser Trp
 1               5                  10

( 2 ) INFORMATION FOR SEQ ID NO:256:

( i ) SEQUENCE CHARACTERISTICS:
  ( A ) LENGTH: 35 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:256:

Lys Ser Phe Ser Ala Ser Tyr Pro Leu Ile Lys Ser Leu Lys Leu Cys
 1               5                  10                  15
Asn Gly Leu Tyr Gln Ser Gly Phe Leu Leu Glu Ile Tyr Val Leu Phe
                20                  25                  30
Ser Ala Pro
            35

( 2 ) INFORMATION FOR SEQ ID NO:257:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:257:

Leu Thr Gly Arg His Val Lys Lys Met Ser
 1               5                  10

( 2 ) INFORMATION FOR SEQ ID NO:258:

( i ) SEQUENCE CHARACTERISTICS:
 ( A ) LENGTH: 66 amino acids
 ( B ) TYPE: amino acid
 ( C ) STRANDEDNESS: single
 ( D ) TOPOLOGY: linear ( i i ) MOLECULE TYPE: protein ( i i i ) HYPOTHETICAL: NO ( x i ) SEQUENCE DESCRIPTION: SEQ ID NO:258:

```
Gln Asn Met Ser Val Ser Arg Phe Val Val Ile Phe Cys Val Val Leu
  1               5                  10                  15
Ile Arg Lys Glu Asn Arg Cys Arg Phe Cys Gly Ser Ala Lys Val Leu
             20                  25                  30
Lys Thr Ser Cys Val Asn Pro Phe Ala Arg Arg Gln Trp Gly Pro Ile
         35                  40                  45
Leu Arg Cys Arg Leu Val Ile Arg Arg Arg Ser Cys Asn Leu Ser Ser
     50                  55                  60
Arg Arg
 65
```

( 2 ) INFORMATION FOR SEQ ID NO:259:

( i ) SEQUENCE CHARACTERISTICS:
  ( A ) LENGTH: 36 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:259:

```
Ser Ser Gln Pro Asn Tyr Ser Leu Ser Leu Leu Ser Thr Pro Asp Val
  1               5                  10                  15
Ser Cys Glu Lys Leu Gln Lys Pro Pro Cys Ser Thr Tyr Arg Phe Cys
             20                  25                  30
His Gly Arg Asn
         35
```

( 2 ) INFORMATION FOR SEQ ID NO:260:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:260:

```
Glu Arg Arg Ala Leu Tyr Lys Trp
  1               5
```

( 2 ) INFORMATION FOR SEQ ID NO:261:

( i ) SEQUENCE CHARACTERISTICS:
  ( A ) LENGTH: 109 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( x i ) SEQUENCE DESCRIPTION: SEQ ID NO:261:

| Lys | Val | Leu | Thr | Leu | Ala | Lys | Arg | Ser | Trp | Arg | Thr | Met | Lys | Asn | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Met | Gln | Arg | Leu | Arg | Leu | Lys | Tyr | Pro | Pro | Pro | Asp | Gly | Tyr | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Trp | Gly | Arg | Ile | Gln | Asp | Val | Ser | Ala | Thr | Leu | Leu | Asn | Ala | Trp |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Leu | Pro | Gly | Val | Phe | Met | Gly | Glu | Leu | Cys | Cys | Ile | Lys | Pro | Gly | Glu |
|-----|-----|-----|-----|-----|-----|-----|-----|-----|-----|-----|-----|-----|-----|-----|-----|
|     |     | 50  |     |     |     | 55  |     |     |     |     |     | 60  |     |     |     |

| Glu | Leu | Ala | Glu | Val | Val | Gly | Ile | Asn | Gly | Ser | Lys | Ala | Leu | Leu | Ser |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Pro | Phe | Thr | Ser | Thr | Ile | Gly | Leu | His | Cys | Gly | Gln | Gln | Val | Met | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Ser | Asp | Ala | Ile | Arg | Phe | Pro | Trp | Ala | Lys | Arg | Tyr |
|-----|-----|-----|-----|-----|-----|-----|-----|-----|-----|-----|-----|-----|
|     |     |     | 100 |     |     |     |     | 105 |     |     |     |     |

( 2 ) INFORMATION FOR SEQ ID NO:262:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:262:

| Gly | Glu | Leu | Leu | Met | Ala | Leu | Val | Val | Pro | Leu | Met | Ala | Ala | Asn | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Thr | Ser | Ala | Gly | Lys | Thr | Met | Met | Gln | Cys | Leu | Leu | Pro | Gln | Trp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Asp | Ser | Leu | Ser | Leu | Asn | His |
|-----|-----|-----|-----|-----|-----|-----|-----|
|     |     |     | 35  |     |     |     | 40  |

( 2 ) INFORMATION FOR SEQ ID NO:263:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:263:

| Arg | Gly | Phe | Ala | Leu | Leu | Ile | Ala | Leu | Arg | Pro | Val | Ala | Lys | Gly | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Trp | Val | Phe | Phe | Leu | Leu | Leu | Ala | Trp | Gly | Lys | Ala | Arg | Phe | Trp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Cys | Cys | Val | Met | Arg | Gln | Thr | Gln | Thr | Ala | Met | Phe | Trp | Cys |
|-----|-----|-----|-----|-----|-----|-----|-----|-----|-----|-----|-----|-----|-----|-----|
|     |     |     | 35  |     |     |     | 40  |     |     |     |     | 45  |     |

( 2 ) INFORMATION FOR SEQ ID NO:264:

( i ) SEQUENCE CHARACTERISTICS:
        ( A ) LENGTH: 35 amino acids
        ( B ) TYPE: amino acid ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:264:

```
Leu  Val  Asn  Val  Asp  Glu  Lys  Ser  Ala  Asn  Ser  Ser  Ile  Leu  His  Cys
 1              5                        10                       15
Leu  Lys  Arg  Pro  Glu  Asn  Val  Val  Ser  Leu  Leu  Ser  Gln  Pro  Leu  Thr
              20                        25                       30
Asp  Pro  Pro
          35
```

( 2 ) INFORMATION FOR SEQ ID NO:265:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:265:

```
Gly  Arg  Cys  Leu  Trp  Pro  Pro  Arg
 1              5
```

( 2 ) INFORMATION FOR SEQ ID NO:266:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:266:

```
Gln  Asn  Phe  Phe  Ala  Ile  Met  Glu  Ser  Glu  Ser  Ser  Cys  Leu  Pro  Thr
 1              5                        10                       15
His
```

( 2 ) INFORMATION FOR SEQ ID NO:267:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:267:

```
Arg  Val  Met  Pro  Gly  Pro  His  Gly  Asn  Arg  Ser  Gly  Ala  Gly  Glu  Thr
 1              5                        10                       15
Ala  Val  Ser  Gly  Glu  Tyr  Arg  Gln  Ala  Tyr  Leu  Val  His  Cys  His  Asp
              20                        25                       30
Phe
```

(2) INFORMATION FOR SEQ ID NO:268:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:268:

```
Asn Val Arg Glu Trp Glu Lys Lys Ala Val Leu Pro His Phe Ile Arg
 1               5                  10                  15
Tyr Trp Trp Lys Ala Met Ile
             20
```

(2) INFORMATION FOR SEQ ID NO:269:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:269:

```
Met Lys Pro Leu Ala Asp Glu Val Arg Ser Leu Leu Asp Gly His Ile
 1               5                  10                  15
Val Leu Ser Arg Arg Leu Ala Glu Arg Gly His Tyr Pro Ala Ile Asp
                20                  25                  30
Val Leu Ala Thr Leu Ser Arg Val Phe Pro Val Val Thr Ser His Glu
                35                  40                  45
His Arg Gln Leu Ala Ala Ile Leu Arg Arg Cys Leu Ala Leu Tyr Gln
                50                  55                  60
Glu Val Glu Leu Leu Ile Arg Ile Gly Glu Tyr Gln Arg Gly Val Asp
65                  70                  75                  80
Thr Asp Thr Asp Lys Ala Ile Asp Thr Tyr Pro Asp Ile Cys Thr Phe
                85                  90                  95
Leu Arg Gln Ser Lys Asp Glu Val Cys Gly Pro Glu Leu Leu Ile Glu
                100                 105                 110
Lys Leu His Gln Ile Leu Thr Glu
                115                 120
```

(2) INFORMATION FOR SEQ ID NO:270:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:270:

```
Ser Trp Lys Leu Cys Trp Arg
 1               5
```

(2) INFORMATION FOR SEQ ID NO:271:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:271:

```
Lys Ala Ile Thr Arg Gln Ala Tyr Arg Thr
 1               5                  10
```

(2) INFORMATION FOR SEQ ID NO:272:

(i) SEQUENCE CHARACTERISTICS:
(A) LENGTH: 41 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:272:

```
Ser Ala Ala Thr Gly Asp Tyr Tyr Gly Thr Ala Asp Leu Pro Asp Ala
 1               5                  10                  15
Arg Phe Ser Ser Val Tyr Gln Thr Glu Arg Ile Asn Gly Leu Ala Arg
                20                  25                  30
Tyr Val Ile Leu Ser Phe Ile Val Gly
                35                  40
```

(2) INFORMATION FOR SEQ ID NO:273:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:273:

```
Glu Thr Thr Asn Gly Arg Val Ile His Ser Gly Ala Glu Leu Phe Asp
 1               5                  10                  15
Ala Thr Ala Ser Ser
                20
```

(2) INFORMATION FOR SEQ ID NO:274:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:274:

```
Arg Ile Ser Ile Ser Ser Leu Ser Pro Gly Glu Ala Asn Tyr Arg Arg
 1               5                  10                  15
Ile Leu Met Arg Leu
                20
```

( 2 ) INFORMATION FOR SEQ ID NO:275:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:275:

```
Lys Arg Lys Lys Lys Leu Leu Trp Tyr
 1               5
```

( 2 ) INFORMATION FOR SEQ ID NO:276:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:276:

```
Ala Met Arg Ile Thr Lys Val Glu Gly Ser Leu Gly Leu Pro Cys Gln
 1               5                  10                  15
Ser Tyr Gln Asp Asp Asn Glu Ala Glu Ala Glu Arg Met Asp Phe Glu
                20                  25                  30
Gln Leu Met His Gln Ala Leu Pro Ile Gly Glu Asn Asn Pro Pro Ala
                35                  40                  45
Ala Leu Asn Lys Asn Val Val Phe Thr Gln Arg Tyr Arg Val Ser Gly
         50                  55                  60
Gly Tyr Leu Asp Gly Val Glu Cys Glu Val Cys Glu Ser Gly Gly Leu
 65                  70                  75                  80
Ile Gln Leu Arg Ile Asn Val Pro His His Glu Ile Tyr Arg Ser Met
                85                  90                  95
Lys Ala Leu Lys Gln Trp Leu Glu Ser Gln Leu Leu His Met Gly Tyr
                100                 105                 110
Ile Ile Ser Leu Glu Ile Phe Tyr Val Lys Asn Ser Glu
                115                 120                 125
```

( 2 ) INFORMATION FOR SEQ ID NO:277:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:277:

```
Arg Ala Ser Val Gly Gly Asp Thr Ser Asn Ala Arg Arg Tyr His Trp
 1               5                  10                  15
```

( 2 ) INFORMATION FOR SEQ ID NO:278:

( i ) SEQUENCE CHARACTERISTICS:

( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:278:

Ala Asp Ile Glu Tyr Ala Thr Ile Ser Ser Thr Ala Arg Asp Ile Ile
1               5                   1 0                      1 5
Tyr His Lys Leu Ser
            2 0

( 2 ) INFORMATION FOR SEQ ID NO:279:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:279:

Gly Val Asp Cys Arg Thr Met Leu Ala Ala Leu Val
1               5                   1 0

( 2 ) INFORMATION FOR SEQ ID NO:280:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:280:

Arg Ala Asn Trp His Arg
1               5

( 2 ) INFORMATION FOR SEQ ID NO:281:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:281:

Ser Ile Gly Tyr Arg Ser
1               5

( 2 ) INFORMATION FOR SEQ ID NO:282:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:282:

Ile Ala Ile Trp Asn Ser
1               5

(2) INFORMATION FOR SEQ ID NO:283:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:283:

Met Gly Ala Gly Ala Val Ile Ala Ser Gln
1               5                   10

(2) INFORMATION FOR SEQ ID NO:284:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:284:

Cys Asn Pro Leu Ser Glu Arg Ala Ala Asn Ile Leu Gln
1               5                   10

(2) INFORMATION FOR SEQ ID NO:285:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:285:

Ser Thr Thr Ser Ala Ser Val Ala Tyr
1               5

(2) INFORMATION FOR SEQ ID NO:286:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:286:

His Tyr Phe Tyr Met Ala Asn Gly Phe Phe Ala Gln Tyr Ser Arg Arg
1               5                   10                  15

Ala Phe Cys (2) INFORMATION FOR SEQ ID NO:287:

(i) SEQUENCE CHARACTERISTICS:
  (A) LENGTH: 26 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:287:

```
Ala Thr Thr Asp Leu Ser Cys Pro Ser Cys Gly Ser Pro Cys Ile Phe
 1               5                  10                  15
Arg Leu Val Pro Ala Tyr Ile Asn Arg Thr
                20                  25
```

(2) INFORMATION FOR SEQ ID NO:288:

(i) SEQUENCE CHARACTERISTICS:
  (A) LENGTH: 38 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:288:

```
Val Tyr Arg Asn Arg His Gly Arg Ser Asp Ser Leu Leu Arg Arg His
 1               5                  10                  15
Gln Thr Arg Phe Phe Cys Tyr Ser Thr Thr Trp Gly Asn Leu Arg Lys
                20                  25                  30
Gly Val Ala Asp Arg Gly
                35
```

(2) INFORMATION FOR SEQ ID NO:289:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:289:

```
His Asp Glu Ile
 1
```

(2) INFORMATION FOR SEQ ID NO:290:

(i) SEQUENCE CHARACTERISTICS:
  (A) LENGTH: 19 amino acids
  (B) TYPE: amino acid
  (C) STRANDEDNESS: single
  (D) TOPOLOGY: linear (ii) MOLECULE TYPE: protein (iii) HYPOTHETICAL: NO (xi) SEQUENCE DESCRIPTION: SEQ ID NO:290:

```
Arg  Ile  Ser  Pro  Gly  Tyr  Arg  Asn  Ala  Thr  Cys  Val  Arg  Glu  Pro  Asn
1                   5                   10                  15

Val  Lys  Glu
```

(2) INFORMATION FOR SEQ ID NO:291:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:291:

```
Arg  Asn  Val  Phe  Ser  Arg  Thr
1                   5
```

(2) INFORMATION FOR SEQ ID NO:292:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:292:

```
Ala  Asp  Thr  Thr  Thr  Gly  Ala  Leu
1                   5
```

(2) INFORMATION FOR SEQ ID NO:293:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:293:

```
Gly  Arg  Thr  Cys  Glu  Ser  Gly  Asn  Trp  Thr  Ile  Thr  Thr  Thr
1                   5                        10
```

(2) INFORMATION FOR SEQ ID NO:294:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:294:

```
Asn  Gly  Gly  Arg  Phe  Ala  Cys  Arg  Trp  Met  Phe  Cys  Ala  Arg  Gly  Asp
1                   5                   10                  15

Asp  Lys  Ser  Lys
                20
```

( 2 ) INFORMATION FOR SEQ ID NO:295:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:295:

```
Pro  Tyr  Tyr  Trp  Ala  Arg
 1                    5
```

( 2 ) INFORMATION FOR SEQ ID NO:296:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:296:

```
Val  Asp  Cys  Leu  Trp  Gln
 1                    5
```

( 2 ) INFORMATION FOR SEQ ID NO:297:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:297:

```
Ile  Tyr  Gly  Ala  Tyr  Tyr  Thr  Leu  Val  Ser  Leu  Gln  Lys  Tyr  Ser  Val
 1                    5                        10                            15
Asn  Leu  Ile  Arg  Lys  Ile  Ile  Cys  Glu  Gln  Tyr  Asn  Ser  Val  Pro  Gly
                     20                        25                       30
Arg  Val  Met  Arg  Asp  Thr  Val  Cys  Leu  Tyr  Pro  Ile  Arg  Leu  Cys  Asn
                35                        40                       45
```

( 2 ) INFORMATION FOR SEQ ID NO:298:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:298:

```
Leu  Val  Tyr  Cys  Phe  Cys  Phe  Gln  Tyr  Cys  Leu  Ser  Leu  Ser  Ser  Trp
 1                    5                        10                            15
Glu  Leu  Leu  Ser  Leu  Asn  Trp  Arg  Trp  Tyr  Phe  Arg  Phe  Tyr  Glu  Met
```

```
                      20                          25                          30
Leu  Trp  Val  Phe  Asn  Lys  Ser  Pro  Gln  Ile  Ser  His  Cys  Met  Ala  Leu
                35                          40                          45
Arg  Leu  Tyr  Phe  Pro  Tyr  Ser  Leu  Trp  Gly  Arg  Arg  Tyr
          50                          55                          60
```

( 2 ) INFORMATION FOR SEQ ID NO:299:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:299:

```
Lys  Ser  Ala  Gly  Ile  Arg  Phe  Arg  Ser  Leu  Ala  Leu  Leu  Ser  Gly  Arg
  1                 5                          10                          15
Leu  Ser  Gly  Thr  Val  Lys  His
                20
```

( 2 ) INFORMATION FOR SEQ ID NO:300:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:300:

```
Arg  Leu  Ile  Asp  Ser  Phe  Cys  Lys  Lys  Thr  Leu  Lys  Arg  Arg  Lys  Pro
  1                 5                          10                          15
Ile  Ile  Phe  Gly  Ile
                20
```

( 2 ) INFORMATION FOR SEQ ID NO:301:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:301:

```
Asn  Glu  Pro  Gly  Leu  Lys  Thr
  1                 5
```

( 2 ) INFORMATION FOR SEQ ID NO:302:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:302:

Asn Leu Ile Leu Cys Ser Tyr
 1               5

( 2 ) INFORMATION FOR SEQ ID NO:303:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:303:

Phe Arg His Leu Arg
 1               5

( 2 ) INFORMATION FOR SEQ ID NO:304:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:304:

Arg Arg His Phe Gly Leu Asp Tyr Leu Phe Ile Phe Pro Phe Trp Leu
 1               5                   1 0                  1 5
Leu Thr Cys Leu Phe Gln Ile Tyr Cys Trp Leu Trp Gly
             2 0                  2 5

( 2 ) INFORMATION FOR SEQ ID NO:305:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:305:

Trp Cys Arg Arg
 1

( 2 ) INFORMATION FOR SEQ ID NO:306:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:306:

Pro Phe His Tyr Arg Leu Ser Cys
 1               5

( 2 ) INFORMATION FOR SEQ ID NO:307:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:307:

Tyr Phe Tyr Trp Gln Ala Val Gly Ile
 1               5

( 2 ) INFORMATION FOR SEQ ID NO:308:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:308:

His Trp Arg Asn Trp Tyr Arg Ala Phe His Glu
 1               5                 10

( 2 ) INFORMATION FOR SEQ ID NO:309:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:309:

Ile Asp Ala Ile Cys Asn Ala Thr Phe Met Asp Arg Pro Phe Tyr Val
 1               5                 10                15

Tyr Ala Gly Ser Val Gly Gly Ile Gly Ser Trp Cys His Arg Lys Pro
                20                 25                30

Cys Ser Gly Leu Asp Ser Asn Thr Gly Pro Asn Ala Thr Val His Asp
                35                 40                45

( 2 ) INFORMATION FOR SEQ ID NO:310:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:310:

Ile Ile Gly Asn Cys Asn Asn Leu Asn Gly Gln Leu Pro Met Ala
 1               5                 10                15

( 2 ) INFORMATION FOR SEQ ID NO:311:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:311:

```
Arg Tyr Pro Val Glu Leu Tyr Pro Ala Asp Asn Val Thr Asn Trp Arg
 1               5                  10                  15
Ala Trp Leu Asn Gly Thr Thr Gly Lys
            20                  25
```

( 2 ) INFORMATION FOR SEQ ID NO:312:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:312:

```
Val Ala Tyr Cys Ile Gly Cys Gly Phe Tyr Ser Thr Ile Glu Pro Phe
 1               5                  10                  15
Phe Ile Thr Ser Leu Ile Lys Lys Trp Gln Phe Arg Gly Arg Thr Phe
            20                  25                  30
Thr
```

( 2 ) INFORMATION FOR SEQ ID NO:313:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:313:

```
Trp Arg Ala Tyr Val Thr Tyr Leu Ser Asp Ile Thr Asn His Leu Pro
 1               5                  10                  15
Ala Glu Asp Tyr Asp Ala Tyr Trp
            20
```

( 2 ) INFORMATION FOR SEQ ID NO:314:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:314:

```
Arg Leu Gln Leu Val Arg Val Ser His Trp Arg Gly Asp Tyr Trp Phe
```

```
                1               5              10              15
Phe  Asn  Trp  Val  Leu  Cys  Gly  Gly  Ser  Leu  Leu  Gly  Arg
                    20                        25
```

( 2 ) INFORMATION FOR SEQ ID NO:315:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:315:

```
Tyr  Gly  Gly  Val  Ser  Ala
 1                    5
```

( 2 ) INFORMATION FOR SEQ ID NO:316:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:316:

```
Tyr  Phe  Thr  Trp  Arg  Asp  Asn  Gly  Tyr  Asp  Ile  Gln  Phe  Tyr  Asn  Arg
 1                   5                        10                       15
Ser
```

( 2 ) INFORMATION FOR SEQ ID NO:317:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:317:

```
Asn  Leu  Thr  Phe  Trp  Leu  Ala  Phe  Gln  Pro  Val  Leu  Val  Cys  Tyr  Phe
 1                   5                        10                       15
Leu  Tyr  Lys  Arg  Arg  His  Gly  Val  Tyr  Ile  Lys  His  Ser  Val
                    20                        25                       30
```

( 2 ) INFORMATION FOR SEQ ID NO:318:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:318:

```
Val  Ile  Ser  Ile  Phe  Thr  Thr  Arg  Ala  Tyr  Phe  Ile  Ile
```

(2) INFORMATION FOR SEQ ID NO:319:

(i) SEQUENCE CHARACTERISTICS:
      (A) LENGTH: 93 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:319:

```
Pro Ala Ile Phe Lys Ile Tyr Pro Gly Arg Val Glu Asn Ala Leu Ser
 1               5                  10                  15

Ile Met Tyr Gln Leu Leu Ser Ser Cys His Asn Met Tyr Gly Ile Ser
            20                  25                  30

Arg Ser Gly Phe Arg Ser Phe Lys Ser Val Gly Thr Thr Ile Glu Cys
            35                  40                  45

Val Phe Leu Leu Asn Ala Ala Gln Lys Tyr Ile Gly Ser Thr Asp Xaa
        50                  55                  60

Leu Ile Ser Phe Pro Tyr Ala Leu His His Tyr Leu Val Glu Ser Asp
 65                  70                  75                  80

Lys Phe Tyr Ile Tyr Leu Lys Asp Trp Phe Pro Ser Val
                 85                  90
```

(2) INFORMATION FOR SEQ ID NO:320:

(i) SEQUENCE CHARACTERISTICS:
      (A) LENGTH: 26 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:320:

```
Ala Arg Lys Gln Asn Ser Leu Gln Lys Arg Asn Tyr Val Met Ala Val
 1               5                  10                  15

Arg Lys Gly Arg Leu Ser Lys Val Leu Lys
                20                  25
```

(2) INFORMATION FOR SEQ ID NO:321:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:321:

```
His His Tyr Phe Ser
 1               5
```

(2) INFORMATION FOR SEQ ID NO:322:

(i) SEQUENCE CHARACTERISTICS:
      (A) LENGTH: 13 amino acids
      (B) TYPE: amino acid (C) STRANDEDNESS: single
(D) TOPOLOGY: linear (i i) MOLECULE TYPE: protein (i i i) HYPOTHETICAL: NO (x i) SEQUENCE DESCRIPTION: SEQ ID NO:322:

Leu Arg Phe Ile Cys Ile Phe Ile Ser Leu Leu Lys Arg
 1               5                   10

(2) INFORMATION FOR SEQ ID NO:323:

(i) SEQUENCE CHARACTERISTICS:
    (A) LENGTH: 5 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:323:

Leu Ser His Tyr Asn
 1               5

(2) INFORMATION FOR SEQ ID NO:324:

(i) SEQUENCE CHARACTERISTICS:
    (A) LENGTH: 7 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:324:

Ile Asn His Phe Leu Met His
 1               5

(2) INFORMATION FOR SEQ ID NO:325:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:325:

Leu Leu His Cys Cys Phe Trp Ala Leu Gly
 1               5                   10

(2) INFORMATION FOR SEQ ID NO:326:

(i) SEQUENCE CHARACTERISTICS:
    (A) LENGTH: 26 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:326:

```
Leu Leu Leu Trp Val Ala Cys Phe Phe Arg Trp Gly Trp Leu Leu Pro
 1               5                   10                  15
Ala Arg Pro Leu Val Leu Lys Ala Ser Ile
            20              25
```

(2) INFORMATION FOR SEQ ID NO:327:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:327:

```
Val Ile Leu Ser Arg Tyr Ser Leu Tyr Ile Ala
 1               5                   10
```

(2) INFORMATION FOR SEQ ID NO:328:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:328:

```
Asn Tyr Val Asn Pro Ala
 1               5
```

(2) INFORMATION FOR SEQ ID NO:329:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:329:

```
Lys Leu Ser Cys Tyr Leu Leu Ser Leu Pro Phe Ser Phe Ile Ile Met
 1               5                   10                  15
Pro Val Leu Phe Gly Arg Tyr Arg Thr Val Gly
            20                  25
```

(2) INFORMATION FOR SEQ ID NO:330:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:330:

```
Pro Val Ala Cys Leu Trp Phe Leu Leu
```

(2) INFORMATION FOR SEQ ID NO:331:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:331:

```
Asn  Gly  Tyr  Gly
 1
```

(2) INFORMATION FOR SEQ ID NO:332:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:332:

```
Trp  Phe  Phe  Ile  Ser  Ser  Leu  Ala  Tyr  Trp  Thr  Ile  Leu  Phe  Asn  Ile
 1                 5                          10                         15
Ile  Arg  Leu  Glu  Lys  Leu  Ser  Lys  Asn  Glu
                20                          25
```

(2) INFORMATION FOR SEQ ID NO:333:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:333:

```
Arg  Lys  Thr  Gly  Ala
 1                  5
```

(2) INFORMATION FOR SEQ ID NO:334:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:334:

```
Arg  Ser  Gly  Gly  Arg  Pro  Ser  Asn  Glu  Asp  Ala  Ala  Ser  Glu  Met  Gln
 1                 5                          10                         15
Ser  Glu  Ile  Gln  Ser  Gly  Ser  Leu  Ala  Gln  Ser  Val  Lys  Gln  Ser  Val
                20                          25                         30
```

Ala Val Val Arg Asn Pro Thr His Ile Ala Val Cys Leu Gly Tyr His
            35                    40                   45

Pro Thr Asp Met Pro Ile Pro Arg Val Leu Glu Lys Gly Ser Asp Ala
        50                   55                  60

Gln Ala Asn Tyr Ile Val Asn Ile Ala Glu Arg Asn Cys Ile Pro Val
65                       70                  75                   80

Val Glu Asn Val Glu Leu Ala Arg Ser Leu Phe Phe Glu Val Glu Arg
                85                       90                  95

Gly Asp Lys Ile Pro Glu Thr Leu Phe Glu Pro Val Ala Ala Leu Leu
                100                  105                 110

Arg Met Val Met Lys Ile Asp Tyr Ala His Ser Thr Glu Thr Pro
        115                  120                 125

(2) INFORMATION FOR SEQ ID NO:335:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:335:

Met Leu Leu Val Cys Phe Phe Arg Pro Leu Arg Arg Leu Arg Gly
1                   5                   10                  15

(2) INFORMATION FOR SEQ ID NO:336:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:336:

Arg Ile Glu Gln Cys Leu Thr Ile Lys Val Arg Asp
1                   5                   10

(2) INFORMATION FOR SEQ ID NO:337:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:337:

Ser Leu Leu Ala Trp His Lys His Gln Ile Ala Tyr Tyr Lys Ile Lys
1                   5                   10                  15

Gln Asp Asn Gly Leu Val Arg Leu Asn Gly Leu Glu Pro Leu Asp Pro
                20                  25                  30

His His Val Lys Val Val Leu
            35

(2) INFORMATION FOR SEQ ID NO:338:

( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL: NO ( x i ) SEQUENCE DESCRIPTION: SEQ ID NO:338:

Pro Thr Glu Leu
 1

( 2 ) INFORMATION FOR SEQ ID NO:339:

( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL: NO ( x i ) SEQUENCE DESCRIPTION: SEQ ID NO:339:

Thr Ala Thr Leu
 1

( 2 ) INFORMATION FOR SEQ ID NO:340:

( i ) SEQUENCE CHARACTERISTICS:
                ( A ) LENGTH: 26 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL: NO ( x i ) SEQUENCE DESCRIPTION: SEQ ID NO:340:

Val Thr Thr Gly Thr Asn Ile Ser Val Thr Thr Ala Met Arg Gln Glu
 1               5                  10                  15
Gly Asn Arg Asn Phe Leu Pro Glu Ile Thr
            20                  25

( 2 ) INFORMATION FOR SEQ ID NO:341:

( i ) SEQUENCE CHARACTERISTICS:
                ( A ) LENGTH: 27 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL: NO ( x i ) SEQUENCE DESCRIPTION: SEQ ID NO:341:

Leu Arg Trp Lys Tyr Ala Thr Cys Arg Glu Asn Ser Arg His Ala Thr
 1               5                  10                  15
Ala Ile Val Val Leu Ser Glu Arg Ala Ala Lys
            20                  25

( 2 ) INFORMATION FOR SEQ ID NO:342:

( i ) SEQUENCE CHARACTERISTICS:

(A) LENGTH: 23 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:342:

Trp Arg Thr Ala Asp Val Val Asp Ser Ala Ser Val Ala Ser Leu Thr
1               5                   10                  15

Pro Pro Pro Arg Ser Gly Arg
            20

(2) INFORMATION FOR SEQ ID NO:343:

(i) SEQUENCE CHARACTERISTICS:
(A) LENGTH: 32 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:343:

Thr Pro Ser Arg Ser Leu Pro Val Pro Tyr Asp Pro Pro Pro Asn Pro
1               5                   10                  15

Leu Thr Pro Gly Tyr Asn Arg Trp Val Asn Leu Thr Pro Ser Arg Arg
            20                  25                  30

(2) INFORMATION FOR SEQ ID NO:344:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:344:

Lys Arg Trp Asn Ala Tyr Leu Tyr Asn Arg Ala Glu Tyr Arg Cys Arg
1               5                   10                  15

(2) INFORMATION FOR SEQ ID NO:345:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:345:

Ser Arg Lys Ser Gly Lys Pro Gln Arg Ala Ala Leu Ile Ala Ala Ser
1               5                   10                  15

Ala Thr Thr Ser Gly Leu Ser Leu
            20

(2) INFORMATION FOR SEQ ID NO:346:

( i ) SEQUENCE CHARACTERISTICS:
    ( A ) LENGTH: 42 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:346:

| Ser | Lys | Ala | Ile | Cys | Leu | Arg | Arg | Val | Thr | Val | Lys | Ile | Ala | Val | Thr |
|---|---|---|---|---|---|---|---|---|---|---|---|---|---|---|---|
| 1 |  |  |  | 5 |  |  |  |  | 10 |  |  |  |  | 15 |  |
| Thr | Ala | Ile | Gln | Met | Pro | Thr | Pro | Lys | Pro | Val | Arg | Ala | Ala | Phe | Ala |
|  |  |  |  | 20 |  |  |  | 25 |  |  |  |  | 30 |  |  |
| His | Pro | Ala | Leu | Ser | Pro | Gly | Pro | Asp | Arg |
|  |  |  |  | 35 |  |  |  | 40 |  |

( 2 ) INFORMATION FOR SEQ ID NO:347:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:347:

| Pro | Thr | Arg | Ile | Val | Thr | Ala | Ala | Ala | Ser | Asp | Ile | Gly | Ser | Thr | Asn |
|---|---|---|---|---|---|---|---|---|---|---|---|---|---|---|---|
| 1 |  |  |  | 5 |  |  |  |  | 10 |  |  |  |  | 15 |  |
| Ile | Ser | Glu | Leu | Lys | Leu | Ser | Ala | Ile |
|  |  |  |  | 20 |  |  |  | 25 |

( 2 ) INFORMATION FOR SEQ ID NO:348:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:348:

| Pro | Ala | Thr | Ser | Thr | Ile | Pro | Asn | Gly | Glu | Thr | Ser | Ser | Ala | Thr | Thr |
|---|---|---|---|---|---|---|---|---|---|---|---|---|---|---|---|
| 1 |  |  |  | 5 |  |  |  |  | 10 |  |  |  |  | 15 |  |
| Ala | Asn | Asn | Val | Thr | Ser | Lys | Asn | Ser | Gln | Arg | Asn | Arg | Gln | Pro | Gln |
|  |  |  |  | 20 |  |  |  | 25 |  |  |  |  | 30 |  |  |
| Leu | Asn | Gln | Ala | Leu | His | Asp | Asp | Ala | Ile | Gly | Phe | Ala | Lys | Ala | Phe |
|  |  |  |  | 35 |  |  |  | 40 |  |  |  |  | 45 |  |  |
| Phe | Ile | Thr | Asn | Ile | Thr | His |
|  |  |  |  | 50 |  |  |  | 55 |

( 2 ) INFORMATION FOR SEQ ID NO:349:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i i ) MOLECULE TYPE: protein (  i i i  ) HYPOTHETICAL: NO ( x i ) SEQUENCE DESCRIPTION: SEQ ID NO:349:

```
Thr  Arg  Val  Phe  Asn  Val  Arg  Lys  His  Gly  Asp  Lys  His  His  Pro  Ile
 1              5                        10                             15

Asp  Arg  Arg  Ser  Arg  Asn  Ala  Ala  Ala  Asp  Thr  Ala  Glu  Phe  Arg  His
              20                        25                        30

Thr  Lys  Met  Ala  Ile  Asp  Lys  Asn  Ile  Val  His  Arg  Asn  Ile  His  Gln
              35                        40                        45

Gln  Ala  Gln  Lys  Ser  His  His  His  Thr  Arg  Phe  Gly  Phe  Gly  Gln  Thr
         50                        55                        60

Phe  Ala  Leu  Val  Ser  Arg  Tyr  Leu  Lys  Glu  Lys  Val  Ser  Cys  Ala  Pro
 65                       70                        75                        80

Gln  Gln  Arg  Ala  Lys  Ile  Thr  His  Gly  Phe  Ile  Gly  Gln  Arg  Arg  Ile
                   85                        90                        95

Asn  Ile  Met  His  Arg  Ala  Asp  Asn  Val  Ser  Gly  Ile  Pro  Gln  Asp  Asp
              100                       105                       110

His  His  Gln  His  Gly  Asp  Lys  Ala  Arg  Gln  Pro  Glu  Pro  Leu  Ser  Asn
              115                       120                       125

Leu  Met  Arg  Asp  Thr  Leu  Thr  Thr  Ala  Gly  Ala  Ile  Glu  Leu  Arg  Asn
         130                       135                       140

His  Arg  Arg  Gln  Gly  Gln  Gln
 145                       150
```

( 2 ) INFORMATION FOR SEQ ID NO:350:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: protein (  i i i  ) HYPOTHETICAL: NO ( x i ) SEQUENCE DESCRIPTION: SEQ ID NO:350:

```
Ala  Val  Thr  Lys  Gln  Asn  Gly  Gly  Lys  Gln  Ile  Glu  Val  Pro  Ile  Ala
 1              5                        10                             15

Thr  Ala  Ala  Met  Ser  Val  Ala  Leu
              20
```

( 2 ) INFORMATION FOR SEQ ID NO:351:

( i ) SEQUENCE CHARACTERISTICS:
( A ) LENGTH: 25 amino acids
( B ) TYPE: amino acid
( C ) STRANDEDNESS: single
( D ) TOPOLOGY: linear ( i i ) MOLECULE TYPE: protein (  i i i  ) HYPOTHETICAL: NO ( x i ) SEQUENCE DESCRIPTION: SEQ ID NO:351:

```
Pro  Pro  Ala  Met  Thr  Val  Ser  Thr  Asn  Pro  Leu  Arg  Ser  Ile  Pro  Leu
 1              5                        10                             15

Ala  Gln  Gly  Ser  Pro  Val  Ser  Glu  Arg
              20                        25
```

( 2 ) INFORMATION FOR SEQ ID NO:352:

( i ) SEQUENCE CHARACTERISTICS:

(A) LENGTH: 19 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:352:

Leu Thr Arg Phe Thr Gly Ile Leu Leu His Val Phe Thr Phe Tyr Phe
 1               5                   10                  15
Val Val Ile (2) INFORMATION FOR SEQ ID NO:353:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:353:

Lys Thr Lys Lys Pro Pro Lys Trp Gln Pro Lys Glu Ile Ala Gly Glu
 1               5                   10                  15
Ile Ser Val Tyr Cys Ser Gly Val Leu Leu Phe Leu Gln
            20                  25

(2) INFORMATION FOR SEQ ID NO:354:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:354:

Lys Asn Ser Cys
 1

(2) INFORMATION FOR SEQ ID NO:355:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:355:

Arg Arg Ile Ala Gly Lys Leu Phe Phe His Leu Leu Leu Cys
 1               5                   10

(2) INFORMATION FOR SEQ ID NO:356:

(i) SEQUENCE CHARACTERISTICS:
            (A) LENGTH: 27 amino acids
            (B) TYPE: amino acid
            (C) STRANDEDNESS: single ( D ) TOPOLOGY: linear ( i i ) MOLECULE TYPE: protein ( i i i ) HYPOTHETICAL: NO ( x i ) SEQUENCE DESCRIPTION: SEQ ID NO:356:

```
Thr Val Leu Leu Leu Phe Ile Ser Gly Val Glu Asp Met Phe Thr Gly
 1               5                  10                 15
Ile Val Gln Gly Thr Ala Lys Leu Val Ser Ile
                20                  25
```

( 2 ) INFORMATION FOR SEQ ID NO:357:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:357:

```
Ala Glu Pro Ser Gln Glu Gln Ile Asn Phe Phe Glu Gln Leu Leu Lys
 1               5                  10                 15
Asp Glu Ala Ser Thr Ser Asn Ala Ser Ala Leu Leu Pro Gln Val Met
                20                  25                 30
Leu Thr Arg Gln Met Asp Tyr Met Gln Leu Thr Val Gly Val Asp Tyr
             35                  40                 45
Leu Ala Arg Ile Ser Arg Arg Ser Met Pro Ser Ala
          50                  55                 60
```

( 2 ) INFORMATION FOR SEQ ID NO:358:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:358:

```
His Gly Met Lys Val His Arg Ile Val Phe Leu Thr Val Leu Thr Phe
 1               5                  10                 15
Phe Leu Thr Ala Cys Asp Val Asp Leu Tyr Arg Ser Leu Pro Glu Asp
                20                  25                 30
Glu Ala Asn Gln Met Leu Ala Leu Leu Met Gln His His Ile Asp Ala
             35                  40                 45
Lys Lys Asn Arg Lys Arg Met Val
          50                  55
```

( 2 ) INFORMATION FOR SEQ ID NO:359:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:359:

Pro Tyr Val Ser Ser Ser Arg Gln Phe Ile Asn Ala Val Glu Ala Thr
1               5                   10                  15

( 2 ) INFORMATION FOR SEQ ID NO:360:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:360:

Arg Leu Ser Ala
1

( 2 ) INFORMATION FOR SEQ ID NO:361:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:361:

Gly Ser Leu Gln Arg Arg Ile Arg Cys Phe Arg Leu Ile Ser
1               5                   10

( 2 ) INFORMATION FOR SEQ ID NO:362:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:362:

Trp Tyr His Pro Arg Lys Asn Arg Gln Lys Ile Asn Phe Leu Lys Glu
1               5                   10                  15

Gln Arg Ile Glu Gly Met Leu Ser Gln Met Glu Gly Arg Asp
            20                  25                  30

( 2 ) INFORMATION FOR SEQ ID NO:363:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:363:

Pro Leu Arg Tyr Arg Leu Met Met Arg Glu Val Thr Leu Leu Arg Ala
1               5                   10                  15

```
Gln Leu Pro Tyr Leu
             20
```

( 2 ) INFORMATION FOR SEQ ID NO:364:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:364:

```
Asn Ile His Leu Arg Ser Ile Trp Arg Pro Phe Gly
 1               5                   10
```

( 2 ) INFORMATION FOR SEQ ID NO:365:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:365:

```
Lys Leu Lys Ile
 1
```

( 2 ) INFORMATION FOR SEQ ID NO:366:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:366:

```
Arg Cys Gln Ser Leu Gly Cys Asn Thr Val Arg Leu Val Ser
 1               5                   10
```

( 2 ) INFORMATION FOR SEQ ID NO:367:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:367:

```
Cys Ser Leu Leu Asn Ser Glu Trp
 1               5
```

( 2 ) INFORMATION FOR SEQ ID NO:368:

( i ) SEQUENCE CHARACTERISTICS:

(A) LENGTH: 22 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:368:

Leu Thr Tyr Pro Arg Asp Lys His Ser Gly Leu Trp Thr Leu Ser Thr
1               5                   10                  15
Pro Ile Lys Gly Arg Trp
            20

(2) INFORMATION FOR SEQ ID NO:369:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:369:

Asn Thr Leu Ile Arg
1               5

(2) INFORMATION FOR SEQ ID NO:370:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:370:

Gln Asp Cys Tyr
1

(2) INFORMATION FOR SEQ ID NO:371:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:371:

Glu Trp Ala Ser
1

(2) INFORMATION FOR SEQ ID NO:372:

(i) SEQUENCE CHARACTERISTICS:
(A) LENGTH: 5 amino acids
(B) TYPE: amino acid
(C) STRANDEDNESS: single
(D) TOPOLOGY: linear (  i  i  ) MOLECULE TYPE: protein (  i  i  i  ) HYPOTHETICAL: NO (  x  i  ) SEQUENCE DESCRIPTION: SEQ ID NO:372:

Ser  Ala  Ile  Phe  Ala
 1                  5

( 2 ) INFORMATION FOR SEQ ID NO:373:

( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( x i ) SEQUENCE DESCRIPTION: SEQ ID NO:373:

Asp  Ala  Val  Phe  Glu  Pro  Thr
 1                  5

( 2 ) INFORMATION FOR SEQ ID NO:374:

( i ) SEQUENCE CHARACTERISTICS:
            ( A ) LENGTH: 23 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( x i ) SEQUENCE DESCRIPTION: SEQ ID NO:374:

Ser  Arg  Gly  Val  Ala  Thr  Leu  Ser  Leu  Phe  Leu  Ala  Thr  Cys  Ser  Leu
 1                  5                                  10                                 15

Arg  Cys  Thr  Gly  Met  Ala  Gly
                    20

( 2 ) INFORMATION FOR SEQ ID NO:375:

( i ) SEQUENCE CHARACTERISTICS:
            ( A ) LENGTH: 384 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( x i ) SEQUENCE DESCRIPTION: SEQ ID NO:375:

Ala  Gly  Leu  Ser  Ser  Ser  Asn  Cys  Trp  Arg  Tyr  Gly  Asp  Arg  Pro  Glu
 1                  5                                  10                                 15

Leu  Asp  Arg  Leu  Leu  Asp  Arg  Ala  Leu  Asn  Arg  Leu  Arg  Gly  Ser  Ser
                    20                                 25                                 30

Val  Ile  Pro  Ala  Cys  Leu  Asn  Asp  Arg  Gln  Lys  Arg  Gln  Val  Arg  Leu
                    35                                 40                                 45

Ala  Pro  Arg  Ile  Ser  Ala  Phe  Ala  Phe  Gly  Leu  Gly  Leu  Phe  Lys  Leu
        50                                 55                                 60

Arg  Cys  Ser  Asp  Tyr  Phe  Met  Leu  Pro  Glu  Tyr  Arg  Gln  Leu  Leu  Leu
 65                                 70                                 75                              80

Gln  Trp  Phe  Ser  Glu  Asp  Glu  Ile  Trp  Gln  Leu  Tyr  Gly  Trp  Leu  Gly
                    85                                 90                                 95

```
Gln  Arg  Asp  Gly  Lys  Leu  Leu  Pro  Pro  Gln  Val  Met  Gln  Gln  Thr  Ala
               100                 105                           110

Leu  Gln  Ile  Gly  Thr  Ala  Ile  Leu  Asn  Arg  Glu  Ala  His  Asp  Asp  Ala
               115                 120                           125

Gly  Phe  Thr  Cys  Ala  Ile  Ser  Ile  Ile  Thr  Pro  Ser  Ala  Ala  Tyr  Thr
          130                 135                      140

Leu  Ala  Glu  Asp  Phe  Ser  Tyr  Arg  Asp  Tyr  Leu  His  Gly  Ala  Phe  Ala
145                      150                      155                      160

Met  Ser  Phe  Thr  Ser  Leu  Pro  Leu  Thr  Glu  Ile  Asn  His  Lys  Leu  Pro
                    165                      170                     175

Ala  Arg  Asn  Ile  Ile  Glu  Ser  Gln  Trp  Ile  Thr  Leu  Gln  Leu  Thr  Leu
               180                      185                      190

Phe  Ala  Gln  Glu  Gln  Ala  Lys  Arg  Val  Ser  His  Ala  Ile  Val  Ser
          195                 200                      205

Ser  Ala  Tyr  Arg  Lys  Ala  Glu  Lys  Ile  Ile  Arg  Asp  Ala  Tyr  Arg  Tyr
          210                 215                      220

Gln  Arg  Glu  Gln  Lys  Val  Glu  Gln  Gln  Glu  Leu  Ala  Cys  Leu  Arg
225                      230                      235                      240

Lys  Asn  Thr  Leu  Glu  Lys  Met  Glu  Val  Glu  Trp  Leu  Glu  Gln  His  Val
                    245                      250                      255

Lys  His  Leu  Gln  Asp  Asp  Glu  Asn  Gln  Phe  Arg  Ser  Leu  Val  Asp  His
               260                      265                      270

Ala  Ala  His  His  Ile  Lys  Asn  Ser  Ile  Glu  Gln  Val  Leu  Leu  Ala  Trp
          275                      280                      285

Phe  Asp  Gln  Gln  Ser  Val  Asp  Ser  Val  Met  Cys  His  Arg  Leu  Ala  Arg
          290                      295                      300

Gln  Ala  Thr  Ala  Met  Ala  Glu  Glu  Gly  Ala  Leu  Tyr  Leu  Arg  Ile  His
305                           310                      315                 320

Pro  Glu  Lys  Glu  Ala  Leu  Met  Arg  Glu  Thr  Phe  Gly  Lys  Arg  Phe  Thr
                    325                      330                      335

Leu  Ile  Ile  Glu  Pro  Gly  Phe  Ser  Pro  Asp  Gln  Ala  Glu  Leu  Ser  Ser
               340                      345                      350

Thr  Arg  Tyr  Ala  Val  Glu  Phe  Ser  Leu  Ser  Arg  His  Phe  Asn  Ala  Leu
          355                      360                      365

Leu  Lys  Trp  Leu  Arg  Asn  Gly  Glu  Asp  Lys  Arg  Gly  Ser  Asp  Glu  Tyr
          370                      375                      380
```

( 2 ) INFORMATION FOR SEQ ID NO:376:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:376:

```
Asp  Lys  Asn  Asp  Ala  Pro  Tyr  Ser  Ile  Tyr  Pro  Trp  Pro  Gly  Tyr  Arg
 1                   5                        10                       15

Gly  Thr  Arg  Gly  Tyr  Phe  Ala  Phe  Asn  Val  Ser  Ser  Pro  Gly  Val  Thr
               20                      25                       30

Gly  Asn  Asp  Gly  Gly  Ser  Ala  Leu
               35                      40
```

( 2 ) INFORMATION FOR SEQ ID NO:377:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:377:

Asp Asp Gly Arg Asn Arg Asn Gly Ala Glu Trp
1               5                   10

( 2 ) INFORMATION FOR SEQ ID NO:378:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:378:

Thr Ala Arg Lys Leu
1               5

( 2 ) INFORMATION FOR SEQ ID NO:379:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:379:

Glu Thr Gly Ala Gln Thr Ala Gly Phe Ala Ala Phe Asp Lys Thr Asn
1               5                   10                  15
Thr Gly Gly ( 2 ) INFORMATION FOR SEQ ID NO:380:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:380:

Trp Gly Asn Val Ala Ser Ala Tyr Arg Arg Glu
1               5                   10

( 2 ) INFORMATION FOR SEQ ID NO:381:

( i ) SEQUENCE CHARACTERISTICS:
        ( A ) LENGTH: 60 amino acids
        ( B ) TYPE: amino acid
        ( C ) STRANDEDNESS: single (D) TOPOLOGY: linear (ii) MOLECULE TYPE: protein (iii) HYPOTHETICAL: NO (xi) SEQUENCE DESCRIPTION: SEQ ID NO:381:

| Phe | Thr | Glu | Cys | Val | Ser | Asn | Tyr | Arg | Ser | Cys | Asn | Gly | Ala | Tyr | Cys |
|---|---|---|---|---|---|---|---|---|---|---|---|---|---|---|---|
| 1 | | | | 5 | | | | | 10 | | | | | 15 | |

| Arg | Arg | Val | Val | Lys | Lys | Glu | Lys | Thr | Arg | Phe | Ala | Ile | Ala | Thr | Gly |
|---|---|---|---|---|---|---|---|---|---|---|---|---|---|---|---|
| | | | 20 | | | | | 25 | | | | | 30 | | |

| Tyr | Val | Thr | Ala | Glu | Glu | Gly | Trp | Glu | Leu | Ala | Val | Phe | Ser | Leu | Leu |
|---|---|---|---|---|---|---|---|---|---|---|---|---|---|---|---|
| | | 35 | | | | | 40 | | | | | 45 | | | |

| Glu | Leu | Gly | Glu | Val | Asp | Thr | Val | Arg | Cys | Pro | Leu |
|---|---|---|---|---|---|---|---|---|---|---|---|
| | 50 | | | | | 55 | | | | 60 | |

(2) INFORMATION FOR SEQ ID NO:382:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:382:

| Ser | Val | Leu | Cys | Asn | Arg | Arg |
|---|---|---|---|---|---|---|
| 1 | | | | 5 | | |

(2) INFORMATION FOR SEQ ID NO:383:

(i) SEQUENCE CHARACTERISTICS:
(A) LENGTH: 27 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:383:

| Thr | Thr | Met | Lys | Cys | Pro | Tyr | Arg | Ser | Gly | Ser | Asp | Ala | Trp | Gln | Thr |
|---|---|---|---|---|---|---|---|---|---|---|---|---|---|---|---|
| 1 | | | | 5 | | | | | 10 | | | | | 15 | |

| Gly | Arg | Ile | Ala | Val | Asn | Gly | Ser | Val | Phe | Cys |
|---|---|---|---|---|---|---|---|---|---|---|
| | | | 20 | | | | | 25 | | |

(2) INFORMATION FOR SEQ ID NO:384:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:384:

| Pro | Leu | Asn | Leu | Ala | Tyr | Ala | Ser | Asn | Pro | Arg | Ser | Lys | Val | Val | Trp |
|---|---|---|---|---|---|---|---|---|---|---|---|---|---|---|---|
| 1 | | | | 5 | | | | | 10 | | | | | 15 | |

| Pro | Gln | His |
|---|---|---|
| | | |

(2) INFORMATION FOR SEQ ID NO:385:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:385:

Tyr Val Cys Val Val Cys Cys Tyr Ser Leu Ala Leu Lys Lys Ser Ala
 1               5                   10               15

Ser Val Arg Ser Gly Phe Ala Ser Cys Arg Leu Ile His Tyr Cys Arg
             20                      25                  30

Tyr Tyr Ser Ile Leu Phe Val Ser Ala Gly Phe Ser Val Ile Gly Cys
        35                  40                 45

Leu Ile Asp Leu Pro Leu
    50

(2) INFORMATION FOR SEQ ID NO:386:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:386:

Phe Leu His Arg Arg Cys Ser Ile Gly Tyr Ser Asn Asn Leu Met Arg
 1               5                   10               15

Ser Leu Cys (2) INFORMATION FOR SEQ ID NO:387:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:387:

Tyr Pro Ile Thr Val Leu Thr Thr Lys Ile Asn Val Asn Lys Phe Ser
 1               5                   10               15

Lys Arg Phe Val Lys
        20

(2) INFORMATION FOR SEQ ID NO:388:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO ( x i ) SEQUENCE DESCRIPTION: SEQ ID NO:388:

Ile Arg Phe Tyr Ser Asp Thr Trp Leu Ser Ile Phe Arg
 1               5                  10

( 2 ) INFORMATION FOR SEQ ID NO:389:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:389:

Ile Gly Phe Leu Ala His His Glu Ala Ser Gly Trp Ile Gly Ile Ser
 1               5                  10                          15
Leu Leu Asn Val Ile Phe Ser Phe Leu Phe Asn
             20                  25

( 2 ) INFORMATION FOR SEQ ID NO:390:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:390:

Leu Asn Gly Leu
 1

( 2 ) INFORMATION FOR SEQ ID NO:391:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:391:

Gln Pro Ile Cys Ser Gly Gly Lys Asp Asn Met Lys Leu Ser
 1               5                  10

( 2 ) INFORMATION FOR SEQ ID NO:392:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:392:

Arg Ser Tyr Ser Leu Met Ser Asp Thr Gln Ala Asn Leu Leu Arg Arg
 1               5                  10                          15

Arg Thr Ala Phe
        20

( 2 ) INFORMATION FOR SEQ ID NO:393:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:393:

Leu Glu Thr Arg Ser Val Pro Gly Tyr Ser Ser Thr Ile Ile Phe Val
 1               5                  10                      15

Ala Arg Trp Ala Cys Asn Glu Leu Phe Ser Thr Ser Phe Gln Leu Arg
            20                  25                  30

Arg Ala Leu Val Thr Ile Thr Ser Ser Thr Asn Lys Ile Xaa Trp Ser
            35                  40                  45

Arg Asn Ala Phe Met Val Arg
        50                  55

( 2 ) INFORMATION FOR SEQ ID NO:394:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:394:

Gly Ser Gln Gly Ala Thr Val Ala Gln Cys Met Arg Gly Ser Ala Gly
 1               5                  10                      15

Tyr Gly Ser Gly Asp Gly Val Ile Asn Arg Tyr Cys Asp Asp Ala Val
            20                  25                  30

Thr Leu Ala Asp Leu Asp Gly
        35

( 2 ) INFORMATION FOR SEQ ID NO:395:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:395:

Tyr Pro Asp Tyr Tyr Gln Pro Tyr Val Phe Ser Asp Pro Ala Leu Asn
 1               5                  10                      15

Cys Tyr Leu Ser
        20

( 2 ) INFORMATION FOR SEQ ID NO:396:

( i ) SEQUENCE CHARACTERISTICS:
        ( A ) LENGTH: 33 amino acids (B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:396:

```
Pro Ser Arg Phe Ile Gly Ile Ser Val Phe Ile Thr Tyr Tyr Tyr Ile
 1               5                  10                  15
Ile Ser Phe Val Thr His Asn Gln His Ile Thr Ala Gly Thr Val Thr
                20                  25                  30
Thr
```

(2) INFORMATION FOR SEQ ID NO:397:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:397:

```
Tyr Cys Gly Cys Phe Arg
 1               5
```

(2) INFORMATION FOR SEQ ID NO:398:

(i) SEQUENCE CHARACTERISTICS:
(A) LENGTH: 35 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:398:

```
Val Cys Arg Arg Arg Lys Ser His Arg Trp Val Gly Arg Ile Tyr His
 1               5                  10                  15
His Tyr Tyr Arg Ala Ile Tyr Cys His Tyr Lys Arg Tyr Arg Glu Gly
                20                  25                  30
Gly Gly Ser
        35
```

(2) INFORMATION FOR SEQ ID NO:399:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:399:

```
Arg Thr Phe Leu Ala
 1               5
```

(2) INFORMATION FOR SEQ ID NO:400:

( i ) SEQUENCE CHARACTERISTICS:
   ( A ) LENGTH: 47 amino acids
   ( B ) TYPE: amino acid
   ( C ) STRANDEDNESS: single
   ( D ) TOPOLOGY: linear ( i i ) MOLECULE TYPE: protein ( i i i ) HYPOTHETICAL: NO ( x i ) SEQUENCE DESCRIPTION: SEQ ID NO:400:

```
Trp Asp Ala Arg Gln Thr Asn Glu Tyr Arg Trp Arg Phe Ala Cys Arg
 1               5                  10                  15
Ser Tyr Arg Cys Arg Pro Cys Pro Tyr Ile Lys Thr Ala Cys Pro Ala
            20                  25                  30
Gly Lys Pro Leu Ser Arg Cys Asp Gly Arg Cys Asp Glu Ile Cys
            35                  40                  45
```

( 2 ) INFORMATION FOR SEQ ID NO:401:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:401:

```
Arg Arg Tyr Asp Cys Arg Tyr Tyr Cys Cys Ser Gly Glu His Tyr Arg
 1               5                  10                  15
Arg Tyr His Tyr Arg Tyr Arg Thr Ile
            20                  25
```

( 2 ) INFORMATION FOR SEQ ID NO:402:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:402:

```
Tyr Val Asp Glu
 1
```

( 2 ) INFORMATION FOR SEQ ID NO:403:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:403:

```
Gly Cys Ser His Leu
 1               5
```

(2) INFORMATION FOR SEQ ID NO:404:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:404:

```
Arg Thr Val Asn Arg Arg Trp Phe Met Trp Ala Asn Ser Ile Ala Ala
 1               5                  10                  15
Asp Phe Pro
```

(2) INFORMATION FOR SEQ ID NO:405:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:405:

```
Arg Gly Asn Tyr Cys His Pro Cys Pro Gly
 1               5                  10
```

(2) INFORMATION FOR SEQ ID NO:406:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:406:

```
Glu Thr Pro Glu Pro Gly Asp Arg Val Glu Phe Ser Asn Cys Gln Thr
 1               5                  10                  15
Thr Ser Val Ala His Ile Asn Arg Cys Gly Phe Asn Ala Pro Arg Phe
                20                  25                  30
Asn Ser Trp Leu Ser Phe Tyr His Ser Arg Phe Leu Phe Ser Val Val
                35                  40                  45
Ser Ile Ala Asn Tyr Pro His Ser Pro Gln Lys Val Cys Gly Phe Arg
                50                  55                  60
Lys Trp Arg Arg Ser Thr Gly Lys Arg
 65                  70
```

(2) INFORMATION FOR SEQ ID NO:407:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO ( x i ) SEQUENCE DESCRIPTION: SEQ ID NO:407:

Tyr Gly Ser Arg Arg Met Ser Ser Asn Leu Thr Ser
 1               5                   1 0

( 2 ) INFORMATION FOR SEQ ID NO:408:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:408:

Pro Asp Val Thr Phe Cys Arg Pro Asp Ser
 1               5                   1 0

( 2 ) INFORMATION FOR SEQ ID NO:409:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:409:

Arg His Glu Met Val Phe Ile
 1               5

( 2 ) INFORMATION FOR SEQ ID NO:410:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:410:

Gly Tyr Arg Arg Pro Ser Pro
 1               5

( 2 ) INFORMATION FOR SEQ ID NO:411:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:411:

Thr His Arg Lys Ile Asp Gly Thr Ala Ile Ser Gly Thr Arg Ile
 1               5                   1 0                 1 5

( 2 ) INFORMATION FOR SEQ ID NO:412:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:412:

Phe Ile Tyr Ser Arg Ser Gly Gly Leu Phe Ile Asp Arg Arg Gly Arg
1               5                   10                  15

(2) INFORMATION FOR SEQ ID NO:413:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:413:

Gln Pro Asp Val Thr Glu Arg Asp Gly Ala Asp Leu Leu Ala Tyr Lys
1               5                   10                  15

Arg His Gly Pro
            20

(2) INFORMATION FOR SEQ ID NO:414:

(i) SEQUENCE CHARACTERISTICS:
(A) LENGTH: 48 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:414:

Gly Ala Arg Phe Trp Thr Gly Arg Phe Arg Gly Gln Pro Thr Tyr Leu
1               5                   10                  15

Cys Leu Ile Lys Met Cys Pro Ala Ser Ala Tyr Gly Arg Val Tyr Trp
                20                  25                  30

Cys Ser Gly Asn Ala Leu Ser Asn Glu Cys Asp Gly Lys Lys Leu Leu
            35                  40                  45

(2) INFORMATION FOR SEQ ID NO:415:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:415:

Ala Gly Glu Arg Ala Ser Ala Pro Val Thr His
1               5                   10

(2) INFORMATION FOR SEQ ID NO:416:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:416:

Asn Phe Ala Thr Ala Cys Ile Arg Ala Gly Phe Tyr
1               5                   1 0

( 2 ) INFORMATION FOR SEQ ID NO:417:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:417:

Arg Phe Thr Ser Tyr Phe Arg His Leu Asn
1               5                   1 0

( 2 ) INFORMATION FOR SEQ ID NO:418:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:418:

Leu Gly Ala Thr
1

( 2 ) INFORMATION FOR SEQ ID NO:419:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:419:

Lys Arg Cys Pro Asp Val Asp Arg Ile Cys Pro Tyr Arg Ala Ser Ser
1               5                   1 0                  1 5
Ser Tyr Ser Ala Ser Ser
            2 0

( 2 ) INFORMATION FOR SEQ ID NO:420:

( i ) SEQUENCE CHARACTERISTICS:
    ( A ) LENGTH: 15 amino acids
    ( B ) TYPE: amino acid
    ( C ) STRANDEDNESS: single (D) TOPOLOGY: linear (ii) MOLECULE TYPE: protein (iii) HYPOTHETICAL: NO (xi) SEQUENCE DESCRIPTION: SEQ ID NO:420:

Ser Gly Arg Lys Thr Ala Ala Asp Phe Ala Asp Arg Arg Arg Tyr
1               5                   10                  15

(2) INFORMATION FOR SEQ ID NO:421:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:421:

Lys Pro Arg Ala
1

(2) INFORMATION FOR SEQ ID NO:422:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:422:

Ile His Ser Pro Asp Gly Asn Gly Asp Leu Tyr Cys Ala Val Val Ser
1               5                   10                  15
Ser (2) INFORMATION FOR SEQ ID NO:423:

(i) SEQUENCE CHARACTERISTICS:
(A) LENGTH: 60 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:423:

Asp Ala Asp Pro Ala Thr Tyr Arg Ala Gly Ala Glu Ala Val Ser Gln
1               5                   10                  15

Ile Ile His Cys His Phe Cys Arg His Pro Thr Phe Leu Ala Lys Asn
                20                  25                  30

Tyr Arg Ser His Leu Val Arg Arg Thr Asp Phe Val Met Ala Gly Ile
                35                  40                  45

Arg Arg Gly Glu Pro Tyr Thr Ser Gly Arg Lys Tyr
            50                  55                  60

(2) INFORMATION FOR SEQ ID NO:424:

(i) SEQUENCE CHARACTERISTICS:

(A) LENGTH: 7 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:424:

Arg Arg Gly Val Gly Gly Gln
1               5

(2) INFORMATION FOR SEQ ID NO:425:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:425:

Asn Ile Arg Pro Pro Met Val Ile Val Asp Gly Ala Glu Phe Arg Met
1               5                   10                  15
Ser Ala Gln Arg Cys
            20

(2) INFORMATION FOR SEQ ID NO:426:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:426:

Met Arg Gly Cys Leu Gly Tyr Leu Trp Ala Ser Cys Ala Val
1               5                   10

(2) INFORMATION FOR SEQ ID NO:427:

(i) SEQUENCE CHARACTERISTICS:
(A) LENGTH: 33 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:427:

Ser Leu Glu Lys Asn Leu Leu Lys Ser Trp Gly Leu Met Ala Ala Lys
1               5                   10                  15
Leu Cys Tyr Leu Leu Leu Arg Val Gln Ser Gly Phe Thr Ala Gly Ser
            20                  25                  30
Lys (2) INFORMATION FOR SEQ ID NO:428:

(i) SEQUENCE CHARACTERISTICS:

( A ) LENGTH: 16 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( x i ) SEQUENCE DESCRIPTION: SEQ ID NO:428:

Ala Thr Pro Ser Gly Ser Arg Gly Arg Ser Val Ile Arg Ala Ser Tyr
 1               5                  10                  15

( 2 ) INFORMATION FOR SEQ ID NO:429:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( x i ) SEQUENCE DESCRIPTION: SEQ ID NO:429:

Trp Leu Trp Ser Ser Pro
 1               5

( 2 ) INFORMATION FOR SEQ ID NO:430:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( x i ) SEQUENCE DESCRIPTION: SEQ ID NO:430:

Trp Pro Arg Thr Ala Arg Arg Leu Leu Glu Arg Leu
 1               5                  10

( 2 ) INFORMATION FOR SEQ ID NO:431:

( i ) SEQUENCE CHARACTERISTICS:
            ( A ) LENGTH: 23 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( x i ) SEQUENCE DESCRIPTION: SEQ ID NO:431:

Cys Asn Ala Ser Ser Arg Asn Gly Ser Thr Ala Tyr His Ser Thr Ile
 1               5                  10                  15
Asn Asp Gly Asp Ser Arg Tyr
                20

( 2 ) INFORMATION FOR SEQ ID NO:432:

( i ) SEQUENCE CHARACTERISTICS:
            ( A ) LENGTH: 28 amino acids
            ( B ) TYPE: amino acid
            ( C ) STRANDEDNESS: single
            ( D ) TOPOLOGY: linear (i i) MOLECULE TYPE: protein (i i i) HYPOTHETICAL: NO (x i) SEQUENCE DESCRIPTION: SEQ ID NO:432:

Arg Cys Asp Leu Trp Arg Arg Ala Thr Ser Gly Tyr Phe Phe Cys Ser
1               5                   10                  15
Trp Arg Gly Glu Lys His Ala Ser Gly Asp Ala Val
            20                  25

(2) INFORMATION FOR SEQ ID NO:433:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:433:

Cys Ala Arg Arg Arg Gln Gln Cys Ser Gly Val Asn Trp
1               5                   10

(2) INFORMATION FOR SEQ ID NO:434:

(i) SEQUENCE CHARACTERISTICS:
        (A) LENGTH: 14 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:434:

Thr Trp Thr Arg Ser Pro Arg Ile His Arg Phe Tyr Thr Val
1               5                   10

(2) INFORMATION FOR SEQ ID NO:435:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:435:

Arg Asp Pro Lys Thr Leu Cys His Cys Cys Arg Asn Leu
1               5                   10

(2) INFORMATION FOR SEQ ID NO:436:

(i) SEQUENCE CHARACTERISTICS:
        (A) LENGTH: 22 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:436:

```
Gln  Thr  Arg  Leu  Arg  Ala  Arg  Glu  Gly  Ala  Val  Cys  Gly  His  His  Asp
 1              5                        10                            15

Ser  Arg  Ile  Phe  Ser  Arg
                20
```

(2) INFORMATION FOR SEQ ID NO:437:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:437:

```
Trp  Lys  Ala  Ser  Arg  Leu  Ala  Cys  Arg  Leu  Thr  Asp  Ala  Leu  Cys  Gln
 1              5                        10                            15

Gly  Arg  Thr  Glu  Ile  Ala  Leu  Ala  Pro  Glu  Arg  Pro  Arg  Phe  Leu  Glu
               20                       25                       30

Asn  Ile  Ala  Arg  Arg  Ile
               35
```

(2) INFORMATION FOR SEQ ID NO:438:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:438:

```
Cys  Ile  Ala  Thr  Thr  Phe  Arg  Thr  Tyr  Gly  Asn  Gly  Arg  Lys  Arg  Gln
 1              5                        10                            15

Tyr  Tyr  Arg  Ile  Leu  Tyr  Gly  Thr  Gly  Gly  Arg  Arg
               20                       25
```

(2) INFORMATION FOR SEQ ID NO:439:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:439:

```
Ser  Arg  Trp  Arg  Met  Lys  Ser  Val  His  Cys  Leu  Met  Asp  Ile  Leu  Tyr
 1              5                        10                            15

Tyr  Pro  Asp  Gly  Leu  Gln  Arg  Gly  Gly  Ile  Ile  Leu  Pro  Leu  Thr  Cys
               20                       25                       30

Trp  Gln  Arg  Ser  Ala  Ala  Phe  Phe  Gln  Ser  Leu  Pro  Ala  Met  Ser  Ile
               35                       40                       45

Val  Asn  Trp  Arg  Arg  Tyr  Cys  Asp  Gly  Ala  Trp  Arg  Phe  Thr  Arg  Arg
          50                       55                       60

Leu  Asn  Cys
```

65

( 2 ) INFORMATION FOR SEQ ID NO:440:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:440:

```
Tyr Ala Leu Gly Asn Thr Ser Glu Glu Leu Ile Gln Ile Leu Thr Lys
 1               5                  10                  15
Pro Leu Ile Pro Ile Arg Ile Phe Ala His Phe Cys Asp Lys Val Arg
                20                  25                  30
Met Lys Tyr Ala Asp Pro Ser Tyr Leu
                35                  40
```

( 2 ) INFORMATION FOR SEQ ID NO:441:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:441:

```
Lys Asn Tyr Thr Lys Tyr Ser Pro Ser Asp His Gly Asn Phe Ala Gly
 1               5                  10                  15
Asp Asn Arg Ala Ala Glu Lys Gln Leu Arg Gly Lys Leu Thr Val Leu
                20                  25                  30
Asp Gln Gln Gln Gln Ala Ile Ile Thr Glu Gln Gln Ile Cys Gln Thr
                35                  40                  45
Arg Ala Leu Ala Val Ser Thr Arg Leu Lys Glu Leu Met Gly Trp Gln
        50                  55                  60
Gly Thr Leu Ser Cys His Leu Leu Leu Asp Lys Lys Gln Gln Met Ala
 65                  70                  75              80
Gly Leu Phe Thr Gln Ala Gln Ser Phe Leu Thr Gln Arg Gln Ala Val
                    85                  90                  95
Arg Glu Ser Val Ser Ala Ala Cys Leu Pro Ala Lys Arg Ile Thr Glu
                100                 105                 110
Glu Phe
```

( 2 ) INFORMATION FOR SEQ ID NO:442:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:442:

```
Cys Ala Tyr Glu Lys Glu Arg Lys Asn Tyr Tyr Gly Ile Lys Arg Cys
```

```
             1               5                    10                      15
Val  Leu  Pro  Lys  Leu  Arg  Glu  Val  Leu  Gly  Cys  His  Ala  Ser  Leu  Ile
                    20                       25                       30

Arg  Met  Ile  Thr  Arg  Arg  Arg  Asn  Val  Trp  Thr  Leu  Asn  Asn  Ser
               35                       40                       45

Cys  Thr  Arg  His  Tyr  Pro  Leu  Val  Arg  Ile  Ile  Leu  Leu  Gln  His
          50                       55                       60
```

( 2 ) INFORMATION FOR SEQ ID NO:443:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:443:

```
Ile  Arg  Thr  Trp  Phe  Ser  Arg  Asn  Val  Ile  Val  Leu  Val  Ala  Val  Ile
 1                   5                        10                       15

Leu  Thr  Val
```

( 2 ) INFORMATION FOR SEQ ID NO:444:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:444:

```
Ser  Val  Lys  Tyr  Val  Asn  Gln  Gly  Gly
 1                   5
```

( 2 ) INFORMATION FOR SEQ ID NO:445:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:445:

```
Glu  Ser  Met  Ser  Leu  Ile  Met  Lys  Phe  Thr  Val  Arg
 1                   5                        10
```

( 2 ) INFORMATION FOR SEQ ID NO:446:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:446:

| Ser | Ser | Gly | Trp | Ser | Leu | Ser | Cys | Cys | Ile | Trp | Gly | Ile |
|---|---|---|---|---|---|---|---|---|---|---|---|---|
| 1 | | | | 5 | | | | | 10 | | | |

( 2 ) INFORMATION FOR SEQ ID NO:447:

( i ) SEQUENCE CHARACTERISTICS:
        ( A ) LENGTH: 328 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:447:

| Phe | Pro | Trp | Arg | Tyr | Ser | Met | Leu | Arg | Ile | Ala | Asn | Glu | Glu | Arg | Pro |
|---|---|---|---|---|---|---|---|---|---|---|---|---|---|---|---|
| 1 | | | | 5 | | | | | 10 | | | | | 15 | |
| Trp | Val | Glu | Ile | Leu | Pro | Thr | Gln | Gly | Ala | Thr | Ile | Gly | Glu | Leu | Thr |
| | | | 20 | | | | | 25 | | | | | 30 | | |
| Leu | Ser | Met | Gln | Gln | Tyr | Pro | Val | Gln | Gln | Gly | Thr | Leu | Phe | Thr | Ile |
| | | 35 | | | | | 40 | | | | | 45 | | | |
| Asn | Tyr | His | Asn | Glu | Leu | Gly | Arg | Val | Trp | Ile | Ala | Glu | Gln | Cys | Trp |
| | 50 | | | | | 55 | | | | | 60 | | | | |
| Gln | Arg | Trp | Cys | Glu | Gly | Leu | Ile | Gly | Thr | Ala | Asn | Arg | Ser | Ala | Ile |
| 65 | | | | | 70 | | | | | 75 | | | | | 80 |
| Asp | Pro | Glu | Leu | Leu | Tyr | Gly | Ile | Ala | Glu | Trp | Gly | Leu | Ala | Pro | Leu |
| | | | | 85 | | | | | 90 | | | | | 95 | |
| Leu | Gln | Ala | Ser | Asp | Ala | Thr | Leu | Cys | Gln | Asn | Glu | Pro | Pro | Thr | Ser |
| | | | | 100 | | | | | 105 | | | | | 110 | |
| Cys | Ser | Asn | Leu | Pro | His | Gln | Leu | Ala | Leu | His | Ile | Lys | Trp | Thr | Val |
| | | | 115 | | | | | 120 | | | | | 125 | | |
| Glu | Glu | His | Glu | Phe | His | Ser | Ile | Ile | Phe | Thr | Trp | Pro | Thr | Gly | Phe |
| | | | 130 | | | | | 135 | | | | | 140 | | |
| Leu | Arg | Asn | Ile | Val | Gly | Glu | Leu | Ser | Ala | Glu | Arg | Gln | Gln | Ile | Tyr |
| 145 | | | | | 150 | | | | | 155 | | | | | 160 |
| Pro | Ala | Pro | Pro | Val | Val | Val | Pro | Val | Tyr | Ser | Gly | Trp | Cys | Gln | Leu |
| | | | | 165 | | | | | 170 | | | | | 175 | |
| Thr | Leu | Ile | Glu | Leu | Glu | Ser | Ile | Glu | Ile | Gly | Met | Gly | Val | Arg | Ile |
| | | | 180 | | | | | 185 | | | | | 190 | | |
| His | Cys | Phe | Gly | Asp | Ile | Arg | Leu | Gly | Phe | Phe | Ala | Ile | Gln | Leu | Pro |
| | | | 195 | | | | | 200 | | | | | 205 | | |
| Gly | Gly | Ile | Tyr | Ala | Arg | Val | Leu | Leu | Thr | Glu | Asp | Asn | Thr | Met | Lys |
| | | 210 | | | | | 215 | | | | | 220 | | | |
| Phe | Asp | Glu | Leu | Val | Gln | Asp | Ile | Glu | Thr | Leu | Leu | Ala | Ser | Gly | Ser |
| 225 | | | | | 230 | | | | | 235 | | | | | 240 |
| Pro | Met | Ser | Lys | Ser | Asp | Gly | Thr | Ser | Ser | Val | Glu | Leu | Glu | Gln | Ile |
| | | | | 245 | | | | | 250 | | | | | 255 | |
| Pro | Gln | Gln | Val | Leu | Phe | Glu | Val | Gly | Arg | Ala | Ser | Leu | Glu | Ile | Gly |
| | | | 260 | | | | | 265 | | | | | 270 | | |
| Gln | Leu | Arg | Gln | Leu | Lys | Thr | Gly | Asp | Val | Leu | Pro | Val | Gly | Gly | Cys |
| | | 275 | | | | | 280 | | | | | 285 | | | |
| Phe | Ala | Pro | Glu | Val | Thr | Ile | Arg | Val | Asn | Asp | Arg | Ile | Ile | Gly | Gln |
| | 290 | | | | | 295 | | | | | 300 | | | | |
| Gly | Glu | Leu | Ile | Ala | Cys | Gly | Asn | Glu | Phe | Met | Val | Arg | Ile | Thr | Arg |
| 305 | | | | | 310 | | | | | 315 | | | | | 320 |

Trp Tyr Leu Cys Lys Asn Thr Ala
            325

( 2 ) INFORMATION FOR SEQ ID NO:448:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:448:

Tyr Ala Asn Asn Ile Ile Ala Phe Gln Val Val Ser
 1               5                   10

( 2 ) INFORMATION FOR SEQ ID NO:449:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:449:

Glu Ile Gln Tyr Val Phe Thr Arg Phe Ala Phe Ala Thr Asp Trp Tyr
 1               5                   10                  15

Ile Val Ser Ala Phe Asn Thr Ala Ser His Tyr Arg His Gly Asn Phe
            20                  25                  30

Phe Pro ( 2 ) INFORMATION FOR SEQ ID NO:450:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:450:

Thr Gly Gly Gly Ile Phe Asp Phe Thr Lys Cys Ser Gly Tyr Ser Thr
 1               5                   10                  15

Ser Pro Pro Lys Tyr Arg Thr Val Trp Pro Cys Ala Cys Thr Phe Leu
            20                  25                  30

Ile His Tyr Gly Ala Asp Ala Ile Ser Cys Lys Arg Ala Leu Ala Ser
            35                  40                  45

Gly Ser Gly Arg Trp Arg Ser Phe Leu Asp Val
            50                  55

( 2 ) INFORMATION FOR SEQ ID NO:451:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear (i i) MOLECULE TYPE: protein (i i i) HYPOTHETICAL: NO (x i) SEQUENCE DESCRIPTION: SEQ ID NO:451:

Ser Ile Ser Ala Leu Ser Thr Val Phe Ala Lys Lys Leu
1               5                   10

(2) INFORMATION FOR SEQ ID NO:452:

(i) SEQUENCE CHARACTERISTICS:
    (A) LENGTH: 16 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:452:

Arg Glu Gly Ser Gln Leu Phe Ser Glu Phe Asp Lys Thr Asn Leu Ala
1               5                   10                  15

(2) INFORMATION FOR SEQ ID NO:453:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:453:

Arg His Lys Lys Lys Asp Lys Thr
1               5

(2) INFORMATION FOR SEQ ID NO:454:

(i) SEQUENCE CHARACTERISTICS:
    (A) LENGTH: 31 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:454:

Phe Phe Ala His Ile Asn Ser Gly Ile Tyr Gly Glu Ser Val Asn Ala
1               5                   10                  15
Gly Ile Ser Asp Trp Ile Thr Tyr Leu Ser Ser Leu Ser Gly Tyr
            20                  25                  30

(2) INFORMATION FOR SEQ ID NO:455:

(i) SEQUENCE CHARACTERISTICS:
    (A) LENGTH: 24 amino acids
    (B) TYPE: amino acid
    (C) STRANDEDNESS: single
    (D) TOPOLOGY: linear (i i) MOLECULE TYPE: protein (i i i) HYPOTHETICAL: NO (x i) SEQUENCE DESCRIPTION: SEQ ID NO:455:

Pro Ala Tyr Phe Lys Tyr Thr Ala Gly Tyr Gly Asp Asp Asp Gly Val
1               5                   10                  15

Ala Asp Asp His Phe Ile Thr Val
            20

(2) INFORMATION FOR SEQ ID NO:456:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:456:

Ala Ala Asn Ile Phe Thr Gly Arg Arg Leu Gly Ser Asp Thr Gly Ala
1               5                   10                  15

Ile Gly Thr Glu Leu Phe Met Asn Asp Ser Glu Leu Thr Gln Phe Val
                20                  25                  30

Thr Gln Leu Leu Trp Ile Val Leu Phe Thr Ser Met Pro Val Val Leu
            35                  40                  45

Val Ala Ser Val Val Gly Val Ile Val Ser Leu Val Gln Ala Leu Thr
        50                  55                  60

Gln Ile Gln Asp Gln Thr Leu Gln Phe Met Ile Lys Leu Leu Ala Ile
65                      70                  75                  80

Ala Ile Thr Leu Met Val Ser Tyr Pro Trp Leu Ser Gly Ile Leu Leu
                85                  90                  95

Asn Tyr Thr Arg Gln Ile Met Leu Arg Ile Gly Glu His Gly
                100                 105                 110

(2) INFORMATION FOR SEQ ID NO:457:

(i) SEQUENCE CHARACTERISTICS:
        (A) LENGTH: 230 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:457:

Met Ala Gln Gln Val Asn Glu Trp Leu Ile Ala Leu Ala Val Ala Phe
1               5                   10                  15

Ile Arg Pro Leu Ser Leu Ser Leu Leu Leu Pro Leu Leu Lys Ser Gly
                20                  25                  30

Ser Leu Gly Ala Ala Leu Leu Arg Asn Gly Val Leu Met Ser Leu Thr
            35                  40                  45

Phe Pro Ile Leu Pro Ile Ile Tyr Gln Gln Lys Ile Met Met His Ile
        50                  55                  60

Gly Lys Asp Tyr Ser Trp Leu Gly Leu Val Thr Gly Glu Val Ile Ile
65                      70                  75                  80

Gly Phe Ser Ile Gly Phe Cys Ala Ala Val Pro Phe Trp Ala Val Asp
                85                  90                  95

Met Ala Gly Phe Leu Leu Asp Thr Leu Arg Gly Ala Thr Met Gly Thr
                100                 105                 110

Ile Phe Asn Ser Thr Ile Glu Ala Glu Thr Ser Leu Phe Gly Leu Leu

-continued

```
                    115                           120                           125
Phe  Ser  Gln  Phe  Leu  Cys  Val  Ile  Phe  Phe  Ile  Ser  Gly  Gly  Met  Glu
     130                      135                      140
Phe  Ile  Leu  Asn  Ile  Leu  Tyr  Glu  Ser  Tyr  Gln  Tyr  Leu  Pro  Pro  Gly
145                           150                      155                     160
Arg  Thr  Leu  Leu  Phe  Asp  Gln  Gln  Phe  Leu  Lys  Tyr  Ile  Gln  Ala  Glu
                    165                      170                      175
Trp  Arg  Thr  Leu  Tyr  Gln  Leu  Cys  Ile  Ser  Phe  Ser  Leu  Pro  Ala  Ile
               180                      185                      190
Ile  Cys  Met  Val  Leu  Ala  Asp  Leu  Ala  Leu  Gly  Leu  Leu  Asn  Arg  Ser
          195                      200                      205
Ala  Gln  Gln  Leu  Asn  Val  Phe  Phe  Phe  Ser  Met  Pro  Leu  Lys  Ser  Ile
     210                      215                      220
Leu  Val  Leu  Leu  Thr  Xaa
225                 230
```

( 2 ) INFORMATION FOR SEQ ID NO:458:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:458:

```
Ser  His  Ser  Leu  Met  Leu  Phe  Ile  Thr  Ile  Trp  Leu  Lys  Ala  Ile  Asn
1                   5                        10                       15
Phe  Ile  Phe  Ile
               20
```

( 2 ) INFORMATION FOR SEQ ID NO:459:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:459:

```
Lys  Thr  Gly  Phe  His  Leu  Tyr  Glu  Arg  Glu  Asn  Arg  Thr  Ala  Tyr  Arg
1                   5                        10                       15
Lys  Glu  Ile  Thr
               20
```

( 2 ) INFORMATION FOR SEQ ID NO:460:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:460:

Gly Arg Ala Gly Cys Gln Lys Tyr
1               5

(2) INFORMATION FOR SEQ ID NO:461:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:461:

Asn Asn Ile Ile Ile Ser Ala Asp Cys Ala Leu Phe Val Phe Ser Phe
1               5                   10                  15

Leu Tyr (2) INFORMATION FOR SEQ ID NO:462:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:462:

Lys Asp Asp Phe Asp Thr Asp
1               5

(2) INFORMATION FOR SEQ ID NO:463:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:463:

Val Asn Asn Phe His Ile Thr Ile Ser Lys
1               5                   10

(2) INFORMATION FOR SEQ ID NO:464:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:464:

Thr Ile Phe Leu Cys Ile Asn Ala Ile Glu Ser Cys Phe Asn Arg Val
1               5                   10                  15

Thr Asp Phe Cys Thr Ala Val Ser Gly Arg Trp Gly Asn Ser Cys Tyr
            20                  25                  30

Cys Gly ( 2 ) INFORMATION FOR SEQ ID NO:465:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:465:

Arg Val Ser Ser Gly Gly Gly Gly Tyr Cys Gln Gln Gly His Trp Phe
1               5                   10                  15

( 2 ) INFORMATION FOR SEQ ID NO:466:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:466:

Lys Arg Ala Tyr Lys Ser Gly Lys
1               5

( 2 ) INFORMATION FOR SEQ ID NO:467:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:467:

Ala Asp Ile Leu Phe Thr
1               5

( 2 ) INFORMATION FOR SEQ ID NO:468:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:468:

Arg Ser Arg Ile Met
1               5

( 2 ) INFORMATION FOR SEQ ID NO:469:

( i ) SEQUENCE CHARACTERISTICS:
        ( A ) LENGTH: 66 amino acids
        ( B ) TYPE: amino acid (C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:469:

| Ile | Gln | Pro | Lys | Ser | Tyr | His | Ala | Ile | Ser | Tyr | Leu | Cys | Leu | Phe | Leu |
|---|---|---|---|---|---|---|---|---|---|---|---|---|---|---|---|
| 1 | | | | 5 | | | | | 10 | | | | | 15 | |

| Leu | Leu | Leu | Cys | Gln | Tyr | Phe | Ser | Gly | Ala | Thr | Val | Leu | Trp | Val | Ser |
|---|---|---|---|---|---|---|---|---|---|---|---|---|---|---|---|
| | | | | 20 | | | | 25 | | | | | 30 | | |

| Leu | Trp | Arg | Ala | Cys | Gly | Phe | Phe | Phe | Asn | Lys | Met | Val | Met | Gly | Arg |
|---|---|---|---|---|---|---|---|---|---|---|---|---|---|---|---|
| | | 35 | | | | | 40 | | | | | 45 | | | |

| Gly | Asp | Gly | Phe | Leu | Tyr | Arg | Arg | Trp | His | Thr | Gly | Leu | Phe | Phe | Ser |
|---|---|---|---|---|---|---|---|---|---|---|---|---|---|---|---|
| | 50 | | | | | 55 | | | | | 60 | | | | |

| Ile | Leu |
|---|---|
| 65 | |

(2) INFORMATION FOR SEQ ID NO:470:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:470:

| Lys | Ser | Tyr | Leu | Lys | Met | Ser | Lys | Asp | Asp | Val | Lys | Gln | Glu | His | Lys |
|---|---|---|---|---|---|---|---|---|---|---|---|---|---|---|---|
| 1 | | | | 5 | | | | | 10 | | | | | 15 | |

| Asp | Leu | Glu | Gly | Asp | Pro | Gln | Met | Lys | Thr | Arg | Arg | Arg | Lys | Cys | Arg |
|---|---|---|---|---|---|---|---|---|---|---|---|---|---|---|---|
| | | | 20 | | | | 25 | | | | | 30 | | | |

| Val | Lys | Tyr | Lys | Val | Gly | Val |
|---|---|---|---|---|---|---|
| | | 35 | | | | |

(2) INFORMATION FOR SEQ ID NO:471:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:471:

| Leu | Asn | Leu | Leu | Asn | Asn | Leu | Leu | Arg |
|---|---|---|---|---|---|---|---|---|
| 1 | | | | 5 | | | | |

(2) INFORMATION FOR SEQ ID NO:472:

(i) SEQUENCE CHARACTERISTICS:
(A) LENGTH: 80 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:472:

```
Cys  Val  Ile  Gln  Arg  Ile  Leu  Arg  Phe  Val  Leu  Ala  Ile  Ile  Pro  Pro
 1                   5                   10                            15

Ile  Cys  Gln  Tyr  His  Ala  Ser  Trp  Lys  Lys  Ala  Val  Met  Leu  Lys  Leu
               20                        25                   30

Thr  Ile  Leu  Leu  Thr  Ser  Leu  Asn  Ala  Thr  Ala  Ser  Pro  Leu  Leu  Lys
               35                        40                   45

Met  Leu  Ser  Trp  Pro  Ala  His  Tyr  Phe  Leu  Lys  Trp  Asn  Ala  Glu  Ile
      50                        55                        60

Lys  Phe  Leu  Lys  Arg  Tyr  Leu  Asn  Pro  Leu  Gln  Pro  Cys  Tyr  Val  Trp
 65                        70                       75                        80
```

( 2 ) INFORMATION FOR SEQ ID NO:473:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:473:

```
Ile  Met  Arg  Ile  Leu  Pro  Lys  His  His  Lys  Cys  Phe  Trp  Tyr  Ala  Ser
 1                   5                        10                            15

Ser  Gly  His  Cys  Glu  Gly
               20
```

( 2 ) INFORMATION FOR SEQ ID NO:474:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:474:

```
Glu  Gly  Asn  Ser  Val
 1                    5
```

( 2 ) INFORMATION FOR SEQ ID NO:475:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:475:

```
Glu  Thr  Glu  Asn  Asn  Arg  Phe
 1                    5
```

( 2 ) INFORMATION FOR SEQ ID NO:476:

( i ) SEQUENCE CHARACTERISTICS:
        ( A ) LENGTH: 6 amino acids
        ( B ) TYPE: amino acid
        ( C ) STRANDEDNESS: single ( D ) TOPOLOGY: linear ( i i ) MOLECULE TYPE: protein ( i i i ) HYPOTHETICAL: NO ( x i ) SEQUENCE DESCRIPTION: SEQ ID NO:476:

Pro  Gly  Thr  Ser  Thr  Arg
 1                    5

( 2 ) INFORMATION FOR SEQ ID NO:477:

( i ) SEQUENCE CHARACTERISTICS:
                    ( A ) LENGTH: 13 amino acids
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL: NO ( x i ) SEQUENCE DESCRIPTION: SEQ ID NO:477:

Arg  Ile  Ile  Lys  Leu  Asn  Lys  Ile  Met  Asp  Trp  Cys  Val
 1                    5                        1 0

( 2 ) INFORMATION FOR SEQ ID NO:478:

( i ) SEQUENCE CHARACTERISTICS:
                    ( A ) LENGTH: 26 amino acids
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL: NO ( x i ) SEQUENCE DESCRIPTION: SEQ ID NO:478:

Met  Asp  Ser  Asn  His  Ser  Thr  Pro  Thr  Met  Ser  Arg  Trp  Cys  Ser  Asn
 1                    5                        1 0                           1 5
Gln  Leu  Ser  Tyr  Glu  Arg  Gln  Arg  Cys  Arg
                 2 0                        2 5

( 2 ) INFORMATION FOR SEQ ID NO:479:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL: NO ( x i ) SEQUENCE DESCRIPTION: SEQ ID NO:479:

Gln  Arg  Gly  Arg  Ile  Leu  Ala  Ser  Gln  Pro  Gln
 1                    5                        1 0

( 2 ) INFORMATION FOR SEQ ID NO:480:

( i ) SEQUENCE CHARACTERISTICS:
                    ( A ) LENGTH: 48 amino acids
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL: NO ( x i ) SEQUENCE DESCRIPTION: SEQ ID NO:480:

Gly Lys Arg Glu Ile Ala Ile Phe Phe Leu Lys Ser Pro Asp Cys Gly
1               5                   10                  15

Gly Asn Met Gln His Val Glu Lys Ile Ala Ala Met Arg Arg Leu Ser
            20                  25                  30

Ser Tyr Tyr Arg Ser Ala Leu Gln Asn Asp Gly Gly Arg Leu Thr Leu
        35                  40                  45

( 2 ) INFORMATION FOR SEQ ID NO:481:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:481:

Ile Ala His Pro
1

( 2 ) INFORMATION FOR SEQ ID NO:482:

( i ) SEQUENCE CHARACTERISTICS:
      ( A ) LENGTH: 26 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:482:

His Arg Arg Arg Gly Gln Ala Asp Asp Glu Pro His Pro Glu Ala Cys
1               5                   10                  15

Arg Ser His Thr Ile His His Gln Ile Arg
            20                  25

( 2 ) INFORMATION FOR SEQ ID NO:483:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:483:

Arg Gln Asp Ile Thr Ala Gly
1               5

( 2 ) INFORMATION FOR SEQ ID NO:484:

( i ) SEQUENCE CHARACTERISTICS:
      ( A ) LENGTH: 40 amino acids
      ( B ) TYPE: amino acid
      ( C ) STRANDEDNESS: single
      ( D ) TOPOLOGY: linear ( i i ) MOLECULE TYPE: protein -continued (i i i) HYPOTHETICAL: NO (x i) SEQUENCE DESCRIPTION: SEQ ID NO:484:

His Pro Val Gly Gly Lys Gly Asp Lys Lys Asp Gly Thr Arg Ile Phe
1               5                   1 0                  1 5

Ile Thr Ala Gln Asn Thr Ala Ala Asp Asn Leu Tyr Arg Val Gly Asn
            2 0                  2 5                  3 0

Leu Val Asn Arg Ser Glu Gln His
            3 5                  4 0

(2) INFORMATION FOR SEQ ID NO:485:

(i) SEQUENCE CHARACTERISTICS:
        (A) LENGTH: 21 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:485:

Leu Arg Gln Ala Pro Arg Pro Gln Gly Cys His Cys Arg Ala Lys Gln
1               5                   1 0                  1 5

Tyr Ala Tyr Ala Glu
            2 0

(2) INFORMATION FOR SEQ ID NO:486:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:486:

Pro Gln Pro Tyr Lys Cys Arg Arg Leu Asn Arg Tyr Ala Leu Arg Leu
1               5                   1 0                  1 5

Arg Ile Gln Arg
            2 0

(2) INFORMATION FOR SEQ ID NO:487:

(i) SEQUENCE CHARACTERISTICS:
        (A) LENGTH: 26 amino acids
        (B) TYPE: amino acid
        (C) STRANDEDNESS: single
        (D) TOPOLOGY: linear (i i) MOLECULE TYPE: protein (i i i) HYPOTHETICAL: NO (x i) SEQUENCE DESCRIPTION: SEQ ID NO:487:

Ala Leu Ala Gln Thr Asp Asn Pro Leu Glu Ser Leu Pro Pro Gln Pro
1               5                   1 0                  1 5

Ala Thr Ser Ala Val Arg Thr Ser Ala Ser
            2 0                  2 5

(2) INFORMATION FOR SEQ ID NO:488:

(i) SEQUENCE CHARACTERISTICS:

(A) LENGTH: 37 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:488:

```
Ala Gln Ser Asp Asp Arg Arg His Pro Gln Tyr Leu Met Ala Lys Pro
 1               5                  10                  15
Ala Ala Gln Arg Pro Gln Ile Thr Ser Leu Gln Arg Thr Ala Ser Ala
            20                  25                  30
Ile Gly Asn Pro Ser
            35
```

(2) INFORMATION FOR SEQ ID NO:489:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:489:

```
Ile Arg Arg Phe Met Thr Thr Leu Ser Gly Leu Pro Lys Pro Phe Ser
 1               5                  10                  15
Leu Arg Ile Ser Arg Ile Glu Arg Ala Cys Leu Met
            20                  25
```

(2) INFORMATION FOR SEQ ID NO:490:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:490:

```
Glu Ser Met Ala Ile Asn Ile Thr Gln
 1               5
```

(2) INFORMATION FOR SEQ ID NO:491:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:491:

```
Thr Ala Ala Val Ala Thr Pro Gln Pro Ile Pro Pro Ser Ser Gly Ile
 1               5                  10                  15
Pro Lys Trp Pro
            20
```

( 2 ) INFORMATION FOR SEQ ID NO:492:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:492:

```
Phe Thr Gly Ile Phe Thr Ser Arg Pro Lys Asn Pro Ile Thr Ile Pro
 1               5                  10                  15
Gly Leu Val Leu Ala Arg Pro Ser His Trp Phe Arg Ala Thr
            20                  25                  30
```

( 2 ) INFORMATION FOR SEQ ID NO:493:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:493:

```
Lys Lys Arg Tyr Pro Ala Pro His Ser Ser Ala Arg Arg
 1               5                  10
```

( 2 ) INFORMATION FOR SEQ ID NO:494:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:494:

```
Pro Thr Ala Leu Ser Ala Ser Ala Gly Ser Ile Leu Cys Ile Glu Arg
 1               5                  10                  15
Ile Met Tyr Pro Ala Phe His Arg Thr Ile Ile Thr Ser Thr Glu Thr
            20                  25                  30
Lys Pro Ala Ser Gln Asn Pro Cys Arg Thr
            35                  40
```

( 2 ) INFORMATION FOR SEQ ID NO:495:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:495:

```
Cys Ala Ile Arg Ser Arg Arg Pro Glu Pro Leu Ser Cys Ala Ile Thr
 1               5                  10                  15
```

Gly Val Lys Ala Ser Ser Lys Pro
            20

( 2 ) INFORMATION FOR SEQ ID NO:496:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:496:

Pro Asn Lys Met Ala Gly Ser Arg
 1                   5

( 2 ) INFORMATION FOR SEQ ID NO:497:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:497:

Arg Arg Gln Pro Cys Pro
 1               5

( 2 ) INFORMATION FOR SEQ ID NO:498:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:498:

Arg Tyr Ser Leu Pro Pro
 1               5

( 2 ) INFORMATION FOR SEQ ID NO:499:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:499:

Arg Tyr Arg Arg Ile His Cys Gly Leu Tyr His Leu Arg Lys Asp His
 1               5                   10                  15
Arg Tyr Leu Asn Ala Asn Asn
            20

(2) INFORMATION FOR SEQ ID NO:500:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:500:

```
Arg Ala Ser Leu Val Tyr Phe Cys Thr Tyr Ser Pro Phe Ile Leu Leu
 1               5                  10                  15
Leu Tyr Glu Arg Leu Lys Ser Arg Arg Ser Gly Ser Gln Lys Lys
            20                  25                  30
```

(2) INFORMATION FOR SEQ ID NO:501:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:501:

```
Gln Gly Lys Phe Gln Ser Ile Val Ala Gly Tyr Tyr Tyr Phe Ser Ser
 1               5                  10                  15
Glu Lys Thr Val Val Asn Gly Ala Leu Leu Ala Ser Cys Phe Ser Thr
            20                  25                  30
Cys Tyr Cys Ala Glu Gln Phe Cys Phe Tyr Leu Phe Gln Glu Leu Lys
            35                  40                  45
Ile Cys Leu Arg Gly Ser Tyr Arg Val Pro Arg Asn Trp Tyr Arg
            50                  55                  60
```